(12) United States Patent
Reed et al.

(10) Patent No.: US 12,344,641 B2
(45) Date of Patent: *Jul. 1, 2025

(54) **IMMUNOGENIC COMPOSITIONS COMPRISING *MYCOBACTERIUM TUBERCULOSIS* POLYPEPTIDES AND FUSIONS THEREOF**

(71) Applicant: ACCESS TO ADVANCED HEALTH INSTITUTE, Seattle, WA (US)

(72) Inventors: Steven G. Reed, Bellevue, WA (US); Rhea N. Coler, Seattle, WA (US); Gregory C. Ireton, Seattle, WA (US); Sylvie Bertholet, Gaithersburg, MD (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/407,367

(22) Filed: Jan. 8, 2024

(65) Prior Publication Data

US 2024/0140997 A1 May 2, 2024

Related U.S. Application Data

(60) Division of application No. 17/367,812, filed on Jul. 6, 2021, now Pat. No. 11,897,922, which is a division of application No. 15/815,512, filed on Nov. 16, 2017, now Pat. No. 11,091,521, which is a division of application No. 13/791,511, filed on Mar. 8, 2013, now Pat. No. 9,822,152, which is a continuation of application No. 12/594,806, filed as application No. PCT/US2008/059500 on Apr. 4, 2008, now Pat. No. 8,486,414.

(60) Provisional application No. 60/910,169, filed on Apr. 4, 2007.

(51) Int. Cl.
| | | |
|---|---|---|
| *C07K 14/35* | (2006.01) |
| *A61K 39/00* | (2006.01) |
| *A61K 39/04* | (2006.01) |
| *C07K 14/285* | (2006.01) |
| *G01N 33/569* | (2006.01) |
| *G01N 33/68* | (2006.01) |

(52) U.S. Cl.
CPC ............. *C07K 14/35* (2013.01); *A61K 39/04* (2013.01); *C07K 14/285* (2013.01); *G01N 33/5695* (2013.01); *G01N 33/68* (2013.01); *A61K 2039/55561* (2013.01); *C07K 2319/00* (2013.01); *G01N 2469/20* (2013.01); *Y02A 50/30* (2018.01)

(58) Field of Classification Search
CPC .. C07K 14/35; C07K 14/285; C07K 2319/00; A61K 39/04; A61K 2039/55561; G01N 33/5695; G01N 33/68; G01N 469/20; Y02A 50/30
See application file for complete search history.

(56) References Cited

PUBLICATIONS

Notification of Reexamination for related family Chinese Patent Application No. 201410837977.9, mailed Jul. 16, 2024, 14 pages. Related matter patent CN Office Action for application No. 201410837977.9, issued Jan. 23, 2025, 34 pages (translation included).

*Primary Examiner* — Robert A Zeman
(74) *Attorney, Agent, or Firm* — Benjamin Keim; Newport IP, LLC

(57) ABSTRACT

The present invention relates to compositions and fusion proteins containing at least two *Mycobacterium* sp. antigens, and polynucleotides encoding such compositions and fusion proteins. The invention also relates to methods for their use in the treatment, prevention and/or diagnosis of tuberculosis infections.

15 Claims, 9 Drawing Sheets
Specification includes a Sequence Listing.

Levels of IFN-γ released by antigen stimulated human PBMC

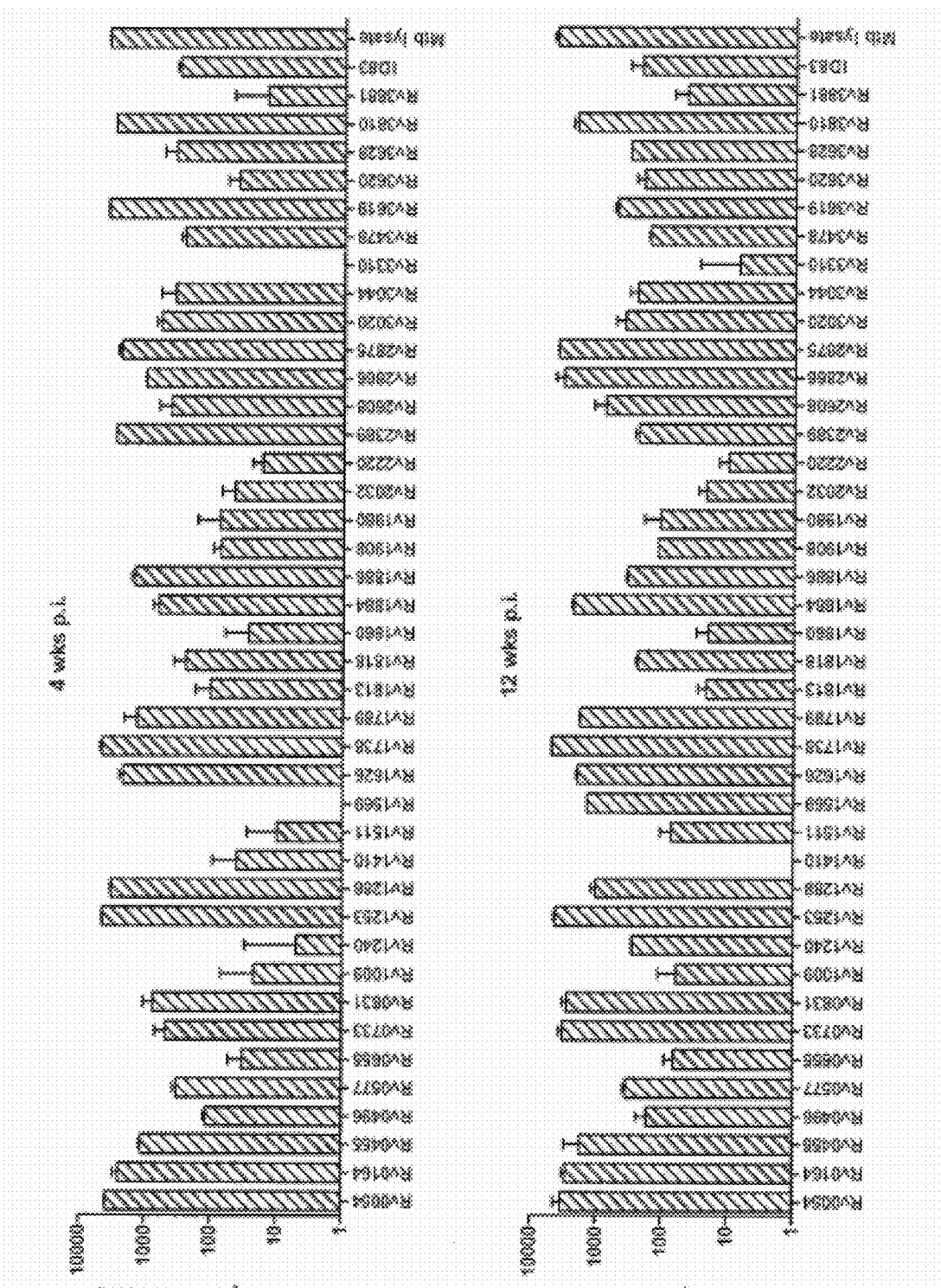

Immune responses to Rv1813, Rv2608, and Rv3620 with CpG in C57BL/6 mice and protection against aerosol challenge with Mtb Immune responses ID83 and ID93 fusion proteins with
GLA-SE in C57BL/6 mice

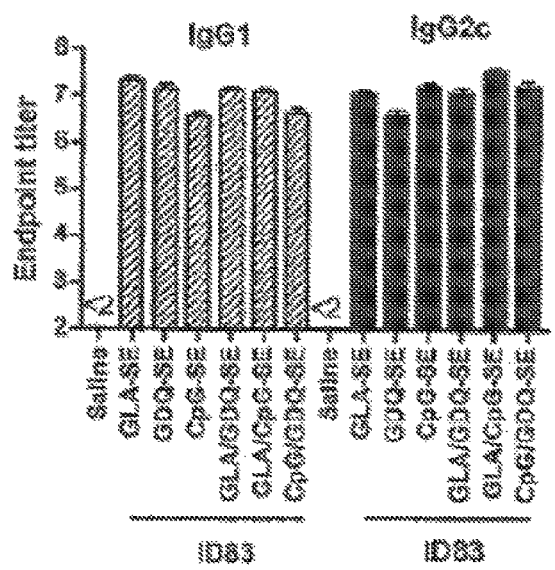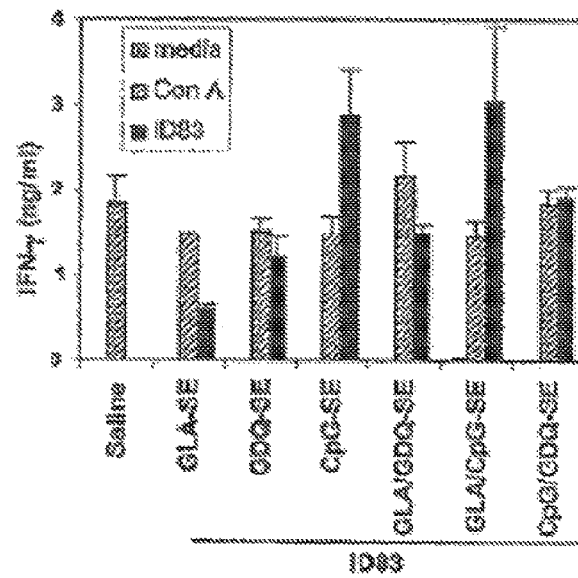
Immune responses ID83 with different adjuvant formulations in C57BL/6 mice Survival of Mtb-infected guinea pigs vaccinated with ID83 in
different adjuvant formulations

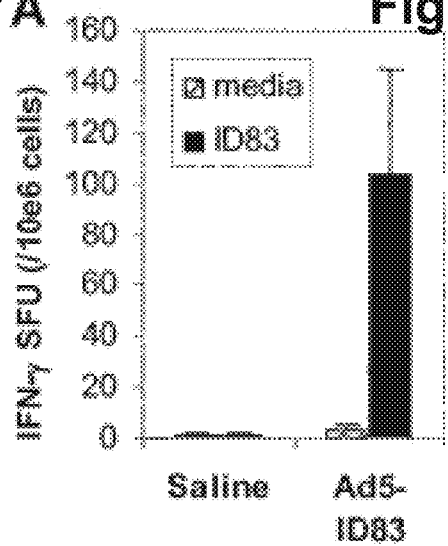 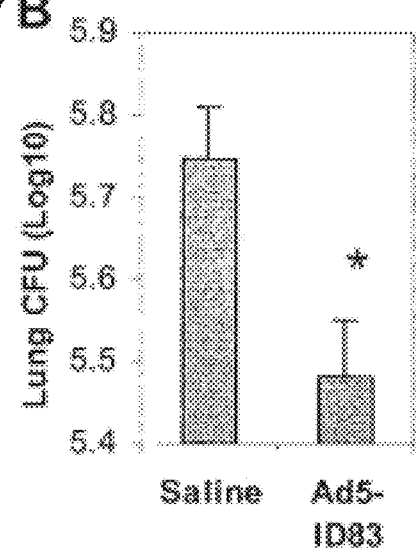
**Ad5-ID83-dependent IFN-γ responses and protection against *M. tuberculosis* in C57BL/6 mice**

Survival of Mtb-infected SWR mice after antibiotics + immunotherapy with Rv1813, Rv2608, Rv3620 and GLA-SE Serological diagnostic of TB

```
                       SEQUENCE LISTING

Sequence total quantity: 318
SEQ ID NO: 1           moltype = AA   length = 161
FEATURE                Location/Qualifiers
source                 1..161
                       mol_type = protein
                       organism = Mycobacterium tuberculosis
SEQUENCE: 1
MTAISCSPRP RYASRMPVLS KTVEVTADAA SIMAIVADIE RYPEWNEGVK GAWVLARYDD   60
GRPSQVRLDT AVQGIEGTYI HAVYYPGENQ IQTVMQQGEL FAKQEQLFSV VATGAASLLT  120
VDMDVQVTMP VPEPMVKMLL NNVLEHLAEN LKQRAEQLAA S                      161

SEQ ID NO: 2           moltype = DNA   length = 495
FEATURE                Location/Qualifiers
source                 1..495
                       mol_type = genomic DNA
                       organism = Mycobacterium tuberculosis
SEQUENCE: 2
catatgacgg caatctcgtg ctcaccgcga cccaggtatg cttcccgaat gccagttttg    60
agcaagaccg tcgaggtcac cgccgacgcc gcatcgatca tggccatcgt tgccgatatc   120
gagcgctacc cagagtggaa tgaaggggtc aagggcgcat gggtgctcgc tcgctacgat   180
gacgggcgtc ccagccaggt gcggctcgac accgctgttc aaggcatcga gggcacctat   240
atccacgccg tgtactaccc aggcgaaaac cagattcaaa ccgtcatgca gcagggtgaa   300
ctgtttgcca agcaggagca gctgttcagt gtggtggcaa ccggcgccgc gagcttgctc   360
acggtggaca tggacgtcca ggtcaccatg ccggtgcccg agccgatggt gaagatgctg   420
ctcaacaacg tcctggagca tctcgccgaa aatctcaagc agcgcgccga gcagctggcg   480
gccagctaaa agctt                                                    495

SEQ ID NO: 3           moltype = AA   length = 181
FEATURE                Location/Qualifiers
source                 1..181
                       mol_type = protein
                       organism = Mycobacterium tuberculosis
SEQUENCE: 3
MGSSHHHHHH SSGLVPRGSH MTAISCSPRP RYASRMPVLS KTVEVTADAA SIMAIVADIE   60
RYPEWNEGVK GAWVLARYDD GRPSQVRLDT AVQGIEGTYI HAVYYPGENQ IQTVMQQGEL  120
FAKQEQLFSV VATGAASLLT VDMDVQVTMP VPEPMVKMLL NNVLEHLAEN LKQRAEQLAA  180
S                                                                  181

SEQ ID NO: 4           moltype = DNA   length = 33
FEATURE                Location/Qualifiers
misc_feature           1..33
                       note = Cloning primer
source                 1..33
                       mol_type = other DNA
                       organism = synthetic construct
SEQUENCE: 4
taggatccca tatgacggca atctcgtgct cac                                33

SEQ ID NO: 5           moltype = DNA   length = 35
FEATURE                Location/Qualifiers
misc_feature           1..35
                       note = Cloning primer
source                 1..35
```

```
                            mol_type = other DNA
                            organism = synthetic construct
SEQUENCE: 5
tagaattcaa gcttttagct ggccgccagc tgctc                              35

SEQ ID NO: 6                moltype = AA   length = 328
FEATURE                     Location/Qualifiers
source                      1..328
                            mol_type = protein
                            organism = Mycobacterium tuberculosis
SEQUENCE: 6
VVDAHRGGHP TPMSSTKATL RLAEATDSSG KITKRGADKL ISTIDEFAKI AISSGCAELM    60
AFATSAVRDA ENSEDVLSRV RKETGVELQA LRGEDESRLT FLAVRRWYGW SAGRILNLDI   120
GGGSLEVSSG VDEEPEIALS LPLGAGRLTR EWLPDDPPGR RRVAMLRDWL DAELAEPSVT   180
VLEAGSPDLA VATSKTFRSL ARLTGAAPSM AGPRVKRTLT ANGLRQLIAF ISRMTAVDRA   240
ELEGVSADRA PQIVAGALVA EASMRALSIE AVEICPWALR EGLILRKLDS EADGTALIES   300
SSVHTSVRAV GGQPADRNAA NRSRGSKP                                     328

SEQ ID NO: 7                moltype = DNA   length = 996
FEATURE                     Location/Qualifiers
source                      1..996
                            mol_type = genomic DNA
                            organism = Mycobacterium tuberculosis
SEQUENCE: 7
catatggtcg atgccaccg cggcggccac ccgaccccga tgagctcgac gaaggccacg    60
ctgcggctgg ccgaggccac cgacagctcg gcaagatca ccaagcgcgg agccgacaag   120
ctgatttcca ccatcgacga attcgccaag attgccatca gctcgggctg tgccgagctg   180
atggccttcg ccacgtcggc ggtccgcgac gccgagaatt ccgaggacgt cctgtcccgg   240
gtgcgcaaag agaccggtgt cgagttgcag cgctgcgtg gggaggacga gtcacggctg   300
accttcctgg ccgtgcgacg atggtacggg tggagccgtg ggcgcatcct caacctcgac   360
atcggcggcg gctcgctgga agtgtccagt ggcgtggacg aggagcccga gattgcgtta   420
tcgctgcccc tgggcgccgg acggttgacc cgagagtggc tgcccgacga tccgccgggc   480
cggcgccggg tggcgatgct gcgagactgg ctggatgccg agctggccga gcccagtgtg   540
accgtcctgg aagccggcag ccccgacctg gcggtcgcaa cgtcgaagac gtttcgtctg   600
ttggcgcgac taaccggtgc ggccccatcc atggccgggc cgcgggtgaa gaggaccctt   660
acggcaaatg gtctcgggca actcatcgcg tttatctcta ggatgacggc ggttgaccgt   720
gcagaactgg aagggtaag cgccgaccga gcgccgcaga ttgtggccgg cgccctggtg   780
gcagaggcga gcatgcgagc actgtcgata gaagcggtgg aaatctgccc gtgggcgctg   840
cgggaaggtc tcatcttgcg caaactcgac agcgaagccg acggaaccgc cctcatcgag   900
tcttcgtctg tgcacacttc ggtgcgtgcc gtcggaggtc agccagctga tcggaacgcg   960
gccaaccgat cgagaggcag caaaccatga aagctt                            996

SEQ ID NO: 8                moltype = AA   length = 348
FEATURE                     Location/Qualifiers
source                      1..348
                            mol_type = protein
                            organism = Mycobacterium tuberculosis
SEQUENCE: 8
MGSSHHHHHH SSGLVPRGSH MVDAHRGGHP TPMSSTKATL RLAEATDSSG KITKRGADKL    60
ISTIDEFAKI AISSGCAELM AFATSAVRDA ENSEDVLSRV RKETGVELQA LRGEDESRLT   120
FLAVRRWYGW SAGRILNLDI GGGSLEVSSG VDEEPEIALS LPLGAGRLTR EWLPDDPPGR   180
RRVAMLRDWL DAELAEPSVT VLEAGSPDLA VATSKTFRSL ARLTGAAPSM AGPRVKRTLT   240
ANGLRQLIAF ISRMTAVDRA ELEGVSADRA PQIVAGALVA EASMRALSIE AVEICPWALR   300
EGLILRKLDS EADGTALIES SSVHTSVRAV GGQPADRNAA NRSRGSKP                348

SEQ ID NO: 9                moltype = DNA   length = 32
FEATURE                     Location/Qualifiers
misc_feature                1..32
                            note = Cloning primer
source                      1..32
                            mol_type = other DNA
                            organism = synthetic construct
SEQUENCE: 9
taggatccca tatggtcgat gcccaccgcg gc                                  32

SEQ ID NO: 10               moltype = DNA   length = 35
FEATURE                     Location/Qualifiers
misc_feature                1..35
                            note = Cloning primer
source                      1..35
                            mol_type = other DNA
                            organism = synthetic construct
SEQUENCE: 10
tagaattcaa gctttcatgg tttgctgcct ctcga                               35

SEQ ID NO: 11               moltype = AA   length = 94
FEATURE                     Location/Qualifiers
source                      1..94
                            mol_type = protein
```

```
                        organism = Mycobacterium tuberculosis
SEQUENCE: 11
MCGDQSDHVL QHWTVDISID EHEGLTRAKA RLRWREKELV GVGLARLNPA DRNVPEIGDE    60
LSVARALSDL GKRMLKVSTH DIEAVTHQPA RLLY                                94

SEQ ID NO: 12           moltype = DNA   length = 315
FEATURE                 Location/Qualifiers
source                  1..315
                        mol_type = genomic DNA
                        organism = Mycobacterium tuberculosis
SEQUENCE: 12
catatgcatc accatcacca tcacatgtgc ggcgaccagt cggatcacgt gctgcagcac    60
tggaccgtcg acatatcgat cgacgaacac gaaggattga ctcgggcgaa ggcacggctg   120
cgttggcggg aaaaggaatt ggtgggtgtt ggcctcaatc ggccgaccgc                180
aacgtccccg agatcggcga tgaactctcg gtcgcccgag ccttgtccga cttggggaag   240
cgaatgttga aggtgtcgac ccacgacatc gaagctgtta cccatcagcc ggcgcgattg   300
ttgtattgag aattc                                                    315

SEQ ID NO: 13           moltype = AA   length = 101
FEATURE                 Location/Qualifiers
source                  1..101
                        mol_type = protein
                        organism = Mycobacterium tuberculosis
SEQUENCE: 13
MHHHHHHMCG DQSDHVLQHW TVDISIDEHE GLTRAKARLR WREKELVGVG LARLNPADRN    60
VPEIGDELSV ARALSDLGKR MLKVSTHDIE AVTHQPARLL Y                       101

SEQ ID NO: 14           moltype = DNA   length = 51
FEATURE                 Location/Qualifiers
misc_feature            1..51
                        note = Cloning primer
source                  1..51
                        mol_type = other DNA
                        organism = synthetic construct
SEQUENCE: 14
caattacata tgcatcacca tcaccatcac atgtgcggcg accagtcgga t              51

SEQ ID NO: 15           moltype = DNA   length = 33
FEATURE                 Location/Qualifiers
misc_feature            1..33
                        note = Cloning primer
source                  1..33
                        mol_type = other DNA
                        organism = synthetic construct
SEQUENCE: 15
caattagaat tctcaataca caatcgcgc cgg                                   33

SEQ ID NO: 16           moltype = AA   length = 143
FEATURE                 Location/Qualifiers
source                  1..143
                        mol_type = protein
                        organism = Mycobacterium tuberculosis
SEQUENCE: 16
MITNLRRRTA MAAAGLGAAL GLGILLVPTV DAHLANGSMS EVMMSEIAGL PIPPIIHYGA    60
IAYAPSGASG KAWHQRTPAR AEQVALEKCG DKTCKVVSRF TRCGAVAYNG SKYQGGTGLT   120
RRAAEDDAVN RLEGGRIVNW ACN                                           143

SEQ ID NO: 17           moltype = DNA   length = 363
FEATURE                 Location/Qualifiers
source                  1..363
                        mol_type = genomic DNA
                        organism = Mycobacterium tuberculosis
SEQUENCE: 17
catatgcatc accatcacca tcatctcgcc aacggttcga tgtcggaagt catgatgtcg    60
gaaattgccg ggttgcctat ccctccgatt atccattacg ggcgattgc ctatgccccc   120
agcggcgcgt cgggcaaagc gtggcaccag cgcacaccgg cgcgagcaga gcaagtcgca   180
ctagaaaagt gcggtgacaa gacttgcaaa gtggttagtc gcttcaccag gtgcggcgcg   240
gtcgcctaca acgctcgaa ataccaaggc ggaaccggac tcacgcgccg cgcggcagaa   300
gacgacgccg tgaaccgact cgaaggcggg cggatcgtca ctgggcgtg caactaagaa   360
ttc                                                                 363

SEQ ID NO: 18           moltype = AA   length = 117
FEATURE                 Location/Qualifiers
source                  1..117
                        mol_type = protein
                        organism = Mycobacterium tuberculosis
SEQUENCE: 18
MHHHHHHLAN GSMSEVMMSE IAGLPIPPII HYGAIAYAPS GASGKAWHQR TPARAEQVAL    60
EKCGDKTCKV VSRFTRCGAV AYNGSKYQGG TGLTRRAAED DAVNRLEGGR IVNWACN      117
```

```
SEQ ID NO: 19              moltype = DNA  length = 51
FEATURE                    Location/Qualifiers
misc_feature               1..51
                           note = Cloning primer
source                     1..51
                           mol_type = other DNA
                           organism = synthetic construct
SEQUENCE: 19
caattacata tgcatcacca tcaccatcac catctcgcca acggttcgat g       51

SEQ ID NO: 20              moltype = DNA  length = 33
FEATURE                    Location/Qualifiers
misc_feature               1..33
                           note = Cloning primer
source                     1..33
                           mol_type = other DNA
                           organism = synthetic construct
SEQUENCE: 20
caattagaat tcttagttgc acgcccagtt gac                            33

SEQ ID NO: 21              moltype = AA  length = 154
FEATURE                    Location/Qualifiers
source                     1..154
                           mol_type = protein
                           organism = Mycobacterium tuberculosis
SEQUENCE: 21
MTPGLLTTAG AGRPRDRCAR IVCTVFIETA VVATMFVALL GLSTISSKAD DIDWDAIAQC    60
ESGGNWAANT GNGLYGGLQI SQATWDSNGG VGSPAAASPQ QQIEVADNIM KTQGPGAWPK   120
CSSCSQGDAP LGSLTHILTF LAAETGGCSG SRDD                              154

SEQ ID NO: 22              moltype = DNA  length = 347
FEATURE                    Location/Qualifiers
source                     1..347
                           mol_type = genomic DNA
                           organism = Mycobacterium tuberculosis
SEQUENCE: 22
catatgcatc accatcacca tcacgacgac atcgattggg acgccatcgc gcaatgcgaa    60
tccggcggca attgggcggc caacaccggt aacgggttat acggtggtct gcagatcagc   120
caggcgacgt gggattccaa cggtggtgtc gggtcgccgg cggccgcgag tccccagcaa   180
cagatcgagg tcgcagacaa cattatgaaa acccaaggcc cgggtgcgtg gccgaaatgt   240
agttcttgta gtcagggaga cgcaccgctg ggctgctcac ccacatcctg acgttcctcg   300
cggccgagac tggaggttgt tcggggagca gggacgattg agaattc                347

SEQ ID NO: 23              moltype = AA  length = 112
FEATURE                    Location/Qualifiers
source                     1..112
                           mol_type = protein
                           organism = Mycobacterium tuberculosis
SEQUENCE: 23
MHHHHHHDDI DWDAIAQCES GGNWAANTGN GLYGGLQISQ ATWDSNGGVG SPAAASPQQQ    60
IEVADNIMKT QGPGAWPKCS SCSQGDAPLG SLTHILTFLA AETGGCSGSR DD           112

SEQ ID NO: 24              moltype = DNA  length = 51
FEATURE                    Location/Qualifiers
misc_feature               1..51
                           note = Cloning primer
source                     1..51
                           mol_type = other DNA
                           organism = synthetic construct
SEQUENCE: 24
caattacata tgcatcacca tcaccatcac gacgacatcg attgggacgc c        51

SEQ ID NO: 25              moltype = DNA  length = 33
FEATURE                    Location/Qualifiers
misc_feature               1..33
                           note = Cloning primer
source                     1..33
                           mol_type = other DNA
                           organism = synthetic construct
SEQUENCE: 25
caattagaat tctcaatcgt ccctgctccc cga                            33

SEQ ID NO: 26              moltype = AA  length = 580
FEATURE                    Location/Qualifiers
source                     1..580
                           mol_type = protein
                           organism = Mycobacterium tuberculosis
SEQUENCE: 26
```

```
MNFAVLPPEV NSARIFAGAG LGPMLAAASA WDGLAEELHA AAGSFASVTT GLAGDAWHGP   60
ASLAMTRAAS PYVGWLNTAA GQAAQAAGQA RLAASAFEAT LAATVSPAMV AANRTRLASL  120
VAANLLGQNA PAIAAAEAEY EQIWAQDVAA MFGYHSAASA VATQLAPIQE GLQQQLQNVL  180
AQLASGNLGS GNVGVGNIGN DNIGNANIGF GNRGDANIGI GNIGDRNLGI GNTGNWNIGI  240
GITGNGQIGF GKPANPDVLV VGNGGPGVTA LVMGGTDSLL PLPNIPLLEY AARFITPVHP  300
GYTATFLETP SQFFPFTGLN SLTYDVSVAQ GVTNLHTAIM AQLAAGNEVV VFGTSQSATI  360
ATFEMRYLQS LPAHLRPGLD ELSFTLTGNP NRPDGGILTR FGFSIPQLGF TLSGATPADA  420
YPTVDYAFQY DGVNDFPKYP LNVFATANAI AGILFLHSGL IALPPDLASG VVQPVSSPDV  480
LTTYILLPSQ DLPLLVPLRA IPLLGNPLAD LIQPDLRVLV ELGYDRTAHQ DVPSPFGLFP  540
DVDWAEVAAD LQQGAVQGVN DALSGLGLPP PWQPALPRLF                       580

SEQ ID NO: 27           moltype = DNA   length = 1752
FEATURE                 Location/Qualifiers
source                  1..1752
                        mol_type = genomic DNA
                        organism = Mycobacterium tuberculosis
SEQUENCE: 27
catatgaatt tcgccgtttt gccgccggag gtgaattcgg cgcgcatatt cgccggtgcg   60
ggcctgggcc caatgctggc ggcggcgtcg gcctgggacg ggttggccga ggagttgcat  120
gccgcggcgg gctcgttcgc gtcggtgacc accgggttgg cgggcgacgc gtggcatggt  180
ccggcgtcgc tggcgatgac ccgcgcggcc agcccgtatg tgggtggtt gaacacggcg   240
gcgggtcagg ccgcgcaggc ggccgggcag gcgcggctag gcgagcgc gttcgaggcg    300
acgctggcgg ccaccgtgtc tccagccatg gtcgcggcca accggacacg gctggcgtcg  360
ctggtggcag ccaacttgct gggccagaac gccccggcga tcgcggccgc ggaggctgaa  420
tacgagcaga tatgggccca ggacgtggcc gcgatgttcg gctatcactc cgccgcgtcg  480
gcggtggcca cgcagctggc gcctattcaa gagggtttgc agcagcagct gcaaaacgtg  540
ctggcccagt tggctagcgg gaacctgggc agcggaaatg tgggcgtcgg caacatcggc  600
aacgacaaca ttggcaacgc aaacatcggc ttcggaaatc gaggcgacgc caacatcggc  660
atcgggaata tcggcgacag aaacctcggc attgggaaca ccggcaattg gaatatcggc  720
atcggcatca ccggcaacgg acaaatcggc ttcggcaagc ctgccaaccc cgacgtcttg  780
gtggtgggca acggcggccc gggagtaacc gcgttggtca tgggcggcac cgacagccta  840
ctgccgctgc caacatccc cttactcgag tacgctgcgc ggttcatcac ccccgtgcat   900
cccggataca ccgctacgtt cctggaaacg ccatcgcagt ttttcccatt caccgggctg  960
aatagcctga cctatgacgt ctccgtggcc cagggcgtaa cgaatctgca caccgcgatc 1020
atggcgcaac tcgcggcggg aaacgaagtc gtcgtcttcg gcaccctccca aagccgcacg 1080
atagccacct tcgaaatgcg ctatctgcaa tccctgccag cacacctgcg tccgggtctc 1140
gacgaattgt cctttacgtt gaccggcaat cccaaccggc ccgacggtgg cattcttacg 1200
cgttttggct ctctccatac cgcagttggt ttcacattgt ccggcgcgac gccgccgac   1260
gcctacccca ccgtcgatta cgcgttccag tacgacgcg tcaacgactt ccccaaatac  1320
ccgctgaatg tcttcgcgac cgccaacgcg atcgcgggca tccttttcct gcactccggg 1380
ttgattgcgt tgccgcccga tcttgcctcg ggcgtggtc aaccggtgtc ctcaccggac  1440
gtcctgacca cctacatcct gctgcccagc caagatctgc cgctgctggt cccgctgcgt 1500
gctatccccc tgctgggaaa cccgcttgcc gacctcatcc agccgggcgg cgggtgctcc 1560
gtcgagttgg gttatgaccg caccgcccac caggacgcc ccagcccgtt cggactgttt   1620
ccggacgtcg attgggccga ggtggccgcg gacctcagc aaggcgccgt gcaaggcgtc  1680
aacgacgccc tgtccggact ggggctgccg ccgccgtggc agccggcgct accccgactt 1740
ttctaaaagc tt                                                    1752

SEQ ID NO: 28           moltype = AA   length = 600
FEATURE                 Location/Qualifiers
source                  1..600
                        mol_type = protein
                        organism = Mycobacterium tuberculosis
SEQUENCE: 28
MGSSHHHHHH SSGLVPRGSH MNFAVLPPEV NSARIFAGAG LGPMLAAASA WDGLAEELHA   60
AAGSFASVTT GLAGDAWHGP ASLAMTRAAS PYVGWLNTAA GQAAQAAGQA RLAASAFEAT  120
LAATVSPAMV AANRTRLASL VAANLLGQNA PAIAAAEAEY EQIWAQDVAA MFGYHSAASA  180
VATQLAPIQE GLQQQLQNVL AQLASGNLGS GNVGVGNIGN DNIGNANIGF GNRGDANIGI  240
GNIGDRNLGI GNTGNWNIGI GITGNGQIGF GKPANPDVLV VGNGGPGVTA LVMGGTDSLL  300
PLPNIPLLEY AARFITPVHP GYTATFLETP SQFFPFTGLN SLTYDVSVAQ GVTNLHTAIM  360
AQLAAGNEVV VFGTSQSATI ATFEMRYLQS LPAHLRPGLD ELSFTLTGNP NRPDGGILTR  420
FGFSIPQLGF TLSGATPADA YPTVDYAFQY DGVNDFPKYP LNVFATANAI AGILFLHSGL  480
IALPPDLASG VVQPVSSPDV LTTYILLPSQ DLPLLVPLRA IPLLGNPLAD LIQPDLRVLV  540
ELGYDRTAHQ DVPSPFGLFP DVDWAEVAAD LQQGAVQGVN DALSGLGLPP PWQPALPRLF  600

SEQ ID NO: 29           moltype = DNA   length = 32
FEATURE                 Location/Qualifiers
misc_feature            1..32
                        note = Cloning primer
source                  1..32
                        mol_type = other DNA
                        organism = synthetic construct
SEQUENCE: 29
taggatccca tatgaatttc gccgttttgc cg                                 32

SEQ ID NO: 30           moltype = DNA   length = 36
FEATURE                 Location/Qualifiers
misc_feature            1..36
                        note = Cloning primer
```

```
source                  1..36
                        mol_type = other DNA
                        organism = synthetic construct
SEQUENCE: 30
tagaattcaa gcttttagaa aagtcggggt agcgcc                              36

SEQ ID NO: 31           moltype = AA   length = 87
FEATURE                 Location/Qualifiers
source                  1..87
                        mol_type = protein
                        organism = Mycobacterium tuberculosis
SEQUENCE: 31
MPYTVRFTTT ARRDLHKLPP RILAAVVEFA FGDLSREPLR VGKPLRRELA GTFSARRGTY    60
RLLYRIDDEH TTVVILRVDH RADIYRR                                       87

SEQ ID NO: 32           moltype = DNA   length = 33
FEATURE                 Location/Qualifiers
misc_feature            1..33
                        note = Cloning primer
source                  1..33
                        mol_type = other DNA
                        organism = synthetic construct
SEQUENCE: 32
caattacata tgccttccac cgtgcccttc acc                                 33

SEQ ID NO: 33           moltype = DNA   length = 36
FEATURE                 Location/Qualifiers
misc_feature            1..36
                        note = Cloning primer
source                  1..36
                        mol_type = other DNA
                        organism = synthetic construct
SEQUENCE: 33
caattaaagc ttctatcggc ggtagatgtc cgcgcg                              36

SEQ ID NO: 34           moltype = DNA   length = 330
FEATURE                 Location/Qualifiers
source                  1..330
                        mol_type = genomic DNA
                        organism = Mycobacterium tuberculosis
SEQUENCE: 34
atgggcagca gccatcatca tcatcatcac agcagcggcc tggtgccgcg cggcagccat    60
atgccttaca ccgtgcggtt caccacaacc gcgcgtcgag acctccacaa gctgccaccg   120
cgcatcctcg cggcagtggt cgaattcgcc ttcggcgatc tgtcgcgcga gcccctgcgg   180
gtgggcaagc cccttcggcg cgagttggcc ggcacgttca gcgcgcgtcg cggaacgtac   240
cgcctgctgt accggattga cgacgagcac acaacggtag tgatcctgcg cgtcgatcac   300
cgcgcggaca tctaccgccg atagaagctt                                   330

SEQ ID NO: 35           moltype = AA   length = 107
FEATURE                 Location/Qualifiers
VARIANT                 21
                        note = Xaa = Any Amino Acid
source                  1..107
                        mol_type = protein
                        organism = Mycobacterium tuberculosis
SEQUENCE: 35
MGSSHHHHHH SSGLVPRGSH XPYTVRFTTT ARRDLHKLPP RILAAVVEFA FGDLSREPLR    60
VGKPLRRELA GTFSARRGTY RLLYRIDDEH TTVVILRVDH RADIYRR                107

SEQ ID NO: 36           moltype = AA   length = 97
FEATURE                 Location/Qualifiers
source                  1..97
                        mol_type = protein
                        organism = Mycobacterium tuberculosis
SEQUENCE: 36
MSLLDAHIPQ LIASHTAFAA KAGLMRHTIG QAEQQAMSAQ AFHQGESAAA FQGAHARFVA    60
AAAKVNTLLD IAQANLGEAA GTYVAADAAA ASSYTGF                            97

SEQ ID NO: 37           moltype = DNA   length = 303
FEATURE                 Location/Qualifiers
source                  1..303
                        mol_type = genomic DNA
                        organism = Mycobacterium tuberculosis
SEQUENCE: 37
catatgagtt tgttggatgc ccatattccg cagttgatcg cttcgcatac ggcgtttgcc    60
gctaaggcgg ggttgatgcg catacgatc ggtcaggccg agcagcaggc gatgtcggcg   120
caggcgtttc atcagggaga gtccgcggcg gcgtttcagg gtgcgcatgc ccggtttgtg   180
gccgcggccg ccaaggtcaa taccttgctg gatatcgcgc aagccaattt gggtgaggcc   240
gcgggcacgt atgtggccgc cgatgccgcc gccgcgtcca gctacaccgg gttttaaaag   300
```

```
ctt                                                                   303

SEQ ID NO: 38           moltype = AA  length = 117
FEATURE                 Location/Qualifiers
source                  1..117
                        mol_type = protein
                        organism = Mycobacterium tuberculosis
SEQUENCE: 38
MGSSHHHHHH SSGLVPRGSH MSLLDAHIPQ LIASHTAFAA KAGLMRHTIG QAEQQAMSAQ    60
AFHQGESAAA FQGAHARFVA AAAKVNTLLD IAQANLGEAA GTYVAADAAA ASSYTGF      117

SEQ ID NO: 39           moltype = DNA  length = 34
FEATURE                 Location/Qualifiers
misc_feature            1..34
                        note = Cloning primer
source                  1..34
                        mol_type = other DNA
                        organism = synthetic construct
SEQUENCE: 39
taggatccca tatgagtttg ttggatgccc atat                                 34

SEQ ID NO: 40           moltype = DNA  length = 36
FEATURE                 Location/Qualifiers
misc_feature            1..36
                        note = Cloning primer
source                  1..36
                        mol_type = other DNA
                        organism = synthetic construct
SEQUENCE: 40
tagaattcaa gcttttaaaa cccggtgtag ctggac                               36

SEQ ID NO: 41           moltype = AA  length = 393
FEATURE                 Location/Qualifiers
source                  1..393
                        mol_type = protein
                        organism = Mycobacterium tuberculosis
SEQUENCE: 41
VVDFGALPPE INSARMYAGP GSASLVAAAK MWDSVASDLF SAASAFQSVV WGLTVGSWIG    60
SSAGLMAAAA SPYVAWMSVT AGGQAQLTAAQ VRVAAAAYET AYRLTVPPPV IAENRTELMT  120
LTATNLLGQN TPAIEANQAA YSQMWGQDAE AMYGYAATAA TATEALLPFE DAPLITNPGG  180
LLEQAVAVEE AIDTAAANQL MNNVPQALQQ LAQPAQGVVP SSKLGGLWTA VSPHLSPLSN  240
VSSIANNHMS MMGTGVSMTN TLHSMLKGLA PAAAQAVETA AENGVWAMSS LGSQLGSSLG  300
SSGLGAGVAA NLGRAASVGS LSVPPAWAAA NQAVTPAARA LPLTSLTSAA QTAPGHMLGG  360
LPLGHSVNAG SGINNALRVP ARAYAIPRTP AAG                                393

SEQ ID NO: 42           moltype = DNA  length = 1191
FEATURE                 Location/Qualifiers
source                  1..1191
                        mol_type = genomic DNA
                        organism = Mycobacterium tuberculosis
SEQUENCE: 42
catatggtgg atttcggggc gttaccaccg gagatcaact ccgcgaggat gtacgccggc     60
ccgggttcgg cctcgctggt ggccgccgcg aagatgtggg acagcgtggc gagtgacctg   120
ttttcggccg cgtcggcgtt tcagtcggtg gtctggggtc tgacggtggg gtcgtggata   180
ggttcgtcgg cgggtctgat ggcggcggcg gcctcgccgt atgtggcgtg gatgagcgtc   240
accgcgggcg aggcccagct gaccgccgcc caggtccggg ttgctgcggc ggcctacgaa   300
acagcgtata ggctgacggt gccccgccg gtgatcgccg agaaccgtac cgaactgatg   360
acgctgaccg cgaccaacct cttggggcaa aacacgccgg cgatcgaggc caatcaggcc   420
gcatacagcc agatgtgggg ccaagacgcg gaggcgatgt atggctacgc cgccacggcg   480
gcgacggcga ccgaggcgtt gctgccgttc gaggacgccc cactgatcac caaccccggc   540
gggctccttg agcaggccgt cgcggtcgag gaggccatcg acaccgccgc ggcgaaccag   600
ttgatgaaca atgtgcccca agcgctgcaa cagctggccc agccagcgca gggcgtcgta   660
ccttcttcca agctgggtgg gctgtggacg gcggtctcgc cgcatctgtc gccgctcagc   720
aacgtcagtt cgatagccaa caaccacatg tcgatgatgg gacggggtgt gtcgatgacc   780
aacaccttgc actcgatgtt gaagggctta gctccggcgg cggctcaggc cgtggaaacc   840
gcggcggaaa acggggtctg ggcgatgagc tcgctgggca gccagctggg ttcgtcgctg   900
ggttcttcgg gtctgggcgc tggggtggcc gccaacttgg gtcgggcggc ctcggtcggt   960
tcgttgtcgg tgccgccagc gatgggccgc gccaaccagg cggtcacccc ggcggcgcgg  1020
cgcctgccca tgaccagcct gaccagcgcc gcccaaaccg cccccggaca catgctgggc  1080
gggctaccgc tggggcactc ggtcaacgcc ggcagcggta tcaacaatgc gctgcgggtg  1140
ccggcacggg cctacgcgat accccgcaca ccggccgccg gatagaagct t            1191

SEQ ID NO: 43           moltype = AA  length = 413
FEATURE                 Location/Qualifiers
source                  1..413
                        mol_type = protein
                        organism = Mycobacterium tuberculosis
SEQUENCE: 43
MGSSHHHHHH SSGLVPRGSH MVDFGALPPE INSARMYAGP GSASLVAAAK MWDSVASDLF    60
```

```
SAASAFQSVV WGLTVGSWIG SSAGLMAAAA SPYVAWMSVT AGGAQLTAAQ VRVAAAAYET    120
AYRLTVPPPV IAENRTELMT LTATNLLGQN TPAIEANQAA YSQMWGQDAE AMYGYAATAA    180
TATEALLPFE DAPLITNPGG LLEQAVAVEE AIDTAAANQL MNNVPQALQQ LAQPAQGVVP    240
SSKLGGLWTA VSPHLSPLSN VSSIANNHMS MMGTGVSMTN TLHSMLKGLA PAAAQAVETA    300
AENGVWAMSS LGSQLGSSLG SSGLGAGVAA NLGRAASVGS LSVPPAWAAA NQAVTPAARA    360
LPLTSLTSAA QTAPGHMLGG LPLGHSVNAG SGINNALRVP ARAYAIPRTP AAG           413

SEQ ID NO: 44           moltype = DNA  length = 33
FEATURE                 Location/Qualifiers
misc_feature            1..33
                        note = Cloning primer
source                  1..33
                        mol_type = other DNA
                        organism = synthetic construct
SEQUENCE: 44
taggatccca tatggtggat ttcggggcgt tac                                 33

SEQ ID NO: 45           moltype = DNA  length = 35
FEATURE                 Location/Qualifiers
misc_feature            1..35
                        note = Cloning primer
source                  1..35
                        mol_type = other DNA
                        organism = synthetic construct
SEQUENCE: 45
tagaattcaa gcttctatcc ggcggccggt gtgcg                               35

SEQ ID NO: 46           moltype = AA  length = 94
FEATURE                 Location/Qualifiers
source                  1..94
                        mol_type = protein
                        organism = Mycobacterium tuberculosis
SEQUENCE: 46
MTINYQFGDV DAHGAMIRAQ AGSLEAEHQA IISDVLTASD FWGGAGSAAC QGFITQLGRN    60
FQVIYEQANA HGQKVQAAGN NMAQTDSAVG SSWA                                94

SEQ ID NO: 47           moltype = DNA  length = 294
FEATURE                 Location/Qualifiers
source                  1..294
                        mol_type = genomic DNA
                        organism = Mycobacterium tuberculosis
SEQUENCE: 47
catatgacca tcaactatca attcggggac gtcgacgctc acggcgccat gatccgcgct    60
caggccggt cgctggaggc cgagcatcag gccatcattt ctgatgtgtt gaccgcgagt    120
gacttttggg gcggcgccgg ttcggcggcc tgccaggggt tcattaccca gctgggccgt    180
aacttccagg tgatctacga gcaggccaac gcccacgggc agaaggtgca ggctgccggc    240
aacaacatgg cacaaaccga cagcgccgtc ggctccagct gggcctaaaa gctt          294

SEQ ID NO: 48           moltype = AA  length = 114
FEATURE                 Location/Qualifiers
source                  1..114
                        mol_type = protein
                        organism = Mycobacterium tuberculosis
SEQUENCE: 48
MGSSHHHHHH SSGLVPRGSH MTINYQFGDV DAHGAMIRAQ AGSLEAEHQA IISDVLTASD    60
FWGGAGSAAC QGFITQLGRN FQVIYEQANA HGQKVQAAGN NMAQTDSAVG SSWA          114

SEQ ID NO: 49           moltype = DNA  length = 33
FEATURE                 Location/Qualifiers
misc_feature            1..33
                        note = Cloning primer
source                  1..33
                        mol_type = other DNA
                        organism = synthetic construct
SEQUENCE: 49
taggatccca tatgaccatc aactatcaat tcg                                 33

SEQ ID NO: 50           moltype = DNA  length = 35
FEATURE                 Location/Qualifiers
misc_feature            1..35
                        note = Cloning primer
source                  1..35
                        mol_type = other DNA
                        organism = synthetic construct
SEQUENCE: 50
tagaattcaa gcttttaggc ccagctggag ccgac                               35

SEQ ID NO: 51           moltype = AA  length = 98
FEATURE                 Location/Qualifiers
```

| | | |
|---|---|---|
| source | 1..98<br>mol_type = protein<br>organism = Mycobacterium tuberculosis | |
| SEQUENCE: 51 | | |

MTSRFMTDPH AMRDMAGRFE VHAQTVEDEA RRMWASAQNI SGAGWSGMAE ATSLDTMTQM 60
NQAFRNIVNM LHGVRDGLVR DANNYEQQEQ ASQQILSS                        98

| | | |
|---|---|---|
| SEQ ID NO: 52<br>FEATURE<br>source | moltype = DNA  length = 306<br>Location/Qualifiers<br>1..306<br>mol_type = genomic DNA<br>organism = Mycobacterium tuberculosis | |
| SEQUENCE: 52 | | | catatgacct cgcgttttat gacggatccg cacgcgatgc gggacatggc gggccgtttt  60
gaggtgcacg cccagacggt ggaggacgag gctcgccgga tgtgggcgtc cgcgcaaaac 120
atttccggcg cgggctggag tggcatggcc gaggcgacct cgctagacac catgacccag 180
atgaatcagg cgtttcgcaa catcgtgaac atgctgcacg gggtgcgtga cgggctggtt 240
cgcgacgcca acaactacga acagcaagag caggcctccc agcagatcct cagcagctga 300
aagctt                                                           306

| | | |
|---|---|---|
| SEQ ID NO: 53<br>FEATURE<br>source | moltype = AA  length = 118<br>Location/Qualifiers<br>1..118<br>mol_type = protein<br>organism = Mycobacterium tuberculosis | |
| SEQUENCE: 53 | | |

MGSSHHHHHH SSGLVPRGSH MTSRFMTDPH AMRDMAGRFE VHAQTVEDEA RRMWASAQNI  60
SGAGWSGMAE ATSLDTMTQM NQAFRNIVNM LHGVRDGLVR DANNYEQQEQ ASQQILSS  118

| | | |
|---|---|---|
| SEQ ID NO: 54<br>FEATURE<br>misc_feature<br>source | moltype = DNA  length = 32<br>Location/Qualifiers<br>1..32<br>note = Cloning primer<br>1..32<br>mol_type = other DNA<br>organism = synthetic construct | |
| SEQUENCE: 54 | | | taggatccca tatgacctcg cgttttatga cg                               32

| | | |
|---|---|---|
| SEQ ID NO: 55<br>FEATURE<br>misc_feature<br>source | moltype = DNA  length = 35<br>Location/Qualifiers<br>1..35<br>note = Cloning primer<br>1..35<br>mol_type = other DNA<br>organism = synthetic construct | |
| SEQUENCE: 55 | | | tagaattcaa gctttcagct gctgaggatc tgctg                            35

| | | |
|---|---|---|
| SEQ ID NO: 56<br>FEATURE<br>source | moltype = AA  length = 284<br>Location/Qualifiers<br>1..284<br>mol_type = protein<br>organism = Mycobacterium tuberculosis | |
| SEQUENCE: 56 | | |

VPNRRRRKLS TAMSAVAALA VASPCAYFLV YESTETTERP EHHEFKQAAV LTDLPGELMS  60
ALSQGLSQFG INIPPVPSLT GSGDASTGLT GPGLTSPGLT SPGLTSPGLT DPALTSPGLT 120
PTLPGSLAAP GTTLAPTPGV GANPALTNPA LTSPTGATPG LTSPTGLDPA LGGANEIPIT 180
TPVGLDPGAD GTYPILGDPT LGTIPSSPAT TSTGGGGLVN DVMQVANELG ASQAIDLLKG 240
VLMPSIMQAV QNGGAAAPAA SPPVPPIPAA AAVPPTDPIT VPVA                 284

| | | |
|---|---|---|
| SEQ ID NO: 57<br>FEATURE<br>source | moltype = DNA  length = 819<br>Location/Qualifiers<br>1..819<br>mol_type = genomic DNA<br>organism = Mycobacterium tuberculosis | |
| SEQUENCE: 57 | | | catatgcatc accatcacca tcacagtcct tgtgcatatt ttcttgtcta cgaatcaacc  60
gaaacgaccg agcggcccga gcaccatgaa ttcaagcagg cggcggtgtt gaccgacctg 120
cccggcgagc tgatgtccgc gctatcgcag gggttgtccc agttcgggat caacataccg 180
ccggtgccca gctgaccgg gagcggcgat gccagcacgg gtctaaccgg tcctggcctg 240
actagtccgg gattgaccag cccggggattg accagcccgg gctcaccga ccctgccctt 300
accagtccgg gcctgacgcc aaccctgccc ggatcactcg ccgcgcccgg caccaccctg 360
gcgccaacgc ccggctgggg ggccaatccg gcgctcacca acccgccgct gaccagcccg 420
accggggcga cgccgggatt gaccagcccg acgggtttgg atcccgcgct gggcggcgcc 480
aacgaaatcc cgattacgac gccggtcgga ttggatcccg ggctgacgg cacctatccg 540
atcctcggtg atccaacact ggggaccata ccgagcagcc ccgccaccac ctccaccggc 600
ggcggcggtc tcgtcaacga cgtgatgcag gtggccaacg agttgggcgc cagtcaggct 660
atcgacctgc taaaaggtgt gctaatgccg tcgatcatga aggccgtcca gaatggcggc 720

-continued

```
gcggccgcgc cggcagccag cccgccggtc ccgcccatcc ccgcggccgc ggcggtgcca    780
ccgacggacc caatcaccgt gccggtcgcc taactcgag                            819

SEQ ID NO: 58          moltype = AA  length = 269
FEATURE                Location/Qualifiers
source                 1..269
                       mol_type = protein
                       organism = Mycobacterium tuberculosis
SEQUENCE: 58
MHHHHHHSPC AYFLVYESTE TTERPEHHEF KQAAVLTDLP GELMSALSQG LSQFGINIPP     60
VPSLTGSGDA STGLTGPGLT SPGLTSPGLT SPGLTDPALT SPGLTPTLPG SLAAPGTTLA    120
PTPGVGANPA LTNPALTSPT GATPGLTSPT GLDPALGGAN EIPITTPVGL DPGADGTYPI    180
LGDPTLGTIP SSPATTSTGG GGLVNDVMQV ANELGASQAI DLLKGVLMPS IMQAVQNGGA    240
AAPAASPPVP PIPAAAAVPP TDPITVPVA                                      269

SEQ ID NO: 59          moltype = DNA  length = 54
FEATURE                Location/Qualifiers
misc_feature           1..54
                       note = Cloning primer
source                 1..54
                       mol_type = other DNA
                       organism = synthetic construct
SEQUENCE: 59
caattacata tgcatcacca tcaccatcac agtccttgtg catatttct tgtc             54

SEQ ID NO: 60          moltype = DNA  length = 36
FEATURE                Location/Qualifiers
misc_feature           1..36
                       note = Cloning primer
source                 1..36
                       mol_type = other DNA
                       organism = synthetic construct
SEQUENCE: 60
caattactcg agttaggcga ccggcacggt gattgg                               36

SEQ ID NO: 61          moltype = AA  length = 666
FEATURE                Location/Qualifiers
source                 1..666
                       mol_type = protein
                       organism = Mycobacterium tuberculosis
SEQUENCE: 61
MAADYDKLFR PHEGMEAPDD MAAQPFFDPS ASFPPAPASA NLPKPNGQTP PPTSDDLSER     60
FVSAPPPPPP PPPPPPPTPM PIAAGEPPSP EPAASKPPTP PMPIAGPEPA PPKPPTPPMP    120
IAGPEPAPPK PPTPPMPIAG PAPTPTESQL APPRPPTPQT PTGAPQQPES PAPHVPSHGP    180
HQPRRTAPAP PWAKMPIGEP PPAPSRPSAS PAEPPTRPAP QHSRRARRGH RYRTDTERNV    240
GKVATGPSIQ ARLRAEEASG AQLAPGTEPS PAPLGQPRSY LAPPTRPAPT EPPPSPSPQR    300
NSGRRAERRV HPDLAAQHAA AQPDSITAAT TGGRRRKRAA PDLDATQKSL RPAAKGPKVK    360
KVKPQKPKAT KPPKVVSQRG WRHWVHALTR INLGLSPDEK YELDLHARVR RNPRGSYQIA    420
VVGLKGGAGK TTLTAALGST LAQVRADRIL ALDADPGAGN LADRVGRQSG ATIADVLAEK    480
ELSHYNDIRA HTSVNAVNLE VLPAPEYSSA QRALSDADWH FIADPASRFY NLVLADCGAG    540
FFDPLTRGVL STVSGVVVVA SVSIDGAQQA SVALDWLRNN GYQDLASRAC VVINHIMPGE    600
PNVAVKDLVR HFEQQVQPGR VVVMPWDRHI AAGTEISLDL LDPIYKRKVL ELAAALSDDF    660
ERAGRR                                                               666

SEQ ID NO: 62          moltype = DNA  length = 2010
FEATURE                Location/Qualifiers
source                 1..2010
                       mol_type = genomic DNA
                       organism = Mycobacterium tuberculosis
SEQUENCE: 62
catatggcgg ccgactacga caagctcttc cggccgcacg aaggtatgga agctccggac     60
gatatgcag cgcagccgtt cttcgacccc agtgcttcgt ttccgccggc gcccgcatcg    120
gcaaacctac cgaagcccaa cggccagact ccgcccccga cgtccgacga cctgtcggag    180
cggttcgtgt cggccccgcc gccgccaccc cacccccca ctcgcctcc gccaactccg     240
atgccgatcg ccgcaggaga gccgccctcg ccggaaccgg ccgcatctaa accacccaca    300
ccccccatgc ccatcgccgg acccgaaccg gccccaccca aacccaccca cccccccatg    360
cccatcgccg gacccgaacc ggccccacca aaaccaccca cacctccgat gcccatcgcc    420
ggacctgcac ccacccaac cgaatcccag ttggcgcccc ccagaccacc gacaccacaa    480
acgccaaccg gagcgccgca caaccggaa tcaccgcagc agcccacgta ccctcgcacggg    540
ccacatcaac cccggcgcac cgcaccagca ccgccctggg caaagatgcc aatcggcgaa    600
ccccgccg ctccgtccag accgtctgcg tccccggccg aaccaccgac ccggcctgcc    660
ccccaacact cccgacgtgc gcgccggggt caccgctatc gcacagacac cgaacgaaac    720
gtcgggaagg tagcaactgg tccatccatc caggcgcggc tgcgggcaga ggaagcatcc    780
ggcgcgcaac tcgccccggg aacggagccc tcgccagccc cgttggggca accgagatcg    840
tatctggctc cgcccacccg ccccgcgccg acagaacctc ccccagccc tcgccgcag    900
cgcaactccg gtcggcgtgc cgagcgacgc gtccacccg atttagccgc ccaacatgcc    960
gcggcgcaac ctgattcaat tacggccgca accactggcg gtcgtcgccg caagcgtgca   1020
gcgccggatc tcgacgcgac acagaaatcc ttaaggccgc cggccaaggg gccgaaggtg   1080
aagaaggtga agccccagaa accgaaggcc acgaagccgc ccaaagtggt gtcgcagcgc   1140
```

-continued

```
ggctggcgac attgggtgca tgcgttgacg cgaatcaacc tgggcctgtc acccgacgag  1200
aagtacgagc tggacctgca cgctcgagtc cgccgcaatc cccgcgggtc gtatcagatc  1260
gccgtcgtcg gtctcaaagg tggggctggc aaaaccacgc tgacagcagc gttggggtcg  1320
acgttggctc aggtgcgggc cgaccggatc ctggctctag acgcggatcc aggcgccgga  1380
aacctcgccg atcgggtagg gcgacaatcg ggcgcgacca tcgctgatgt gcttgcagaa  1440
aaagagctgt cgcactacaa cgacatccgc gcacacacta gcgtcaatgc ggtcaatctg  1500
gaagtgctgc cggcaccgga atacagctcg gcgcagcgcg cgctcagcga cgccgactgg  1560
catttcatcg ccgatcctgc gtcgaggttt tacaacctcg tcttggctga ttgtggggcc  1620
ggcttcttcg acccgctgac ccgcggcgtg ctgtccacgg tgtccggtgt cgtggtcgtg  1680
gcaagtgtct caatcgacgg cgcacaacag gcgtcggtcg cgttggactg gttgcgcaac  1740
aacggttacc aagatttggc gagccgcgca tgcgtggtca tcaatcacat catgccggga  1800
gaacccaatg tcgcagttaa agacctggtg cggcatttcg aacagcaagt tcaacccggc  1860
cgggtcgtgg tcatgccgtg ggacaggcac attgcggccg gaaccgagat ttcactcgac  1920
ttgctcgacc ctatctacaa gcgcaaggtc ctcgaattgg ccgcagcgct atccgacgat  1980
ttcgagaggg ctggacgtcg ttgaggattc                                    2010

SEQ ID NO: 63          moltype = AA  length = 452
FEATURE                Location/Qualifiers
source                 1..452
                       mol_type = protein
                       organism = Mycobacterium tuberculosis
SEQUENCE: 63
HMHHHHHHSR RARRGHRYRT DTERNVGKVA TGPSIQARLR AEEASGAQLA PGTEPSPAPL  60
GQPRSYLAPP TRPAPTEPPP SPSPQRNSGR RAERRVHPDL AAQHAAAQPD SITAATTGGR  120
RRKRAAPDLD ATQKSLRPAA KGPKVKKVKP QKPKATKPPK VVSQRGWRHW VHALTRINLG  180
LSPDEKYELD LHARVRRNPR GSYQIAVVGL KGGAGKTTLT AALGSTLAQV RADRILALDA  240
DPGAGNLADR VGRQSGATIA DVLAEKELSH YNDIRAHTSV NAVNLEVLPA PEYSSAQRAL  300
SDADWHFIAD PASRFYNLVL ADCGAGFFDP LTRGVLSTVS GVVVVASVSI DGAQQASVAL  360
DWLRNNGYQD LASRACVVIN HIMPGEPNVA VKDLVRHFEQ QVQPGRVVVM PWDRHIAAGT  420
EISLDLLDPI YKRKVLELAA ALSDDFERAG RR                                452

SEQ ID NO: 64          moltype = DNA  length = 32
FEATURE                Location/Qualifiers
misc_feature           1..32
                       note = Cloning primer
source                 1..32
                       mol_type = other DNA
                       organism = synthetic construct
SEQUENCE: 64
gatcccatgg gcatatggcg gccgactacg ac                                 32

SEQ ID NO: 65          moltype = DNA  length = 28
FEATURE                Location/Qualifiers
misc_feature           1..28
                       note = Cloning primer
source                 1..28
                       mol_type = other DNA
                       organism = synthetic construct
SEQUENCE: 65
gtcagaattc tcaacgacgt ccagccct                                      28

SEQ ID NO: 66          moltype = DNA  length = 1185
FEATURE                Location/Qualifiers
misc_feature           1..1185
                       note = Mycobaterium tuberculosi fusion sequence
source                 1..1185
                       mol_type = other DNA
                       organism = synthetic construct
SEQUENCE: 66
atgggcagca gccatcatca tcatcatcac agcagcggcc tggtgccgcg cggcagccat  60
atggacgaca tcgattggga cgccatcgcg caatgcgaat ccggcggcaa ttgggcggcc  120
aacaccggta acgggttata cggtggtctg cagatcagcc aggcgacgtg ggattccaac  180
ggtggtgtcg ggtcgccggc ggccgcgagt ccccagcaac agatcgaggt cgcagacaac  240
attatgaaaa cccaaggccc gggtgcgtgg ccgaaatgta gttcttgtag tcagggagac  300
gcaccgctgg gctcgctcac ccacatcctg acgttcctcg cggccgagac tggaggttgt  360
tcggggagca gggacgatga gctcagtcct tgtgcatatt ttcttgtcta cgaatcaacc  420
gaaacgaccg agcggcccga gcaccatgaa ttcaagcagg cggcggtgtt gaccgacctg  480
cccggcgagc tgatgtccgc gctatcgcag ggttgtcccc agttcgggat caacataccg  540
ccggtgccca gcctgaccgg gagcggcgat gccagcacgg gtctaaccgg tcctggcctg  600
actagtccgg gattgaccag cccgggattg accagcccgg gcctcaccga ccctgccctt  660
accagtccgg gcctgacgcc aaccctgccc ggatcactcg ccgcgcccgg caccaccctg  720
gcgccaacgc ccggcgtggg ggccaatccg gcgctcacca accccgcgct gaccagcccg  780
accggggcga cgccgggatt gaccagcccg acgggtttgg atcccgcgct gggcggcgcc  840
aacgaaatcc cgattacgac gccggtcgga ttggatcccg ggctgacggc cacctatccg  900
atcctcggtg atccaacact ggggaccata ccgagcagcc ccgccaccac ctccaccggc  960
ggcggcggtc tcgtcaacga cgtgatgcag gtggccaacg agttgggcgc cagtcaggct  1020
atcgacctgc taaaaggtgt gctaatgccg tcgatcatgc aggccgtcca gaatggcggc  1080
gcggccgcgc cggcagccag cccgccggtc ccgcccatcc ccgcggccgc ggcggtgcca  1140
ccgacggacc caatcaccgt gccggtcgcc ggtacctaaa agctt                    1185
```

```
SEQ ID NO: 67          moltype = AA  length = 392
FEATURE                Location/Qualifiers
REGION                 1..392
                       note = Mycobaterium tuberculosi fusion sequence
source                 1..392
                       mol_type = protein
                       organism = synthetic construct
SEQUENCE: 67
MGSSHHHHHH SSGLVPRGSH MDDIDWDAIA QCESGGNWAA NTGNGLYGGL QISQATWDSN  60
GGVGSPAAAS PQQQIEVADN IMKTQGPGAW PKCSSCSQGD APLGSLTHIL TFLAAETGGC  120
SGSRDDELSP CAYFLVYEST ETTERPEHHE FKQAAVLTDL PGELMSALSQ GLSQFGINIP  180
PVPSLTGSGD ASTGLTGPGL TSPGLTSPGL TSPGLTDPAL TSPGLTPTLP GSLAAPGTTL  240
APTPGVGANP ALTNPALTSP TGATPGLTSP TGLDPALGGA NEIPITTPVG LDPGADGTYP  300
ILGDPTLGTI PSSPATTSTG GGGLVNDVMQ VANELGASQA IDLLKGVLMP SIMQAVQNGG  360
AAAPAASPPV PPIPAAAAVP PTDPITVPVA GT                                392

SEQ ID NO: 68          moltype = DNA  length = 33
FEATURE                Location/Qualifiers
misc_feature           1..33
                       note = Cloning primer
source                 1..33
                       mol_type = other DNA
                       organism = synthetic construct
SEQUENCE: 68
caattacata tggacgacat cgattgggac gcc                              33

SEQ ID NO: 69          moltype = DNA  length = 33
FEATURE                Location/Qualifiers
misc_feature           1..33
                       note = Cloning primer
source                 1..33
                       mol_type = other DNA
                       organism = synthetic construct
SEQUENCE: 69
caattagagc tcatcgtccc tgctccccga aca                              33

SEQ ID NO: 70          moltype = DNA  length = 34
FEATURE                Location/Qualifiers
misc_feature           1..34
                       note = Cloning primer
source                 1..34
                       mol_type = other DNA
                       organism = synthetic construct
SEQUENCE: 70
caattagagc tcagtccttg tgcatatttt cttg                             34

SEQ ID NO: 71          moltype = DNA  length = 42
FEATURE                Location/Qualifiers
misc_feature           1..42
                       note = Cloning primer
source                 1..42
                       mol_type = other DNA
                       organism = synthetic construct
SEQUENCE: 71
caattaaagc ttttaggtac cggcgaccgg cacggtgatt gg                    42

SEQ ID NO: 72          moltype = DNA  length = 1707
FEATURE                Location/Qualifiers
misc_feature           1..1707
                       note = Mycobacterium tuberculosis fusion sequence
source                 1..1707
                       mol_type = other DNA
                       organism = synthetic construct
SEQUENCE: 72
atgggcagca gccatcatca tcatcatcac agcagcggcc tggtgccgcg cggcagccat  60
atgggtaccc atctcgccaa cggttcgatg tcggaagtca tgatgtcgga aattgccggg  120
ttgcctatcc ctccgattat ccattacggg gcgattgcct atgcccccag cggcgcgtcg  180
ggcaaagcgt ggcaccagcg cacaccggcg cgagcagagc aagtcgcact agaaaagtgc  240
ggtgacaaga cttgcaaagt ggttagtcgc ttcaccaggt gcggcgcggt cgcctacaac  300
ggctcgaaat accaaggcgg aaccggactc acgcgccgcg cggcagaaga cgacgccgtg  360
aaccgactcg aaggcgggcg gatcgtcaac tgggcgtgca acgagctcat gacctcgcgt  420
tttatgacgg atccgcacgc gatgcgggac atggcgggcc gttttgaggt gcacgcccag  480
acggtggagg acgaggctcg ccggatgtgg gcgtccgcgc aaaacatctc gggcgcgggc  540
tggagtggca tggccgaggc gacctcgcta gacaccatga cccagatgaa tcaggcgttt  600
cgcaacatcg tgaacatgct gcacggggtg cgtgacgggc tggttcgcga cgccaacaac  660
tacgaacagc aagagcaggc ctcccagcag atcctcagca gcgtcgacgt ggtcgatgcc  720
caccgcggcg gccacccgac cccgatgagc tcgacgaagg ccacgctgcg gctggccgag  780
gccaccgaca gctcgggcaa gatcaccaag cgcggagccg acaagctgat ttccaccatc  840
```

```
gacgaattcg ccaagattgc catcagctcg ggctgtgccg agctgatggc cttcgccacg    900
tcggcggtcc gcgacgccga gaattccgag gacgtcctgt cccgggtgcg caaagagacc    960
ggtgtcgagt tgcaggcgct gcgtggggag gacgagtcac ggctgacctt cctggccgtg   1020
cgacgatggc acgggtggag cgctgggcgc atcctcaacc tcgacatcgg cggcggctcg   1080
ctgaagtgt ccagtggcgt ggacgaggag cccgagattg cgttatcgct gccctgggc    1140
gccgacggt tgacccgaga gtggctgccc gacgatccgc cgggccggcg ccgggtggcg   1200
atgctgcgag actggctgga tgccgagctg gccgagccca gtgtgaccgt cctggaagcc   1260
ggcagccccg acctggcggt cgcaacgtcg aagacgtttc gctcgttggc gcgactaacc   1320
ggtgcggccc catccatggc cgggccgcgg gtgaagagga ccctaacggc aaatggtctg   1380
cggcaactca tcgcgtttat ctctaggatg acggcggttg accgtgcaga actggaaggg   1440
gtaagcgccg accgagcgcc gcagattgtg ccggcgccc tggtggcaga ggcgagcatg   1500
cgagcactgt cgatagaagc ggtggaaatc tgcccgtggg cgctgcggga aggtctcatc   1560
ttgcgcaaac tcgacagcga agccgacgga accgccctca tcgagtcttc gtctgtgcac   1620
acttcggtgc gtgccgtcgg aggtcagcca gctgatcgga acgcggccaa ccgatcgaga   1680
ggcagcaaac caagtactta aaagctt                                        1707

SEQ ID NO: 73              moltype = DNA   length = 39
FEATURE                    Location/Qualifiers
misc_feature               1..39
                           note = Cloning primer
source                     1..39
                           mol_type = other DNA
                           organism = synthetic construct
SEQUENCE: 73
caattacata tgggtaccca tctcgccaac ggttcgatg                            39

SEQ ID NO: 74              moltype = DNA   length = 33
FEATURE                    Location/Qualifiers
misc_feature               1..33
                           note = Cloning primer
source                     1..33
                           mol_type = other DNA
                           organism = synthetic construct
SEQUENCE: 74
caattagagc tcgttgcacg cccagttgac gat                                  33

SEQ ID NO: 75              moltype = DNA   length = 33
FEATURE                    Location/Qualifiers
misc_feature               1..33
                           note = Cloning primer
source                     1..33
                           mol_type = other DNA
                           organism = synthetic construct
SEQUENCE: 75
caattagagc tcatgacctc gcgttttatg acg                                  33

SEQ ID NO: 76              moltype = DNA   length = 33
FEATURE                    Location/Qualifiers
misc_feature               1..33
                           note = Cloning primer
source                     1..33
                           mol_type = other DNA
                           organism = synthetic construct
SEQUENCE: 76
caattagtcg acgctgctga ggatctgctg gga                                  33

SEQ ID NO: 77              moltype = DNA   length = 33
FEATURE                    Location/Qualifiers
misc_feature               1..33
                           note = Cloning primer
source                     1..33
                           mol_type = other DNA
                           organism = synthetic construct
SEQUENCE: 77
caattagtcg acatggtcga tgcccaccgc ggc                                  33

SEQ ID NO: 78              moltype = DNA   length = 42
FEATURE                    Location/Qualifiers
misc_feature               1..42
                           note = Cloning primer
source                     1..42
                           mol_type = other DNA
                           organism = synthetic construct
SEQUENCE: 78
caattaaagc ttttaagtac ttggtttgct gcctctcgat cg                        42

SEQ ID NO: 79              moltype = AA   length = 566
FEATURE                    Location/Qualifiers
REGION                     1..566
```

-continued

```
                        note = Mycobacterium tuberculosis fusion sequence
source                  1..566
                        mol_type = protein
                        organism = synthetic construct
SEQUENCE: 79
MGSSHHHHHH SSGLVPRGSH MGTHLANGSM SEVMMSEIAG LPIPPIIHYG AIAYAPSGAS  60
GKAWHQRTPA RAEQVALEKC GDKTCKVVSR FTRCGAVAYN GSKYQGGTGL TRRAAEDDAV  120
NRLEGGRIVN WACNELMTSR FMTDPHAMRD MAGRFEVHAQ TVEDEARRMW ASAQNISGAG  180
WSGMAEATSL DTMTQMNQAF RNIVNMLHGV RDGLVRDANN YEQQEQASQQ ILSSVDVVDA  240
HRGGHPTPMS STKATLRLAE ATDSSGKITK RGADKLISTI DEFAKIAISS GCAELMAFAT  300
SAVRDAENSE DVLSRVRKET GVELQALRGE DESRLTFLAV RRWYGWSAGR ILNLDIGGGS  360
LEVSSGVDEE PEIALSLPLG AGRLTREWLP DDPPGRRRVA MLRDWLDAEL AEPSVTVLEA  420
GSPDLAVATS KTFRSLARLT GAAPSMAGPR VKRTLTANGL RQLIAFISRM TAVDRAELEG  480
VSADRAPQIV AGALVAEASM RALSIEAVEI CPWALREGLI LRKLDSEADG TALIESSSVH  540
TSVRAVGGQP ADRNAANRSR GSKPST                                      566

SEQ ID NO: 80           moltype = DNA  length = 2022
FEATURE                 Location/Qualifiers
misc_feature            1..2022
                        note = Mycobacterium tuberculosis fusion sequence
source                  1..2022
                        mol_type = other DNA
                        organism = synthetic construct
SEQUENCE: 80
atgggcagca gccatcatca tcatcatcac agcagcggcc tggtgccgcg cggcagccat  60
atggacgaca tcgattggga cgccatcgcg caatgcgaat ccggcggcaa ttgggcggcc  120
aacaccggta acgggttata cggtggtctg cagatcagcc aggcgacgtg ggattccaac  180
ggtggtgtcg ggtcgccggc ggccgcgagt ccccagcaac agatcgaggt cgcagacaac  240
attatgaaaa cccaaggccc gggtgcgtgg ccgaaatgta gttcttgtag tcagggagac  300
gcaccgctgg gctcgctcac ccacatcctg acgttcctcg cggccgagac tggaggttgt  360
tcggggagca gggacgatgg tacccatctc gccaacggtt cgatgtcgga agtcatgatg  420
tcggaaattg ccgggttgcc tatccctccg attatccatt acggggcgat tgcctatgcc  480
cccagcggcg cgtcgggcaa agcgtggcac cagcgcacac cggcgcgagc agagcaagtc  540
gcactagaaa agtgcggtga caagacttgc aaagtggtta gtcgcttcac caggtgcggc  600
gcggtcgcct acaacggctc gaaataccaa ggcggaaccg gactcacgcg ccgcgcggca  660
gaagacgacg ccgtgaaccg actcgaaggc gggcggatcg tcaactgggc gtgcaacgag  720
ctcatgacct cgcgttttat gacggatccg cacgcgatgc gggacatggc gggccgtttt  780
gaggtgcacg cccagacggt ggaggacgag gctcgccgga tgtgggcgtc cgcgcaaaac  840
atctcgggcg cgggctggag tggcatggcc gaggcgacct cgctagacac catgacccag  900
atgaatcagg cgtttcgcaa catcgtgaac atgctgcacg gggtgcgtga cgggctggtt  960
cgcgacgcca acaactacga acagcaagag caggcctccc agcagatcct cagcagcgtc  1020
gacatggtcg atgcccaccg cggcggccac ccgaccccga tgagctcgac gaaggccacg  1080
ctgcggctgg ccgaggccac cgacagctcg ggcaagatca ccaagcgcgg agccgacaag  1140
ctgatttcca ccatcgacga attcgccaag attgccatca gctcgggctg tgccgagctg  1200
atggccttcg ccacgtcggc ggtccgcgac gccgagaatt ccgaggacgt cctgtcccgg  1260
gtgcgcaaag agaccggtgt cgagttgcag gcgctgcgtg gggaggacga gtcacggctg  1320
accttcctgg ccgtgcgacg atggtacggg tggagcgctg ggcgcatcct caacctcgac  1380
atcggcggcg gctcgctgga agtgtccagt ggcgtggacg aggagcccga gattgcgtta  1440
tcgctgcccc tgggcgccgg acggttgacc cgagagtggc tgcccgacga tccgccgggc  1500
cggcgccggg tggcgatgct gcgagactgg ctggatgccg agctggccga gcccagtgtg  1560
accgtcctgg aagccggcag ccccgacctg gcggtcgcaa cgtcgaagac gtttcgctcg  1620
ttggcgcgac taaccggtgc ggccccatcc atggccgggc cgcgggtgaa gaggaccccta  1680
acggcaaatg gtctgcggca actcatcgcg tttatctcta ggatgacggc ggttgaccgt  1740
gcagaactgg aaggggtaag cgccgaccga gcgccgcaga ttgtggccgg cgccctggtg  1800
gcagaggcga gcatgcgagc actgtcgata gaagcggtgg aaatctgccc gtgggcgctg  1860
cgggaaggtc tcatcttgcg caaactcgac agcgaagccg acggaaccgc cctcatcgag  1920
tcttcgtctg tgcacacttc ggtgcgtgcc gtcggaggtc agccagctga tcggaacgcg  1980
gccaaccgat cgagaggcag caaaccaagt acttaaaagc tt                    2022

SEQ ID NO: 81           moltype = DNA  length = 33
FEATURE                 Location/Qualifiers
misc_feature            1..33
                        note = Cloning primer
source                  1..33
                        mol_type = other DNA
                        organism = synthetic construct
SEQUENCE: 81
caattacata tggacgacat cgattgggac gcc                              33

SEQ ID NO: 82           moltype = DNA  length = 42
FEATURE                 Location/Qualifiers
misc_feature            1..42
                        note = Cloning primer
source                  1..42
                        mol_type = other DNA
                        organism = synthetic construct
SEQUENCE: 82
caattaaagc ttttaagtac ttggtttgct gcctctcgat cg                    42
```

-continued

```
SEQ ID NO: 83          moltype = AA  length = 671
FEATURE                Location/Qualifiers
REGION                 1..671
                       note = Mycobacterium tuberculosis fusion sequence
source                 1..671
                       mol_type = protein
                       organism = synthetic construct
SEQUENCE: 83
MGSSHHHHHH SSGLVPRGSH MDDIDWDAIA QCESGGNWAA NTGNGLYGGL QISQATWDSN  60
GGVGSPAAAS PQQQIEVADN IMKTQGPGAW PKCSSCSQGD APLGSLTHIL TFLAAETGGC  120
SGSRDDGTHL ANGSMSEVMM SEIAGLPIPP IIHYGAIAYA PSGASGKAWH QRTPARAEQV  180
ALEKCGDKTC KVVSRFTRCG AVAYNGSKYQ GGTGLTRRAA EDDAVNRLEG GRIVNWACNE  240
LMTSRFMTDP HAMRDMAGRF EVHAQTVEDE ARRMWASAQN ISGAGWSGMA EATSLDTMTQ  300
MNQAFRNIVN MLHGVRDGLV RDANNYEQQE QASQQILSSV DMVDAHRGGH PTPMSSTKAT  360
LRLAEATDSS GKITKRGADK LISTIDEFAK IAISSGCAEL MAFATSAVRD AENSEDVLSR  420
VRKETGVELQ ALRGEDESRL TFLAVRRWYG WSAGRILNLD IGGGSLEVSS GVDEEPEIAL  480
SLPLGAGRLT REWLPDDPPG RRRVAMLRDW LDAELAEPSV TVLEAGSPDL AVATSKTFRS  540
LARLTGAAPS MAGPRVKRTL TANGLRQLIA FISRMTAVDR AELEGVSADR APQIVAGALV  600
AEASMRALSI EAVEICPWAL REGLILRKLD SEADGTALIE SSSVHTSVRA VGGQPADRNA  660
ANRSRGSKPS T                                                      671

SEQ ID NO: 84          moltype = DNA  length = 2463
FEATURE                Location/Qualifiers
misc_feature           1..2463
                       note = Mycobacterium tuberculosis fusion sequence
source                 1..2463
                       mol_type = other DNA
                       organism = synthetic construct
SEQUENCE: 84
atgggcagca gccatcatca tcatcatcac agcagcggcc tggtgccgcg cggcagccat  60
atgggtaccc atctcgccaa cggttcgatg tcggaagtca tgatgtcgga aattgccggg  120
ttgcctatcc ctccgattat ccattacggg gcgattgcct atgcccccag cggcgcgtcg  180
ggcaaagcgt ggcaccagcg cacaccggcg cgagcagagc aagtcgcact agaaaagtgc  240
ggtgacaaga cttgcaaagt ggttagtcgc ttcaccaggt gcggcgcggt cgcctacaac  300
ggctcgaaat accaaggcgg aaccggactc acgcgccgcg cggcagaaga cgacgccgtg  360
aaccgactcg aaggcgggcg gatcgtcaac tgggcgtgca acgagctcat gacctcgcgt  420
tttatgacgg atccgcacgc gatgcgggac atggcgggcc gttttgaggt gcacgcccag  480
acggtggagg acgaggctcg ccggatgtgg gcgtccgcgc aaaacatctc gggcgcgggc  540
tggagtggca tggccgaggc gacctcgcta gacaccatga cccagatgaa tcaggcgttt  600
cgcaacatcg tgaacatgct gcacggggtg cgtgacgggc tggttcgcga cgccaacaac  660
tacgaacagc aagagcaggc ctcccagcag atcctcagca gcgtcgacat caatttcgcc  720
gttttgccgc cggaggtgaa ttcggcgcgc atattcgccg gtgcgggcct gggcccaatg  780
ctggcggcgg cgtcggcctg ggacgggttg gccgaggagt tgcatgccgc ggcgggctcg  840
ttcgcgtcgg tgaccaccgg gttggcgggc gacgcgtggc atggtccggc gtcgctggcg  900
atgacccgcg cggccagccc gtatgtgggg tggttgaaca cggcggcggg tcaggccgcg  960
caggcggccg gccaggcgcg gctagcggcg agcgcgttcg aggcgacgct ggcggccacc  1020
gtgtctccag cgatggtcgc ggccaaccgg acacggctgg cgtcgctggt ggcagccaac  1080
ttgctgggcc agaacgcccc ggcgatcgcg gccgcggagg ctgaatacga gcagatatgg  1140
gcccaggacg tggccgcgat gttcggctat cactccgccg cgtcggcggt ggccacgcag  1200
ctggcgccta ttcaagaggg tttgcagcag cagctgcaaa acgtgctggc ccagttggct  1260
agcgggaacc tgggcagcgg aaatgtgggc gtcggcaaca tcggcaacga caacattggc  1320
aacgcaaaca tcggcttcgg aaatcgaggc gacgccaaca tcggcatcgg gaatatcggc  1380
gacagaaacc tcggcattgg gaacaccggc aattggaata tcggcatcgg catcaccggc  1440
aacggacaaa tcggcttcgg caagcctgcc aaccccgacg tcttggtggt gggcaacggc  1500
ggcccgggag taaccgcgtt ggtcatgggc ggcaccgaca gcctactgcc gctgcccaac  1560
atccccttac tcgagtacgc tgcgcggttc atcacccccg tgcatcccgg atacaccgct  1620
acgttcctgg aaacgccatc gcagtttttc ccattcaccg ggctgaatag cctgacctat  1680
gacgtctccg tggcccaggg cgtaacgaat ctgcacaccg cgatcatggc gcaactcgcg  1740
gcgggaaacg aagtcgtcgt cttcggcacc tcccaaagcg ccacgatagc caccttcgaa  1800
atgcgctatc tgcaatccct gccagcacac ctgcgtccgg gtctcgacga attgtccttt  1860
acgttgaccg gcaatcccaa ccggcccgac ggtggcattc ttacgcgttt tggcttctcc  1920
ataccgcagt tgggtttcac attgtccggc gcgacgcccg ccgacgccta ccccaccgtc  1980
gattacgcgt tccagtacga cggcgtcaac gacttcccca aatacccgct gaatgtcttc  2040
gcgaccgcca acgcgatcgc gggcatcctt ttcctgcact ccgggttgat tgcgttgccg  2100
cccgatcttg cctcgggcgt ggttcaaccg gtgtcctcac cggacgtcct gaccacctac  2160
atcctgctgc ccagccaaga tctgccgctg ctggtcccgc tgcgtgctat ccccctgctg  2220
ggaaacccgc ttgccgacct catccagccg gacttgcggg tgctcgtcga gttgggttat  2280
gaccgcaccg cccaccagga cgtgcccagc ccgttcggac tgtttccgga cgtcgattgg  2340
gccgaggtgg ccgcggacct gcagcaaggc gccgtgcaag gcgtcaacga cgccctgtcc  2400
ggactggggc tgccgccgcc gtggcagccg gcgctacccc gacttttcag tacttaaaag  2460
ctt                                                               2463

SEQ ID NO: 85          moltype = DNA  length = 39
FEATURE                Location/Qualifiers
misc_feature           1..39
                       note = Cloning primer
source                 1..39
                       mol_type = other DNA
                       organism = synthetic construct
```

| | | |
|---|---|---|
| SEQUENCE: 85 | | |
| caattacata tgggtaccca tctcgccaac ggttcgatg | | 39 |
| | | |
| SEQ ID NO: 86 | moltype = DNA   length = 33 | |
| FEATURE | Location/Qualifiers | |
| misc_feature | 1..33 | |
| | note = Cloning primer | |
| source | 1..33 | |
| | mol_type = other DNA | |
| | organism = synthetic construct | |
| SEQUENCE: 86 | | |
| caattagagc tcgttgcacg cccagttgac gat | | 33 |
| | | |
| SEQ ID NO: 87 | moltype = DNA   length = 33 | |
| FEATURE | Location/Qualifiers | |
| misc_feature | 1..33 | |
| | note = Cloning primer | |
| source | 1..33 | |
| | mol_type = other DNA | |
| | organism = synthetic construct | |
| SEQUENCE: 87 | | |
| caattagagc tcatgacctc gcgttttatg acg | | 33 |
| | | |
| SEQ ID NO: 88 | moltype = DNA   length = 33 | |
| FEATURE | Location/Qualifiers | |
| misc_feature | 1..33 | |
| | note = Cloning primer | |
| source | 1..33 | |
| | mol_type = other DNA | |
| | organism = synthetic construct | |
| SEQUENCE: 88 | | |
| caattagtcg acgctgctga ggatctgctg gga | | 33 |
| | | |
| SEQ ID NO: 89 | moltype = DNA   length = 33 | |
| FEATURE | Location/Qualifiers | |
| misc_feature | 1..33 | |
| | note = Cloning primer | |
| source | 1..33 | |
| | mol_type = other DNA | |
| | organism = synthetic construct | |
| SEQUENCE: 89 | | |
| caattagtcg acatgaattt cgccgttttg ccg | | 33 |
| | | |
| SEQ ID NO: 90 | moltype = DNA   length = 42 | |
| FEATURE | Location/Qualifiers | |
| misc_feature | 1..42 | |
| | note = Cloning primer | |
| source | 1..42 | |
| | mol_type = other DNA | |
| | organism = synthetic construct | |
| SEQUENCE: 90 | | |
| caattaaagc ttttaagtac tgaaaagtcg gggtagcgcc gg | | 42 |
| | | |
| SEQ ID NO: 91 | moltype = AA   length = 818 | |
| FEATURE | Location/Qualifiers | |
| REGION | 1..818 | |
| | note = Mycobacterium tuberculosis fusion sequence | |
| source | 1..818 | |
| | mol_type = protein | |
| | organism = synthetic construct | |
| SEQUENCE: 91 | | |
| MGSSHHHHHH SSGLVPRGSH MGTHLANGSM SEVMMSEIAG LPIPPIIHYG AIAYAPSGAS | | 60 |
| GKAWHQRTPA RAEQVALEKC GDKTCKVVSR FTRCGAVAYN GSKYQGGTGL TRRAAEDDAV | | 120 |
| NRLEGGRIVN WACNELMTSR FMTDPHAMRD MAGRFEVHAQ TVEDEARRMW ASAQNISGAG | | 180 |
| WSGMAEATSL DTMTQMNQAF RNIVNMLHGV RDGLVRDANN YEQQEQASQQ ILSSVDINFA | | 240 |
| VLPPEVNSAR IFAGAGLGPM LAAASAWDGL AEELHAAAGS FASVTTGLAG DAWHGPASLA | | 300 |
| MTRAASPYVG WLNTAAGQAA QAAGQARLAA SAFEATLAAT VSPAMVAANR TRLASLVAAN | | 360 |
| LLGQNAPAIA AAEAEYEQIW AQDVAAMFGY HSAASAVATQ LAPIQEGLQQ QLQNVLAQLA | | 420 |
| SGNLGSGNVG VGNIGNDNIG NANIGFGNRG DANIGIGNIG DRNLGIGNTG NWNIGIGITG | | 480 |
| NGQIGFGKPA NPDVLVVGNG GPGVTALVMG GTDSLLPLPN IPLLEYAARF ITPVHPGYTA | | 540 |
| TFLETPSQFF PFTGLNSLTY DVSVAQGVTN LHTAIMAQLA AGNEVVVFGT SQSATIATFE | | 600 |
| MRYLQSLPAH LRPGLDELSF TLTGNPNRPD GGILTRFGFS IPQLGFTLSG ATPADAYPTV | | 660 |
| DYAFQYDGVN DFPKYPLNVF ATANAIAGIL FLHSGLIALP PDLASGVVQP VSSPDVLTTY | | 720 |
| ILLPSQDLPL LVPLRAIPLL GNPLADLIQP DLRVLVELGY DRTAHQDVPS PFGLFPDVDW | | 780 |
| AEVAADLQQG AVQGVNDALS GLGLPPPWQP ALPRLFST | | 818 |
| | | |
| SEQ ID NO: 92 | moltype = DNA   length = 2778 | |
| FEATURE | Location/Qualifiers | |
| misc_feature | 1..2778 | |

|  |  |
|---|---|
|  | note = Mycobacterium tuberculosis fusion sequence |
| source | 1..2778 |
|  | mol_type = other DNA |
|  | organism = synthetic construct |

SEQUENCE: 92

```
atgggcagca gccatcatca tcatcatcac agcagcggcc tggtgccgcg cggcagccat   60
atggacgaca tcgattggga cgccatcgcg caatgcgaat ccggcggcaa ttgggcggcc  120
aacaccggta acgggttata cggtggtctg cagatcagcc aggcgacgtg ggattccaac  180
ggtggtgtcg ggtcgccggc ggccgcgagt ccccagcaac agatcgaggt cgcagacaac  240
attatgaaaa cccaaggccc gggtgcgtgg ccgaaatgta gttcttgtag tcagggagac  300
gcaccgctgg gctcgctcac ccacatcctg acgttcctcg cggccgagac tggaggttgt  360
tcggggagca gggacgatgg tacccatctc gccaacggtt cgatgtcgga agtcatgatg  420
tcggaaattg ccggggttgcc tatccctccg attatccatt acggggcgat tgcctatgcc  480
cccagcggcg cgtcgggcaa agcgtggcac cagcgcacac cggcgcgagc agagcaagtc  540
gcactagaaa agtgcggtga caagacttgc aaagtggtta gtcgcttcac caggtgcggc  600
gcggtcgcct acaacggctc gaaataccaa ggcggaaccg gactcacgcg ccgcgcggca  660
gaagacgacg ccgtgaaccg actcgaaggc gggcggatcg tcaactgggc gtgcaacgag  720
ctcatgacct cgcgttttat gacgtatccg cacgcgatgc gggacatggc gggccgtttt  780
gaggtcacgc cccagacggt ggaggacgag gctcgccgga tgtgggcgtc cgcgcaaaac  840
atctcgggcg cgggctggag tggcatggcc gaggcgacct cgctagacac catgacccag  900
atgaatcagg cgtttcgcaa catcgtgaac atgctgcacg gggtgcgtga cgggctggtt  960
cgcgagccgca acaactacga acagcaagag caggcctccc agcagatcct cagcagcgtc 1020
gacatcaatt tcgccgtttt gccgccgag gtgaattcgg cgcgcatatt cgccggtgcg 1080
ggcctgggcc caatgctggc ggcggcgtcg gctggacg ggttgccga ggagttgcat 1140
gccgcggcgg gctcgttcgc gtcggtgacc accgggttgg cgggcgacgc gtggcatggt 1200
ccggcgtcgc tggcgatgac ccgcgcgcgc agcccgtatg tgggtggtt gaacacggcg 1260
gcgggtcagg ccgcgcaggc ggccggccag gcgcggctag cggcgagcgc gttcgaggcg 1320
acgctgcgg ccaccgtgtc tccagcgatg gtcgcggcca accggacacg gctggcgtcg 1380
ctggtggcag ccaacttgct gggccagaac gccccgcgca tcgcggccgc ggaggctgaa 1440
tacgagcaga tatgggccca ggacgtggcc gcgatgttcg gctatcactc cgccgcgtcg 1500
gcggtggcca cgcagctggc gcctattcaa gaggggtttgc agcagcagct gcaaacgtg 1560
ctggcccagt tggctagcgg gaacctgggc agcggaaatg tgggcgtcgg caacatcggc 1620
aacgacaaca ttggcaacgc aaacatcggc ttcggaaatc gaggcgacgc caacatcggc 1680
atcgggaata tcggcgacag aaacctcggc attgggaaca ccggcaattg gaatatcggc 1740
atcggcatca ccggcaacgg acaaatcggc ttcgcaagc ctgccaaccc cgacgtcttg 1800
gtggtgggca acggcggccc gggagtaacc gcgttggtca tgggcggcac cgacagccta 1860
ctgccgctgc ccaacatccc cttactcgag tacgctgcgc ggttcatcac ccccgtgcat 1920
cccggataca ccgctacgtt cctggaaacg ccatcgcagt ttttcccatt caccgggctg 1980
aatagcctga cctatgacgt ctccgtggcc cagggcgtaa cgaatctgca caccgcgatc 2040
atggcgcaac tcgcggcggg aaacgaagtc gtcgtcttcg gcacctccca aagcgccacg 2100
atagccacct tcgaaatgcg ctatctgcaa tccctgccag cacacctgcg tccgggtctc 2160
gacgaattgt ccttttacgt tgaccggcat cccaaccggc ccgacggtgg cattcttacg 2220
cgttttggct tctccatacc gcagttgggt ttcacattgt ccggcgcgac gcccgccgaa 2280
gcctacccca ccgtcgatta cgcgttccga tacgacggcg tcaacgactt ccccaaaatac 2340
ccgctgaatg tcttcgcgac cgccaacgcg atcgcgggca tcctttttcct gcactccggg 2400
ttgattgcgt tgccgcccga tcttgcctcg ggcgtggttc aaccggtgtc ctcaccggac 2460
gtcctgacca cctacatcct gctgcccagc caagatctgc ctgctggt ccgctgcgt 2520
gctatccccc tgctgggaaa cccgcttgcc gacctcatcc agccggactt gcgggtgctc 2580
gtcgagttgg gttatgaccg caccgcccac caggacgtgc ccagcccgtt cggactgttt 2640
ccggacgtcg attgggccga ggtggccgcg gacctgcagc aaggcgccgt gcaaggcgtc 2700
aacgacgccc tgtccggact ggggctgcgg ccgccgtggc agcggcgct accccgactt 2760
ttcagtactt aaagctt                                                2778
```

|  |  |
|---|---|
| SEQ ID NO: 93 | moltype = DNA length = 33 |
| FEATURE | Location/Qualifiers |
| misc_feature | 1..33 |
|  | note = Cloning primer |
| source | 1..33 |
|  | mol_type = other DNA |
|  | organism = synthetic construct |

SEQUENCE: 93

```
caattacata tggacgacat cgattgggac gcc                               33
```

|  |  |
|---|---|
| SEQ ID NO: 94 | moltype = DNA length = 42 |
| FEATURE | Location/Qualifiers |
| misc_feature | 1..42 |
|  | note = Cloning primer |
| source | 1..42 |
|  | mol_type = other DNA |
|  | organism = synthetic construct |

SEQUENCE: 94

```
caattaaagc ttttaagtac ttggtttgct gcctctcgat cg                     42
```

|  |  |
|---|---|
| SEQ ID NO: 95 | moltype = AA length = 923 |
| FEATURE | Location/Qualifiers |
| REGION | 1..923 |
|  | note = Mycobacterium tuberculosis fusion sequence |
| source | 1..923 |
|  | mol_type = protein |

```
                        organism = synthetic construct
SEQUENCE: 95
MGSSHHHHHH  SSGLVPRGSH  MD -continued

```
source                  1..935
                        mol_type = protein
                        organism = synthetic construct
SEQUENCE: 97
MGSSHHHHHH SSGLVPRGSH MDDIDWDAIA QCESGGNWAA NTGNGLYGGL QISQATWDSN    60
GGVGSPAAAS PQQQIEVADN IMKTQGPGAW PKCSSCSQGD APLGSLTHIL TFLAAETGGC   120
SGSRDDELSP CAYFLVYEST ETTERPEHHE FKQAAVLTDL PGELMSALSQ GLSQFGINIP   180
PVPSLTGSGD ASTGLTGPGL TSPGLTSPGL TSPGLTDPAL TSPGLTPTLP GSLAAPGTTL   240
APTPGVGANP ALTNPALTSP TGATPGLTSP TGLDPALGGA NEIPITTPVG LDPGADGTYP   300
ILGDPTLGTI PSSPATTSTG GGGLVNDVMQ VANELGASQA IDLLKGVLMP SIMQAVQNGG   360
AAAPAASPPV PPIPAAAAVP PTDPITVPVA GTHLANGSMS EVMMSEIAGL PIPPIIHYGA   420
IAYAPSGASG KAWHQRTPAR AEQVALEKCG DKTCKVVSRF TRCGAVAYNG SKYQGGTGLT   480
RRAAEDDAVN RLEGGRIVNW ACNELMTSRF MTDPHAMRDM AGRFEVHAQT VEDEARRMWA   540
SAQNISGAGW SGMAEATSLD TMTQMNQAFR NIVNMLHGVR DGLVRDANNY EQQEQASQQI   600
LSSVDMVDAH RGGHPTPMSS TKATLRLAEA TDSSGKITKR GADKLISTID EFAKIAISSG   660
CAELMAFATS AVRDAENSED VLSRVRKETG VELQALRGED ESRLTFLAVR RWYGWSAGRI   720
LNLDIGGGSL EVSSGVDEEP EIALSLPLGA GRLTREWLPD DPPGRRRVAM LRDWLDAELA   780
EPSVTVLEAG SPDLAVATSK TFRSLARLTG AAPSMAGPRV KRTLTANGLR QLIAFISRMT   840
AVDRAELEGV SADRAPQIVA GALVAEASMR ALSIEAVEIC PWALREGLIL RKLDSEADGT   900
ALIESSSVHT SVRAVGGQPA DRNAANRSRG SKPST                             935

SEQ ID NO: 98           moltype = DNA  length = 3570
FEATURE                 Location/Qualifiers
misc_feature            1..3570
                        note = Mycobacterium tuberculosis fusion sequence
source                  1..3570
                        mol_type = other DNA
                        organism = synthetic construct
SEQUENCE: 98
atgggcagca gccatcatca tcatcatcac agcagcggcc tggtgccgcg cggcagccat    60
atggacgaca tcgattggga cgccatcgcg caatgcgaat ccggcggcaa ttgggcggcc   120
aacaccgtta acgggttata cggtggtctg cagatcagcc aggcgacgtg ggattccaac   180
ggtggtgtcg gtcgccggc ggccgcgagt ccccagcaac agatcgaggt cgcagacaac   240
attatgaaaa cccaaggccc gggtgcgtgg ccgaaatgta gttcttgtag tcagggagac   300
gcaccgctgg gctcgctcac ccacatcctg acgttcctcg cggccgagac tggaggttgt   360
tcggggagca gggacgatga gctcagtcct tgtgcatatt ttcttgtcta cgaatcaacc   420
gaaacgaccg agcggcccga gcaccatgaa ttcaagcagg cggcggtgtt gaccgacctg   480
cccggcgagc tgatgtccgc gctatcgcag gggttgtccc agttcgggat caacataccg   540
ccggtgccga gcctgaccgg gagcggcgat gccagcaccgg gtctaaccgg tcctggcctg   600
actagtccgg gattgaccag cccgggattg accagcccgg gcctcaccga ccctgccctt   660
accagtccgg gcctgacgcc aaccctgccc ggatcactcg ccgcgccgg caccaccctg   720
gcgccaacgc ccggcgtggg ggccaatccg gcgctcacca ccccgcgct gaccagcccg   780
accggggcga cgccgggatt gaccagcccg acggttttgg atccgccgg gggcgcc     840
aacgaaatcc cgattacgac gccggtcgga ttggatcccg gggctgacgg cacctatccg   900
atcctcggtg atccaacact ggggaccata ccgagcagcc ccgccaccac ctccaccggc   960
ggcggcggtc tcgtcaacga cgtgatgcag gtggccaacg agttgggcgc cagtcaggct  1020
atcgacctgc taaaaggtgt gctaatgccg tcgatcatgc aggccgtcca gaatggcggc  1080
gcggccgcgc cggcagccag cccgccggtc ccgcccatcc ccggcgccgg cggtgccca  1140
ccgacggacc caatcaccgt gccggtcgcc ggtacccatc tcgccaacgg ttcgatgtcg  1200
gaagtcatga tgtcggaaat tgccgggttg cctatcccct cgattatcca ttacggggcg  1260
attgcctatg ccccagcgg cgcgtcggcc aaagcgcac accagcgcac accggcgca  1320
gcagagcaag tcgcactaga aaagtgcggt gacaagactt gcaaagtggt tagtcgcttc  1380
accaggtgcg gcgcggtcgc ctacaacggc tcgaaatacc aaggcggaac cggactcacg  1440
cgccgcgcg cagaagacga cgccgtgaac cgactcgaag cgggcggat cgtcaactgg  1500
gcgtgcaacg agctcatgac ctcgcgtttt atgacggatc cgcacgcgat gcgggacatg  1560
gcgggccgtt ttgaggtgca cgcccagacg gtgaggacg aggctcgccg gatgtgggcg  1620
tccgcgcaaa acatctcggg cgcgggctgg agtggcatgg ccgaggcgac ctcgctagac  1680
accatgaccc agatgaatca ggcgtttcgc aacatcgtga acatgctgca cggggtgcgt  1740
gacgggctgg ttcgcgacgc caacaactac gaacagcaag agcagccctc ccagcagatc  1800
ctcagcagcg tcgacatgca tttcgccgtt ttgccgccgg aggtgaattc ggcgcgcata  1860
ttcgccggtg cgggcctggg cccaatgctg cgcgcggcgt cggcctggga cgggttggcc  1920
gaggagttgc atgccgcggc gggctcgttc cgtcggtga ccaccgggtt ggcgggcgac  1980
gcgtggcatg gtccggcgtc gctggcgatg acccgcgcgg ccagcccgta tgtggggtgg  2040
ttgaacaccgg cggcgggtca ggccgcgcag gcggccggcc agggccggct agccggcgca  2100
gcgttcgagg cgacgctggc ggccaccgtg tctccagcga tggtcgcggc caaccggaca  2160
cggctgcgt cgctggtggc agccaacttg ctgggccaga cgcccggc gatcgcggcc  2220
gcggaggctg aatacgagca gatatgggcc caggacgtgg ccgcgatgtt cggctatcac  2280
tccgccgcgt cggcggtggc cacgcagctg gcgcctattc aagagggttt gcagcagcag  2340
ctgcaaaacg tgctgccca gttggctagc gggaacctgg gcagcggaaa tgtgggcgtc  2400
ggcaacatcg gcaacgacaa cattggcaac gcaaacatcg gcttcggaaa tcgaggcgac  2460
gccaacatcg gcatcgggaa tatcggcgac agaaacctcg gcattgggaa caccggcaat  2520
tggaatatcg gcatcggcat caccggcaac ggacaaatcg gcttcggcaa gcctgccaac  2580
cccgacgtct tggtggtggg caacggcggc ccggagtaa ccgcgttggt catgggcggc  2640
accggcgct tactgccgct gcccaacatc ccttactcg agtacgcgg catgggcggc  2700
accccgtgg atcccggata caccgctacg ttcctggaaa cgccatcgca gttttttcca  2760
ttcaccgggc tgaatagcct gacctatgac gtcccgtgg cccagggcgt aacgaatctg  2820
cacaccgcga tcatgcgca actgcgcggc ggaaacgaag tcgtcgtctt cggcacctcc  2880
caaagcgcca cgatagccac cttcgaaatg cgctatctgc aatccctgcc agcacacctg  2940
cgtccgggtc tcgacgaatt gtcctttacg ttgaccggca atcccaaccg gcccgacggt  3000
```

```
ggcattctta cgcgttttgg cttctccata ccgcagttgg gtttcacatt gtccggcgcg  3060
acgcccgccg acgcctaccc caccgtcgat tacgcgttcc agtacgacgg cgtcaacgac  3120
ttccccaaat acccgctgaa tgtcttcgcg accgccaacg cgatcgcggg catccttttc  3180
ctgcactccg ggttgattgc gttgccgccc gatcttgcct cgggcgtggt tcaaccggtg  3240
tcctcaccgg acgtcctgac cacctacatc ctgctgccca gccaagatct gccgctgctg  3300
gtcccgctgc gtgctatccc cctgctggga aacccgcttg ccgacctcat ccagccggac  3360
ttgcgggtgc tcgtcgagtt gggttatgac cgcaccgccc accaggacgt gcccagcccg  3420
ttcggactgt ttccggacgt cgattgggcc gaggtggccg cggacctgca gcaaggcgcc  3480
gtgcaaggcg tcaacgacgc cctgtccgga ctggggctgc cgccgccgtg gcagccggcg  3540
ctaccccgac ttttcagtac ttaaaagctt                                3570

SEQ ID NO: 99          moltype = AA  length = 1187
FEATURE                Location/Qualifiers
REGION                 1..1187
                       note = Mycobacterium tuberculosis fusion sequence
source                 1..1187
                       mol_type = protein
                       organism = synthetic construct
SEQUENCE: 99
MGSSHHHHHH SSGLVPRGSH MDDIDWDAIA QCESGGNWAA NTGNGLYGGL QISQATWDSN  60
GGVGSPAAAS PQQQIEVADN IMKTQGPGAW PKCSSCSQGD APLGSLTHIL TFLAAETGGC  120
SGSRDDELSP CAYFLVYEST ETTERPEHHE FKQAAVLTDL PGELMSALSQ GLSQFGINIP  180
PVPSLTGSGD ASTGLTGPGL TSPGLTSPGL TSPGLTDPAL TSPGLTPTLP GSLAAPGTTL  240
APTPGVGANP ALTNPALTSP TGATPGLTSP TGLDPALGGA NEIPITTPVG LDPGADGTYP  300
ILGDPTLGTI PSSPATTSTG GGGLVNDVMQ VANELGASQA IDLLKGVLMP SIMQAVQNGG  360
AAAPAASPPV PPIPAAAAVP PTDPITVPVA GTHLANGSMS EVMMSEIAGL PIPPIIHYGA  420
IAYAPSGASG KAWHQRTPAR AEQVALEKCG DKTCKVVSRF TRCGAVAYNG SKYQGGTGLT  480
RRAAEDDAVN RLEGGRIVNW ACNELMTSRF MTDPHAMRDM AGRFEVHAQT VEDEARRMWA  540
SAQNISGAGW SGMAEATSLD TMTQMNQAFR NIVNMLHGVR DGLVRDANNY EQQEQASQQI  600
LSSVDINFAV LPPEVNSARI FAGAGLGPML AAASAWDGLA EELHAAAGSF ASVTTGLAGD  660
AWHGPASLAM TRAASPYVGW LNTAAGQAAQ AAGQARLAAS AFEATLAATV SPAMVAANRT  720
RLASLVAANL LGQNAPAIAA AEAEYEQIWA QDVAAMFGYH SAASAVATQL APIQEGLQQQ  780
LQNVLAQLAS GNLGSGNVGV GNIGNDNIGN ANIGFGNRGD ANIGIGNIGD RNLGIGNTGN  840
WNIGIGITGN GQIGFGKPAN PDVLVVGNGG PGVTALVMGG TDSLLPLPNI PLLEYAARFI  900
TPVHPGYTAT FLETPSQFFP FTGLNSLTYD VSVAQGVTNL HTAIMAQLAA GNEVVVFGTS  960
QSATIATFEM RYLQSLPAHL RPGLDELSFT LTGNPNRPDG GILTRFGFSI PQLGFTLSGA  1020
TPADAYPTVD YAFQYDGVND FPKYPLNVFA TANAIAGILF LHSGLIALPP DLASGVVQPV  1080
SSPDVLTTYI LLPSQDLPLL VPLRAIPLLG NPLADLIQPD LRVLVELGYD RTAHQDVPSP  1140
FGLFPDVDWA EVAADLQQGA VQGVNDALSG LGLPPPWQPA LPRLFST               1187

SEQ ID NO: 100         moltype = AA  length = 164
FEATURE                Location/Qualifiers
source                 1..164
                       mol_type = protein
                       organism = Mycobacterium tuberculosis
SEQUENCE: 100
VAGDTTITIV GNLTADPELR FTPSGAAVAN FTVASTPRIY DRQTGEWKDG EALFLRCNIW  60
REAAENVAES LTRGARVIVS GRLKQRSFET REGEKRTVIE VEVDEIGPSL RYATAKVNKA  120
SRSGGFGSGS RPAPAQTSSA SGDDPWGSAP ASGSFGGGDD EPPF                 164

SEQ ID NO: 101         moltype = DNA  length = 507
FEATURE                Location/Qualifiers
source                 1..507
                       mol_type = genomic DNA
                       organism = Mycobacterium tuberculosis
SEQUENCE: 101
catatggtgg ctggtgacac caccatcacc atcgtcggaa atctgaccgc tgaccccgag  60
ctgcggttca ccccgtccgg tgcggccgtg gcgaatttca ccgtggcgtc aacgccccgg  120
atctatgacc gtcagaccgg cgaatggaaa gacggcgaag cgctgttcct ccggtgcaat  180
atctggcggg aggcggccga gaacgtggcc gagagcctca cccgggggc acgagtcatc  240
gttagcgggc ggcttaagca gcggtcgttt gaaacccgtg agggcgagaa gcgcaccgtc  300
atcgaggtcg aggtcgatga gattgggcct tcgcttcggt acgccaccgc caaggtcaac  360
aaggccagcc gcagcggcgg gtttggcagc ggatcccgtc cggcgccggc gcagaccagc  420
agcgcctcgg gagatgaccc gtggggcagc gcaccggcgt cgggttcgtt cggcggcggc  480
gatgacgaac cgccattctg aaagctt                                   507

SEQ ID NO: 102         moltype = AA  length = 185
FEATURE                Location/Qualifiers
source                 1..185
                       mol_type = protein
                       organism = Mycobacterium tuberculosis
SEQUENCE: 102
MGSSHHHHHH SSGLVPRGSH MVAGDTTITI VGNLTADPEL RFTPSGAAVA NFTVASTPRI  60
YDRQTGEWKD GEALFLRCNI WREAAENVAE SLTRGARVIV SGRLKQRSFE TREGEKRTVI  120
EVEVDEIGPS LRYATAKVNK ASRSGGFGSG SRPAPAQTSS ASGDDPWGSA PASGSFGGGD  180
DEPPF                                                           185

SEQ ID NO: 103         moltype = AA  length = 161
FEATURE                Location/Qualifiers
```

```
source                      1..161
                            mol_type = protein
                            organism = Mycobacterium tuberculosis
SEQUENCE: 103
MTAISCSPRP RYASRMPVLS KTVEVTADAA SIMAIVADIE RYPEWNEGVK GAWVLARYDD    60
GRPSQVRLDT AVQGIEGTYI HAVYYPGENQ IQTVMQQGEL FAKQEQLFSV VATGAASLLT   120
VDMDVQVTMP VPEPMVKMLL NNVLEHLAEN LKQRAEQLAA S                      161

SEQ ID NO: 104              moltype = DNA   length = 495
FEATURE                     Location/Qualifiers
source                      1..495
                            mol_type = genomic DNA
                            organism = Mycobacterium tuberculosis
SEQUENCE: 104
catatgacgg caatctcgtg ctcaccgcga cccaggtatg cttcccgaat gccagttttg    60
agcaagaccg tcgaggtcac cgccgacgcc gcatcgatca tggccatcgt tgccgatatc   120
gagcgctacc cagagtggaa tgaaggggtc aagggcgcat gggtgctcgc tcgctacgat   180
gacggccgtc ccagccaggt gcggctcgac accgctgttc aaggcatcga gggcacctat   240
atccacgccg tgtactaccc aggcgaaaac cagattcaaa ccgtcatgca gcagggtgaa   300
ctgtttgcca agcaggagca gctgttcagt gtggtggcaa ccggcgccgc gagcttgctc   360
acggtggaca tggacgtcca ggtcaccatg ccggtgcccg agccgatggt gaagatgctg   420
ctcaacaacg tcctggagca tctcgccgaa aatctcaagc agcgcgccga gcagctggcg   480
gccagctaaa agctt                                                   495

SEQ ID NO: 105              moltype = AA    length = 181
FEATURE                     Location/Qualifiers
source                      1..181
                            mol_type = protein
                            organism = Mycobacterium tuberculosis
SEQUENCE: 105
MGSSHHHHHH SSGLVPRGSH MTAISCSPRP RYASRMPVLS KTVEVTADAA SIMAIVADIE    60
RYPEWNEGVK GAWVLARYDD GRPSQVRLDT AVQGIEGTYI HAVYYPGENQ IQTVMQQGEL   120
FAKQEQLFSV VATGAASLLT VDMDVQVTMP VPEPMVKMLL NNVLEHLAEN LKQRAEQLAA   180
S                                                                  181

SEQ ID NO: 106              moltype = AA    length = 750
FEATURE                     Location/Qualifiers
source                      1..750
                            mol_type = protein
                            organism = Mycobacterium tuberculosis
SEQUENCE: 106
MAKASETERS GPGTQPADAQ TATSATVRPL STQAVFRPDF GDEDNFPHPT LGPDTEPQDR    60
MATTSRVRPP VRRLGGGLVE IPRAPDIDPL EALMTNPVVP ESKRFCWNCG RPVGRSDSET   120
KGASEGWCPY CGSPYSFLPQ LNPGDIVAGQ YEVKGCIAHG GLGWIYLALD RNVNGRPVVL   180
KGLVHSGDAE AQAMAMAERQ FLAEVVHPSI VQIFNFVEHT DRHGDPVGYI VMEYVGGQSL   240
KRSKGQKLPV AEAIAYLLEI LPALSYLHSI GLVYNDLKPE NIMLTEEQLK LIDLGAVSRI   300
NSFGYLYGTP GFQAPEIVRT GPTVATDIYT VGRTLAALTL DLPTRNGRYV DGLPEDDPVL   360
KTYDSYGRLL RRAIDPDPRQ RFTTAEEMSA QLTGVLREVV AQDTGVPRPG LSTIFSPSRS   420
TFGVDLLVAH TDVYLDGQVH AEKLTANEIV TALSVPLVDP TDVAASVLQA TVLSQPVQTL   480
DSLRAARHGA LDADGVDFSE SVELPLMEVR ALLDLGDVAK ATRKLDDLAE RVGWRWRLVW   540
YRAVAELLTG DYDSATKHFT EVLDTFPGEL APKLALAATA ELAGNTDEHK FYQTVWSTND   600
GVISAAFGLA RARSAEGDRV GAVRTLDEVP PTSRHFTTAR LTSAVTLLSG RSTSEVTEEQ   660
IRDAARRVEA LPPTEPRVLQ IRALVLGGAL DWLKDNKAST NHILGFPFTS HGLRLGVEAS   720
LRSLARVAPT QRHRYTLVDM ANKVRPTSTF                                   750

SEQ ID NO: 107              moltype = DNA   length = 2289
FEATURE                     Location/Qualifiers
source                      1..2289
                            mol_type = genomic DNA
                            organism = Mycobacterium tuberculosis
SEQUENCE: 107
catatgcata tgcatcacca tcaccatcac atggccaaag cgtcagagac cgaacgttcg    60
ggccccggca cccaaccggc ggacgcccag accgcgacgt ccgcgacggt tcgcccctg   120
agcacccagg cggtgttccg ccccgatttc ggcgatgagg acaacttccc ccatccgact   180
ctcggcccgg acaccgagcc gcaagaccgg atgccacca ccagccgggt gcgccccgcg   240
gtcagacggc tgggcggcgg cctggtggaa atcccgcggg cgccgatat cgatccgctt   300
gaggccctga tgaccaaccc ggtggtgccg agtccaagc ggttctgctg gaactgtgga   360
cgtcccgtcg gccggtccga ctcggagacc aagggagctt cagagggctg gtgtcccgtat   420
tgcggcagcc cgtattcgtt cctgccgcag ctaaatcccg gggacatcgt cgccggccag   480
tacgaggtca aaggctgcat cgcgcacggc ggactgggct ggatctacct cgctctcgac   540
cgcaatgtca acgccgtcc ggtggtgctc aagggcctgg tgcattccgg tgatgccgaa   600
gcgcaggcaa tggcgatggc gaacgccag ttcctggccg aggtggtgca cccgtcgatc   660
gtgcagatct tcaactttgt cgagcacacc gacaggcacg gggatccggt cggctacatc   720
gtgatggaat acgtcggcgg gcaatcgctc aaacgcagca aaggtcagaa actgcccgtc   780
gcggaggcca tcgcctacct gctggagatc ctgccggcgc tgagctacct gcattccatc   840
ggcttggtct acaacgacct gaagccgaa aacatcatgc tgaccgagga acagctcaag   900
ctgatcgacc tgggcgcggt atcgcggatc aactcgttcg gctacctcta cgggaccca   960
ggcttccagg cgcccgagat cgtcggacc ggtccgacgg tggccaccga catctacacc  1020
gtgggacgca cgctcgcggc gctcacgctg gacctgccca ccgcaatgg ccgttatgtg  1080
```

```
gatgggctac ccgaagacga cccggtgctg aaaacctacg actcttacgg ccggttgctg   1140
cgcagggcca tcgaccccga tccgcggcaa cggttcacca ccgccgaaga gatgtccgcg   1200
caattgacgg gcgtgttgcg ggaggtggtc gcccaggaca ccggggtgcc gcggccaggg   1260
ctatcaacga tcttcagtcc cagtcggtcg acatttggag tggacctgct ggtggcgcac   1320
accgacgtgt atctggacgg gcaggtgcac gcggagaacg tgaccgccaa cgagatcgtg   1380
accgcgctgt cggtgccgct ggtcgatccg accgacgtcg cagcttcggt cctgcaggcc   1440
acggtgctct cccagccggt gcagacccta gactcgctgc gcgcggcccg ccacggtgcg   1500
ctggacgccg acgcgtcga cttctccgag tcagtggagc tgccgctaat ggaagtccgc   1560
gcgctgctgg atctcggcga tgtggccaag gccacccgaa aactcgacga tctggccgaa   1620
cgcgttggct ggcgatggcg attggtctgg taccgggccg tcgccgagct gctcaccggc   1680
gactatgact cggccaccaa acatttcacc gaggtgctgg ataccttcc cggcgagctg   1740
gcgcccaagc tcgccctggc cgccaccgcc gaactagccg caacaccga cgaacacaag   1800
ttctatcaga cggtgtggag caccaacgac ggcgtgatct cggcggcttt cggactggcc   1860
agagcccggt cggccgaagg tgatcgggtc ggcgccgtga cgaggtaccg   1920
cccacttctc ggcatttcac cacggcacgg ctgaccagcg cggtgactct gttgtccggc   1980
cggtcaacga gtgaagtcac cgaggaacag atccgcgacg ccgcccgaag agtggaggcg   2040
ctgcccccga ccgaaccacg cgtgctgcag atccgcgccc tggtgctggg tggcgcgctg   2100
gactggctga aggacaacaa ggccagcacc aaccacatcc tcggtttccc gttcaccagt   2160
cacgggctgc ggctgggtgt cgaggcgtca ctgcgcagcc tggcccgggt agctcccact   2220
caacggcatc gctacacgct ggtggacatg ccaacaaagg tccggcccac cagcacgttc   2280
taagaattc                                                           2289

SEQ ID NO: 108           moltype = AA   length = 758
FEATURE                  Location/Qualifiers
source                   1..758
                         mol_type = protein
                         organism = Mycobacterium tuberculosis
SEQUENCE: 108
HMHHHHHHMA KASETERSGP GTQPADAQTA TSATVRPLST QAVFRPDFGD EDNFPHPTLG    60
PDTEPQDRMA TTSRVRPPVR RLGGGLVEIP RAPDIDPLEA LMTNPVVPES KRFCWNCGRP   120
VGRSDSETKG ASEGWCPYCG SPYSFLPQLN PGDIVAGQYE VKGCIAHGGL GWIYLALDRN   180
VNGRPVVLKG LVHSGDAEAQ AMAMAERQFL AEVVHPSIVQ IFNFVEHTDR HGDPVGYIVM   240
EYVGGQSLKR SKGQKLPVAE AIAYLLEILP ALSYLHSIGL VYNDLKPENI MLTEEQLKLI   300
DLGAVSRINS FGYLYGTPGF QAPEIVRTGP TVATDIYTVG RTLAALTLDL PTRNGRYVDG   360
LPEDDPVLKT YDSYGRLLRR AIDPDPRQRF TTAEEMSAQL TGVLREVVAQ DTGVPRPGLS   420
TIFSPSRSTF GVDLLVAHTD VYLDGQVHAE KLTANEIVTA LSVPLVDPTD VAASVLQATV   480
LSQPVQTLDS LRAARHGALD ADGVDFSESV ELPLMEVRAL LDLGDVAKAT RKLDDLAERV   540
GWRWRLVWYR AVAELLTGDY DSATKHFTEV LDTFPGELAP KLALAATAEL AGNTDEHKFY   600
QTVWSTNDGV ISAAFGLARA RSAEGDRVGA VRTLDEVPPT SRHFTTARLT SAVTLLSGRS   660
TSEVTEEQIR DAARRVEALP PTEPRVLQIR ALVLGGALDW LKDNKASTNH ILGFPFTSHG   720
LRLGVEASLR SLARVAPTQR HRYTLVDMAN KVRPTSTF                           758

SEQ ID NO: 109           moltype = AA   length = 328
FEATURE                  Location/Qualifiers
source                   1..328
                         mol_type = protein
                         organism = Mycobacterium tuberculosis
SEQUENCE: 109
VVDAHRGGHP TPMSSTKATL RLAEATDSSG KITKRGADKL ISTIDEFAKI AISSGCAELM    60
AFATSAVRDA ENSEDVLSRV RKETGVELQA LRGEDESRLT FLAVRRWYGW SAGRILNLDI   120
GGGSLEVSSG VDEEPEIALS LPLGAGRLTR EWLPDDPPGR RRVAMLRDWL DAELAEPSVT   180
VLEAGSPDLA VATSKTFRSL ARLTGAAPSM AGPRVKRTLT ANGLRQLIAF ISRMTAVDRA   240
ELEGVSADRA PQIVAGALVA EASMRALSIE AVEICPWALR EGLILRKLDS EADGTALIES   300
SSVHTSVRAV GGQPADRNAA NRSRGSKP                                     328

SEQ ID NO: 110           moltype = DNA   length = 996
FEATURE                  Location/Qualifiers
source                   1..996
                         mol_type = genomic DNA
                         organism = Mycobacterium tuberculosis
SEQUENCE: 110
catatggtcg atgccaccg cggcggccac ccgaccccga tgagctcgac gaaggccacg    60
ctgcggctgg ccgaggccac cgacagctcg ggcaagatca ccaagcgcgg agccgacaag   120
ctgatttcca ccatcgacga attcgccaag attgccatca gctcgggctg tgccgagctg   180
atggccttcg ccacgtcggc ggtccgcgac gccgagaatt ccgaggacgt cctgtcccgg   240
gtgcgcaaag agaccggtgt cgagttgcag gcgctgcgtg gggaggacga gtcacggctg   300
accttcctgg ccgtgcgacg atggtacggg tggagcgctg gcgcatcct caacctcgac   360
atcggcggcg gctcgctgga agtgtccagt ggcgtggacg aggagcccga gattgcgtta   420
tcgctgcccc tgggcgccgg acggttgacc cgagagtgg tgctgccgga tgacccgccg   480
cggcgccggg tggcgatgct gcgagactgg ctgatgccg agctggccga gcccagtgtg   540
accgtcctgg aagccggcag ccccgacctg cggtcgcaa cgtcgaagac gtttcgctcg   600
ttggcgcgac taaccggtgc ggccccatcc atggccgggc gcgggtgaa gaggacccta   660
acggcaaatg gtctgcggca actcatcgcg tttatctcta ggatgacggc ggttgaccgt   720
gcagaggcga aaggggtaag cgccgaccga ggccgacaga ttgtggccgg cgccctggtg   780
gcagaggcga gcatgcgagc actgtcgata gaagccgtgg aaatctgccc gtgggcgctg   840
cgggaaggtc tcatccttcg caaactcgac agcgaagccg acggaaccgc cctcatcgag   900
tcttcgtctg tgcacactt ggtcgtgcc gtcggaggtc agccagctga tcggaacgcg   960
gccaaccgat cgagaggcag caaaccatga aagctt                            996
```

```
SEQ ID NO: 111            moltype = AA   length = 348
FEATURE                   Location/Qualifiers
source                    1..348
                          mol_type = protein
                          organism = Mycobacterium tuberculosis
SEQUENCE: 111
MGSSHHHHHH SSGLVPRGSH MVDAHRGGHP TPMSSTKATL RLAEATDSSG KITKRGADKL    60
ISTIDEFAKI AISSGCAELM AFATSAVRDA ENSEDVLSRV RKETGVELQA LRGEDESRLT   120
FLAVRRWYGW SAGRILNLDI GGGSLEVSSG VDEEPEIALS LPLGAGRLTR EWLPDDPPGR   180
RRVAMLRDWL DAELAEPSVT VLEAGSPDLA VATSKTFRSL ARLTGAAPSM AGPRVKRTLT   240
ANGLRQLIAF ISRMTAVDRA ELEGVSADRA PQIVAGALVA EASMRALSIE AVEICPWALR   300
EGLILRKLDS EADGTALIES SSVHTSVRAV GGQPADRNAA NRSRGSKP                348

SEQ ID NO: 112            moltype = AA   length = 359
FEATURE                   Location/Qualifiers
source                    1..359
                          mol_type = protein
                          organism = Mycobacterium tuberculosis
SEQUENCE: 112
VRYSDSYHTT GRWQPRASTE GFPMGVSIEV NGLTKSFGSS RIWEDVTLTI PAGEVSVLLG    60
PSGTGKSVFL KSLIGLLRPE RGSIIIDGTD IIECSAKELY EIRTLFGVLF QDGALFGSMN   120
LYDNTAFPLR EHTKKKESEI RDIVMEKLAL VGLGGDEKKF PGEISGGMRK RAGLARALVL   180
DPQIILCDEP DSGLDPVRTA YLSQLIMDIN AQIDATILIV THNINIARTV PDNMGMLFRK   240
HLVMFGPREV LLTSDEPVVR QFLNGRRIGP IGMSEEKDEA TMAEEQALLD AGHHAGGVEE   300
IEGVPPQISA TPGMPERKAV ARRQARVREM LHTLPKKAQA AILDDLEGTH KYAVHEIGQ    359

SEQ ID NO: 113            moltype = DNA   length = 1088
FEATURE                   Location/Qualifiers
source                    1..1088
                          mol_type = genomic DNA
                          organism = Mycobacterium tuberculosis
SEQUENCE: 113
catatgcgat acagtgactc ataccacaca acgggccggt ggcagccacg agcgtcgaca     60
gagggtttcc catgggcgtc agcatcgagg tcaaacgatc aacgaagtcc ttcgggtcct   120
cgaggatctg ggaagatgtc acgctaacga tccccgccgg ggaggtcagc gtgctgctgg   180
gcccatcggg taccggcaaa tcggtgtttc tgaaatctct gatcggcctc ctgcggccgg   240
agcgcggctc gatcatcatc gacggcaccg acatcatcga atgctcggcc aaggagcttt   300
acgagatccg cacattgttc ggcgtgctgt ttcaggacgg tgccctgttc gggtcgatga   360
acctctacga caacaccgcg ttcccccctgc gtgagcacga caagaaaaag gaaagcgaga   420
tccgtgacat cgtcatggag aagctggccc tagtcggcct gggtggggac gagaagaagt   480
tccccggcga gatctccggc gggatgcgta agcgtgccgg cctagcgcgt gccctggtcc   540
ttgacccgca gatcattctc tgcgacgagc ccgactcggg tctggacccg gttcgtaccg   600
cctacctgag ccagctgatc atggacatca acgcccagat cgacgccacc atcctgatcg   660
tgacgcacaa catcaacatc gcccgcaccg tgccggacaa catgggcatg ttgttccgca   720
agcatttggt gatgttcggg ccgcgggagg tgctactcac cagcgacgag ccggtggtgc   780
ggcagttcct caacggccgg cgcatcggcc cgatcggcat gtccgaggag aaggacgagg   840
ccaccatggc cgaagagcag gccctgctcg atgccggcca ccacgcgggc ggtgtcgagg   900
aaatcgaggg cgtgccgccg cagatcagcg cgacaccggg catgccggag cgcaaagcgg   960
tcgcccggcg tcaggctcgg gttcgcgaga tgttgcacac gctgcccaaa aaggcccagg  1020
cggcgatcct cgacgatctc gagggcacgc acaagtacgc ggtgcacgaa atcggccagt  1080
aaaagctt                                                           1088

SEQ ID NO: 114            moltype = AA   length = 379
FEATURE                   Location/Qualifiers
source                    1..379
                          mol_type = protein
                          organism = Mycobacterium tuberculosis
SEQUENCE: 114
MGSSHHHHHH SSGLVPRGSH MRYSDSYHTT GRWQPRASTE GFPMGVSIEV NGLTKSFGSS    60
RIWEDVTLTI PAGEVSVLLG PSGTGKSVFL KSLIGLLRPE RGSIIIDGTD IIECSAKELY   120
EIRTLFGVLF QDGALFGSMN LYDNTAFPLR EHTKKKESEI RDIVMEKLAL VGLGGDEKKF   180
PGEISGGMRK RAGLARALVL DPQIILCDEP DSGLDPVRTA YLSQLIMDIN AQIDATILIV   240
THNINIARTV PDNMGMLFRK HLVMFGPREV LLTSDEPVVR QFLNGRRIGP IGMSEEKDEA   300
TMAEEQALLD AGHHAGGVEE IEGVPPQISA TPGMPERKAV ARRQARVREM LHTLPKKAQA   360
AILDDLEGTH KYAVHEIGQ                                                379

SEQ ID NO: 115            moltype = AA   length = 270
FEATURE                   Location/Qualifiers
source                    1..270
                          mol_type = protein
                          organism = Mycobacterium tuberculosis
SEQUENCE: 115
MLPETNQDEV QPNAPVALVT VEIRHPTTDS LTESANRELK HLLINDLPIE RQAQDVSWGM    60
TAPGGAPTPV ADRFVRYVNR DNTTAASLKN QAIVVETTAY RSFEAFTDVV MRVVDARAQV   120
SSIVGLERIL RFVLEIRVPA GVDGRITWSN WIDEQLLGPQ RFTPGGLVLT EWQGAAVYRE   180
LQPGKSLIVR YGPGMGQALD PNYHLRRITP AQTGPFFLLD IDSFWTPSGG SIPEYNRDAL   240
VSTFQDLYGP AQVVFQEMIT SRLKDELLRQ                                    270

SEQ ID NO: 116            moltype = DNA   length = 825
```

```
FEATURE                    Location/Qualifiers
source                     1..825
                           mol_type = genomic DNA
                           organism = Mycobacterium tuberculosis
SEQUENCE: 116
catatgctcc ccgagacaaa tcaggatgag gtccagccca acgcaccgt tgccctggtg    60
acggtggaaa tccgtcaccc gacaacggat tcgctcaccg aatcagcgaa ccgggagctc  120
aaacacctgc ttatcaatga tctaccgatc gaacgccagg cgcaggacgt cagctggggg  180
atgacggcgc ccggtggagc ccccacccg gtcgcggatc gtttcgttcg ttatgtcaat   240
cgcgataaca ccaccgccgc ttcactgaag aaccaggcca tagtcgtgga gaccaccgcc  300
taccgcagct tgaggcctt accgacgtt gtgatgcggg tcgtggatgc tcgcgcgcag   360
gtctcgtcaa tcgttgggtt ggagcgtatc ggtcttcgct ttgttctgga gatccgcgtc  420
cccgcgggtg tcgacggccg gatcacgtgg agcaactgga tcgacgagca gctgctcggg  480
cagcagcgtt tcactcccgg cggtctggtc tcgaccgagt ggcagggtgc cgcagtctac  540
cgtgagctac aaccaggcaa atcgctcatc gtgcgctacg gcccgggtat gggccaagcg  600
cttgatccca attaccatct cgccgaata acacccgccc aaaccggacc attcttcctg   660
ctggacatcg atagctttg gactcccagt ggcggctcca ttcccgagta caacaggac   720
gccttagtgt cgacattcca ggacctgtac ggtccggccc aggtcgtgtt tcaggagatg  780
atcaccagtc gcctgaaaga tgagctgctt cgccagtaaa agctt                 825

SEQ ID NO: 117             moltype = AA  length = 291
FEATURE                    Location/Qualifiers
source                     1..291
                           mol_type = protein
                           organism = Mycobacterium tuberculosis
SEQUENCE: 117
MGSSHHHHHH SSGLVPRGSH MMLPETNQDE VQPNAPVALV TVEIRHPTTD SLTESANREL   60
KHLLINDLPI ERQAQDVSWG MTAPGGAPTP VADRFVRYVN RDNTTAASLK NQAIVVETTA  120
YRSFEAFTDV VMRVVDARAQ VSSIVGLERI LRFVLEIRVP AGVDGRITWS NWIDEQLLGP  180
QRFTPGGLVL TEWQGAAVYR ELQPGKSLIV RYGPGMGQAL DPNYHLRRIT PAQTGPFFLL  240
DIDSFWTPSG GSIPEYNRDA LVSTFQDLYG PAQVVFQEMI TSRLKDELLR Q           291

SEQ ID NO: 118             moltype = AA  length = 362
FEATURE                    Location/Qualifiers
source                     1..362
                           mol_type = protein
                           organism = Mycobacterium tuberculosis
SEQUENCE: 118
MLRLVVGALL LVLAFAGGYA VAACKTVTLT VDGTAMRVTT MKSRVIDIVE ENGFSVDDRD   60
DLYPAAGVQV HDADTIVLRR SRPLQISLDG HDAKQVWTTA STVDEALAQL AMTDTAPAAA  120
SRASRVPLSG MALPVVSAKT VQLNDGGLVR TVHLPAPNVA GLLSAAGVPL LQSDHVVPAA  180
TAPIVEGMQI QVTRNRIKKV TERLPLPPNA RRVEDPEMNM SREVVEDPGV PGTQDVTFAV  240
AEVNGVETGR LPVANVVVTP AHEAVRVGT KPGTEVPPVI DGSIWDAIAG CEAGGNWAIN   300
TGNGYYGGVQ FDQGTWEANG GLRYAPRADL ATREEQIAVA EVTRLRQGWG AWPVCAARAG  360
AR                                                                 362

SEQ ID NO: 119             moltype = DNA  length = 1053
FEATURE                    Location/Qualifiers
source                     1..1053
                           mol_type = genomic DNA
                           organism = Mycobacterium tuberculosis
SEQUENCE: 119
catatgcatc accatcacca tcacgcatgc aaaacggtga cgttgaccgt cgacggaacc    60
gcgatgcggg tgaccacgat gaaatcgcgg gtgatcgaca tcgtcgaaga aacgggttc   120
tcagtcgacg accgcgacga cctgtatccc gcggccggtc tgcaggtcca tacgcccac  180
accatcgtgc tgcggcgtag ccgtccgctg cagatctcgc tggatggtca cgacgctaag  240
caggtgtgga cgaccgcgtc gacggtggac gaggcgctgg cccaactcgc gatgaccgac  300
acggcgccgg ccgcggcttc tcgcgccagc gcgtcccgc tgtccgggat ggcgctaccg   360
gtcgtcagcg ccaagacggt gcagctcaac gacggcgggt tggtgcgcac ggtgcacttg  420
cccgccccca atgtcgcggg gctgctgagt gcggccgagc tgccgctgtt gcaaagcgac  480
cacgtggtgc ccgccgcgac ggccccgatc gtcgaaggca tgcagatcca ggtgacccgc  540
aatcggatca gaaggtcac cgagcggctg ccgctgccgc cgaacgcgcg tcgtgtcgag   600
gacccggaga tgaacatgag ccgggaggtc gtcgaagacc cgggggttcc ggggaaccag   660
gatgtgacgt tcgcggtagc tgaggtcaac ggcgtcgaa ccggccgttt ggccgtcgac   720
aacgtcgtgg tgaccccggc ccacgaagcc gtggtgcggg tggcaccaa cccggtacc    780
gaggtgcccc cggtgatcga cggaagcatc tgggacgcga tcgccggctg tgaggccggt  840
ggcaactggg cgatcaacac cggcaacggg tattacggtg gtgtgcagtt tgaccagggc  900
acctgggagg ccaacggcgg gctgcggtat gcaccccgcg ctgacctcgc cacccgcgaa  960
gagcagatcg ccgttgccga ggtgacccga ctgcgtcaag gtttggggcgc ctggccgta  1020
tgtgctgcac gagcgggtgc gcgctgagaa ttc                              1053

SEQ ID NO: 120             moltype = AA  length = 348
FEATURE                    Location/Qualifiers
source                     1..348
                           mol_type = protein
                           organism = Mycobacterium tuberculosis
SEQUENCE: 120
HMHHHHHHAC KTVTLTVDGT AMRVTTMKSR VIDIVEENGF SVDDRDDLYP AAGVQVHDAD    60
TIVLRRSRPL QISLDGHDAK QVWTTASTVD EALAQLAMTD TAPAAASRAS RVPLSGMALP   120
```

```
VVSAKTVQLN DGGLVRTVHL PAPNVAGLLS AAGVPLLQSD HVVPAATAPI VEGMQIQVTR    180
NRIKKVTERL PLPPNARRVE DPEMNMSREV VEDPGVPGTQ DVTFAVAEVN GVETGRLPVA    240
NVVVTPAHEA VVRVGTKPGT EVPPVIDGSI WDAIAGCEAG GNWAINTGNG YYGGVQFDQG    300
TWEANGGLRY APRADLATRE EQIAVAEVTR LRQGWGAWPV CAARAGAR                 348

SEQ ID NO: 121           moltype = AA  length = 328
FEATURE                  Location/Qualifiers
source                   1..328
                         mol_type = protein
                         organism = Mycobacterium tuberculosis
SEQUENCE: 121
MELVRVTEAG AMAAGRWVGR GDKEGGDGAA VDAMRELVNS VSMRGVVVIG EGEKDHAPML     60
YNGEEVGNGD GPECDFAVDP IDGTTLMSKG MTNAISVLAV ADRGTMFDPS AVFYMNKIAV    120
GPDAAHVLDI TAPISENIRA VAKVKDLSVR DMTVCILDRP RHAQLIHDVR ATGARIRLIT    180
DGDVAGAISA CRPHSGTDLL AGIGGTPEGI IAAAAIRCMG GAIQAQLAPR DDAERRKALE    240
AGYDLNQVLT TEDLVSGENV FFCATGVTDG DLLKGVRYYP GGCTTHSIVM RSKSGTVRMI    300
EAYHRLSKLN EYSAIDFTGD SSAVYPLP                                      328

SEQ ID NO: 122           moltype = DNA  length = 999
FEATURE                  Location/Qualifiers
source                   1..999
                         mol_type = genomic DNA
                         organism = Mycobacterium tuberculosis
SEQUENCE: 122
catatgatgg agctggtccg ggtgaccgag gccggagcca tggccgcggg ccgctgggta     60
ggccgcggcg acaaggaggg cggcgacggc gcggcgtcg acgcgatgcg cgaactggtc    120
aactcggttt ccatgcgcgg ggtggtggtc atcggcgaag cgaaaagga ccacgcacca    180
atgctctaca acggcgaaga gtgggcaac ggcgacggac cggaatgcga ctttgccgtc     240
gaccccattg acggcaccac gctgatgagc aagggcatga ccaacgccat ctcggtgctg    300
gcggtagccg atcgcggcac catgttcgac ccgtcgccg tgttctacat gaacaaaatc     360
gccgtcggcc ccgatgccgc acacgtgctg gatatccacg cgccgatctc ggaaaacatc    420
cgagcggtcg ccaaggtcaa ggacctgtcg gtgcgagaca tgacggtgtg catcctggac    480
aggccgcggc acgcgcaact catccacgac gtccgcgcca ccggggcccg gatccggctg    540
atcaccgatg gcgacgtcgc cggcgcgatc tcggcgtgcc gaccgccgac ccggcaccgac    600
ctgctagctg ggatcggcgg caccccggag gaatcatcg ccgccgcggc gatccgctgc     660
atgggcgggg cgatccaggc gcagctcgcc ccgcgacg acgcggaacg ccgcaaggcc      720
ctagaagccg gttacgacct gaaccaggtc ttgaccaccg aagatctggt gtccgggaa     780
aacgtcttct tctgcgccac tggggtcacc gacggcgacc tgctcaaggg agtgcgttac    840
tacccccggg gctgcaccac ccattcgatc gtgatgcgct cgaagtccgg caccgtccgg    900
atgatcgagg cctaccaccg gcttcaaag ctcaacgaat actccgcgat cgacttcacc    960
ggcgacagca gcgccgtgta cccattgccc taaaagctt                           999

SEQ ID NO: 123           moltype = AA  length = 348
FEATURE                  Location/Qualifiers
source                   1..348
                         mol_type = protein
                         organism = Mycobacterium tuberculosis
SEQUENCE: 123
MGSSHHHHHH SSGLVPRGSH MELVRVTEAG AMAAGRWVGR GDKEGGDGAA VDAMRELVNS     60
VSMRGVVVIG EGEKDHAPML YNGEEVGNGD GPECDFAVDP IDGTTLMSKG MTNAISVLAV    120
ADRGTMFDPS AVFYMNKIAV GPDAAHVLDI TAPISENIRA VAKVKDLSVR DMTVCILDRP    180
RHAQLIHDVR ATGARIRLIT DGDVAGAISA CRPHSGTDLL AGIGGTPEGI IAAAAIRCMG    240
GAIQAQLAPR DDAERRKALE AGYDLNQVLT TEDLVSGENV FFCATGVTDG DLLKGVRYYP    300
GGCTTHSIVM RSKSGTVRMI EAYHRLSKLN EYSAIDFTGD SSAVYPLP                 348

SEQ ID NO: 124           moltype = AA  length = 329
FEATURE                  Location/Qualifiers
source                   1..329
                         mol_type = protein
                         organism = Mycobacterium tuberculosis
SEQUENCE: 124
VSASPLKVAV TGAAGQIGYS LLFRLASGSL LGPDRPIELR LLEIEPALQA LEGVVMELDD     60
CAFPLLSGVE IGSDPQKIFD GVSLALLVGA RPRGAGMERS DLLEANGAIF TAQGKALNAV    120
AADDVRVGVT GNPANTNALI AMTNAPDIPR ERFSALTRLD HNRAISQLAA KTGAAVTDIK    180
KMTIWGNHSA TQYPDLFHAE VAGKNAAEVV NDQAWIEDEF IPTVAKRGAA IIDARGASSA    240
ASAASATIDA ARDWLLGTPA DDWVSMAVVS DGSYGVPEGL ISSFPVTTKG GNWTIVSGLE    300
IDEFSRGRID KSTAELADER SAVTELGLI                                     329

SEQ ID NO: 125           moltype = DNA  length = 999
FEATURE                  Location/Qualifiers
source                   1..999
                         mol_type = genomic DNA
                         organism = Mycobacterium tuberculosis
SEQUENCE: 125
catatgagcg ctagtcctct caaggtcgcc gttaccggcg ccgccggcca aatcggctac     60
agcctgttgt tccgcctggc cagcggctct ttgctgggcc ctgaccgtcc gatcgagctg    120
cggctgctcg agatcgagcc ggcactgcag gcgctcgagg tgtggtgat ggaactcgac      180
gactgcgctt cccgctgtt gtccggggtg gagatcggtt cagatcccca agatcttc       240
gatggcgtga gcctggccct gctggtcgga gcccgccccc ggggcgcggg catggagcga    300
```

```
agtgacctgc tggaggccaa cggcgcgatc ttcaccgctc agggcaaagc cctcaacgct    360
gtcgccgcgg atgacgttcg cgtcggggtg accggcaacc ccgccaacac caacgcgctg    420
atcgcgatga ccaatgcgcc cgacattccc cgcgagcggt tctcggcgct cacccggctg    480
gaccacaatc gggcgatctc gcagctggcc gccaagaccg gcgcggcggt caccgacatc    540
aagaagatga cgatctgggg caatcactcg accacccagt acccccgacct gttccacgcg    600
gaggtcgccg gaaagaacgc ggccgaagtg gtcaacgacc aggcctggat cgaggatgaa    660
ttcatcccga cggtcgccaa gcgcggtgcg gcgatcatcg atgcgcgcgg cgcgtcgtcg    720
gccgcctcgg ccgcgtcggc aaccatcgac gctgcccggg actggttgct ggggacgccg    780
gcggacgatt gggtctcgat ggccgtcgtc tccgacgggt cctacggggt gccggagggc    840
ttgatctcct cgtttccggt caccaccaag ggcggcaact ggacgatcgt gagcggcttg    900
gagatcgacg agttctcccg cggccggatc gacaagtcaa ccgccgagtt ggctgacgag    960
cgcagcgcgg tcaccgagct cggcctgatc tgaaagctt                           999

SEQ ID NO: 126           moltype = AA   length = 349
FEATURE                  Location/Qualifiers
source                   1..349
                         mol_type = protein
                         organism = Mycobacterium tuberculosis
SEQUENCE: 126
MGSSHHHHHH SSGLVPRGSH MSASPLKVAV TGAAGQIGYS LLFRLASGSL LGPDRPIELR     60
LLEIEPALQA LEGVVMELDD CAFPLLSGVE IGSDPQKIFD GVSLALLVGA RPRGAGMERS    120
DLLEANGAIF TAQGKALNAV AADDVRVGVT GNPANTNALI AMTNAPDIPR ERFSALTRLD    180
HNRAISQLAA KTGAAVTDIK KMTIWGNHSA TQYPDLFHAE VAGKNAAEVV NDQAWIEDEF    240
IPTVAKRGAA IIDARGASSA ASAASATIDA ARDWLLGTPA DDWVSMAVVS DGSYGVPEGL    300
ISSFPVTTKG GNWTIVSGLE IDEFSRGRID KSTAELADER SAVTELGLI                349

SEQ ID NO: 127           moltype = AA   length = 456
FEATURE                  Location/Qualifiers
source                   1..456
                         mol_type = protein
                         organism = Mycobacterium tuberculosis
SEQUENCE: 127
MVSTHAVVAG ETLSALALRF YGDAELYRLI AAASGIADPD VVNVGQRLIM PDFTRYTVVA     60
GDTLSALALR FYGDAELNWL IAAASGIADP DVVNVGQRLI MPDFTRYTVV AGDTLSALAA    120
RFYGDASLYP LIAAVNGIAD PGVIDVGQVL VIFIGRSDGF GLRIVDRNEN DPRLWYYRFQ    180
TSAIGWNPGV NVLLPDDYRT SGRTYPVLYL FHGGGTDQDF RTFDFLGIRD LTAGKPIIIV    240
MPDGGHAGWY SNPVSSFVGP RNWETFHIAQ LLPWIEANFR TYAEYDGRAV AGFSMGGFGA    300
LKYAAKYYGH FASASSHSGP ASLRRDFGLV VHWANLSSAV LDLGGGTVYG APLWDQARVS    360
ADNPVERIDS YRNKRIFLVA GTSPDPANWF DSVNETQVLA GQREFRERLS NAGIPHESHE    420
VPGGHVFRPD MFRLDLDGIV ARLRPASIGA AAERAD                              456

SEQ ID NO: 128           moltype = DNA   length = 1380
FEATURE                  Location/Qualifiers
source                   1..1380
                         mol_type = genomic DNA
                         organism = Mycobacterium tuberculosis
SEQUENCE: 128
catatggtca gcacacatgc ggttgtcgcg ggggagacgc tgtcggcgtt ggcgttgcgc     60
ttctatggcg acgcggaact gtatcggctg atcgccgccg ccagcgggat cgccgatccc    120
gacgtcgtca atgtggggca gcggctgatt atgcctgact tcacgcgata caccgttgtt    180
gccggggaca cgctgtcggc gttggcgttg cgcttctatg gcgacgcgga attgaattgg    240
ctgatcgccg ccgccagcgg gatcgccgat cccgacgtcg tcaatgtggg gcagcggctg    300
attatgcctg acttcacgcg atacaccgtt gttgccgggg acacgctgtc ggcattggct    360
gcgcgcttct atggcgacgc ctccctatat ccgcttatcg ccgccgtcaa tggcatcgcc    420
gatcctggcg tcatcgacgt cgggcaggta ctggtcatat tcatcgggcg tagcgacggg    480
ttcggcctaa ggatcgtgga ccgcaacgag aacgatcccc gcctgtggta ctaccggttc    540
cagacctccg cgatcggctg gaaccccgga gtcaacgtcc tgcttcccga tgactaccgc    600
accagcggac gcacctatcc cgtcctctac ctgttccacg gcggcggcac cgaccaggat    660
ttccgcacgt tcgactttct gggcatccgc gacctgaccg ccggaaagcc gatcatcatc    720
gtgatgcccg acggcgggca cgcgggctgg tattccaacc cggtcagctc gttcgtcggc    780
ccacggaact gggagacatt ccacatcgcc cagctgctcc cctggatcga ggcgaacttc    840
cgaacctacg ccgaatacga cggccgcgcg gtcgccgggt ttcgatgggg tggcttcggc    900
gcgctgaagt acgcagcaaa gtactacggc cacttcgcgt cggcgagcag ccactccgga    960
ccggcaagtc tgccgccgga cttcggcctg gtagtgcatt gggcaaacct gtcctcggcg   1020
gtgctggatc taggcggcgg cacggtttac ggcgcgccgc tctgggacca agctagggtc   1080
agcgccgaca acccggtcga gcgtatcgac agctaccgca acaagcggat cttcctggtc   1140
gccggcacca gtccggaccc ggccaactgg ttcgacagcg tgaacgagac ccaggtgcta   1200
gccgggcaga gggagttccg cgaacgcctc agcaacgccg gcatcccgca tgaatcgcac   1260
gaggtgcctg gcggtcacgt cttccggccc gacatgttcc gtctcgacct cgacggcatc   1320
gtcgcccggc tgcgccccgc gagcatcggg gcggccgcag aacgcgccga ttagaagctt   1380

SEQ ID NO: 129           moltype = AA   length = 476
FEATURE                  Location/Qualifiers
source                   1..476
                         mol_type = protein
                         organism = Mycobacterium tuberculosis
SEQUENCE: 129
MGSSHHHHHH SSGLVPRGSH MVSTHAVVAG ETLSALALRF YGDAELYRLI AAASGIADPD     60
VVNVGQRLIM PDFTRYTVVA GDTLSALALR FYGDAELNWL IAAASGIADP DVVNVGQRLI    120
```

```
MPDFTRYTVV AGDTLSALAA RFYGDASLYP LIAAVNGIAD PGVIDVGQVL VIFIGRSDGF  180
GLRIVDRNEN DPRLWYYRFQ TSAIGWNPGV NVLLPDDYRT SGRTYPVLYL FHGGGTDQDF  240
RTFDFLGIRD LTAGKPIIIV MPDGGHAGWY SNPVSSFVGP RNWETFHIAQ LLPWIEANFR  300
TYAEYDGRAV AGFSMGGFGA LKYAAKYYGH FASASSHSGP ASLRRDFGLV VHWANLSSAV  360
LDLGGTVYG  APLWDQARVS ADNPVERIDS YRNKRIFLVA GTSPDPANWF DSVNETQVLA  420
GQREFRERLS NAGIPHESHE VPGGHVFRPD MFRLDLDGIV ARLRPASIGA AAERAD      476

SEQ ID NO: 130           moltype = AA  length = 518
FEATURE                  Location/Qualifiers
source                   1..518
                         mol_type = protein
                         organism = Mycobacterium tuberculosis
SEQUENCE: 130
MRAGRRVAIS AGSLAVLLGA LDTYVVVTIM RDIMNSVGIP INQLHRITWI VTMYLLGYIA  60
AMPLLGRASD RFGRKLMLQV SLAGFIIGSV VTALAGHFGD FHMLIAGRTI QGVASGALLP  120
ITLALGADLW SQRNRAGVLG GIGAAQELGS VLGPLYGIFI VWLLHDWRDV FWINVPLTAI  180
AMVMIHFSLP SHDRSTEPER VDLVGGLLLA LALGLAVIGL YNPNPDGKHV LPDYGAPLLV  240
GALVAAVAFF GWERFARTRL IDPAGVHFRP FLSALGASVA AGAALMVTLV DVELFGQGVL  300
QMDQAQAAGM LLWFLIALPI GAVTGGWIAT RAGDRAVAFA GLLIAAYGYW LISHWPVDLL  360
ADRHNILGLF TVPAMHTDLV VAGLGLGLVI GPLSSATLRV VPSAQHGIAS AAVVVARMTG  420
MLIGVAALSA WGLYRFNQIL AGLSAAIPPN ASLLERAAAI GARYQQAFAL MYGEIFTITA  480
IVCVFGAVLG LLISGRKEHA DEPEVQEQPT LAPQVEPL                         518

SEQ ID NO: 131           moltype = DNA  length = 996
FEATURE                  Location/Qualifiers
source                   1..996
                         mol_type = genomic DNA
                         organism = Mycobacterium tuberculosis
SEQUENCE: 131
catatggagc tggtccgggt gaccgaggcc ggagccatgg ccgcgggccg ctgggtaggc   60
cgcggcgaca aggagggcgg cgacggcgcg gcggtcgacg cgatgcgcga actggtcaac  120
tcggttttcca tgcgcggggt ggtggtcatc ggcgaaggca aaaaggacca cgcaccaatg  180
ctctacaacg gcgaagaagt gggcaacggc gacggaccgg aatgcgactt tgccgtcgac  240
cccattgacg gcaccacgct gatgagcaag gcatgacaca acgccatctc ggtgctggcg  300
gtagccgatc gcggcaccat gttcgacccg tcggcggtgt tctacatgaa caaaatcgcc  360
gtcgccccg  atgccgcaca cgtgctggat atcaccgcgc cgatctcgga aacatccga   420
gcggtcgcca aggtcaagga cctgtcggtg cgagacatga cggtgtgcat cctggacagg  480
ccgcggcacg cgcaactcat ccacgacgtc cgcgccaccg gggcccggat ccggctgatc  540
accgatggcg acgtcgccgg cgcgatctcg gcgtgccgc cgcactccgg caccgacctg   600
ctagctggga tcggcggcac cccggaggga atcatcgccg ccggcgat ccgctgcatg    660
ggcggggcga tccaggcgca gctgcccccg cgcgacgacg cggaacgccg caaggcccta  720
gaagccggtt acgacctgaa ccaggtcttg accaccgaag atctggtgtc cggggaaaac  780
gtcttcttct gcgccactgg ggtcaccgac ggcgacctgc tcaaggggagt gcgttactac  840
cccggcggct gcaccaccca ttcgatcgtg atgcgctcga agtccggcac cgtccggatg  900
atcgaggcct accaccggct ttcaaagctc aacgaatact ccgcgatcga cttcaccggc  960
gacagcagcg ccgtgtaccc attgccctaa aagctt                            996

SEQ ID NO: 132           moltype = AA  length = 349
FEATURE                  Location/Qualifiers
source                   1..349
                         mol_type = protein
                         organism = Mycobacterium tuberculosis
SEQUENCE: 132
MGSSHHHHHH SSGLVPRGSH HMELVRVTEA GAMAAGRWVG RGDKEGGDGA AVDAMRELVN  60
SVSMRGVVVI GEGEKDHAPM LYNGEEVGNG DGPECDFAVD VGPDTTLMSK GMTNAISVLA  120
VADRGTMFDP SAVFYMNKIA VGPDAAHVLD ITAPISENIR AVAKVKDLSV RDMTVCILDR  180
PRHAQLIHDV RATGARIRLI TDGDVAGAIS ACRPHSGTDL LAGIGGTPEG IIAAAAIRCM  240
GGAIQAQLAP RDDAERRKAL EAGYDLNQVL TTEDLVSGEN VFFCATGVTD GDLLKGVRYY  300
PGGCTTHSIV MRSKSGTVRM IEAYHRLSKL NEYSAIDFTG DSSAVYPLP             349

SEQ ID NO: 133           moltype = AA  length = 386
FEATURE                  Location/Qualifiers
source                   1..386
                         mol_type = protein
                         organism = Mycobacterium tuberculosis
SEQUENCE: 133
MKAATQARID DSPLAWLDAV QRQRHEAGLR RCLRPRPAVA TELDLASNDY LGLSRHPAVI  60
DGGVQALRIW GAGATGSRLV TGDTKLHQQF EAELAEFVGA AAGLLFSSGY TANLGAVVGL  120
SGPGSLLVSD ARSHASLVDA CRLSRARVVV TPHRDVDAVD AALRSRDEQR AVVVTDSVFS  180
ADGSLAPVRE LLEVCRRHGA LLLVDEAHGL GVRGGGRGLL YELGLAGAPD VVMTTTLSKA  240
LGSQGGVVLG PTPVRAHLID AARPIFDTG  LAPAAVGAAR AALRVLQAEP WRPQAVLNHA  300
GELARMCGVA AVPDSAMVSV ILGEPESAVA AAAACLDAGV KVGCFRPPTV PAGTSRLRLT  360
ARASLNAGEL ELARRVLTDV LAVARR                                      386

SEQ ID NO: 134           moltype = DNA  length = 1170
FEATURE                  Location/Qualifiers
source                   1..1170
                         mol_type = genomic DNA
                         organism = Mycobacterium tuberculosis
```

```
SEQUENCE: 134
catatgaaag ccgccacgca ggcacggatc gacgattcac cgttggcctg gttggacgcg    60
gtgcagcggc agcgccacga ggccggactg cggcgctgcc tgcggccgcg tcccgcggtc   120
gccaccgagc tggacttggc ctccaacgac tatctcggtc tgtcccgaca tcccgccgtc   180
atcgacggcg gcgtccaggc gctgcggatc tggggcgccg gcgccaccgg gtcgcgcctg   240
gttaccggcg acaccaagct gcaccagcaa ttcgaggccg agctcgccga gttygtcggc   300
gctgccgcgg gattgctgtt ctcctctggc tacacggcca acctgggcgc cgtggtcggc   360
ctgtccggcc cgggttccct gctggtgtcc gacgcccgtt cgcatgcgtc gttggtggat   420
gcctgtcggc tgtcgcgggc gcgggttgtg gtgacgccgc accgacgt cgacgccgtg   480
gacgccgacg tgcgatcgcg cgacgagcag cgcgccgtcg tcgtcaccga ctcggtgttc   540
agcgccgacg gctcgctggc gccggttcgg gagttgcttg aggtctgccg gcgtcatggt   600
gcgctgcttc tggtggacga ggcgcacggc ctgggtgtgc gtggcggcgg acgcgggctg   660
ctctacgagt taggtctagc gggtgcgccc gacgtggtga tgaccaccac gctgtccaag   720
gcgctgggca gccagggtgg tgtggtgctc gggccgacgc cggtcgggc ccatctgatc   780
gatgctgccc ggccgttcat cttcgacacc ggtctggccg cggcggcggt gggtgccgca   840
cgggccgcgc tgcgcgtctt gcaggccgag ccgtggcgac cgcaggcggt gctcaaccac   900
gctggtgaac ttgcgcggat gtgcggtgtg gctgcggtgc cggactcggc gatggtgtcg   960
gtgatcctgg gcgagccgga gtcggccagtg gccgccgagg cggcctgcct ggacgccggg  1020
gtcaaggtgg gctgcttccg gccgccgacg gtgcccgcgg gtacgtcgcg gctgcggctg  1080
accgcgcgcg catcgctgaa cgccggcgag ctcgagctgg cccggcgggt gctgacggat  1140
gttctcgccg tggcgcgccg ttgaaagctt                                   1170

SEQ ID NO: 135       moltype = AA  length = 406
FEATURE              Location/Qualifiers
source               1..406
                     mol_type = protein
                     organism = Mycobacterium tuberculosis
SEQUENCE: 135
MGSSHHHHHH SSGLVPRGSH MKAATQARID DSPLAWLDAV QRQRHEAGLR RCLRPRPAVA    60
TELDLASNDY LGLSRHPAVI DGGVQALRIW GAGATGSRLV TGDTKLHQQF EAELAEFVGA   120
AAGLLFSSGY TANLGAVVGL SGPGSLLVSD ARSHASLVDA CRLSRARVVV TPHRDVDAVD   180
AALRSRDEQR AVVVTDSVFS ADGSLAPVRE LLEVCRRHGA LLLVDEAHGL GVRGGGRGLL   240
YELGLAGAPD VVMTTTLSKA LGSQGGVVLG PTPVRAHLID AARPFIFDTG LAPAAVGAAR   300
AALRVLQAEP WRPQAVLNHA GELARMCGVA AVPDSAMVSV ILGEPESAVA AAAACLDAGV   360
KVGCFRPPTV PAGTSRLRLT ARASLNAGEL ELARRVLTDV LAVARR               406

SEQ ID NO: 136       moltype = AA  length = 393
FEATURE              Location/Qualifiers
source               1..393
                     mol_type = protein
                     organism = Mycobacterium tuberculosis
SEQUENCE: 136
MDFGALPPEV NSVRMYAGPG SAPMVAAASA WNGLAAELSS AATGYETVIT QLSSEGWLGP    60
ASAAMAEAVA PYVAWMSAAA AQAEQAATQA RAAAAAFEAA FAATVPPPLI AANRASLMQL   120
ISTNVFGQNT SAIAAAEAQY GEMWAQDSAA MYAYAGSSAS ASAVTPFSTP PQIANPTAQG   180
TQAAAVATAA GTAQSTLTEM ITGLPNALQS LTSPLLQSSN GPLSWLWQIL FGTPNFPTSI   240
SALLTDLQPY ASFFYNTEGL PYFSIGMGNN FIQSAKTLGL IGSAAPAAVA AAGDAAKGLP   300
GLGGMLGGGP VAAGLGNAAS VGKLSVPPVW SGPLPGSVTP GAAPLPVSTV SAAPEAAPGS   360
LLGGLPLAGA GGAGAGPRYG FRPTVMARPP FAG                              393

SEQ ID NO: 137       moltype = DNA  length = 1191
FEATURE              Location/Qualifiers
source               1..1191
                     mol_type = genomic DNA
                     organism = Mycobacterium tuberculosis
SEQUENCE: 137
catatggatt ttggggcgtt gccgccggag gtcaattcgg tgcggatgta tgccggtcct    60
ggctcggcac caatggtcgc tgcggcgtcg gcctggaacg gttggccgc ggagctgagt   120
tcggcggcca ccggttatga gacggtgatc actcagctca gcagtgaggg gtggctaggt   180
ccggcgtcag cggcgatggc cgaggcagtt gcgccgtatg tggcgtggat gagtgccgct   240
gcggcgcaag ccgagcaggc ggccacacag gccaggccg ccggcgc ttttgaggcg   300
gcgtttgccg cgacggtgcc tccgccgttg atcgcggcca accgggcttc gttgatgcag   360
ctgatctcga cgaatgtctt tggtcagaac acctcggcga tcgcggccgc cgaagctcag   420
tacggcggga tgtgggccca agactccgcg gcgatgtatg cctacgcggg cagttcgggg   480
agcgcctcgg cggtcacgcc gtttagcacg ccgccgcaga ttgccaaccc gaccgctcag   540
ggtacgcagg ccgcggccgt ggccaccgcc gccggtaccg cccagtcgac gctgacggag   600
atgatcaccg gctacccaa cgcgctgcaa agcctcacct cacctctgtt gcagtcgtct   660
aacggtccgc tgtcgtggct gtggcagatc ttgttcggca cgcccaattt ccccacctca   720
atttcggcac tgctgaccga cctgcagccc tacgcgagtc tcttctataa caccgagggc   780
ctgccgtact tcagcatcgg catgggcaac aacttcatc agtcggccaa gaccctggga   840
ttgatcggct cggcggcacc ggctgcggtc gcggctgctg gggatgccgc caagggcttg   900
cctggactgg gcgggatgct cggtggcggg ccggtggcgg cgggtctggg caatgcggct   960
tcggttggca agctgtcggt gccgccggtg tggagtggac cgttgccggg tcggtgact  1020
ccgggggctg ctccgctacc ggtgagtacg gtcaatgcg cccggaggc ggcgccaggg  1080
agcctgttgg gcggcctgcc gctagctggt gcgggcgggg ccggcgcggg tccacgctac  1140
ggattccgtc ccaccgtcat ggctcgccca cccttcgccg gatagaagct t            1191

SEQ ID NO: 138       moltype = AA  length = 413
FEATURE              Location/Qualifiers
```

```
source                  1..413
                        mol_type = protein
                        organism = Mycobacterium tuberculosis
SEQUENCE: 138
MGSSHHHHHH SSGLVPRGSH MDFGALPPEV NSVRMYAGPG SAPMVAAASA WNGLAAELSS    60
AATGYETVIT QLSSEGWLGP ASAAMAEAVA PYVAWMSAAA AQAEQAATQA RAAAAAFEAA   120
FAATVPPPLI AANRASLMQL ISTNVFGQNT SAIAAAEAQY GEMWAQDSAA MYAYAGSSAS   180
ASAVTPFSTP PQIANPTAQG TQAAAVATAA GTAQSTLTEM ITGLPNALQS LTSPLLQSSN   240
GPLSWLWQIL FGTPNFPTSI SALLTDLQPY ASFFYNTEGL PYFSIGMGNN FIQSAKTLGL   300
IGSAAPAAVA AAGDAAKGLP GLGGMLGGGP VAAGLGNAAS VGKLSVPPVW SGPLPGSVTP   360
GAAPLPVSTV SAAPEAAPGS LLGGLPLAGA GGAGAGPRYG FRPTVMARPP FAG          413

SEQ ID NO: 139          moltype = AA  length = 498
FEATURE                 Location/Qualifiers
source                  1..498
                        mol_type = protein
                        organism = Mycobacterium tuberculosis
SEQUENCE: 139
MSFVVTIPEA LAAVATDLAG IGSTIGTANA AAAVPTTTVL AAAADEVSAA MAALFSGHAQ    60
AYQALSAQAA LFHEQFVRAL TAGAGSYAAA EAASAAPLEG VLDVINAPAL ALLGRPLIGN   120
GANGAPGTGA NGGDGGILIG NGGAGGSAA GMPGGNGGAA GLFGNGGAGG AGGNVASGTA    180
GFGGAGGAGG LLYGAGGAGG AGGRAGGGVG GIGGAGGAGG NGGLLFGAGG AGGVGGLAAD   240
AGDGGAGGDG GLFFGVGGAG GAGGTGTNVT GGAGGAGGNG GLLFGAGGVG GVGGDGVAFL   300
GTAPGGPGGA GGAGGLFGVG GAGGAGGIGL VGNGGAGGSG GSALLWGDGG AGGAGGVGST   360
TGGAGGAGGN AGLLVGAGGA GGAGALGGGA TGVGGAGGNG GTAGLLFGAG GAGGFGFGGA   420
GGAGGLGGKA GLIGDGGDGG AGGNGTGAKG GDGGAGGGAI LVGNGGNGGN AGSGTPNGSA   480
GTGGAGGLLG KNGMNGLP                                                 498

SEQ ID NO: 140          moltype = DNA  length = 1506
FEATURE                 Location/Qualifiers
source                  1..1506
                        mol_type = genomic DNA
                        organism = Mycobacterium tuberculosis
SEQUENCE: 140
catatgtcat tgtggtcac gatcccggag gcgctagcgg cggtggcgac cgatttggcg     60
ggtatcgggt cgacgatcgg caccgccaac gcggccgccg cggtcccgac cacgacggtg   120
ttggccgccg ccgccgatga ggtgtcggcg gcgatggcgg cattgttctc cggacacgcc   180
caggcctatc aggcgctgag cgcccaggcg gcgctgtttc acgagcagtt cgtgcgggcg   240
ctcaccgccg gggcgggctc gtatgccggc gccgagccag cagcgccgga cccgctagag   300
ggtgtgctcg acgtgatcaa cgcccccgcc ctggcgctgt tggggcgccc actgatcggt   360
aacggagcca acggggcccc ggggaccggg gcaaacggcg gcgacggcgg aatcttgatc   420
ggcaacggcg gggccggcgg ctccggcgcg gccggcatgc cgggggcaa cggcggagcc    480
gctggcctgt tcggcaacgg gggcgccggc ggcgccgggg ggaacgtagc gtccggcacc   540
gcaggggttcg gcggggccgg cggggccggc gggctgctct acggcgcgg cggggccggc   600
ggcgccggcg gacgcgccgg tggtggggtg ggcggtattg gtggggccgg cggggccggc   660
ggcaatggcg ggctgctgtt cggcgccggc ggggccggcg gcgtcggcgg actcgcggct   720
gacgccggtg acggcggggc cggcgagac ggcgggttgt tcttcggcgg gggcgtgcc    780
ggcgggggcc gcggcaccgg cactaatgtc accggcggtg ccgcggggc cggcggcaat   840
ggcgggctcc tgttcggcgc cggcggggtg ggcgtgttg gcgtgacgg tgtggcattc    900
ctgggcaccg ccccggcgg gccggtggt ccggcggggg ccggtgggct gttcggcgtc    960
ggtggggccg gcggcgccgg cggaatcgga ttggtcggga acggcggtgc cgggggtcc   1020
ggcgggtccg ccctgctctg gggcgacgg ggtgccggcg gcgcgggtgg ggtcgggtcc   1080
actaccggcg gtgccggcgg ggcggccgg aacgccggcc tgctggtagg cgccggcggg   1140
gccggcggcc ccgcgcact cggcggtggc gctaccgggg tgggcggcgc cggcggaaac   1200
ggccgcactg cggggcctgct gtttggtgcc ggcggcgccg gcggattcgg cttcggcgga   1260
gccggggccg ccggtgggct cggcggcaaa gccgggctga tcggcgacgg cggtgacggc   1320
ggcgccggag gaaacggcac cggtgccaag ggcggtgacg gcggcgctgg cggcggtgcc   1380
atcctggtcg gcaacggcgg caacggcggc aacgccggga gtggcacacc taacggcagc   1440
gcgggcaccg gcggtgccgg cgggctgttg gtaagaacg ggatgaacgg gttaccgtag    1500
aagctt                                                             1506

SEQ ID NO: 141          moltype = AA  length = 518
FEATURE                 Location/Qualifiers
source                  1..518
                        mol_type = protein
                        organism = Mycobacterium tuberculosis
SEQUENCE: 141
MGSSHHHHHH SSGLVPRGSH MSFVVTIPEA LAAVATDLAG IGSTIGTANA AAAVPTTTVL    60
AAAADEVSAA MAALFSGHAQ AYQALSAQAA LFHEQFVRAL TAGAGSYAAA EAASAAPLEG   120
VLDVINAPAL ALLGRPLIGN GANGAPGTGA NGGDGGILIG NGGAGGSAA GMPGGNGGAA    180
GLFGNGGAGG AGGNVASGTA GFGGAGGAGG LLYGAGGAGG AGGRAGGGVG GIGGAGGAGG   240
NGGLLFGAGG AGGVGGLAAD AGDGGAGGDG GLFFGVGGAG GAGGTGTNVT GGAGGAGGNG   300
GLLFGAGGVG GVGGDGVAFL GTAPGGPGGA GGAGGLFGVG GAGGAGGIGL VGNGGAGGSG   360
GSALLWGDGG AGGAGGVGST TGGAGGAGGN AGLLVGAGGA GGAGALGGGA TGVGGAGGNG   420
GTAGLLFGAG GAGGFGFGGA GGAGGLGGKA GLIGDGGDGG AGGNGTGAKG GDGGAGGGAI   480
LVGNGGNGGN AGSGTPNGSA GTGGAGGLLG KNGMNGLP                           518

SEQ ID NO: 142          moltype = AA  length = 325
FEATURE                 Location/Qualifiers
```

```
source                      1..325
                            mol_type = protein
                            organism = Mycobacterium tuberculosis
SEQUENCE: 142
MHQVDPNLTR RKGRLAALAI AAMASASLVT VAVPATANAD PEPAPPVPTT AASPPSTAAA    60
PPAPATPVAP PPPAAANTPN AQPGDPNAAP PPADPNAPPP PVIAPNAPQP VRIDNPVGGF   120
SFALPAGWVE SDAAHFDYGS ALLSKTTGDP PFPGQPPPVA NDTRIVLGRL DQKLYASAEA   180
TDSKAAARLG SDMGEFYMPY PGTRINQETV SLDANGVSGS ASYYEVKFSD PSKPNGQIWT   240
GVIGSPAANA PDAGPPQRWF VVWLGTANNP VDKGAAKALA ESIRPLVAPP PAPAPAPAEP   300
APAPAPAGEV APTPTTPTPQ RTLPA                                        325

SEQ ID NO: 143              moltype = DNA   length = 873
FEATURE                     Location/Qualifiers
source                      1..873
                            mol_type = genomic DNA
                            organism = Mycobacterium tuberculosis
SEQUENCE: 143
catatggatc cggagccagc gcccccggta cccacaacgg ccgcctcgcc gccgtcgacc    60
gctgcagcgc cacccgcacc ggcgacacct gttgccccc caccaccggc cgccgccaac   120
acgccgaatg cccagccggg cgatcccaac gcagcacctc cgccggccga cccgaacgca   180
ccgccgccac ctgtcattgc cccaaacgca ccccaacctg tccggatcga caacccggtt   240
ggaggattca gcttcgcgct gcctgctggc tgggtggagt ctgacgccgg ccacttcgac   300
tacggttcag cactcctcag caaaaccacc ggggacccgc catttccggg acagccgccg   360
ccggtggcca atgacacccg tatcgtgctc ggccggctag accaaaagct ttacgccagc   420
gccgaagcca ccgactccaa ggccgcggcc cggttgggct cggacatggg tgagttctat   480
atgccctacc cgggcacccg gatcaaccag gaaaccgtct cgctcgacgc caacggggtg   540
tctggaagcg cgtcgtatta cgaagtcaag ttcagcgatc cgagtaagcc gaacggccag   600
atctggacgg gcgtaatcgg ctcgcccgcg gcgaacgcac cggacgccgg ccccctcag   660
cgctggtttg tggtatggct cgggaccgcc aacaacccgg tggacaaggg cgcggccaag   720
gcgctggccg aatcgatccg gcctttggtc gccccgccgc cggcgccggc accggctcct   780
gcagagcccg ctccggccgc ggccgccggc ggggaagtcg ctcctacccc gacgacaccg   840
acaccgcagc ggaccttacc ggcctgagaa ttc                               873

SEQ ID NO: 144              moltype = AA   length = 307
FEATURE                     Location/Qualifiers
source                      1..307
                            mol_type = protein
                            organism = Mycobacterium tuberculosis
SEQUENCE: 144
MGSSHHHHHH SSGLVPRGSH MDPEPAPPVP TTAASPPSTA AAPPAPATPV APPPPAAANT    60
PNAQPGDPNA APPPADPNAP PPVIAPNAP QPVRIDNPVG GFSFALPAGW VESDAAHFDY   120
GSALLSKTTG DPPFPGQPPP VANDTRIVLG RLDQKLYASA EATDSKAAAR LGSDMGEFYM   180
PYPGTRINQE TVSLDANGVS GSASYYEVKF SDPSKPNGQI WTGVIGSPAA NAPDAGPPQR   240
WFVVWLGTAN NPVDKGAAKA LAESIRPLVA PPPAPAPAPA EPAPAPAPAG EVAPTPTTPT   300
PQRTLPA                                                            307

SEQ ID NO: 145              moltype = AA   length = 325
FEATURE                     Location/Qualifiers
source                      1..325
                            mol_type = protein
                            organism = Mycobacterium tuberculosis
SEQUENCE: 145
MTDVSRKIRA WGRRLMIGTA AAVVLPGLVG LAGGAATAGA FSRPGLPVEY LQVPSPSMGR    60
DIKVQFQSGG NNSPAVYLLD GLRAQDDYNG WDINTPAFEW YYQSGLSIVM PVGGQSSFYS   120
DWYSPACGKA GCQTYKWETF LTSELPQWLS ANRAVKPTGS AAIGLSMAGS SAMILAAYHP   180
QQFIYAGSLS ALLDPSQGMG PSLIGLAMGD AGGYKAADMW GPSSDPAWER NDPTQQIPKL   240
VANNTRLWVY CGNGTPNELG GANIPAEFLE NFVRSSNLKF QDAYNAAGGH NAVFNFPPNG   300
THSWEYWGAQ LNAMKGDLQS SLGAG                                        325

SEQ ID NO: 146              moltype = DNA   length = 904
FEATURE                     Location/Qualifiers
source                      1..904
                            mol_type = genomic DNA
                            organism = Mycobacterium tuberculosis
SEQUENCE: 146
catatgcatc accatcacca tcacttctcc cggccgggc tgccggtcga gtacctgcag    60
gtgccgtcgc cgtcgatggg ccgcgacatc aaggttcagt tccagagcgg tgggaacaac   120
tcacctgcgg tttatctgct cgacggcctg cgcgcccaag acgactacaa cggctgggat   180
atcaacaccc cggcgttcga gtggtactac cagtcgggcc tgtcgatagt catgccggtc   240
ggcgggcagt ccagcttcta cagcgactgg tacagcccgg cctgcggtaa ggctggctgc   300
cagacttaca gtgggaaac cttcctgacc agcgagctgc cgcaatggtt gtccgccaac   360
agggccgtga agcccaccgg cagcgctgca atcggcttgt cgatggccgg ctcgtcggca   420
atgatcttgg ccgcctacca ccccagcag ttcatctacg ccggctcgct gtcggccctg   480
ctggacccct ctcaggggat ggggcctagc ctgatcggct tggcgatggg tgacgccggt   540
ggttacaagg ccgcagacat gtggggtccc tcgagtgacc cggcatggga gcgcaacgac   600
cctacgcagc agatccccaa gctggtcgca aacaacaccc ggctatgggt ttattgcggg   660
aacggcaccc cgaacgagtt gggcggtgcc aacatacccg ccgagttctt ggagaacttc   720
gttcgtagca gcaacctgaa gttccaggat gcgtacaacg ccggcggcgg gcacaacgcc   780
gtgttcaact tcccgcccaa cggcacgcac agctgggagt actggggcgc tcagctcaac   840
```

```
gccatgaagg gtgacctgca gagttcgtta ggcgccggct gacgggatca accgaaggga    900
attc                                                                904

SEQ ID NO: 147          moltype = AA   length = 293
FEATURE                 Location/Qualifiers
source                  1..293
                        mol_type = protein
                        organism = Mycobacterium tuberculosis
SEQUENCE: 147
HMHHHHHHFS RPGLPVEYLQ VPSPSMGRDI KVQFQSGGNN SPAVYLLDGL RAQDDYNGWD     60
INTPAFEWYY QSGLSIVMPV GGQSSFYSDW YSPACGKAGC QTYKWETFLT SELPQWLSAN    120
RAVKPTGSAA IGLSMAGSSA MILAAYHPQQ FIYAGSLSAL LDPSQGMGPS LIGLAMGDAG    180
GYKAADMWGP SSDPAWERND PTQQIPKLVA NNTRLWVYCG NGTPNELGGA NIPAEFLENF    240
VRSSNLKFQD AYNAAGGHNA VFNFPPNGTH SWEYWGAQLN AMKGDLQSSL GAG           293

SEQ ID NO: 148          moltype = AA   length = 740
FEATURE                 Location/Qualifiers
source                  1..740
                        mol_type = protein
                        organism = Mycobacterium tuberculosis
SEQUENCE: 148
VPEQHPPITE TTTGAASNGC PVVGHMKYPV EGGGNQDWWP NRLNLKVLHQ NPAVADPMGA     60
AFDYAAEVAT IDVDALTRDI EEVMTTSQPW WPADYGHYGP LFIRMAWHAA GTYRIHDGRG    120
GAGGGMQRFA PLNSWPDNAS LDKARRLLWP VKKKYGKKLS WADLIVFAGN CALESMGFKT    180
FGFGFGRVDQ WEPDEVYWGK EATWLGDERY SGKRDLENPL AAVQMGLIYV NPEGPNGNPD    240
PMAAAVDIRE TFRRMAMNDV ETAALIVGGH TFGKTHGAGP ADLVGPEPEA APLEQMGLGW    300
KSSYGTGTGK DAITSGIEVV WTNTPTKWDN SFLEILYGYE WELTKSPAGA WQYTAKDGAG    360
AGTIPDDPFGG PGRSPTMLAT DLSLRVDPIY ERITRRWLEH PEELADEFAK AWYKLIHRDM   420
GPVARYLGPL VPKQTLLWQD PVPAVSHDLV GEAEIASLKS QIRASGLTVS QLVSTAWAAA    480
SSFRGSDKRG GANGGRIRLQ PQVGWEVNDP DGDLRKVIRT LEEIQESFNS AAPGNIKVSF    540
ADLVVLGGCA AIEKAAKAAG HNITVPFTPG RTDASQEQTD VESFAVLEPK ADGFRNYLGK    600
GNPLPAEYML LDKANLLTLS APEMTVLVGG LRVLGANYKR LPLGVFTEAS ESLTNDFFVN    660
LLDMGITWEP SPADDGTYQG KDGSGKVKWT GSRVDLVFGS NSELRALVEV YGADDAQPKF    720
VQDFVAAWDK VMNLDRFDVR                                                740

SEQ ID NO: 149          moltype = DNA   length = 2157
FEATURE                 Location/Qualifiers
source                  1..2157
                        mol_type = genomic DNA
                        organism = Mycobacterium tuberculosis
SEQUENCE: 149
catatgaaat acccgtcga gggcggcgga aaccaggact ggtggcccaa ccggctcaat      60
ctgaaggtac tgcaccaaaa cccggccgtc gctgacccga tgggtgcggc gttcgactat   120
gccgcggagg tcgcgaccat cgacgttgac gccctgacgc gggacatcga ggaagtgatg   180
accacctcgc agccgtggtg gcccgccgac tacggccact acgggccgct gtttatccgg   240
atggcgtggc acgctgccgg cacctaccgc atccacgacg gccgcggcgg cgccgggggc   300
ggcatgcagc ggttcgcgcc gcttaacagc tggcccgaca acgccagctt ggacaaggcg   360
cgccggctgc tgtggccggt caagaagaag tacggcaaga agctctcatg gcggacctg    420
attgttttcg ccggcaactg cgcgctggaa tcgatgggct tcaagacgtt cgggttcggc   480
ttcggccggg tcgaccagtg ggagcccgat gaggtctatt gggcaagga agccacctgg    540
ctcggcgatg agcgttacag cggtaagcgg gatctggaga acccgctggc cgcggtgcag   600
atggggctga tctacgtgaa cccggagggg ccgaacggca acccggaccc catgccgcg    660
gcggtcgaca ttcgcgagac gtttcggcgc atgccatga cgacgtcga aacagcggcg    720
ctgatcgtcg gcggtcacac tttcggtaag cccatggcg ccggcccggc cgatctggtc    780
ggcccgaac ccgaggctgc tccgctggag cagatgggct tgggctgaa gagctgtat    840
ggcaccggaa ccggtaagga cgcgatcacc agcggcatcg aggtcgtatg gacgaacacc   900
ccgacgaaat gggacaacag tttcctcgag atcctgtacg gctacgagtg ggagctgacg   960
aagagccctg ctgcgcttg gcaatacacc gccaaggacg gcgccggtgc cggcaccatc   1020
ccggacccgt tcggcgggcc agggcgctcc ccgacgatgc tggccactga cctctcgctg   1080
cgggtggatc cgatctatga gcggatcacg cgtcgctggc tggaacaccc cgaggaattg   1140
gccgacgagt tcgccaaggc ctggtacaag ctgatccacc gagacatggg tcccgttgcg   1200
agataccttg ggccgctggt ccccaagcag accctgctgt ggcaggatcc ggtccctgcg   1260
gtcagccacg acctcgtcgg cgaagccgag attgccagcc ttaagagcca gatccgggca   1320
tcgggattga ctgtctcaca gctagtttcg accgcatggg cggcggcgtc gtcgttcgt   1380
ggtagcgaca agcgcggcgg cgccaacggt ggtcgcatcc gcctgcagcc acaagtcggg   1440
tgggaggtca acgaccccga cggggatctg cgcaaggtca ttcgcaccct ggaagagatc   1500
caggagtcat tcaactccgc ggcgccgggg aacatcaaaa tgtccttcgc cgacctcgtc   1560
gtgctcggtg gctgtgccgc catagagaaa gcagcaaagg cggctggcca caacatcacg   1620
gtgcccttca ccccggggccg cacgatgcg tcgcaggaaa aaaccgacgt ggaatccttt   1680
gccgtgctgg agcccaaggc agatggcttc cgaaactacc tcggaaaggg caacccgttg   1740
ccggccgagt acatgctgct cgacaaggcg aacctgctta cgtcagtgc ccctgagatg   1800
acggtgctgg taggtggcct gcgcgtcctc ggcgcaaact acaagcgctt accgctgggc   1860
gtgttcaccg aggcctccga gtcactgacc aacgacttct tcgtgaacct gctcgacatg   1920
ggtatcactt gggagccctc gccagcagat gacgggacct accagggcaa ggatggcagt   1980
ggcaaggtga agtggaccgg cagccgcgtg gacctggtct tcgggtccaa ctcgagttg    2040
cgggcgcttg tcgaggtcta tggcgccgat gacgcgcagc cgaagttcgt gcaggacttc   2100
gtcgctgcct gggacaaggt gatgaacctc gacaggttcg acgtgcgctg aaagctt      2157

SEQ ID NO: 150          moltype = AA   length = 735
```

```
FEATURE                 Location/Qualifiers
source                  1..735
                        mol_type = protein
                        organism = Mycobacterium tuberculosis
SEQUENCE: 150
MGSSHHHHHH SSGLVPRGSH MKYPVEGGGN QDWWPNRLNL KVLHQNPAVA DPMGAAFDYA    60
AEVATIDVDA LTRDIEEVMT TSQPWWPADY GHYGPLFIRM AWHAAGTYRI HDGRGGAGGG   120
MQRFAPLNSW PDNASLDKAR RLLWPVKKKY GKKLSWADLI VFAGNCALES MGFKTFGFGF   180
GRVDQWEPDE VYWGKEATWL GDERYSGKRD LENPLAAVQM GLIYVNPEGP NGNPDPMAAA   240
VDIRETFRRM AMNDVETAAL IVGGHTFGKT HGAGPADLVG PEPEAAPLEQ MGLGWKSSYG   300
TGTGKDAITS GIEVVWTNTP TKWDNSFLEI LYGYEWELTK SPAGAWQYTA KDGAGAGTIP   360
DPFGGPGRSP TMLATDLSLR VDPIYERITR RWLEHPEELA DEFAKWYKL IHRDMGPVAR    420
YLGPLVPKQT LLWQDPVPAV SHDLVGEAEI ASLKSQIRAS GLTVSQLVST AWAAASSFRG   480
SDKRGGANGG RIRLQPQVGW EVNDPDGDLR KVIRTLEEIQ ESFNSAAPGN IKVSFADLVV   540
LGGCAAIEKA AKAAGHNITV PFTPGRTDAS QEQTDVESFA VLEPKADGFR NYLGKGNPLP   600
AEYMLLDKAN LLTLSAPEMT VLVGGLRVLG ANYKRLPLGV FTEASESLTN DFFVNLLDMG   660
ITWEPSPADD GTYQGKDGSG KVKWTGSRVD LVFGSNSELR ALVEVYGADD AQPKFVQDFV   720
AAWDKVMNLD RFDVR                                                   735

SEQ ID NO: 151          moltype = AA   length = 331
FEATURE                 Location/Qualifiers
source                  1..331
                        mol_type = protein
                        organism = Mycobacterium tuberculosis
SEQUENCE: 151
MPDTMVTTDV IKSAVQLACR APSLHNSQPW RWIAEDHTVA LFLDKDRVLY ATDHSGREAL    60
LGCGAVLDHF RVAMAAAGTT ANVERFPNPN DPLHLASIDF SPADFVTEGH RLRADAILLR   120
RTDRLPFAEP PDWDLVESQL RTTVTADTVR IDVIADDMRP ELAAASKLTE SLRLYDSSYH   180
AELFWWTGAF ETSEGIPHSS LVSAAESDRV TFGRDFPVVA NTDRRPEFGH DRSKVLVLST   240
YDNERASLLR CGEMLSAVLL DATMAGLATC TLTHITELHA SRDLVAALIG QPATPQALVR   300
VGLAPEMEEP PPATPRRPID EVFHVRAKDH R                                 331

SEQ ID NO: 152          moltype = DNA   length = 1026
FEATURE                 Location/Qualifiers
source                  1..1026
                        mol_type = genomic DNA
                        organism = Mycobacterium tuberculosis
SEQUENCE: 152
catatgcatc accatcacca tcacatgccg acaccatgg tgaccaccga tgtcatcaag    60
agcgcggtgc agttggcctg ccgcgcaccg tcgctccaca acagccagcc ctggcgctgg   120
atagccgagg accacgggt tgcgctgttc ctcgacaagg atcgggtgct ttacgcgacc    180
gaccactccg gccgggaagc gctgctgggg tgcggcgccg tactcgacca cttttcgggtg   240
gcgatgcgg ccgcgggtac caccgccaat gtggaacggt ttcccaacc caacgatcct    300
ttgcatctgg cgtcaattga cttcagcccg gccgatttcg tcaccgaggg ccaccgtcta   360
agggcggatg cgatcctact gcgcgtacc gaccggctgc cttcgccga gccgccggat     420
tgggacttgg tggagtcgca gttgcgcacg accgtcaccg ccgacacggt gcgcatcgac   480
gtcatcgccg acgatatgcg tcccgaactg gcggcggcct ccaaactcac cgaatcgctg   540
cggctctacg attcgtcgta tcatgccgaa ctcttttggt ggacagggc ttttgagact    600
tctgagggca taccgcacag ttcattggta tcgcggccg aaagtgaccg gtcaccttc     660
ggacgcgact tccggtcgt cgccaacacc gataggcgcc cggagttttg ccacgaccgc   720
tctaaggtcc tggtgctctc cacctacgac aacgaacgcc cagcctact gcgctgcggc   780
gagatgcttt ccgccgtatt gcttgacgcc accatggctg gcttgccac ctgcacgctg    840
acccacatca ccgaactgca cgccagccga gacctggtcg cagcgctgat gggcagccc    900
gcaactccgc aagccttggt tcgcgtcggt ctggccccgg agatgaaga gccgccaccg   960
gcaacgcctc ggcgaccaat cgatgaagtg tttcacgttc gggctaagga tcaccggtag   1020
gaattc                                                             1026

SEQ ID NO: 153          moltype = AA   length = 338
FEATURE                 Location/Qualifiers
source                  1..338
                        mol_type = protein
                        organism = Mycobacterium tuberculosis
SEQUENCE: 153
MHHHHHHMPD TMVTTDVIKS AVQLACRAPS LHNSQPWRWI AEDHTVALFL DKDRVLYATD    60
HSGREALLGC GAVLDHFRVA MAAAGTTANV ERFPNPNDPL HLASIDFSPA DFVTEGHRLR   120
ADAILLRRTD RLPFAEPPDW DLVESQLRTT VTADTVRIDV IADDMRPELA AASKLTESLR   180
LYDSSYHAEL FWWTGAFETS EGIPHSSLVS AAESDRVTFG RDFPVVANTD RRPEFGHDRS   240
KVLVLSTYDN ERASLLRCGE MLSAVLLDAT MAGLATCTLT HITELHASRD LVAALIGQPA   300
TPQALVRVGL APEMEEPPPA TPRRPIDEVF HVRAKDHR                          338

SEQ ID NO: 154          moltype = AA   length = 478
FEATURE                 Location/Qualifiers
source                  1..478
                        mol_type = protein
                        organism = Mycobacterium tuberculosis
SEQUENCE: 154
VTEKTPDDVF KLAKDEKVEY VDVRFCDLPG IMQHFTIPAS AFDKSVFDDG LAFDGSSIRG    60
FQSIHESDML LLPDPETARI DPFRAAKTLN INFFVHDPFT LEPYSRDPRN IARKAENYLI   120
STGIADTAYF GAEAEFYIFD SVSFDSRANG SFYEVDAISG WWNTGAATEA DGSPNRGYKV   180
```

```
RHKGGYFPVA PNDQYVDLRD KMLTNLINSG FILEKGHHEV GSGGQAEINY QFNSLLHAAD  240
DMQLYKYIIK NTAWQNGKTV TFMPKPLFGD NGSGMHCHQS LWKDGAPLMY DETGYAGLSD  300
TARHYIGGLL HHAPSLLAFT NPTVNSYKRL VPGYEAPINL VYSQRNRSAC VRIPITGSNP  360
KAKRLEFRSP DSSGNPYLAF SAMLMAGLDG IKNKIEPQAP VDKDLYELPP EEAASIPQTP  420
TQLSDVIDRL EADHEYLTEG GVFTNDLIET WISFKRENEI EPVNIRPHPY EFALYYDV    478

SEQ ID NO: 155          moltype = DNA   length = 1445
FEATURE                 Location/Qualifiers
source                  1..1445
                        mol_type = genomic DNA
                        organism = Mycobacterium tuberculosis
SEQUENCE: 155
catatgacgg aaaagacgcc cgacgacgtc ttcaaacttg ccaaggacga gaaggtcgaa   60
tatgcgacgt ccggttctgt gacctgcctg gcatcatgca gcacttcacg attccggctt  120
cggcctttga caagagcgtg tttgacgacg gcttggcctt tgacggctcg tcgattcgcg  180
ggttccagtc gatccacgaa tccgacatgt tgcttcttcc cgatcccgag acggcgcgca  240
tcgacccgtt ccgcgcggcc aagacgctga atatcaactt ctttgtgcac gacccgttca  300
ccctggagcc gtactcccgc gacccgcgca acatcgccga caaggccgga aactacctga  360
tcagcactgg catcgccgac accgcatact tcggcgccga ggccgagttc tacatttcg  420
attcggtgag cttcgactcg cgcgccaacg gctccttcta cgaggtggac gccatctcgg  480
ggtggtggaa caccggcgcg gcgaccgagg ccgacggcag tcccaaccgg ggctacaagg  540
tccgccacaa gggcgggtat ttcccagtgg ccccaacga cggcctgcg  600
acaagatgct gaccaacctg atcaactccg gcttcatcct ggagaagggc caccacgagg  660
tgggcagcgg cggacaggcc gagatcaact accagttcaa ttcgctgctg cacgccgccg  720
acgacatgca gttgtacaag tacatcatca agaaccccgc ctggcagaac ggcaaaacgg  780
tcacgttcat gcccaagccg ctgttcggcg acaacggcag cggcatgcac tgtcatcagt  840
cgctgtggaa ggacggggcc ccgctgatgt acgacgagac gggttatgcc ggtctgtcgg  900
acacggcccg tcattacatc ggcggcctgt tacaccacgc gccgtcgctg ctggccttca  960
ccaacccgac ggtgaactcc tacaagcggc tggttcccgg ttacgaggcc ccgatcaacc  1020
tggtctatag ccagcgcaac cggtcggcat gcgtgcgcat cccgatcacc ggcagcaacc  1080
cgaaggccaa gcggctggag ttccgaagcc ccgactcgtc gggcaacccc tatctggcct  1140
tctcggccat gctgatggca ggcctggacg gtatcaagaa caagatcgag ccgcaggcgc  1200
ccgtcgacaa ggatctctac gagctgccgc cggaagaggc cgcgagtatc ccgcagactc  1260
cgacccagct gtcagatgtg atcgaccgtc tcgaggccga ccacgaatac ctcaccgaag  1320
gagggggtgtt cacaaacgac ctgatcgaga cgtggatcag tttcaagcgc gaaaacgaga  1380
tcgagccggt caacatccgg ccgcatcctt acgaattcgc gctgtactac gacgtttaaa  1440
agctt                                                              1445

SEQ ID NO: 156          moltype = AA   length = 498
FEATURE                 Location/Qualifiers
source                  1..498
                        mol_type = protein
                        organism = Mycobacterium tuberculosis
SEQUENCE: 156
MGSSHHHHHH SSGLVPRGSH MTEKTPDDVF KLAKDEKVEY VDVRFCDLPG IMQHFTIPAS   60
AFDKSVFDDG LAFDGSSIRG FQSIHESDML LLPDPETARI DPFRAAKTLN INFFVHDPFT  120
LEPYSRDPRN IARKAENYLI STGIADTAYF GAEAEFYIFD SVSFDSRANG SFYEVDAISG  180
WWNTGAATEA DGSPNRGYKV RHKGGYFPVA PNDQYVDLRD KMLTNLINSG FILEKGHHEV  240
GSGGQAEINY QFNSLLHAAD DMQLYKYIIK NTAWQNGKTV TFMPKPLFGD NGSGMHCHQS  300
LWKDGAPLMY DETGYAGLSD TARHYIGGLL HHAPSLLAFT NPTVNSYKRL VPGYEAPINL  360
VYSQRNRSAC VRIPITGSNP KAKRLEFRSP DSSGNPYLAF SAMLMAGLDG IKNKIEPQAP  420
VDKDLYELPP EEAASIPQTP TQLSDVIDRL EADHEYLTEG GVFTNDLIET WISFKRENEI  480
EPVNIRPHPY EFALYYDV                                                498

SEQ ID NO: 157          moltype = AA   length = 580
FEATURE                 Location/Qualifiers
source                  1..580
                        mol_type = protein
                        organism = Mycobacterium tuberculosis
SEQUENCE: 157
MNFAVLPPEV NSARIFAGAG LGPMLAAASA WDGLAEELHA AAGSFASVTT GLAGDAWHGP   60
ASLAMTRAAS PYVGWLNTAA GQAAQAAGQA RLAASAFEAT LAATVSPAMV AANRTRLASL  120
VAANLLGQNA PAIAAAEAEY EQIWAQDVAA MFGYHSAASA VATQLAPIQE GLQQQLQNVL  180
AQLASGNLGS GNVGVGNIGN DNIGNANIGF GNRGDANIGI GNIGDRNLGI GNTGNWNIGI  240
GITGNGQIGF GKPANPDVLV VGNGGPGVTA LVMGGTDSLL PLPNIPLLEY AARFITPVHP  300
GYTATFLETP SQFFPFTGLN SLTYDVSVAQ GVTNLHTAIM AQLAAGNEVV VFGTSQSATI  360
ATFEMRYLQS LPAHLRPGLD ELSFTLTGNP NRPDGGILTR FGFSIPQLGF TLSGATPADA  420
YPTVDYAFQY DGVNDPFKYP LNVFATANAI AGILFLHSGL IALPPDLASG VVQPVSSPDV  480
LTTYILLPSQ DLPLLVPLRA IPLLGNPLAD LIQPDLRVLV ELGYDRTAHQ DVPSPFGLFP  540
DVDWAEVAAD LQQGAVQGVN DALSGLGLPP PWQPALPRLF                        580

SEQ ID NO: 158          moltype = DNA   length = 1752
FEATURE                 Location/Qualifiers
source                  1..1752
                        mol_type = genomic DNA
                        organism = Mycobacterium tuberculosis
SEQUENCE: 158
catatgaatt tcgccgtttt gccgccggag gtgaattcgg cgcgcatatt cgccggtgcg   60
ggcctggggcc caatgctggc ggcggcgtcg gcctgggacg ggttggccga ggagttgcat  120
```

```
gccgcggcgg gctcgttcgc gtcggtgacc accgggttgg cgggcgacgc gtggcatggt    180
ccggcgtcgc tggcgatgac ccgcgcggcc agcccgtatg tggggtggtt gaacacggcg    240
gcgggtcagg ccgcgcaggc ggccggccag gcgcggctag cggcgagcgc gttcgaggcg    300
acgctggcgg ccaccgtgtc tccagcgatg gtcgcggcca accggacacg gctggcgtcg    360
ctggtggcag ccaacttgct gggccagaac gccccggcga tcgcggccgc ggaggctgaa    420
tacgagcaga tatgggccca ggacgtggcc gcgatgttcg gctatcactc cgccgcgtcg    480
gcggtggcca cgcagctggc gcctattcaa gagggtttgc agcagcagct gcaaaacgtg    540
ctggcccagt tggctagcgg gaacctgggc agcggaaatg tgggcgtcgg caacatcggc    600
aacgacaaca ttggcaacgc aaacatcggc ttcggaaatc gaggcgacgc caacatcggc    660
atcgggaata tcggcgacag aaacctcggc attgggaaca ccggcaattg gaatatcggc    720
atcggcatca ccggcaacgg acaaatcggc ttcggcaagc ctgccaaccc cgacgtcttg    780
gtggtgggca acggcggccc gggagtaacc gcgttggtca tgggcggcac cgacagccta    840
ctgccgctgc ccaacatccc cttactcgag tacgctgcgc ggttcatcac ccccgtgcat    900
cccggataca ccgctacgtt cctggaaacg ccatcgcagt ttttcccatt caccgggctg    960
aatagcctga cctatgacgt ctccgtggcc cagggcgtaa cgaatctgca caccgcgatc   1020
atggcgcaac tcgcggcggg aaacgaagtc gtcgtcttcg gcacctccca aagcgccacg   1080
atagccacct tcgaaatgcg ctatctgcaa tccctgccag cacacctgcg tccgggtctc   1140
gacgaattgt cctttacgtt gaccggcaat cccaaccggc ccgacggtgg cattcttacg   1200
cgttttggct tctccatacc gcagttgggt ttcacattgt ccggcgcgac gcccgccgac   1260
gcctaccccca ccgtcgatta cgcgttccag tacgacggcg tcaacgactt ccccaaatac   1320
ccgctgaatg tcttcgcgac cgccaacgcg atcgcgggca tccttttcct gcactccggg   1380
ttgattgcgt tgccgcccga tcttgcctcg ggcgtggttc aaccggtgtc ctcaccggac   1440
gtcctgacca cctacatcct gctgccagc caagatctgc cgctgctggt cccgctgcgt   1500
gctatccccc tgctgggaaa cccgcttgcc gacctcatcc agccggactt gcgggtgctc   1560
gtcgagttgg gttatgaccg caccgccac caggacgtgc ccagcccgtt cggactgttt   1620
ccggacgtcg attgggccga ggtggccgcg gacctgcagc aaggcgccgt gcaaggcgtc   1680
aacgacgccc tgtccggact ggggctgccg ccgccgtggc agccggcgct accccgactt   1740
ttctaaaagc tt                                                       1752

SEQ ID NO: 159        moltype = AA  length = 600
FEATURE               Location/Qualifiers
source                1..600
                      mol_type = protein
                      organism = Mycobacterium tuberculosis
SEQUENCE: 159
MGSSHHHHHH SSGLVPRGSH MNFAVLPPEV NSARIFAGAG LGPMLAAASA WDGLAEELHA    60
AAGSFASVTT GLAGDAWHGP ASLAMTRAAS PYVGWLNTAA GQAAQAAGQA RLAASAFEAT   120
LAATVSPAMV AANRTRLASL VAANLLGQNA PAIAAAEAEY EQIWAQDVAA MFGYHSAASA   180
VATQLAPIQE GLQQQLQNVL AQLASGNLGS GNVGVGNIGN DNIGNANIGF GNRGDANIGI   240
GNIGDRNLGI GNTGNWNIGI GITGNGQIGF GKPANPDVLV VGNGGPGVTA LVMGGTDSLL   300
PLPNIPLLEY AARFITPVHP GYTATFLETP SQFFPFTGLN SLTYDVSVAQ GVTNLHTAIM   360
AQLAAGNEVV VFGTSQSATI ATFEMRYLQS LPAHLRPGLD ELSFTLTGNP NRPDGGILTR   420
FGFSIPQLGF TLSGATPADA YPTVDYAFQY DGVNDFPKYP LNVFATANAI AGILFLHSGL   480
IALPPDLASG VVQPVSSPDV LTTYILLPSQ DLPLLVPLRA IPLLGNPLAD LIQPDLRVLV   540
ELGYDRTAHQ DVPSPFGLFP DVDWAEVAAD LQQGAVQGVN DALSGLGLPP PWQPALPRLF   600

SEQ ID NO: 160        moltype = AA  length = 297
FEATURE               Location/Qualifiers
source                1..297
                      mol_type = protein
                      organism = Mycobacterium tuberculosis
SEQUENCE: 160
MSSGNSSLGI IVGIDDSPAA QVAVRWAARD AELRKIPLTL VHAVSPEVAT WLEVPLPPGV    60
LRWQQDHGRH LIDDALKVVE QASLRAGPPT VHSEIVPAAA VPTLVDMSKD AVLMVVGCLG   120
SGRWPGRLLG SVSSGLLRHA HCPVVIIHDE DSVMPHPQQA PVLVGVDGSS ASELATAIAF   180
DEASRRNVDL VALHAWSDVD VSEWPGIDWP ATQSMAEQVL AERLAGWQER YPNVAITRVV   240
VRDQPARQLV QRSEEAQLVV VGSRGRGGYA GMLVGSVGET VAQLARTPVI VARESLT     297

SEQ ID NO: 161        moltype = DNA  length = 903
FEATURE               Location/Qualifiers
source                1..903
                      mol_type = genomic DNA
                      organism = Mycobacterium tuberculosis
SEQUENCE: 161
catatgtcat cgggcaattc atctctggga attatcgtcg ggatcgacga ttcaccggcc    60
gcacaggttg cggtgcggtg ggcagctcgg gatgcggagt tgcgaaaaat ccctctgacg   120
ctcgtgcacg cggtgtcgcc ggaagtagcc acctggctgg aggtgccact gccgccgggc   180
gtgctgcgat ggcagcagga tcacgggcgc cacctgatcg acgacgcact caaggtggtt   240
gaacaggctt cgctgcgcgc tggtcccccc acggtccaca gtgaaatcgt tccggcggca   300
gccgttccca cattggtcga catgtccaaa gacgcagtgc tgatggtcgt gggttgtctc   360
ggaagtgggc ggtggccggg ccggctgctc ggttcggtca gttccggcct gctccgccac   420
gcgcactgtc cggtcgtgat catccacgac gaagattcgg tgatgccgca tccccagcaa   480
gcgccggtgc tagttggcgt tgacggctcg tcggcctccg agctggcgac cgcaatcgca   540
ttcgacgaag cgtcgcggcg aaacgtcgac ctggtcgcat tggcacgacg gagcgacgtc   600
gatgtgtcga gtggcccgg aatcgattgg ccggcaactc agtcgatggc cgagcaggtg   660
ctggccgagc ggttggcggg ttggcaggag cggtatccca acgtagccat aacccgcgtg   720
gtggtgcgcg atcagccggc ccgccagctc gtccaacgct ccgaggaagc ccagctggtc   780
gtggtcggca gccggggccg cggcggctac gccggaatgc tggtggggtc ggtaggcgaa   840
accgttgctc agctggcgcg gacgccggtc atcgtggcac gcgagtcgct gacttagaag   900
```

```
ctt                                                                     903

SEQ ID NO: 162          moltype = AA  length = 317
FEATURE                 Location/Qualifiers
source                  1..317
                        mol_type = protein
                        organism = Mycobacterium tuberculosis
SEQUENCE: 162
MGSSHHHHHH SSGLVPRGSH MSSGNSSLGI IVGIDDSPAA QVAVRWAARD AELRKIPLTL        60
VHAVSPEVAT WLEVPLPPGV LRWQQDHGRH LIDDALKVVE QASLRAGPPT VHSEIVPAAA       120
VPTLVDMSKD AVLMVVGCLG SGRWPGRLLG SVSSGLLRHA HCPVVIIHDE DSVMPHPQQA       180
PVLVGVDGSS ASELATAIAF DEASRRNVDL VALHAWSDVD VSEWPGIDWP ATQSMAEQVL       240
AERLAGWQER YPNVAITRVV VRDQPARQLV QRSEEAQLVV VGSRGRGGYA GMLVGSVGET       300
VAQLARTPVI VARESLT                                                     317

SEQ ID NO: 163          moltype = AA  length = 193
FEATURE                 Location/Qualifiers
source                  1..193
                        mol_type = protein
                        organism = Mycobacterium tuberculosis
SEQUENCE: 163
MKVKNTIAAT SFAAAGLAAL AVAVSPPAAA GDLVGPGCAE YAAANPTGPA SVQGMSQDPV        60
AVAASNNPEL TTLTAALSGQ LNPQVNLVDT LNSGQYTVFA PTNAAFSKLP ASTIDELKTN       120
SSLLTSILTY HVVAGQTSPA NVVGTRQTLQ GASVTVTGQG NSLKVGNADV VCGGVSTANA       180
TVVYMIDSVLM PPA                                                        193

SEQ ID NO: 164          moltype = DNA  length = 503
FEATURE                 Location/Qualifiers
source                  1..503
                        mol_type = genomic DNA
                        organism = Mycobacterium tuberculosis
SEQUENCE: 164
catatgggcg atctggtgag cccgggctgc gcgaatacg cggcagccaa tcccactggg         60
ccggcctcgg tgcagggaat gtcgcaggac ccggtcgcgg tggcggcctc gaacaatccg       120
gagttgacaa cgctgacggc tgcactgtcg ggccagctca atccgcaagt aaacctggtg       180
gacacccctca acagcggtca gtacacggtg ttcgcaccga ccaacgcggc atttagcaag      240
ctgccggcat ccacgatcga cgagctcaag accaattcgt cactgctgac cagcatcctg      300
acctaccacg tagtggccgg ccaaaccagc ccggccaacg tcgtcggcac ccgtcagacc      360
ctccagggcg ccagcgtgac ggtgaccggt cagggtaaca gcctcaaggt cggtaacgcc      420
gacgtcgtct gtggtgggt gtctaccgcc aacgcgacgg tgtacatgat tgacagcgtg      480
ctaatgcctc cggcgtaaaa gct                                              503

SEQ ID NO: 165          moltype = AA  length = 185
FEATURE                 Location/Qualifiers
source                  1..185
                        mol_type = protein
                        organism = Mycobacterium tuberculosis
SEQUENCE: 165
MGSSHHHHHH SSGLVPRGSH MMGDLVSPGC AEYAAANPTG PASVQGMSQD PVAVAASNNP        60
ELTTLTAALS GQLNPQVNLV DTLNSGQYTV FAPTNAAFSK LPASTIDELK TNSSLLTSIL       120
TYHVVAGQTS PANVVGTRQT LQGASVTVTG QGNSLKVGNA DVVCGGVSTA NATVYMIDSV       180
LMPPA                                                                  185

SEQ ID NO: 166          moltype = AA  length = 359
FEATURE                 Location/Qualifiers
source                  1..359
                        mol_type = protein
                        organism = Mycobacterium tuberculosis
SEQUENCE: 166
MRSTVAVAVA AAVIAASSGC GSDQPAHKAS QSMITPTTQI AGAGVLGNDR KPDESCARAA        60
AAADPGPPTR PAHNAAGVSP EMVQVPAEAQ RIVVLSGDQL DALCALGLQS RIVAAALPNS       120
SSSQPSYLGT TVHDLPGVGT RSAPDLRAIA AAHPDLILGS QGLTPQLYPQ LAAIAPTVFT       180
AAPGADWENN LRGVGAATAR IAAVDALITG FAEHATQVPG KHDATHFQAS IVQLTANTMR       240
VYGANNFPAS VLSAVGVDRP PSQRFTDKAY IEIGTTAADL AKSPDFSAAD ADIVYLSCAS       300
EAAAERAAVI LDSDPWRKLS ANRDNRVFVV NDQVWQTGEG MVAARGIVDD LRWVDAPIN       359

SEQ ID NO: 167          moltype = DNA  length = 1071
FEATURE                 Location/Qualifiers
source                  1..1071
                        mol_type = genomic DNA
                        organism = Mycobacterium tuberculosis
SEQUENCE: 167
atgggcagca gccatcatca tcatcatcac agcagcggcc tggtgccgcg cggcagccat        60
atgcataagg cgtcacaatc gatgatcacg cccaccaccc agatcgccgc cggcggggtg       120
ctggaaaacg acagaaagcc ggatgagtcg tgcgcgcgtg cggcggccgc ggccgatccg       180
gggccaccga cccgaccagc gcacaatgcg cgggagtcac gcccgagat ggtgcaggtg       240
ccggcggagg cgcagcgcat cgtggtgctc tccggtgacc agctcgacgc gctgtgcgcg       300
ctgggcctgc aatcgcggat cgtcgccgcc gcgttgccga cagctcctc aagtcaacct       360
tcctatctgg gcacgaccgt gcatgatctg cccggtgtcg gtactcgcag cgcccccgac       420
```

```
ctgcgcgcca ttgcggcggc tcacccggat ctgatcctgg gttcgcaggg tttgacgccg    480
cagttgtatc cgcagctggc ggcgatcgcc ccgacggtgt ttaccgcggc accgggcgcg    540
gactgggaaa taacctgcg tggtgtcggt gccgccacgg cccgtatcgc cgcggtggac     600
gcgctgatca ccgggttcgc cgaacacgcc acccaggtcg ggaccaagca tgacgcgacc    660
cacttccaag cgtcgatcgt gcagctgacc gccaacacca tgcgggtata cggcgccaac    720
aacttcccgg ccagcgtgct gagcgcggtc ggcgtcgacc gaccgccgtc tcaacggttc    780
accgacaagg cctacatcga gatcggcacc acggccgccg acctggcgaa atcaccggac    840
ttctcggcgg ccgacgccga tatcgtctac ctgtcgtgcg cgtcggaagc agccgcggaa    900
cgcgcggccg tcatcctgga tagcgaccca tggcgcaagc tgtccgccaa ccgtgacaac    960
cgggtcttcg tcgtcaacga ccaggtatgg cagaccggcg agggtatggt cgctgcccgc   1020
ggcattgtcg atgatctgcg ctgggtcgac gcgccgatca actagaagct t            1071

SEQ ID NO: 168          moltype = AA   length = 354
FEATURE                 Location/Qualifiers
source                  1..354
                        mol_type = protein
                        organism = Mycobacterium tuberculosis
SEQUENCE: 168
MGSSHHHHHH SSGLVPRGSH MHKASQSMIT PTTQIAGAGV LGNDRKPDES CARAAAAADP    60
GPPTRPAHNA AGVSPEMVQV PAEAQRIVVL SGDQLDALCA LGLQSRIVAA ALPNSSSSQP   120
SYLGTTVHDL PGVGTRSAPD LRAIAAAHPD LILGSQGLTP QLYPQLAAIA PTVFTAAPGA   180
DWENNLRGVG AATARIAAVD ALITGFAEHA TQVGTKHDAT HFQASIVQLT ANTMRVYGAN   240
NFPPASVLSAV GVDRPPSQRF TDKAYIEIGT TAADLAKSPD FSAADADIVY LSCASEAAAE   300
RAAVILDSDP WRKLSANRDN RVFVVNDQVW QTGEGMVAAR GIVDDLRWVD APIN          354

SEQ ID NO: 169          moltype = AA   length = 299
FEATURE                 Location/Qualifiers
source                  1..299
                        mol_type = protein
                        organism = Mycobacterium tuberculosis
SEQUENCE: 169
MLRGIQALSR PLTRVYRALA VIGVLAASLL ASWVGAVPQV GLAASALPTF AHVVIVVEEN    60
RSQAAIIGNK SAPFINSLAA NGAMMAQAFA ETHPSEPNYL ALFAGNTFGL TKNTCPVNGG   120
ALPNLGSELL SAGYTFMGFA EDLPAVGSTV CSAGKYARKH VPWVNFSNVP TTLSVPFSAF   180
PKPQNYPGLP TVSFVIPNAD NDMHDGSIAQ GDAWLNRHLS AYANWAKTNN SLLVVTWDED   240
DGSSRNQIPT VFYGAHVRPG TYNETISHYN VLSTLEQIYG LPKTGYATNA PPITDIWGD    299

SEQ ID NO: 170          moltype = DNA   length = 789
FEATURE                 Location/Qualifiers
source                  1..789
                        mol_type = genomic DNA
                        organism = Mycobacterium tuberculosis
SEQUENCE: 170
catatggcta gcatgagtgc cctgccgacc ttcgcgcacg tggtcatcgt ggtggaggag    60
aaccgctcgc aggccgccat catcggtaac aagtcggctc ccttcatcaa ttcgctggcc   120
gccaacggcg cgatgatggc ccaggcgttc gccgaaacac acccgagcga accgaactac   180
ctggcactgt tcgctggcaa cacattcggg ttgacgaaga cacctgccc cgtcaacggc    240
ggcgcgctgc ccaacctggg ttctgagttg ctcagcgccg gttacacatt catggggttc    300
gccgaagact gcctgcggt cggctccacg gtgtgcagtg cggcaaata cgcacgcaaa    360
cacgtgccgt gggtcaactt cagtaacgtg ccgacgcac tgtcggtgcc gttttcggca    420
tttccgaagc cgcagaatta ccccgcctg tcgacggtgt cgtttgtcat ccctaacgc    480
gacaacgaca tgcacgacgg ctcgatcgcc caaggcgacg cctggctgaa ccgccacctg    540
tcggcatatg ccaactgggc caagacaaac aacagcctgc tcgttgtgac ctgggacgaa    600
gacgacggca gcagccgcaa tcagatcccg acggtgttct acggcgcgca cgtgcggccc    660
ggaacttaca cgagaccat cagccactac aacgtgctgt ccacattgga gcagatctac    720
ggactgccca gagggttac gcgaccaat gctccgccaa taaccgatat ttggggcgac    780
tagaagctt                                                             789

SEQ ID NO: 171          moltype = AA   length = 279
FEATURE                 Location/Qualifiers
source                  1..279
                        mol_type = protein
                        organism = Mycobacterium tuberculosis
SEQUENCE: 171
MGSSHHHHHH SSGLVPRGSH MASMSALPTF AHVVIVVEEN RSQAAIIGNK SAPFINSLAA    60
NGAMMAQAFA ETHPSEPNYL ALFAGNTFGL TKNTCPVNGG ALPNLGSELL SAGYTFMGFA   120
EDLPAVGSTV CSAGKYARKH VPWVNFSNVP TTLSVPFSAF PKPQNYPGLP TVSFVIPNAD   180
NDMHDGSIAQ GDAWLNRHLS AYANWAKTNN SLLVVTWDED DGSSRNQIPT VFYGAHVRPG   240
TYNETISHYN VLSTLEQIYG LPKTGYATNA PPITDIWGD                            279

SEQ ID NO: 172          moltype = AA   length = 94
FEATURE                 Location/Qualifiers
source                  1..94
                        mol_type = protein
                        organism = Mycobacterium tuberculosis
SEQUENCE: 172
MTINYQFGDV DAHGAMIRAQ AGSLEAEHQA IISDVLTASD FWGGAGSAAC QGFITQLGRN    60
FQVIYEQANA HGQKVQAAGN NMAQTDSAVG SSWA                                 94
```

```
SEQ ID NO: 173              moltype = DNA  length = 294
FEATURE                     Location/Qualifiers
source                      1..294
                            mol_type = genomic DNA
                            organism = Mycobacterium tuberculosis
SEQUENCE: 173
catatgacca tcaactatca attcggggac gtcgacgctc acggcgccat gatccgcgct    60
caggccgggt cgctggaggc cgagcatcag gccatcattt ctgatgtgtt gaccgcgagt   120
gacttttggg gcggcgccgg ttcggcggcc tgccaggggt tcattaccca gctgggccgt   180
aacttccagg tgatctacga gcaggccaac gcccacgggc agaaggtgca ggctgccggc   240
aacaacatgg cacaaaccga cagcgccgtc ggctccagct gggcctaaaa gctt         294

SEQ ID NO: 174              moltype = AA  length = 114
FEATURE                     Location/Qualifiers
source                      1..114
                            mol_type = protein
                            organism = Mycobacterium tuberculosis
SEQUENCE: 174
MGSSHHHHHH SSGLVPRGSH MTINYQFGDV DAHGAMIRAQ AGSLEAEHQA IISDVLTASD    60
FWGGAGSAAC QGFITQLGRN FQVIYEQANA HGQKVQAAGN NMAQTDSAVG SSWA          114

SEQ ID NO: 175              moltype = AA  length = 284
FEATURE                     Location/Qualifiers
source                      1..284
                            mol_type = protein
                            organism = Mycobacterium tuberculosis
SEQUENCE: 175
VPNRRRRKLS TAMSAVAALA VASPCAYFLV YESTETTERP EHHEFKQAAV LTDLPGELMS    60
ALSQGLSQFG INIPPVPSLT GSGDASTGLT GPGLTSPGLT SPGLTSPGLT DPALTSPGLT   120
PTLPGSLAAP GTTLAPTPGV GANPALTNPA LTSPTGATPG LTSPTGLDPA LGGANEIPITT  180
TPVGLDPGAD GTYPILGDPT LGTIPSSPAT TSTGGGGLVN DVMQVANELG ASQAIDLLKG   240
VLMPSIMQAV QNGGAAAPAA SPPVPPIPAA AAVPPTDPIT VPVA                    284

SEQ ID NO: 176              moltype = DNA  length = 858
FEATURE                     Location/Qualifiers
source                      1..858
                            mol_type = genomic DNA
                            organism = Mycobacterium tuberculosis
SEQUENCE: 176
atgggcagca gccatcatca tcatcatcac agcagcggcc tggtgccgcg cggcagccat    60
atgagtcctt gtgcatattt tcttgtctac gaatcaaccg aaacgaccga gcggcccgag   120
caccatgaat tcaagcaggc ggcggtgttg accgacctgc ccggcgagct gatgtccgcg   180
ctatcgcagg ggttgtccca gttcgggatc aacatacccg tgccggccag cctgaccggg   240
agcggcgatg ccagcacggg tctaaccggt cctggcctga ctagtccggg attgaccagc   300
ccgggattga ccagcccggg cctcaccgac ctgccctta ccagtccggg cctgacgcca    360
acctgcccg atcactcgc cgcgcccggc accaccctgg cgccaacgcc cggcgtgggg    420
gccaatccgg cgctcaccaa ccccgcgctg accagccga gccgggattg                480
accagcccga cgggtttgga tcccgcgctg gcggcgcca acgaaatccc gattacgacg   540
ccggtcggat tggatcccgg ggctgacggc acctatccga tcctcggtga tccaacactg   600
gggaccatac cgagcagccc cgccaccacc tccaccggcg gcggcggtct cgtcaacgac   660
gtgatgcagg tggccaacga gttgggcgcc agtcaggcta tcgacctgct caaaggtgtg   720
ctaatgccgt cgatcatgca ggccgtccag aatggcggcg cggccgcgcc ggcagccagc   780
ccgccggtcc cgcccatccc cgcggccgcg gcggtgccac cgacggaccc aatcaccgtg   840
ccggtcgcct aaaagctt                                                 858

SEQ ID NO: 177              moltype = AA  length = 283
FEATURE                     Location/Qualifiers
source                      1..283
                            mol_type = protein
                            organism = Mycobacterium tuberculosis
SEQUENCE: 177
MGSSHHHHHH SSGLVPRGSH MSPCAYFLVY ESTETTERPE HHEFKQAAVL TDLPGELMSA    60
LSQGLSQFGI NIPPVPSLTG SGDASTGLTG PGLTSPGLTS PGLTSPGLTD PALTSPGLTP   120
TLPGSLAAPG TTLAPTPGVG ANPALTNPAL TSPTGATPGL TSPTGLDPAL GGANEIPITT   180
PVGLDPGADG TYPILGDPTL GTIPSSPATT STGGGGLVND VMQVANELGA SQAIDLLKGV   240
LMPSIMQAVQ NGGAAAPAAS PPVPPIPAAA AVPPTDPITV PVA                     283

SEQ ID NO: 178              moltype = AA  length = 460
FEATURE                     Location/Qualifiers
source                      1..460
                            mol_type = protein
                            organism = Mycobacterium tuberculosis
SEQUENCE: 178
MTQSQTVTVD QQEILNRANE VEAPMADPPT DVPITPCELT AKNAAQQLV LSADNMREYL    60
AAGAKERQRL ATSLRNAAKA YGEVDEEAAT ALDNDGEGTV QAESAGAVGG DSSAELTDTP   120
RVATAGEPNF MDLKEAARKL ETGDQGASLA HFADGWNTFN LTLQGDVKRF RGFDNWEGDA   180
ATACEASLDQ QRQWILHMAK LSAAMAKQAQ YVAQLHVWAR REHPTYEDIV GLERLYAENP   240
SARDQILPVY AEYQQRSEKV LTEYNNKAAL EPVNPPKPPP AIKIDPPPPP QEQGLIPGFL   300
MPPSDGSGVT PGTGMPAAPM VPPTGSPGGG LPADTAAQLT SAGREAAALS GDVAVKAASL   360
```

```
GGGGGGGVPS APLGSAIGGA ESVRPAGAGD IAGLGQGRAG GGAALGGGGM GMPMGAAHQG   420
QGGAKSKGSQ QEDEALYTED RAWTEAVIGN RRRQDSKESK                        460

SEQ ID NO: 179          moltype = DNA  length = 1449
FEATURE                 Location/Qualifiers
source                  1..1449
                        mol_type = genomic DNA
                        organism = Mycobacterium tuberculosis
SEQUENCE: 179
atgggcagca gccatcatca tcatcatcac agcagcggcc tggtgccgcg cggcagccat    60
atgacgcagt cgcagaccgt gacggtggat cagcaagaga ttttgaacag ggccaacgag   120
gtggaggccc cgatggcgga cccaccgact gatgtcccca tcacaccgtg cgaactcacg   180
gcggctaaaa acgccgccca acagctggta ttgtccgccg acaacatgcg ggaatacctg   240
gcggccggtg ccaaagagcg gcagcgtctg gcgacctcgc tgcgcaacgc ggccaaggcg   300
tatggcgagg ttgatgagga ggctgcgacc gcgctggaca acgacggcga aggaactgtg   360
caggcagaat cggccggggc cgtcggaggg gacagttcgg ccgaactaac cgatacgccg   420
agggtggcca cggccggtga acccaacttc atggatctca agaagcggc aaggaagctc   480
gaaacgggcg accaaggcgc atcgctcgcg cactttgcgg atgggtggaa cacttttcaac   540
ctgacgctgc aaggcgacgt caagcggttc cggggggttg acaactggga aggcgatgcg   600
gctaccgctt gcgaggcttc gctcgatcaa aacggcaatg gatactcca catggccaaa   660
ttgagcgctg cgatggccaa gcaggctcaa tatgtcgcgc agctgcacgt gtgggctagg   720
cgggaacatc cgacttatga agacatagtc gggctgcagc ggctttacgc ggaaaaccct   780
tcggcccgcg accaaattct cccggtgtac gcggagtatc agcagaggtc ggagaaggtg   840
ctgaccgaat acaacaacaa ggcagccctg aaccggtaa acccgccgaa gcctccccc   900
gccatcaaga tcgaccgcc cccgcctccg caagagcagg gattgatccc tggcttcctg   960
atgccgccgt ctgacggctc cggtgtgact cccggtatgc cagccagcc cgcaccgatg  1020
gttccgccta ccggatcgcc gggtggtggc ctcccggctg acacggcggc acagctgacg  1080
tcggctgggc gggaagccgc agcgctgtcg ggcgacgtgg cggtcaaagc ggcatcgctc  1140
ggtggcggtg gaggcggcgg ggtgccgtcg gcgccgttgg gatccgcgat cggggggcgcc  1200
gaatcggtgc ggccgcctgg cgctggtgac attgccgact taggccaggg aagggccggc  1260
ggcggcgccg cgctgggcgg cggtggcatg gaatgccga tgggtgccgc gcatcaggga  1320
caaggggggcc ccaagtccaa gggttctcag caggaagacg aggcgctcta caccgaggat  1380
cgggcatgga ccgaggccgt cattggtaac cgtcggcgcc aggacagtaa ggagtcgaag  1440
tgaaagctt                                                          1449

SEQ ID NO: 180          moltype = AA  length = 480
FEATURE                 Location/Qualifiers
source                  1..480
                        mol_type = protein
                        organism = Mycobacterium tuberculosis
SEQUENCE: 180
MGSSHHHHHH SSGLVPRGSH MTQSQTVTVD QQEILNRANE VEAPMADPPT DVPITPCELT    60
AAKNAAQQLV LSADNMREYL AAGAKERQRL ATSLRNAAKA YGEVDEEAAT ALDNDGEGTV   120
QAESAGAVGG DSSAELTDTP RVATAGEPNF MDLKEAARKL ETGDQGASLA HFADGWNTFN   180
LTLQGDVKRF RGFDNWEGDA ATACEASLDQ QRQWILHMAK LSAAMAKQAQ YVAQLHVWAR   240
REHPTYEDIV GLERLYAENP SARDQILPVY AEYQQRSEKV LTEYNNKAAL EPVNPPKPPP   300
AIKIDPPPPP QEQGLIPGFL MPPSDGSGVT PGTGMPAAPM VPPTGSPGGG LPADTAAQLT   360
SAGREAAALS GDVAVKAASL GGGGGGGVPS APLGSAIGGA ESVRPAGAGD IAGLGQGRAG   420
GGAALGGGGM GMPMGAAHQG QGGAKSKGSQ QEDEALYTED RAWTEAVIGN RRRQDSKESK   480

SEQ ID NO: 181          moltype = AA  length = 148
FEATURE                 Location/Qualifiers
source                  1..148
                        mol_type = protein
                        organism = Mycobacterium tuberculosis
SEQUENCE: 181
MSRLSSILRA GAAFLVLGIA AATFPQSAAA DSTEDFPIPR RMIATTCDAE QYLAAVRDTS    60
PVYYQRYMID FNNHANLQQA TINKAHWFFS LSPAERRDYS EHFYNGDPLT FAWVNHMKIF   120
FNNKGVVAKG TEVCNGYPAG DMSVWNWA                                     148

SEQ ID NO: 182          moltype = DNA  length = 372
FEATURE                 Location/Qualifiers
source                  1..372
                        mol_type = genomic DNA
                        organism = Mycobacterium tuberculosis
SEQUENCE: 182
catatggccg actccacgga agactttcca ataccctcgcc ggatgatcgc aaccacctgc    60
gacgccgaac aatatctggc ggcggtgcgg gataccagtc cggtgtacta ccagcggtac   120
atgatcgact tcaacaacca tgcaaacctt cagcaagcga cgatcaacaa ggcgcactgg   180
ttcttctcgc tgtcaccggc ggagcgccga gactactccg aacacttttta caatggcgat   240
ccgctgacgt ttgcctgggt caatcacatg aaaatcttct tcaacaacaa gggcgtcgtc   300
gctaaaggga ccgaggtgtg caatggatac ccagccggcg acatgtcggt gtggaactgg   360
gcctaaaagc tt                                                      372

SEQ ID NO: 183          moltype = AA  length = 140
FEATURE                 Location/Qualifiers
source                  1..140
                        mol_type = protein
                        organism = Mycobacterium tuberculosis
```

```
SEQUENCE: 183
MGSSHHHHHH SSGLVPRGSH MADSTEDFPI PRRMIATTCD AEQYLAAVRD TSPVYYQRYM    60
IDFNNHANLQ QATINKAHWF FSLSPAERRD YSEHFYNGDP LTFAWVNHMK IFFNNKGVVA   120
KGTEVCNGYP AGDMSVWNWA                                              140

SEQ ID NO: 184           moltype = AA  length = 261
FEATURE                  Location/Qualifiers
source                   1..261
                         mol_type = protein
                         organism = Mycobacterium tuberculosis
SEQUENCE: 184
MPKRSEYRQG TPNWVDLQTT DQSAAKKFYT SLFGWGYDDN PVPGGGGVYS MATLNGEAVA    60
AIAPMPPGAP EGMPPIWNTY IAVDDVDAVV DKVVPGGGQV MMPAFDIGDA GRMSFITDPT   120
GAAVGLWQAN RHIGATLVNE TGTLIWNELL TDKPDLALAF YEAVVGLTHS SMEIAAGQNY   180
RVLKAGDAEV GGCMEPPMPG VPNHWHVYFA VDDADATAAK AAAAGGQVIA EPADIPSVGR   240
FAVLSDPQGA IFSVLKPAPQ Q                                            261

SEQ ID NO: 185           moltype = DNA  length = 853
FEATURE                  Location/Qualifiers
source                   1..853
                         mol_type = genomic DNA
                         organism = Mycobacterium tuberculosis
SEQUENCE: 185
atgggcagca gccatcatca tcatcatcac agcagcggcc tggtgccgcg cggcagccat    60
atgcccaaga gaagcgaata caggcaaggc acgccgaact gggtcgacct tcagaccacc   120
gatcagtccg ccgccaaaaa gttctacaca tcgttgttcg gctggggtta cgacgacaac   180
ccggtccccg gaggcggtgg ggtctattcc atggccacgc tgaacggcga agccgtggcc   240
gccatcgcac cgatgccccc gggtgcaccg gaggggatgc cgccgatctg gaacacctat   300
atcgcggtgg acgacgtcga tgcggtggtg acaaggtgg tgcccggggg cgggcaggtg   360
atgatgccgg ccttcgacat cggcgatgcc ggccgtgatg cgttcatcac cgatccgacc   420
ggcgctgccg tgggcctatg caggccaat cggcacatcg gagcgacgtt ggtcaacgag   480
acgggcacgc tcatctggaa cgaactgctc acggacaagc cggatttggc gctagcgttc   540
tacgaggctg tggttggcct cacccactcg agcatggaga tagctgcggg ccagaactat   600
cgggtgctca aggccggcga cgcggaagtc ggcggctgta tggaaccgcc gatgcccggc   660
gtgccgaatc attggcacgt ctactttgcg gtggatgacg ccgacgccac cgcggccaaa   720
gccgccgcag cgggcggcca ggtcattgcg gaaccggctg acattccgtc ggtgggccgg   780
ttcgccgtgt tgtccgatcc gcagggcgcg atcttcagtg tgttgaagcc cgcaccgcag   840
caataggaag ctt                                                     853

SEQ ID NO: 186           moltype = AA  length = 281
FEATURE                  Location/Qualifiers
source                   1..281
                         mol_type = protein
                         organism = Mycobacterium tuberculosis
SEQUENCE: 186
MGSSHHHHHH SSGLVPRGSH MPKRSEYRQG TPNWVDLQTT DQSAAKKFYT SLFGWGYDDN    60
PVPGGGGVYS MATLNGEAVA AIAPMPPGAP EGMPPIWNTY IAVDDVDAVV DKVVPGGGQV   120
MMPAFDIGDA GRMSFITDPT GAAVGLWQAN RHIGATLVNE TGTLIWNELL TDKPDLALAF   180
YEAVVGLTHS SMEIAAGQNY RVLKAGDAEV GGCMEPPMPG VPNHWHVYFA VDDADATAAK   240
AAAAGGQVIA EPADIPSVGR FAVLSDPQGA IFSVLKPAPQ Q                      281

SEQ ID NO: 187           moltype = AA  length = 205
FEATURE                  Location/Qualifiers
source                   1..205
                         mol_type = protein
                         organism = Mycobacterium tuberculosis
SEQUENCE: 187
MTGPTTDADA AVPRRVLIAE DEALIRMDLA EMLREEGYEI VGEAGDGQEA VELAELHKPD    60
LVIMDVKMPR RDGIDAASEI ASKRIAPIVV LTAFSQRDLV ERARDAGAMA YLVKPFSISD   120
LIPAIELAVS RFREITALEG EVATLSERLE TRKLVERAKG LLQTKHGMTE PDAFKWIQRA   180
AMDRRTTMKR VAEVVLETLG TPKDT                                        205

SEQ ID NO: 188           moltype = DNA  length = 684
FEATURE                  Location/Qualifiers
source                   1..684
                         mol_type = genomic DNA
                         organism = Mycobacterium tuberculosis
SEQUENCE: 188
atgggcagca gccatcatca tcatcatcac agcagcggcc tggtgccgcg cggcagccat    60
atgaccggcc ccaccaccga cgccgatgcc gctgtcccac gtcgggtctt gatcgcggaa   120
gatgaagcgc tcatccgcat ggacctggcc gagatgttgc gagaggaggg atatgaaatt   180
gtcggcgagg ccggcgacgg ccaggaagcc gtcgagctgg ccgagctgca caagcccgac   240
ctggtgatca tggacgtgaa gatgccgcgc cgggacggga tcgacgccgc atccgaaatc   300
gccagcaaac gtattgcccc gatcgtggtg ctgaccgcgt tcagccagcg cgatctggtc   360
gaacgtgcgc gtgatgccgg ggcgatggca tacctggtaa agcctttcag catcagcgac   420
ctgattccag cgattgaatt ggcggtcagc cggttcaggg agatcaccgc gttggaaggc   480
gaggtggcga cgctatctga acggttggaa acccgcaagc tggtggaacg agcaaaaggc   540
ctgctgcaga ccaaacatgg gatgaccgag ccggacgctt caagtggat caacgtgcc   600
gccatggatc ggcgcaccac catgaagcgg gtggccgaag tcgtgctgga aaccctcgga   660
```

```
acacccaaag acacctgaaa gctt                                             684

SEQ ID NO: 189          moltype = AA  length = 225
FEATURE                 Location/Qualifiers
source                  1..225
                        mol_type = protein
                        organism = Mycobacterium tuberculosis
SEQUENCE: 189
MGSSHHHHHH SSGLVPRGSH MTGPTTDADA AVPRRVLIAE DEALIRMDLA EMLREEGYEI       60
VGEAGDGQEA VELAELHKPD LVIMDVKMPR RDGIDAASEI ASKRIAPIVV LTAFSQRDLV      120
ERARDAGAMA YLVKPFSISD LIPAIELAVS RFREITALEG EVATLSERLE TRKLVERAKG      180
LLQTKHGMTE PDAFKWIQRA AMDRRTTMKR VAEVVLETLG TPKDT                     225

SEQ ID NO: 190          moltype = AA  length = 181
FEATURE                 Location/Qualifiers
source                  1..181
                        mol_type = protein
                        organism = Mycobacterium tuberculosis
SEQUENCE: 190
MRVLLLGPPG AGKGTQAVKL AEKLGIPQIS TGELFRRNIE EGTKLGVEAK RYLDAGDLVP       60
SDLTNELVDD RLNNPDAANG FILDGYPRSV EQAKALHEML ERRGTDIDAV LEFRVSEEVL      120
LERLKGRGRA DDTDDVILNR MKVYRDETAP LLEYYRDQLK TVDAVGTMDE VFARALRALG      180
K                                                                    181

SEQ ID NO: 191          moltype = DNA  length = 613
FEATURE                 Location/Qualifiers
source                  1..613
                        mol_type = genomic DNA
                        organism = Mycobacterium tuberculosis
SEQUENCE: 191
atgggcagca gccatcatca tcatcatcac agcagcggcc tggtgccgcg cggcagccat       60
atgagagttt tgttgctggg accgcccggg gcgggcaagg gacgcaggc ggtgaagctg      120
gccgagaagc tcgggatccc gcagatctcc accggcgaac tcttccggcg caacatcgaa      180
gagggcacca agctcggcgt ggaagccaaa cgctacttgg atgccggtga cttggtgccg      240
tccgacttga ccaatgaact cgtcgacgac cggctgaaca atccggacgc ggccaacgga      300
ttcatcttgg atggctatcc acgctcggtc gagcaggcca aggcgcttca cgagatgctc      360
gaacgccggg gaaccgacat cgacgcggtg ctggagtttc gtgtgtccga ggaggtgttg      420
ttggagcgac tcaaggggcg tggccgcgcc gacgacaccg acgacgtcat cctcaacggg      480
atgaaggtct accgcgacga gaccgcgccg ctgctggagt actaccgcga ccaattgaag      540
accgtcgacg ccgtcggcac catggacgag gtgttcgccc gtgcgttgcg ggctctggga      600
aagttagaag ctt                                                       613

SEQ ID NO: 192          moltype = AA  length = 201
FEATURE                 Location/Qualifiers
source                  1..201
                        mol_type = protein
                        organism = Mycobacterium tuberculosis
SEQUENCE: 192
MGSSHHHHHH SSGLVPRGSH MRVLLLGPPG AGKGTQAVKL AEKLGIPQIS TGELFRRNIE       60
EGTKLGVEAK RYLDAGDLVP SDLTNELVDD RLNNPDAANG FILDGYPRSV EQAKALHEML      120
ERRGTDIDAV LEFRVSEEVL LERLKGRGRA DDTDDVILNR MKVYRDETAP LLEYYRDQLK      180
TVDAVGTMDE VFARALRALG K                                              201

SEQ ID NO: 193          moltype = AA  length = 75
FEATURE                 Location/Qualifiers
source                  1..75
                        mol_type = protein
                        organism = Mycobacterium tuberculosis
SEQUENCE: 193
MVDRDPNTIK QEIDQTRDQL AATIDSLAER ANPRRLADDA KTRVIAFLRK PIVTVSLVGI       60
GSVVVVVVIH KIRNR                                                      75

SEQ ID NO: 194          moltype = DNA  length = 258
FEATURE                 Location/Qualifiers
source                  1..258
                        mol_type = genomic DNA
                        organism = Mycobacterium tuberculosis
SEQUENCE: 194
catatgcatc accatcacca tcacgtggtg accgcgatc ccaataccat caagcaggag        60
atcgaccaaa cccgcgacca actggcggcg accatcgatt ccctcgccga gcgcgccaac      120
ccccgccgcc tcgccgacga cgcaaaaact cgggtgatcg ccttcctcag gaagcccatc      180
gtgaccgtgt cactggtcgg gatcgggtct gtggtcgtcg tcgtggtcat ccacaagatc      240
aggaatcgct gagaattc                                                  258

SEQ ID NO: 195          moltype = AA  length = 82
FEATURE                 Location/Qualifiers
source                  1..82
                        mol_type = protein
                        organism = Mycobacterium tuberculosis
```

```
SEQUENCE: 195
MHHHHHHVVD RDPNTIKQEI DQTRDQLAAT IDSLAERANP RRLADDAKTR VIAFLRKPIV    60
TVSLVGIGSV VVVVVIHKIR NR                                             82

SEQ ID NO: 196         moltype = AA   length = 563
FEATURE                Location/Qualifiers
source                 1..563
                       mol_type = protein
                       organism = Mycobacterium tuberculosis
SEQUENCE: 196
MAFPEYSPAA SAATFADLQI HPRVLRAIGD VGYESPTAIQ AATIPALMAG SDVVGLAQTG    60
TGKTAAFAIP MLSKIDITSK VPQALVLVPT RELALQVAEA FGRYGAYLSQ LNVLPIYGGS   120
SYAVQLAGLR RGAQVVVGTP GRMIDHLERA TLDLSRVDFL VLDEADEMLT MGFADDVERI   180
LSETPEYKQV ALFSATMPPA IRKLSAKYLH DPFEVTCKAK TAVAENISQS YIQVARKMDA   240
LTRVLEVEPF EAMIVFVRTK QATEEIAEKL RARGFSAAAI SGDVPQAQRE RTITALRDGD   300
IDILVATDVA ARGLDVERIS HVLNYDIPHD TESYVHRIGR TGRAGRSGAA LIFVSPRELH   360
LLKAIEKATR QTLTEAQLPT VEDVNTQRVA KFADSITNAL GGPGIELFRR LVEEYEREHD   420
VPMADIAAAL AVQCRGGEAF LMAPDPPLSR RNRDQRRDRP QRPKRRPDLT TYRVAVGKRH   480
KIGPGAIVGA IANEGGLHRS DFGQIRIGPD FSLVELPAKL PRATLKKLAQ TRISGVLIDL   540
RPYRPPDAAR RHNGGKPRRK HVG                                           563

SEQ ID NO: 197         moltype = DNA   length = 1758
FEATURE                Location/Qualifiers
source                 1..1758
                       mol_type = genomic DNA
                       organism = Mycobacterium tuberculosis
SEQUENCE: 197
atgggcagca gccatcatca tcatcatcac agcagcggcc tggtgccgcg cggcagccat    60
atggccttcc cggaatattc gcctgcggcg tccgctgcga cgtttgctga cctgcagatt   120
catcccgcg tcttgcgggc gatcggcgac gtcggttacg agtcaccgac ggctatccga   180
gcggctacga tcccggcgtt gatggcaggc tccgacgtgg tggggctggc gcagaccggc   240
accggcaaga cggcggcatt tgcgattccg atgctgtcca agatcgacat caccagcaag   300
gtgccccagg cgctggtgct ggtgccacc cgggagctgg ctctgcaggt ggccgaggcg   360
ttcggccgct acggtgccta tctgtcgcaa ctcaacgtgc tgccgatcta cggcggatcg   420
tcgtatgccg tgcaactggc cggattgaga cgcggcgcg aggtggtggt tggcaccccc   480
ggtcgtatga tagaccatct cgaacggggc accttggacc tgtcgcgggt ggactttcta   540
gtgctcgatg aggccgatga gatgctgacc atgggtttcg ccgacgacgt tgagcgcatt   600
ctgtccgaga ccccgaata caagcaggtc gcctgttt ccgcgaccat gccgccggcg   660
atccgcaaac tcagcgccaa gtatctgcac gatccgttcg aagtcacttg taaggcgaaa   720
accgctgtgg ccgagaatat ttcgcagagc tacattcagg tagcacgaa gatgacgcg   780
ctcaccagag tgctcgaagt cgagccgttc gaggcgatga tcgtctttgt ccgcaccaag   840
caggcgaccg aggagattgc cgaaaagctg cgtgcccgag gttttccgc ggctgccatc   900
agcggtgacg tcccgcaggc gcagcgggag cggaccatcc cggcgctgcg ggacggcgag   960
atcgatatcc tggtcgccac cgatgtggcg gcgcgcggac tcgacgtgga gcggatatca  1020
cacgtgctta actacgacat cccgcacgac accgagtcct acgtacaccg gatcgggcgc  1080
accggcaggg ccgggcgttc gggagccgcg ctgatattcg tctcgccacg ggagcttcac  1140
ctgctcaagg cgatcgaaaa ggctacgcgg caaacgctta cgcaggcgca attgcccact  1200
gtcgaggatg tcaacaccca gcgggtggcc aagttcgccg attccatcac caatgcgctg  1260
ggcggtccgg gaatcgagct gttccgccga ctggtcgagg agtatgaacg cgagcatgat  1320
gtcccgatgg ctgacatcgc cgcggcactg gccgtgcagt gccgcggcgg tgaggcattc  1380
ctgatggcac ccgaccgcc gctttgcgg cgcaaccgcg accagcgtcg ggaccgtccg  1440
caaaggccca agcgtagacc ggacttgacc acctaccgcg tcgccgtcgg caagcggcac  1500
aagatcggtc caggcgccat cgtcggcgcc atcgccaatg agggtgggct gcaccgcagc  1560
gacttcggtc agatccgtat cgggccagac ttctcgctag tagaattgcc ggcgaagctg  1620
ccccgcgcga cgctcaaaaa gcttgcacag acccgtatct cgggtgtgct gatcgacctt  1680
cggccatacc ggccgcccga cgcggcgcgc cggcataatg gcggcaaacc acggcggaaa  1740
cacgtcggat gagaattc                                                1758

SEQ ID NO: 198         moltype = AA   length = 583
FEATURE                Location/Qualifiers
source                 1..583
                       mol_type = protein
                       organism = Mycobacterium tuberculosis
SEQUENCE: 198
MGSSHHHHHH SSGLVPRGSH MAFPEYSPAA SAATFADLQI HPRVLRAIGD VGYESPTAIQ    60
AATIPALMAG SDVVGLAQTG TGKTAAFAIP MLSKIDITSK VPQALVLVPT RELALQVAEA   120
FGRYGAYLSQ LNVLPIYGGS SYAVQLAGLR RGAQVVVGTP GRMIDHLERA TLDLSRVDFL   180
VLDEADEMLT MGFADDVERI LSETPEYKQV ALFSATMPPA IRKLSAKYLH DPFEVTCKAK   240
TAVAENISQS YIQVARKMDA LTRVLEVEPF EAMIVFVRTK QATEEIAEKL RARGFSAAAI   300
SGDVPQAQRE RTITALRDGD IDILVATDVA ARGLDVERIS HVLNYDIPHD TESYVHRIGR   360
TGRAGRSGAA LIFVSPRELH LLKAIEKATR QTLTEAQLPT VEDVNTQRVA KFADSITNAL   420
GGPGIELFRR LVEEYEREHD VPMADIAAAL AVQCRGGEAF LMAPDPPLSR RNRDQRRDRP   480
QRPKRRPDLT TYRVAVGKRH KIGPGAIVGA IANEGGLHRS DFGQIRIGPD FSLVELPAKL   540
PRATLKKLAQ TRISGVLIDL RPYRPPDAAR RHNGGKPRRK HVG                     583

SEQ ID NO: 199         moltype = AA   length = 228
FEATURE                Location/Qualifiers
source                 1..228
                       mol_type = protein
```

```
                         organism = Mycobacterium tuberculosis
SEQUENCE: 199
MRIKIFMLVT AVVLLCCSGV ATAAPKTYCE ELKGTDTGQA CQIQMSDPAY NINISLPSYY    60
PDQKSLENYI AQTRDKFLSA ATSSTPREAP YELNITSATY QSAIPPRGTQ AVVLKVYQNA   120
GGTHPTTTYK AFDWDQAYRK PITYDTLWQA DTDPLPVVFP IVQGELSKQT GQQVSIAPNA   180
GLDPVNYQNF AVTNDGVIFF FNPGELLPEA AGPTQVLVPR SAIDSMLA                228

SEQ ID NO: 200           moltype = DNA   length = 687
FEATURE                  Location/Qualifiers
source                   1..687
                         mol_type = genomic DNA
                         organism = Mycobacterium tuberculosis
SEQUENCE: 200
atgggcagca gccatcatca tcatcatcac agcagcggcc tggtgccgcg cggcagccat    60
atggcgccca agacctactg cgaggagttg aaaggcaccg ataccggcca ggcgtgccag   120
attcaaatgt ccgacccggc ctacaacatc aacatcagcc tgcccagtta ctaccccgac   180
cagaagtcgc tggaaaatta catcgcccag acgcgcgaca agttcctcag cgcggccaca   240
tcgtccactc cacgcgaagc ccctacgaa ttgaatatca cctcggccac ataccagtcc   300
gcgataccgc cgcgtggtac gcaggccgtg gtgctcaagg tctaccagaa cgccggcggc   360
acgcacccaa cgaccacgta caaggccttc gattgggacc aggcctatcg caagccaatc   420
acctatgaca cgctgtggca ggctgacacc gatccgctgc cagtcgtctt ccccattgtg   480
caaggtgaac tgagcaagca gaccggacaa caggtatcga tcgccgcaaa tgccggcttg   540
gacccggtga attatcagaa cttcgcagtc acgaacgacg gggtgatttt cttcttcaac   600
ccgggggagt tgctgcccga agcagccggc ccaacccagg tattggtccc acgttccgcg   660
atcgactcga tgctggccta gaagctt                                       687

SEQ ID NO: 201           moltype = AA   length = 226
FEATURE                  Location/Qualifiers
source                   1..226
                         mol_type = protein
                         organism = Mycobacterium tuberculosis
SEQUENCE: 201
MGSSHHHHHH SSGLVPRGSH MAPKTYCEEL KGTDTGQACQ IQMSDPAYNI NISLPSYYPD    60
QKSLENYIAQ TRDKFLSAAT SSTPREAPYE LNITSATYQS AIPPRGTQAV VLKVYQNAGG   120
THPTTTYKAF DWDQAYRKPI TYDTLWQADT DPLPVVFPIV QGELSKQTGQ QVSIAPNAGL   180
DPVNYQNFAV TNDGVIFFFN PGELLPEAAG PTQVLVPRSA IDSMLA                  226

SEQ ID NO: 202           moltype = AA   length = 162
FEATURE                  Location/Qualifiers
source                   1..162
                         mol_type = protein
                         organism = Mycobacterium tuberculosis
SEQUENCE: 202
MQFDVTIEIP KGQRNKYEVD HETGRVRLDR YLYTPMAYPT DYGFIEDTLG DDGDPLDALV    60
LLPQPVFPGV LVAARPVGMF RMVDEHGGDD KVLCVPAGDP RWDHVQDIGD VPAFELDAIK   120
HFFVHYKDLE PGKFVKAADW VDRAEAEAEV QRSVERFKAG TH                      162

SEQ ID NO: 203           moltype = DNA   length = 519
FEATURE                  Location/Qualifiers
source                   1..519
                         mol_type = genomic DNA
                         organism = Mycobacterium tuberculosis
SEQUENCE: 203
catatgcatc accatcacca tcacatgcaa ttcgacgtga ccatcgaaat tccaagggc    60
cagcgcaaca aatacgaggt cgaccatgag acggggcggg ttcgtctgga ccggtacctg   120
tacaccccga tggcctaccc gaccgactac ggcttcatcg aggacaccct aggtgacgat   180
ggcgacccgc tggacgcgct ggtgctgcta ccgcagccgg tcttccccgg ggtgctggtg   240
gcggcgcggc cggtggggat gttccggatg gtcgacgagc acggcggcga cgacaaagtg   300
ctgtgcgtcc cagccggtga ccccggtgg gaccacgtcc aagacatcgg gacgttccg   360
gctttcgagc tggatgcgat caagcatttc tttgtgcact acaaggacct ggaaccaggt   420
aagttcgtca aggcggccga ctgggtcgac cgcgccgaag ccgaggcaga ggtgcagcgt   480
tcagtggagc gcttcaaggc cggtacacac tgagaattc                          519

SEQ ID NO: 204           moltype = AA   length = 169
FEATURE                  Location/Qualifiers
source                   1..169
                         mol_type = protein
                         organism = Mycobacterium tuberculosis
SEQUENCE: 204
MHHHHHHMQF DVTIEIPKGQ RNKYEVDHET GRVRLDRYLY TPMAYPTDYG FIEDTLGDDG    60
DPLDALVLLP QPVFPGVLVA ARPVGMFRMV DEHGGDDKVL CVPAGDPRWD HVQDIGDVPA   120
FELDAIKHFF VHYKDLEPGK FVKAADWVDR AEAEAEVQRS VERFKAGTH               169

SEQ ID NO: 205           moltype = AA   length = 176
FEATURE                  Location/Qualifiers
source                   1..176
                         mol_type = protein
                         organism = Mycobacterium tuberculosis
SEQUENCE: 205
```

```
MHPLPADHGR SRCNRHPISP LSLIGNASAT SGDMSSMTRI AKPLIKSAMA AGLVTASMSL    60
STAVAHAGPS PNWDAVAQCE SGGNWAANTG NGKYGGLQFK PATWAAFGGV GNPAAASREQ   120
QIAVANRVLA EQGLDAWPTC GAASGLPIAL WSKPAQGIKQ IINEIIWAGI QASIPR       176

SEQ ID NO: 206              moltype = DNA   length = 474
FEATURE                     Location/Qualifiers
source                      1..474
                            mol_type = genomic DNA
                            organism = Mycobacterium tuberculosis
SEQUENCE: 206
catatgcatc accatcacca tcacacttcc ggcgatatgt cgagcatgac aagaatcgcc    60
aagccgctca tcaagtccgc catggccgca ggactcgtca cggcatccat gtcgctctcc   120
accgccgttg cccacgccgg tcccagcccg aactgggacg ccgtcgcgca gtgcgaatcc   180
gggggcaact gggcggccaa caccggaaac ggcaaatacg gcgggctgca gttcaagccg   240
gccacctggg ccgcattcgg cggtgtcggc aacccagcag ctgcctctcg ggaacaacaa   300
atcgcagttg ccaatcgggt tctcgccgaa cagggattgg acgcgtggcc gacgtgcggc   360
gccgcctctg gccttccgat cgcactgtgg tcgaaacccg cgcagggcat caagcaaatc   420
atcaacgaga tcatttgggc aggcattcag gcaagtattc gcgcgtgaga attc         474

SEQ ID NO: 207              moltype = AA    length = 154
FEATURE                     Location/Qualifiers
source                      1..154
                            mol_type = protein
                            organism = Mycobacterium tuberculosis
SEQUENCE: 207
MHHHHHHTSG DMSSMTRIAK PLIKSAMAAG LVTASMSLST AVAHAGPSPN WDAVAQCESG    60
GNWAANTGNG KYGGLQFKPA TWAAFGGVGN PAAASREQQI AVANRVLAEQ GLDAWPTCGA   120
ASGLPIALWS KPAQGIKQII NEIIWAGIQA SIPR                                154

SEQ ID NO: 208              moltype = AA    length = 99
FEATURE                     Location/Qualifiers
source                      1..99
                            mol_type = protein
                            organism = Mycobacterium tuberculosis
SEQUENCE: 208
MEKMSHDPIA ADIGTQVSDN ALHGVTAGST ALTSVTGLVP AGADEVSAQA ATAFTSEGIQ    60
LLASNASAQD QLHRAGEAVQ DVARTYSQID DGAAGVFAE                           99

SEQ ID NO: 209              moltype = DNA   length = 366
FEATURE                     Location/Qualifiers
source                      1..366
                            mol_type = genomic DNA
                            organism = Mycobacterium tuberculosis
SEQUENCE: 209
atgggcagca gccatcatca tcatcatcac agcagcggcc tggtgccgcg cggcagccat    60
atggaaaaaa tgtcacatga tccgatcgct gccgacattg gcacgcaagt gagcgacaac   120
gctctgcacg gcgtgacggc cggctcgacg gcgctgacgt ccgtgaccgg gctggttccc   180
gcggggggccg atgaggtctc cgcccaagcg gcgacggcgt tcacatcgga gggcatccaa   240
ttgctggctt ccaatgcatc ggcccaagac cagctccacc gtgcgggcga agcggttcag   300
gacgtcgccc gcacctattc gcaaatcgac gacggcgccg ccggcgtctt cgccgaatag   360
aagctt                                                               366

SEQ ID NO: 210              moltype = AA    length = 119
FEATURE                     Location/Qualifiers
source                      1..119
                            mol_type = protein
                            organism = Mycobacterium tuberculosis
SEQUENCE: 210
MGSSHHHHHH SSGLVPRGSH MEKMSHDPIA ADIGTQVSDN ALHGVTAGST ALTSVTGLVP    60
AGADEVSAQA ATAFTSEGIQ LLASNASAQD QLHRAGEAVQ DVARTYSQID DGAAGVFAE    119

SEQ ID NO: 211              moltype = AA    length = 367
FEATURE                     Location/Qualifiers
source                      1..367
                            mol_type = protein
                            organism = Mycobacterium tuberculosis
SEQUENCE: 211
MLWHAMPPEL NTARLMAGAG PAPMLAAAAG WQTLSAALDA QAVELTARLN SLGEAWTGGG    60
SDKALAAATP MVVWLQTAST QAKTRAMQAT AQAAAYTQAM ATTPSLPEIA ANHITQAVLT   120
ATNFFGINTI PIALTEMDYF IRMWNQAALA MEVYQAETAV NTLFEKLEPM ASILDPGASQ   180
STTNPIFGMP SPGSSTPVGQ LPPAATQTLG QLGEMSGPMQ QLTQPLQQVT SLFSQVGGTG   240
GGNPADEEAA QMGLLGTSPL SNHPLAGGSG PSAGAGLRAE SLPGAGGSLT RTPLMSQLIE   300
KPVAPSVMPA AAAGSSATGG AAPVGAGAMG QGAQSGGSTR PGLVAPAPLA QEREEDDEDD   360
WDEEDDW                                                              367

SEQ ID NO: 212              moltype = DNA   length = 1173
FEATURE                     Location/Qualifiers
source                      1..1173
                            mol_type = genomic DNA
```

```
                         organism = Mycobacterium tuberculosis
SEQUENCE: 212
atgggcagca gccatcatca tcatcatcac agcagcggcc tggtgccgcg cggcagccat    60
atgctgtggc acgcaatgcc accggagcta aataccgcac ggctgatggc cggcgcgggt   120
ccggctccaa tgcttgcggc ggccgcggga tggcagacgc tttcaggctg tctggacgct   180
caggccgtcg agttgaccgc gcgcctgaac tctctgggag aagcctggac tggaggtggc   240
agcgacaagg cgcttgcggc tgcaacgccg atggtggtct ggctacaaac cgcgtcaaca   300
caggccaaga cccgtgcgat gcaggcgacg gcgcaagccg cggcatacac ccaggccatg   360
gccacgacgc cgtcgctgcc ggagatcgcc gccaaccaca tcacccaggc cgtccttacg   420
gccaccaact tcttcggtat caacacgatc ccgatcgcgt tgaccgagat tggattattc   480
atccgtatgt ggaaccaggc agccctggca atggaggtct accaggccga gaccgcggtt   540
aacacgcttt tcgagaagct cgagccgatg gcgtcgatcc ttgatcccgg cgcgagccag   600
agcacgacga acccgatctt cggaatgccc tcccctggca gctcaacacc ggttggccag   660
ttgccgccgg cggctaccca gaccctcggc caactggtga agatgagcgg cccgatgcag   720
cagctgaccc agccgctgca gcaggtgacg tcgttgttca gccaggtggg cggcaccggc   780
ggcggcaacc cagccgacga ggaagccgcg cagatgggcc tgctcggcac cagtccgctg   840
tcgaaccatc cgctggctgg tggatcaggc cccagcgcgg gcgcgggcct gctgcgcgcg   900
gagtcgctac ctggcgcagg tgggtcgttg acccgcacgc cgctgatgtc tcagctgatc   960
gaaaagccgg ttgccccctc ggtgatgccg gcggctgctg ccggatcgtc ggcgacgggt  1020
ggcgccgctc cggtgggtgc gggagcgatg gccagggtg cgcaatccgg cggctccacc  1080
aggcggggtc tggtcgcgcc ggcaccgctc gcgcaggagc gtgaagaaga cgacgaggac  1140
gactgggacg aagaggacga ctggtgaaag ctt                               1173

SEQ ID NO: 213           moltype = AA  length = 388
FEATURE                  Location/Qualifiers
source                   1..388
                         mol_type = protein
                         organism = Mycobacterium tuberculosis
SEQUENCE: 213
MGSSHHHHHH SSGLVPRGSH MLWHAMPPEL NTARLMAGAG PAPMLAAAAG WQTLSAALDA    60
QAVELTARLN SLGEAWTGGG SDKALAAATP MVVWLQTAST QAKTRAMQAT AQAAAYTQAM   120
ATTPSLPEIA ANHITQAVLT ATNFFGINTI PIALTEMDYF IRMWNQAALA MEVYQAETAV   180
NTLFEKLEPM ASILDPGASQ STTNPIFGMP SPGSSTPVGQ LPPAATQTLG QLGEMSGPMQ   240
QLTQPLQQVT SLFSQVGGTG GGNPADEEAA QMGLLGTSPL SNHPLAGGSG PSAGAGLLRA   300
ESLPGAGGSL TRTPLMSQLI EKPVAPSVMP AAAAGSSATG GAAPVGAGAM GQGAQSGGST   360
RPGLVAPAPL AQEREEDDED DWDEEDDW                                     388

SEQ ID NO: 214           moltype = AA  length = 340
FEATURE                  Location/Qualifiers
source                   1..340
                         mol_type = protein
                         organism = Mycobacterium tuberculosis
SEQUENCE: 214
MKRALITGIT GQDGSYLAEL LLAKGYEVHG LIRRASTFNT SRIDHLYVDP HQPGARLFLH    60
YGDLIDGTRL VTLLSTIEPD EVYNLAAQSH VRVSFDEPVH TGDTTGMGSM RLLEAVRLSR   120
VHCRFYQASS SEMFGASPPP QNELTPFYPR SPYGAAKVYS YWATRNYREA YGLFAVNGIL   180
FNHESPRRGE TFVTRKITRA VARIKAGIQS EVYMGNLDAV RDWGYAPEYV EGMWRMLQTD   240
EPDDFVLATG RGFTVREFAR AAFEHAGLDW QQYVKFDQRY LRPTEVDSLI GDATKAAELL   300
GWRASVHTDE LARIMVDADM AALECEGKPW IDKPMIAGRT                        340

SEQ ID NO: 215           moltype = DNA  length = 1053
FEATURE                  Location/Qualifiers
source                   1..1053
                         mol_type = genomic DNA
                         organism = Mycobacterium tuberculosis
SEQUENCE: 215
catatgcatc accatcacca tcacgtgaag cgagcgctca tcaccggaat caccggccag    60
gacggctcgt atctcgccga actgctgctg gccaaggggt atgaggttca cgggctcatc   120
cggcgcgctt cgacgttcaa cacctcgcgg atcgatcacc tctacgtcga cccgcaccaa   180
ccggggcgcg ggctgttttt gcactatggt gacctgatcg acggaaccg gttggtgacc   240
ctgctgagca ccatcgaacc cgacgaggtg tacaacctgg cggcgcagtc acacgtgcgg   300
gtgagcttcg acgaacccgt gcacaccggt gacaccaccg gcatgggatc catgcgactg   360
ctggaagccg ttcggctctc tcgggtgcac tgccgcttct atcaggcgtc ctcgtcggag   420
atgttcggcg cctcgccgcc accgcagaac gagctgaccc cgttctaccc gcggtcaccg   480
tatggcgccg ccaaggtcta ttcgtactgg gcgacccgca attatcgcga agcgtacgga   540
ttgttcgccg ttaacggcat cttgttcaat cacgaatcac cgcggcgcgg tgagacgttc   600
gtgacccgaa agatcaccag ggccgtgca cgcatcaagg ccggtatcca gtccgaggtc   660
tatatgggca atctggatgc ggtccgcgac tgggggtacg cgcccgaata cgtcgaaggc   720
atgtggcgga tgctgcagac cgacgagccc gacgacttcg ttttggcgac cgggcgcggt   780
ttcaccgtgc gtgagttcgc gcgggccgcg ttcgagcatg ccggtttgga ctggcagcag   840
tacgtgaaat cgaccaacg ctatctgcgg cccaccgagg tggattcgct gatcggcgac   900
gcgaccaagg ctgccgaatt gctgggctgg agggcttcgg tgcacactga cgagttggct   960
cggatcatgg tcgacgcgga catggcggcg ctggagtgcg aaggcaagcc gtggatcgac  1020
aagccgatga tcgccggccg gacatgagaa ttc                               1053

SEQ ID NO: 216           moltype = AA  length = 347
FEATURE                  Location/Qualifiers
source                   1..347
                         mol_type = protein
```

```
                      organism = Mycobacterium tuberculosis
SEQUENCE: 216
MHHHHHHVKR ALITGITGQD GSYLAELLLA KGYEVHGLIR RASTFNTSRI DHLYVDPHQP    60
GARLFLHYGD LIDGTRLVTL LSTIEPDEVY NLAAQSHVRV SFDEPVHTGD TTGMGSMRLL   120
EAVRLSRVHC RFYQASSSEM FGASPPPQNE LTPFYPRSPY GAAKVYSYWA TRNYREAYGL   180
FAVNGILFNH ESPRRGETFV TRKITRAVAR IKAGIQSEVY MGNLDAVRDW GYAPEYVEGM   240
WRMLQTDEPD DFVLATGRGF TVREFARAAF EHAGLDWQQY VKFDQRYLRP TEVDSLIGDA   300
TKAAELLGWR ASVHTDELAR IMVDADMAAL ECEGKPWIDK PMIAGRT                347

SEQ ID NO: 217         moltype = DNA    length = 2742
FEATURE                Location/Qualifiers
source                 1..2742
                       mol_type = genomic DNA
                       organism = Mycobacterium tuberculosis
SEQUENCE: 217
atgggcagca gccatcatca tcatcatcac agcagcggcc tggtgccgcg cggcagccat    60
atgaccatca actatcaatt cggggacgtc gacgctcacg cgccatgat  ccgcgctcag   120
gccgggtcgc tggaggccga gcatcaggcc atcatttctg atgtgttgac cgcgagtgac   180
ttttggggcg cgccggttc  ggcggcctgc cagggttca  ttacccagct gggccgtaac   240
ttccaggtga tctacgagca ggccaacgcc cacgggcaga aggtgcaggc tgccggcaac   300
aacatgcac  aaaccgacag cgccgtcggc tccagctggg ccggtaccca tctcgccaac   360
ggttcgatgt cggaagtcat gatgtcggaa attgccgatt tgcctatccc tccgattatc   420
cattacgggg cgattgccta tgccccagc  ggcgcgtcgg gcaaagcgtg gcaccagcgc   480
acaccggcgc gagcagagca agtcgcacta gaaaagtgcg gtgacaagac ttgcaaagtg   540
gttagtcgct tcaccaggtg cggcgcgtc  gcctacaacg gctcgaaata ccaaggcgga   600
accggactca cgcgccgcgc ggcagaagac gacgccgtga accgactcga aggcgggcgg   660
atcgtcaact gggcgtgcaa cgagctcatg acctcgcgtt ttatgacgga tccgcacgcg   720
atgcgggaca tggcgggccg ttttgaggtg cacgcccaga cggtggagga cgaggctcgc   780
cggatgtggg cgtccgcgca aaacatctcg gcgcgggct  ggagtggcat ggccgaggcg   840
acctcgctag acaccatgac ccagatgaat caggcgtttc gcaacatcgt gaacatgcgg   900
cacggggtgc gtgacgggct ggttcgcgac gccaacaact acgaacagca agagcaggcc   960
tcccagcaga tcctcagcag cgtcgacatc aatttcgccg ttttgccgcc ggaggtgaat  1020
tcggcgcgca tattcgccgg tgcgggcctg gcccaatgc  tggcggcggc gtcggcctgg  1080
gacgggttgg ccgaggagtt gcatgccgcg gcgggctcgt tcgcgtcggt gaccaccggg  1140
tggcgggacg acgcgtggca tggtccggcg tcgctgcgcg tgacccgcgc ggccagcccg  1200
tatgtggggt ggttgaacac ggcggcgggt caggccgcgc aggcggccgg ccaggcgcgg  1260
ctagcggcga gcgcgttcga ggcgacgctg gcggccaccg tgtctccagc gatggtcgcg  1320
gccaaccgga cacggctggc gtcgctggtg gcagccaact gctgggcca  gaacgccccg  1380
gcgatcgcgg ccgcggaggc tgaatacgag cagatatggg cccaggacgt ggccgcgatg  1440
ttcggctatc actccgccgc gtcggcggtg gccacgcagc tggcgcctat tcaagagggt  1500
ttgcagcagc agctgcaaaa cgtgctggcc cagttggcta gcgggaacct gggcagcgga  1560
aatgtgggcg tcggcaacat cggcaacgac aacattggca acgcaaacat cggcttcgga  1620
aatcgaggcg agccaaacat cggcaacggg aatatcggca acagaaacct cggcattggg  1680
aacaccggca attggaatat cggcatcggc atcaccggca acggacaaat cggcttcggc  1740
aagcctgcca accccgacgt cttggtggtg ggcaacggcg gccgggagt  aaccgcgttg  1800
gtcatgggcg gcaccgacag cctactgccg ctgcccaaca tccccttact cgagtacgct  1860
gcgcggttca tcaccccgt  gcatcccgga tacaccgcta cgttcctgga aacgccatcg  1920
cagttttttcc cattcaccgg gctgaatagc ctgacctatg acgtctccgt ggcccagggc  1980
gtaacgaatc tgcacaccgc gatcatggcg caactcgcgg cgggaaacga agtcgtcgtc  2040
ttcggcacct cccaaagcgc cacgatagcc accttcgaaa tgcgctatct gcaatccctg  2100
ccagcacacc tgcgtccggg tctcgacgaa ttgtccttta cgttgaccgg caatcccaat  2160
cggcccgacg gtggcattct tacgcgtttt ggcttctcca taccgcagtt gggtttcaca  2220
ttgtccggcg cgacgcccgc cgacgcctac cccaccgtcg attacgcgtt ccagtacgac  2280
ggcgtcaacg acttccccaa ataccccgcta aatgtcttcg cgaccgccaa cgcgatcgcg  2340
ggcatcctttt tcctgcactc cgggttgatt gcgttgccgc ccgatcttgc ctcgggcgtg  2400
gttcaaccgg tgtcctcacc ggacgtcctg accacctaca tcctgctgcc cagccaagat  2460
ctgccgctgc tggtcccgct gcgtgctatc cccctgctgg gaaacccgct tgccgacctc  2520
atccagccgc acttgcgggt gctcgtcgag ttgggttatg accgcaccgc ccaccaggac  2580
gtgcccagcc cgttcggact gttttccggac gtcgattggg ccgaggtggc cgcggacctg  2640
cagcaaggcg ccgtgcaagg cgtcaacgac gccctgtccg gactgggcgct gccgccgccg  2700
tggcagccgg cgctaccccg acttttcagt acttaaaagc tt                     2742

SEQ ID NO: 218         moltype = DNA    length = 39
FEATURE                Location/Qualifiers
misc_feature           1..39
                       note = Primer
source                 1..39
                       mol_type = other DNA
                       organism = synthetic construct
SEQUENCE: 218
caattacata tgggtaccca tctcgccaac ggttcgatg                           39

SEQ ID NO: 219         moltype = DNA    length = 33
FEATURE                Location/Qualifiers
misc_feature           1..33
                       note = Primer
source                 1..33
                       mol_type = other DNA
                       organism = synthetic construct
```

```
SEQUENCE: 219
caattagagc tcgttgcacg cccagttgac gat                                   33

SEQ ID NO: 220          moltype = DNA   length = 33
FEATURE                 Location/Qualifiers
misc_feature            1..33
                        note = Primer
source                  1..33
                        mol_type = other DNA
                        organism = synthetic construct
SEQUENCE: 220
caattagagc tcatgacctc gcgttttatg acg                                   33

SEQ ID NO: 221          moltype = DNA   length = 33
FEATURE                 Location/Qualifiers
misc_feature            1..33
                        note = Primer
source                  1..33
                        mol_type = other DNA
                        organism = synthetic construct
SEQUENCE: 221
caattagtcg acgctgctga ggatctgctg gga                                   33

SEQ ID NO: 222          moltype = DNA   length = 33
FEATURE                 Location/Qualifiers
misc_feature            1..33
                        note = Primer
source                  1..33
                        mol_type = other DNA
                        organism = synthetic construct
SEQUENCE: 222
caattagtcg acatgaattt cgccgttttg ccg                                   33

SEQ ID NO: 223          moltype = DNA   length = 42
FEATURE                 Location/Qualifiers
misc_feature            1..42
                        note = Primer
source                  1..42
                        mol_type = other DNA
                        organism = synthetic construct
SEQUENCE: 223
caattaaagc ttttaagtac tgaaaagtcg gggtagcgcc gg                         42

SEQ ID NO: 224          moltype = DNA   length = 30
FEATURE                 Location/Qualifiers
misc_feature            1..30
                        note = Primer
source                  1..30
                        mol_type = other DNA
                        organism = synthetic construct
SEQUENCE: 224
caattacata tgaccatcaa ctatcaattc                                       30

SEQ ID NO: 225          moltype = DNA   length = 33
FEATURE                 Location/Qualifiers
misc_feature            1..33
                        note = Primer
source                  1..33
                        mol_type = other DNA
                        organism = synthetic construct
SEQUENCE: 225
caattaggta ccggcccagc tggagccgac ggc                                   33

SEQ ID NO: 226          moltype = AA    length = 911
FEATURE                 Location/Qualifiers
source                  1..911
                        mol_type = protein
                        organism = Mycobacterium tuberculosis
SEQUENCE: 226
MGSSHHHHHH SSGLVPRGSH MTINYQFGDV DAHGAMIRAQ AGSLEAEHQA IISDVLTASD       60
FWGGAGSAAC QGFITQLGRN FQVIYEQANA HGQKVQAAGN NMAQTDSAVG SSWAGTHLAN      120
GSMSEVMMSE IAGLPIPPII HYGAIAYAPS GASGKAWHQR TPARAEQVAL EKCGDKTCKV      180
VSRFTRCGAV AYNGSKYQGG TGLTRRAAED DAVNRLEGGR IVNWACNELM TSRFMTDPHA      240
MRDMAGRFEV HAQTVEDEAR RMWASAQNIS GAGWSGMAEA TSLDTMTQMN QAFRNIVNML      300
HGVRDGLVRD ANNYEQQEQA SQQILSSVDI NFAVLPPEVN SARIFAGAGL GPMLAAASAW      360
DGLAEELHAA AGSFASVTTG LAGDAWHGPA SLAMTRAASP YVGWLNTAAG QAAQAAGQAR      420
LAASAFEATL AATVSPAMVA ANRTRLASLV AANLLGQNAP AIAAAEAEYE QIWAQDVAAM      480
FGYHSAASAV ATQLAPIQEG LQQQLQNVLA QLASGNLGSG NVGVGNIGND NIGNANIGFG      540
NRGDANIGIG NIGDRNLGIG NTGNWNIGIG ITGNGQIGFG KPANPDVLVV GNGGPGVTAL      600
```

```
VMGGTDSLLP LPNIPLLEYA ARFITPVHPG YTATFLETPS QFFPFTGLNS LTYDVSVAQG  660
VTNLHTAIMA QLAAGNEVVV FGTSQSATIA TFEMRYLQSL PAHLRPGLDE LSFTLTGNPN  720
RPDGGILTRF GFSIPQLGFT LSGATPADAY PTVDYAFQYD GVNDFPKYPL NVFATANAIA  780
GILFLHSGLI ALPPDLASGV VQPVSSPDVL TTYILLPSQD LPLLVPLRAI PLLGNPLADL  840
IQPDLRVLVE LGYDRTAHQD VPSPFGLFPD VDWAEVAADL QQGAVQGVND ALSGLGLPPP  900
WQPALPRLFS T                                                      911

SEQ ID NO: 227          moltype = DNA  length = 2664
FEATURE                 Location/Qualifiers
source                  1..2664
                        mol_type = genomic DNA
                        organism = Mycobacterium tuberculosis
SEQUENCE: 227
catatgatga ccatcaacta tcaattcggg gacgtcgacg ctcacggcgc catgatccgc    60
gctcaggccg ggtcgctgga ggccgagcat caggccatca tttctgatgt gttgaccgcg   120
agtgactttt ggggcggcgc cggttcggcg gcctgccagg ggtcattac ccagctgggc    180
cgtaacttcc aggtgatcta cgagcaggcc aacgcccacg ggcagaaggt gcaggctgcc   240
ggcaacaaca tggcacaaac cgacagcgcc gtcggctcca gctgggccgg taccgacgac   300
atcgattggg acgccatcgc gcaatgcgaa tccggcggca attgggcggc caacaccggt   360
aacgggttat acgtggtcct gcagatcagc caggcgacgt gggattccaa cggtggtgtc   420
gggtcgccgg cggccgcgag tccccagcaa cagatcgagg tcgcagacaa cattatgaaa   480
acccaaggcc cgggtgcgtg gccgaaatgt agttcttgta gtcagggaga cgcaccgctg   540
ggctcgctca cccacatcct gacgttcctc gcggccgaga ctggaggttg ttcggggagc   600
agggacgatg gatccgtggt ggatttcggg gcgttaccac cggagatcaa ctccgcgagg   660
atgtacgccg gcccggttc ggcctcgctg gtggccgccg cgaagatgtg ggacagcgtg    720
gcgagtgacc tgttttcggc cgcgtcggcg tttcagtcgg tggtctgggg tctgacggtg   780
gggtcgtgga taggttcgtc ggcgggtctg atggcggccg cggcctcgcc gtatgtggcg   840
tggatgagcg tcaccgcggg gcaggcccag ctgaccgccg cccagtccg ggttgctgcg    900
gcggcctacg agacagcgta taggctgacg gtgcccccgc cggtgatcgc cgagaaccgt   960
accgaactga tgacgctgac cgcgaccaac ctcttgggc aaaacacgcc ggcgatcgag   1020
gccaatcagg ccgcatacag ccagatgtgg ggccaagacg cggaggcgat gtatggctac  1080
gccgccacgg cggcgacggc gaccgaggcg ttgctgccgt tcgaggacgc ccactgatc   1140
accaaccccg gcgggctcct tgagcaggcc gtcgcggtcg aggaggccat cgacaccgcc  1200
gcggcgaacc agttgatgaa caatgtgccc caagcgctgc aacagctgc ccagccagcg   1260
caggcgtcg taccttcttc caagctgggt gggtcgtgga cggcggtctc gccgcatctg   1320
tcgccgctca gcaacgtcag ttcgatagcc aacaaccaca tgtcgatgat gggcacgggt  1380
gtgtcgatga ccaacacctt gcactcgatg ttgaagggct tagctccggc ggcggctcag  1440
gccgtggaaa ccgcggcgga aaacgggtc tgggcgatga gctcgctggg cagccagctg   1500
ggttcgtcgc tgggttcttc gggtctgggc gctggggtg ccgccaactt gtctcggggcg   1560
gcctcggtcg gttcgttgtc ggtgccgcca gcatgggccg cggccaacca ggcggtcacc  1620
ccggcggcgc gggcgctgcc gctgaccagc ctgaccagcg ccgcccaaac cgcccccgga  1680
cacatgctgg gcgggctacc gctggggcac tcggtcaacg ccggcagcgg tatcaacaat  1740
gcgctgcggg tgccggcacg ggcctacgcg ataccccgca caccggccgc cggagaattc  1800
ttctcccggc cggggctgcc ggtcgagtac ctgcaggtgc cgtcgccgtc gatgggccgc  1860
gacatcaagg ttcagttcca gagcggtggg aacaactcac ctgcggttta tctgctcgac  1920
ggcctgcgcg cccaagacga ctacaacggc tgggatatca caccccggc gttcgagtgg   1980
tactaccagt cgggactgtc gatagtcatg ccggtcggcg ggcagtccag cttctacagc  2040
gactggtaca gcccggcctg cggtaaggct ggctgccaga cttacaagtg gaaaccttc    2100
ctgaccagcg agctgccgca atggttgtcc gccaacaggg ccgtgaagcc caccggcagc  2160
gctgcaatcg gcttgtcgat ggccggctcg tcggcaatga tcttggccgc ctaccacccc  2220
cagcagttca tctacgccgg ctcgctgtcg gccctgctgg accctctca ggggatgggg    2280
cctagcctga tcggcctcgc gatgggtgac gccggcggtt acaaggccgc agacatgtgg  2340
ggtccctcga gtgacccggc atgggagcgc aacgaccta cgcagcagat ccccaagctg   2400
gtcgcaaaca cacccggct atgggtttat tgcgggaacg gcaccccgaa cgagttgggc   2460
ggtgccaaca tacccgccga gttcttggag aacttcgttc gtagcagcaa cctgaagttc  2520
caggatgcgt acaacgccgc gggcgggcac aacgccgtgt tcaacttccc gcccaacggc  2580
acgcacagct gggagtactg gggcgctcag ctcaacgcca tgaagggtga cctgcagagt  2640
tcgttaggcg ccggctgaaa gctt                                         2664

SEQ ID NO: 228          moltype = DNA  length = 30
FEATURE                 Location/Qualifiers
misc_feature            1..30
                        note = Primer
source                  1..30
                        mol_type = other DNA
                        organism = synthetic construct
SEQUENCE: 228
caattacata tgaccatcaa ctatcaattc                                    30

SEQ ID NO: 229          moltype = DNA  length = 32
FEATURE                 Location/Qualifiers
misc_feature            1..32
                        note = Primer
source                  1..32
                        mol_type = other DNA
                        organism = synthetic construct
SEQUENCE: 229
caattaggta ccggcccagc tggagccgac gg                                 32
```

```
SEQ ID NO: 230            moltype = DNA   length = 33
FEATURE                   Location/Qualifiers
misc_feature              1..33
                          note = Primer
source                    1..33
                          mol_type = other DNA
                          organism = synthetic construct
SEQUENCE: 230
tgggccggta ccgacgacat cgattgggac gcc                                    33

SEQ ID NO: 231            moltype = DNA   length = 36
FEATURE                   Location/Qualifiers
misc_feature              1..36
                          note = Primer
source                    1..36
                          mol_type = other DNA
                          organism = synthetic construct
SEQUENCE: 231
aatccaccac ggatccatcg tccctgctcc ccgaac                                 36

SEQ ID NO: 232            moltype = DNA   length = 38
FEATURE                   Location/Qualifiers
misc_feature              1..38
                          note = Primer
source                    1..38
                          mol_type = other DNA
                          organism = synthetic construct
SEQUENCE: 232
cagggacgat ggatccgtgg tggatttcgg ggcgttac                               38

SEQ ID NO: 233            moltype = DNA   length = 35
FEATURE                   Location/Qualifiers
misc_feature              1..35
                          note = Primer
source                    1..35
                          mol_type = other DNA
                          organism = synthetic construct
SEQUENCE: 233
ccgggagaag aattctccgg cggccggtgt gcggg                                  35

SEQ ID NO: 234            moltype = DNA   length = 35
FEATURE                   Location/Qualifiers
misc_feature              1..35
                          note = Primer
source                    1..35
                          mol_type = other DNA
                          organism = synthetic construct
SEQUENCE: 234
gccgccggag aattcttctc ccggccgggg ctgcc                                  35

SEQ ID NO: 235            moltype = DNA   length = 32
FEATURE                   Location/Qualifiers
misc_feature              1..32
                          note = Primer
source                    1..32
                          mol_type = other DNA
                          organism = synthetic construct
SEQUENCE: 235
gatatcaagc tttcagccgg cgcctaacga ac                                     32

SEQ ID NO: 236            moltype = AA    length = 905
FEATURE                   Location/Qualifiers
source                    1..905
                          mol_type = protein
                          organism = Mycobacterium tuberculosis
SEQUENCE: 236
MGSSHHHHHH SSGLVPRGSH HMMTINYQFG DVDAHGAMIR AQAGSLEAEH QAIISDVLTA    60
SDFWGGAGSA ACQGFITQLG RNFQVIYEQA NAHGQKVQAA GNNMAQTDSA VGSSWAGTDD   120
IDWDAIAQCE SGGNWAANTG NGLYGGLQIS QATWDSNGGV GSPAAASPQQ QIEVADNIMK   180
TQGPGAWPKC SSCSQGDAPL GSLTHILTFL AAETGGCSGS RDDGSVVDFG ALPPEINSAR   240
MYAGPGSASL VAAAKMWDSV ASDLFSAASA FQSVVWGLTV GSWIGSSAGL MAAAASPYVA   300
WMSVTAGQAQ LTAAQVRVAA AAYETAYRLT VPPPVIAENR TELMTLTATN LLGQNTPAIE   360
ANQAAYSQMW GQDAEAMYGY AATAATATEA LLPFEDAPLI TNPGGLLEQA VAVEEAIDTA   420
AANQLMNNVP QALQQLAQPA QGVVPSSKLG GLWTAVSPHL SPLSNVSSIA NNHMSMMGTG   480
VSMTNTLHSM LKGLAPAAAQ AVETAAENGV WAMSSLGSQL GSSLGSSGLG AGVAANLGRA   540
ASVGSLSVPP AWAANQAVT PAARALPLTS LTSAAQTAPG HMLGGLPLGH SVNAGSGINN    600
ALRVPARAYA IPRTPAAGEF FSRPGLPVEY LQVPSPSMGR DIKVQFQSGG NNSPAVYLLD   660
GLRAQDDYNG WDINTPAFEW YYQSGLSIVM PVGGQSSFYS DWYSPACGKA GCQTYKWETF   720
LTSELPQWLS ANRAVKPTGS AAIGLSMAGS SAMILAAYHP QQFIYAGSLS ALLDPSQGMG   780
```

```
PSLIGLAMGD AGGYKAADMW GPSSDPAWER NDPTQQIPKL VANNTRLWVY CGNGTPNELG    840
GANIPAEFLE NFVRSSNLKF QDAYNAAGGH NAVFNFPPNG THSWEYWGAQ LNAMKGDLQS    900
SLGAG                                                                905

SEQ ID NO: 237           moltype = DNA  length = 2025
FEATURE                  Location/Qualifiers
source                   1..2025
                         mol_type = genomic DNA
                         organism = Mycobacterium tuberculosis
SEQUENCE: 237
catatgatga ccatcaacta tcaattcggg gacgtcgacg ctcacggcgc catgatccgc     60
gctcaggccg ggtcgctgga ggccgagcat caggccatca tttctgatgt gttgaccgcg    120
agtgactttt ggggcggcgc cggttcggcg gcctgccagg ggttcattac ccagctgggc    180
cgtaacttcc aggtgatcta cgagcaggcc aacgcccacg ggcagaaggt gcaggctgcc    240
ggcaacaaca tggcacaaac cgacagcgcc gtcggctcca gctgggccgg taccgacgac    300
atcgattggg acgccatcgc gcaatgcgaa tccggcggca attgggcggc caacaccggt    360
aacgggttat acgtggtcct gcagatcagc caggcgacgt gggattccaa cggtggtgtc    420
gggtcgccgg cggccgcgag tccccagcaa cagatcgcat tcgcagacaa cattatgaaa    480
acccaaggcc cggtgcgtg gccgaaatgt agttcttgta gtcagggaga cgcaccgctg    540
ggctcgctca cccacatcct gacgttcctc gcggccgaga ctggaggttg ttcggggagc    600
agggacgatg gatccgtggt ggatttcggg gcgttaccac cggagatcaa ctccgcgagg    660
atgtacgccg gcccgggttc ggcctcgctg gtggccgccg gaagatgtg ggacagcgtg    720
gcgagtgacc tgttttcggc cgcgtcggcg tttcagtcgg tggtctgggg tctgacggtg    780
gggtcgtgga taggttcgtc ggcgggtctg atggcggcgg cggcctcgcc gtatgtggcg    840
tggatgagcg tcaccgcggg gcaggccag ctgaccgccg cccaggtccg ggttgctgcg    900
gcggcctacg agacagcgta taggctgacg tgcgcccgc ggtcgatcgc cgagaaccgt    960
accgaactga tgacgctgac cgcgaccaac ctcttgggc aaaacacgcc ggcgatcgag   1020
gccaatcagg ccgcatacag ccagatgtgg ggccaagacg cggaggcgat gtatggctac   1080
gccgccacgg cggcgacggc gaccgaggcg ttgctgccgt tcgaggacgc cccactgatc   1140
accaaccccg gcggggaatt cttctcccgg ccggggctgc cggtcgagta cctgcaggtg   1200
ccgtcgccgt cgatgggccg cgacatcaag gttcagttcc agagcggtgg gaacaactca   1260
cctgcggttt atctgctcga cggcctgcgc gcccaagacg actacaacgg ctgggatatc   1320
aacacccccg gcgttcgagtg gtactaccag tcgggactgt cgatagtcat gccggtcggc   1380
gggcagtcca gcttctacag cgactggtac agcccggcct gcggtaaggc tggctgccag   1440
acttacaagt gggaaacctt cctgaccagc gagctgccgc aggttgtc cgccaacagg   1500
gccgtgaagc ccaccggcag cgctgcaatc ggcttgtcga tggccggctc gtcggcaatg   1560
atcttggccg cctaccaccc ccagcagttc atctacgccg ctcgctgtc ggccctgctg   1620
gaccctctc agggatggg gcctagcctg atcggcctcg cgatgggtga cgccggcggt   1680
tacaaggccg cagacatgtg gggtccctcg agtgaccgg catgggagcg caacgaccct   1740
acgcagcaga tccccaagct ggtcgcaaac aacaccccgg ctatgggttta ttgcgggaac   1800
ggcaccccga acgagttggg cggtgccaac ataccgccg agttcttgga gaacttcgtt   1860
cgtagcagca acctgaagtt ccaggatgcg tacaacgccg cgggcgggca acgccgtg   1920
ttcaacttcc cgcccaacgg cacgcacagc tgggagtact ggggcgctca gctcaacgcc   1980
atgaagggtg acctgcagag ttcgttaggc gccggctgaa agctt                    2025

SEQ ID NO: 238           moltype = DNA  length = 30
FEATURE                  Location/Qualifiers
misc_feature             1..30
                         note = Primer
source                   1..30
                         mol_type = other DNA
                         organism = synthetic construct
SEQUENCE: 238
caattacata tgaccatcaa ctatcaattc                                      30

SEQ ID NO: 239           moltype = DNA  length = 32
FEATURE                  Location/Qualifiers
misc_feature             1..32
                         note = Primer
source                   1..32
                         mol_type = other DNA
                         organism = synthetic construct
SEQUENCE: 239
caattaggta ccggcccagc tggagccgac gg                                   32

SEQ ID NO: 240           moltype = DNA  length = 33
FEATURE                  Location/Qualifiers
misc_feature             1..33
                         note = Primer
source                   1..33
                         mol_type = other DNA
                         organism = synthetic construct
SEQUENCE: 240
tgggccggta ccgacgacat cgattgggac gcc                                  33

SEQ ID NO: 241           moltype = DNA  length = 36
FEATURE                  Location/Qualifiers
misc_feature             1..36
                         note = Primer
```

```
source                    1..36
                          mol_type = other DNA
                          organism = synthetic construct
SEQUENCE: 241
aatccaccac ggatccatcg tccctgctcc ccgaac                                36

SEQ ID NO: 242            moltype = DNA  length = 39
FEATURE                   Location/Qualifiers
misc_feature              1..39
                          note = Primer
source                    1..39
                          mol_type = other DNA
                          organism = synthetic construct
SEQUENCE: 242
cggccgggag aagaattccc cgccggggtt ggtgatcag                             39

SEQ ID NO: 243            moltype = DNA  length = 35
FEATURE                   Location/Qualifiers
misc_feature              1..35
                          note = Primer
source                    1..35
                          mol_type = other DNA
                          organism = synthetic construct
SEQUENCE: 243
gccgccggag aattcttctc ccggccgggg ctgcc                                 35

SEQ ID NO: 244            moltype = DNA  length = 32
FEATURE                   Location/Qualifiers
misc_feature              1..32
                          note = Primer
source                    1..32
                          mol_type = other DNA
                          organism = synthetic construct
SEQUENCE: 244
gatatcaagc tttcagccgg cgcctaacga ac                                   32

SEQ ID NO: 245            moltype = AA  length = 672
FEATURE                   Location/Qualifiers
source                    1..672
                          mol_type = protein
                          organism = Mycobacterium tuberculosis
SEQUENCE: 245
HMMTINYQFG DVDAHGAMIR AQAGSLEAEH QAIISDVLTA SDFWGGAGSA ACQGFITQLG      60
RNFQVIYEQA NAHGQKVQAA GNNMAQTDSA VGSSWAGTDD IDWDAIAQCE SGGNWAANTG     120
NGLYGGLQIS QATWDSNGGV GSPAAASPQQ QIEVADNIMK TQGPGAWPKC SSCSQGDAPL     180
GSLTHILTFL AAETGGCSGS RDDGSVVDFG ALPPEINSAR MYAGPGSASL VAAAKMWDSV     240
ASDLFSAASA FQSVVWGLTV GSWIGSSAGL MAAAASPYVA WMSVTAGOAQ LTAAQVRVAA     300
AAYETAYRLT VPPPVIAENR TELMTLTATN LLGQNTPAIE ANQAAYSQMW GQDAEAMYGY     360
AATAATATEA LLPFEDAPLI TNPGGEFFSR PGLPVEYLQV PSPSMGRDIK VQFQSGGNNS     420
PAVYLLDGLR AQDDYNGWDI NTPAFEWYYQ SGLSIVMPVG GQSSFYSDWY SPACGKAGCQ     480
TYKWETFLTS ELPQWLSANR AVKPTGSAAI GLSMAGSSAM ILAAYHPQQF IYAGSLSALL     540
DPSQGMGPSL IGLAMGDAGG YKAADMWGPS SDPAWERNDP TQQIPKLVAN NTRLWVYCGN     600
GTPNELGGAN IPAEFLENFV RSSNLKFQDA YNAAGGHNAV FNFPPNGTHS WEYWGAQLNA     660
MKGDLQSSLG AG                                                        672

SEQ ID NO: 246            moltype = DNA  length = 3318
FEATURE                   Location/Qualifiers
source                    1..3318
                          mol_type = genomic DNA
                          organism = Mycobacterium tuberculosis
SEQUENCE: 246
atgggcagca gccatcatca tcatcatcac agcagcggcc tggtgccgcg cggcagccat      60
atgggtaccc atctcgccaa cggttcgatg tcggaagtca tgatgtcgga aattgccggg     120
ttgcctatcc ctccgattat ccattacggg gcgattgcct atgccccgag cggccgtcg      180
ggcaaagcgt ggcaccagcg cacaccggcc cgagcgagag aagtcgcact agaaaagtcg     240
ggtgacaaga cttgcaaagt ggttagtcgc ttcaccaggt gcggcgcggt cgcctacaac     300
ggctcgaaat accaaggcgg aaccggactc acgcgccgcg cggcagaaga cgacgccgtg     360
aaccgactcg aaggcgggcg gatcgtcaac tgggcgtgca acgagctcat gacctcgcgt     420
tttatgacgg atccgcacgc gatgcgggac atggccggac gttttgaggt cgcacgcccag    480
acggtggagg acgaggctcg ccggatgtgg cgctccgcgc aaaacatctc gggcgcgggc     540
tggagtggca tggccgaggc gacctcgcta gacaccatga cccagatgaa tcaggcgttt     600
cgcaacatct gaacatgct gcacggggtg cgtgacgggc tggttcgcga cgccaacaac     660
tacgaacagc aagagcaggc ctcccagcag atcctcagca gcgtcgacat caatttcgcc     720
gttttgccgc cggaggtgaa ttcggcgcgc atattcgggc gtgcgccaatg                780
ctggcggcgg cgtcggcctg ggacggggttg gccgaggagt gcatgccgc ggcggggctcg    840
ttcgcgtcgg tgaccaccgg gttcggcggc gacgcgtggc atggtccggc gtcgctggcg     900
atgacccgcg cggccagccc gtatgtgggg tggttgaaca cggcggcggg tcaggccgcg     960
caggcggccg ccaggcgcg gctagcggcg agcgcgttcg aggcgacgct ggcggccacc     1020
gtgtctccaa cgatggtcgc ggccaaccgg acacggctgg cgtcgctggt ggcagccaac    1080
```

```
ttgctgggcc agaacgcccc ggcgatcgcg gccgcggagg ctgaatacga gcagatatgg   1140
gcccaggacg tggccgcgat gttcggctat cactccgccg cgtcggcggt ggccacgcag   1200
ctggcgccta ttcaagaggg tttgcagcag cagtcgcaaa acgtgctggc ccagttggct   1260
agcgggaacc tgggcagcgg aaatgtgggc gtcggcaaca tcggcaacga caacattggc   1320
aacgcaaaca tcggcttcgg aaatcgaggc gacgccaaca tcggcatcgg gaatatcggc   1380
gacagaaacc tcggcattgg gaacaccggc aattggaata tcggcatcgg catcaccggc   1440
aacgacaaa tcggcttcgg caagcctgcc aaccccgacg tcttggtggt gggcaacggc   1500
ggcccgggag taaccgcgtt ggtcatgggc ggcaccgaca gcctactgcc gctgcccaac   1560
atccccttac tcgagtacgc tgcgcggttc atcaccccg tgcatccgg atacaccgct   1620
acgttcctgg aaaacgccatc gcagtttttc ccattcaccg ggctgaatag cctgacctat   1680
gacgtctccg tggcccaggg cgtaacgaat ctgcacaccg cgatcatggc gcaactcgcg   1740
gcgggaaacg aagtcgtcgt cttcggcacc tcccaaagcg ccacgatagc caccttcgaa   1800
atgcgctatc tgcaatccct gccagcacac ctgcgtccgg gtctcgacga attgtccttt   1860
acgttgaccg gcaatcccaa ccgggcccga cggtggcatt c ttacgcgttt tggcttctcc   1920
ataccgcagt tgggtttcac attgtccggc gcgacgcccg ccgacgccta ccccaccgtc   1980
gattacgcgt tccagtacga cggcgtcaac gacttcccca atacccgct gaatgtcttc   2040
gcgaccgcca acgcgatcgc gggcatcctt ttcctgcact ccgggttgat tgcgttgccg   2100
cccgatcttg cctcgggcgt ggttcaaccg gtgtcctcac cggacgtcct gaccacctac   2160
atcctgctgc ccagccaaga tctgccgctg ctggtcccgc tgcgtgctat cccccctgctg   2220
ggaaaccccgc ttgccgacct catccagccg gacttgcggg tgctcgtcga gttgggttat   2280
gaccgcaccg cccaccagga cgtgcccagc ccgttcggac tgtttccgga cgtcgattgg   2340
gccgaggtgg ccgcggaacg gcagcaaggc gccgtgcaag gcgtcaacga cgcccgtgtcc   2400
ggactggggc tgccgccgcc gtggcagccg gcgctacccc gacttttcag tactttctcc   2460
cggccgggc tgcggtcga gtacctgcag gtgccgtcgc cgtcgatggg ccgcgacatc   2520
aaggttcagt tccagagcgg tgggaacaac tcacctgcgg tttatctgct cgacggcctg   2580
cgcgcccaag acgactacaa cggctgggat atcaacaccc cggcgttcga gtggtactac   2640
cagtcgggac tgtcgatagt catgccggtc ggcgggcagt ccagcttcta cagcgactgg   2700
tacagcccgg cctgcgtaa ggctggctgc cagacttaca agtgggaaac cttcctgacc   2760
agcgagctgc cgcaatggtt gtccgccaac agggccgtga agcccaccgg cagcgctgca   2820
atcgcttgt cgatgccgg ctcgtcggca atgatcttgg ccgcctacca cccccagcag   2880
ttcatctacg ccggctcgct gtcggccctg ctggacccct ctcaggggat ggggcctagc   2940
ctgatcggcc tcgcgatggg tgacgccggc ggttacaagg ccgcagacat gtggggtccc   3000
tcgagtgacc cggcatggga gcgcaacgac cctacgcagc agatcccaa gctggtcgca   3060
aacaacaccc ggctatgggt ttattgcggg aacggcaccc cgaacgagtt gggcggtgcc   3120
aacatacccg ccgagttctt ggagaacttc gttcgtagca gcaacctgaa gttccaggat   3180
gcgtacaacg ccgcgggcgg gcacaacgcc gtgttcaact tccgcccaa cggcacgcac   3240
agctgggagt actggggcgc tcagctcaac gccatgaagg gtgacctgca gagttcgtta   3300
ggcgccggct gaaagctt                                                  3318

SEQ ID NO: 247          moltype = DNA   length = 33
FEATURE                 Location/Qualifiers
misc_feature            1..33
                        note = Primer
source                  1..33
                        mol_type = other DNA
                        organism = synthetic construct
SEQUENCE: 247
caattagtcg acatgaattt cgccgttttg ccg                                 33

SEQ ID NO: 248          moltype = DNA   length = 42
FEATURE                 Location/Qualifiers
misc_feature            1..42
                        note = Primer
source                  1..42
                        mol_type = other DNA
                        organism = synthetic construct
SEQUENCE: 248
caattaaagc ttttaagtac tgaaaagtcg gggtagcgcc gg                       42

SEQ ID NO: 249          moltype = DNA   length = 47
FEATURE                 Location/Qualifiers
misc_feature            1..47
                        note = Primer
source                  1..47
                        mol_type = other DNA
                        organism = synthetic construct
SEQUENCE: 249
cggcgctacc ccgacttttc agtactttct cccggccggg gctgccg                  47

SEQ ID NO: 250          moltype = DNA   length = 32
FEATURE                 Location/Qualifiers
misc_feature            1..32
                        note = Primer
source                  1..32
                        mol_type = other DNA
                        organism = synthetic construct
SEQUENCE: 250
gatatcaagc tttcagccgg cgcctaacga ac                                  32
```

```
SEQ ID NO: 251         moltype = AA   length = 1103
FEATURE                Location/Qualifiers
source                 1..1103
                       mol_type = protein
                       organism = Mycobacterium tuberculosis
SEQUENCE: 251
MGSSHHHHHH SSGLVPRGSH MGTHLANGSM SEVMMSEIAG LPIPPIIHYG AIAYAPSGAS    60
GKAWHQRTPA RAEQVALEKC GDKTCKVVSR FTRCGAVAYN GSKYQGGTGL TRRAAEDDAV   120
NRLEGGRIVN WACNELMTSR FMTDPHAMRD MAGRFEVHAQ TVEDEARRMW ASAQNISGAG   180
WSGMAEATSL DTMTQMNQAF RNIVNMLHGV RDGLVRDANN YEQQEQASQQ ILSSVDMNFA   240
VLPPEVNSAR IFAGAGLGPM LAAASAWDGL AEELHAAAGS FASVTTGLAG DAWHGPASLA   300
MTRAASPYVG WLNTAAGQAA QAAGQARLAA SAFEATLAAT VSPAMVAANR TRLASLVAAN   360
LLGQNAPAIA AAEAEYEQIW AQDVAAMFGY HSAASAVATQ LAPIQEGLQQ QLQNVLAQLA   420
SGNLGSGNVG VGNIGNDNIG NANIGFGNRG DANIGIGNIG DRNLGIGNTG NWNIGIGITG   480
NGQIGFGKPA NPDVLVVGNG GPGVTALVMG GTDSLLPLPN IPLLEYAARF ITPVHPGYTA   540
TFLETPSQFF PFTGLNSLTY DVSVAQGVTN LHTAIMAQLA AGNEVVVFGT SQSATIATFE   600
MRYLQSLPAH LRPGLDELSF TLTGNPNRPD GGILTRFGFS IPQLGFTLSG ATPADAYPTV   660
DYAFQYDGVN DFPKYPLNVF ATANAIAGIL FLHSGLIALP PDLASGVVQP VSSPDVLTTY   720
ILLPSQDLPL LVPLRAIPLL GNPLADLIQP DLRVLVELGY DRTAHQDVPS PFGLFPDVDW   780
AEVAADLQQG AVQGVNDALS GLGLPPPWQP ALPRLFSTFS RPGLPVEYLQ VPSPSMGRDI   840
KVQFQSGGNN SPAVYLLDGL RAQDDYNGWD INTPAFEWYY QSGLSIVMPV GGQSSFYSDW   900
YSPACGKAGC QTYKWETFLT SELPQWLSAN RAVKPTGSAA IGLSMAGSSA MILAAYHPQQ   960
FIYAGSLSAL LDPSQGMGPS LIGLAMGDAG GYKAADMWGP SSDPAWERND PTQQIPKLVA  1020
NNTRLWVYCG NGTPNELGGA NIPAEFLENF VRSSNLKFQD AYNAAGGHNA VFNFPPNGTH  1080
SWEYWGAQLN AMKGDLQSSL GAG                                         1103

SEQ ID NO: 252         moltype = DNA   length = 3597
FEATURE                Location/Qualifiers
source                 1..3597
                       mol_type = genomic DNA
                       organism = Mycobacterium tuberculosis
SEQUENCE: 252
atgggcagca gccatcatca tcatcatcac agcagcggcc tggtgccgcg cggcagccat    60
atgaccatca actatcaatt cggggacgtc gacgctcacg cgccatgat ccgcgctcag    120
gccgggtcgc tggaggccga gcatcaggcc atcatttctg atgtgttgac ggcgagtgac   180
tttttggggcg cgccggttc ggcggcctgc caggggttca ttaccagct gggccgtaac    240
ttccaggtga tctacgagca ggccaacgcc acgggcagaa aggtgcaggc tgccggcaac   300
aacatgcac aaaccgacag cgccgtcggc tccagctggg ccggtaccca tctcgccaac   360
ggttcgatgt cggaagtcat gatgtcggaa attgccgggt tgcctatccc tccgattatc   420
cattacgggg cgattgccta tgcccccagc ggccgtcgg gcaaagcgtg gcaccagcgc    480
acaccggcgc gagcagagca agtcgcacta gaaaagtgcg gtgacaagac ttgcaaagtg   540
gttagtcgct tcaccaggtg cggcgcggtc gcctacaacg gctcgaaata ccaaggcgga   600
accggactca cgcgccgcgc ggcagaagac gacgccgtga acgactcga aggcgggcgg   660
atcgtcaact gggcgtgcaa cgagctcatg acctcgcgtt ttatgacgga tccgcacgcg   720
atgcgggaca tggcggggcg ttttgaggtg cacgcccaga cggtcgagga cgaggctcgc   780
cggatgtggg cgtccgcgca aaacatctcg ggcgcgggct ggagtggcat ggccgaggcg   840
acctcgctag acaccatgac ccagatgaat caggcgtttc gcaacatcgt gaacatgctg   900
cacggggtgc gtgacgggct ggttcgcgac gccaacaact acgaacagca agagcaggcc   960
tcccagcaga tcctcagcag cgtcgacatc aatttcgccg ttttgccgcc ggaggtgaat  1020
tcggcgcgca tattcgccgg tgcgggcctg ggcccaatgc tggcggcggc gtcggcctgg  1080
gacggttgg ccgaggagtt gcatgccgcg gcgggctcgt tcgcgtcggt gaccaccgag  1140
ttggcgggcg acgcgtggca tggtccggcg tcgctggcga tgacccgcgc ggccagcccg   1200
tatgtgggt ggttgaacac ggcggcgggt caggccgcgc aggcggccgg ccaggcgcgg  1260
ctagcggcga gcgcgttcga ggcgacgctg gcggccaccg tgtctccagc gatggtcgcg  1320
gccaaccgga cacggctggc gtcgctggtg gcagccaata tgctgggcca gaacgcccca  1380
gcgatcgcgg ccgcggaggc tgaatacgag cagatatggg cccaggacgt ggccgcgatg  1440
ttcggctatc actccgccgc gtcggcggtg gccacgcagc tggcgcctat tcaagagggt  1500
ttgcagcagc agctgcaaaa cgtgctggcc cagttggcta gcgggaacct gggcagcgga  1560
aatgtgggcg tcggcaacat cggcaacgac aacattggca acgcaaacat cggcttcgga  1620
aatcgaggcg acgccaacat cggcatcggc aatatcggcg acagaaacct cggcattggc  1680
aacaccggca attggaatat cggcatcggc atcaccggca acggacaaat cggcttcggc  1740
aagcctgcca accccgacgt cttggtggtg ggcaacggcg gccgggagt aaccgcgttg  1800
gtcatgggcg gcaccgacag cctactgccg ctgcccaaca tccccttact cgagtacgct  1860
gcgcggttca tcaccccggt gcatcccgga tacaccgtca cgttcctgga aacgccatcg  1920
cagttttttcc cattcaccgg gctgaatagc ctgacctatg acgtctccgt ggcccagggc  1980
gtaacgaatc tgcacaccgc gatcatggcg caactcgcgg cggaaacga agtcgtcgtc  2040
ttcggcacct cccaaagcgc cacgatagcc accttcgaaa tgcgctatct gcaatccctg  2100
ccagcacacc tgcgtccggg tctcgacgaa ttgtccttta cgttgaccgg caatcccgac  2160
cggcccgacg gtggcattct tacgcgtttt ggcttctcca tacccgcagt gggttttcaca  2220
ttgtccggcg cgacgcccgc cgacgcctac cccaccgtcg attacgcgtt ccagtacgac  2280
ggcgtcaacg acttccccaa ataccccgctg aatgtcttcg cgaccgccaa cgcgatcgcg  2340
ggcatccttt tcctgcactc cgggttgatt gcgttgccgc cgatcttgc ctcgggcgtg  2400
gttcaaccgg tgtcctcacc ggacgtcctg accacctaca tcctgctgcc cagccaagat  2460
ctgccgctgc tggttccgct gcgtgctatc ccctgcttgg gaaacctgct tgccgactcg  2520
atccagccgc acttgcgggt gctcgtcgag ttgggttatg accgcaccgc ccaccaggac  2580
gtgcccagcc cgttcggact gtttccggac gtcgattggg ccgaggtggc cggggacctg  2640
cagcaaggcc ccgtgcaagg cgtcaacgac gccctgtccg gactgggggct gccgccgccg  2700
tggcagccgg cgctaccccg acttttcagt actttctccc ggccggggct gccggtcgag  2760
tacctgcagg tgccgtcgcc gtcgatgggc cgcgacatca aggttcagtt ccagagcggt  2820
```

```
gggaacaact cacctgcggt ttatctgctc gacggcctgc gcgcccaaga cgactacaac   2880
ggctgggata tcaacacccc ggcgttcgag tggtactacc agtcgggact gtcgatagtc   2940
atgccggtcg gcgggcagtc cagcttctac agcgactggt acagcccggc ctgcggtaag   3000
gctggctgcc agacttacaa gtgggaaacc ttcctgacca gcgagctgcc gcaatggttg   3060
tccgccaaca gggccgtgaa gcccaccggc agcgctgaca tcggcttgtc gatggccggc   3120
tcgtcggcaa tgatcttggc cgcctaccac ccccagcagt tcatctacgc cggctcgctg   3180
tcggccctgc tggaccccta tcaggggatg gggcctagcc tgatcggcct cgcgatgggt   3240
gacgccggcg gttacaaggc cgcagacatg tgggtccct cgagtgaccc ggcatggag   3300
cgcaacgcc ctacgcagca gatccccaag ctggtcgcaa acaacacccg gctatggtt   3360
tattgcggga acggcacccc gaacgagttg ggcggtgcca acatacccgc cgagttcttg   3420
gagaacttcg ttcgtagcag caacctgaag ttccaggatg cgtacaacgc cgcgggcggg   3480
cacaacgccg tgttcaactt cccgcccaac ggcacgcaca ctgggagta ctggggcgct   3540
cagctcaacg ccatgaaggg tgacctgcag agttcgttag cgccggctg aaagctt      3597

SEQ ID NO: 253          moltype = DNA  length = 33
FEATURE                 Location/Qualifiers
misc_feature            1..33
                        note = Primer
source                  1..33
                        mol_type = other DNA
                        organism = synthetic construct
SEQUENCE: 253
caattagtcg acatgaattt cgccgttttg ccg                                   33

SEQ ID NO: 254          moltype = DNA  length = 42
FEATURE                 Location/Qualifiers
misc_feature            1..42
                        note = Primer
source                  1..42
                        mol_type = other DNA
                        organism = synthetic construct
SEQUENCE: 254
caattaaagc ttttaagtac tgaaaagtcg gggtagcgcc gg                         42

SEQ ID NO: 255          moltype = DNA  length = 47
FEATURE                 Location/Qualifiers
misc_feature            1..47
                        note = Primer
source                  1..47
                        mol_type = other DNA
                        organism = synthetic construct
SEQUENCE: 255
cggcgctacc ccgactttc agtactttct cccggccggg gctgccg                     47

SEQ ID NO: 256          moltype = DNA  length = 32
FEATURE                 Location/Qualifiers
misc_feature            1..32
                        note = Primer
source                  1..32
                        mol_type = other DNA
                        organism = synthetic construct
SEQUENCE: 256
gatatcaagc tttcagccgg cgcctaacga ac                                    32

SEQ ID NO: 257          moltype = AA   length = 1196
FEATURE                 Location/Qualifiers
source                  1..1196
                        mol_type = protein
                        organism = Mycobacterium tuberculosis
SEQUENCE: 257
MGSSHHHHHH SSGLVPRGSH MTINYQFGDV DAHGAMIRAQ AGSLEAEHQA IISDVLTASD      60
FWGGAGSAAC QGFITQLGRN FQVIYEQANA HGQKVQAAGN NMAQTDSAVG SSWAGTHLAN     120
GSMSEVMMSE IAGLPIPPII HYGAIAYAPS GASGKAWHQR TPARAEQVAL EKCGDKTCKV     180
VSRFTRCGAV AYNGSKYQGG TGLTRRAAED DAVNRLEGGR IVNWACNELM TSRFMTDPHA     240
MRDMAGRFEV HAQTVEDEAR RMWASAQNIS GAGWSGMAEA TSLDTMTQMN QAFRNIVNML     300
HGVRDGLVRD ANNYEQQEQA SQQILSSVDI NFAVLPPEVN SARIFAGAGL GPMLAAASAW     360
DGLAEELHAA AGSFASVTTG LAGDAWHGPA SLAMTRAASP YVGWLNTAAG QAAQAAGQAR     420
LAASAFEATL AATVSPAMVA ANRTRLASLV AANLLGQNAP AIAAAEAEYE QIWAQDVAAM     480
FGYHSAASAV ATQLAPIQEG LQQQLQNVLA QLASGNLGSG NVGVGNIGND NIGNANIGFG     540
NRGDANIGIG NIGDRNLGIG NTGNWNIGIG ITGNGQIGFG KPANPDVLVV GNGGPGVTAL     600
VMGGTDSLLP LPNIPLLEYA ARFITPVHPG YTATFLETPS QFFPFTGLNS LTYDVSVAQG     660
VTNLHTAIMA QLAAGNEVVV FGTSQSATIA TFEMRYLQSL PAHLRPGLDE LSFTLTGNPN     720
RPDGGILTRF GFSIPQLGFT LSGATPADAY PTVDYAFQYD GVNDFPKYPL NVFATANAIA     780
GILFLHSGLI ALPPDLASGV VQPVSSPDVL TTYILLPSQD LPLLVPLRAI PLLGNPLADL     840
IQPDLRVLVE LGYDRTAHQD VPSPFGLFPD VDWAEVAADL QQGAVQGVND ALSGLGLPPP     900
WQPALPRLFS TFSRPGLPVE YLQVPSPSMG RDIKVQFQSG GNNSPAVYLL DGLRAQDDYN     960
GWDINTPAFE WYYQSGLSIV MPVGGQSSFY SDWYSPACGK AGCQTYKWET FLTSELPQWL    1020
SANRAVKPTG SAAIGLSMAG SSAMILAAYH PQQFIYAGSL SALLDPSQGM GPSLIGLAMG    1080
DAGGYKAADM WGPSSDPAWE RNDPTQQIPK LVANNTRLWV YCGNGTPNEL GGANIPAEFL    1140
```

```
ENFVRSSNLK FQDAYNAAGG HNAVFNFPPN GTHSWEYWGA QLNAMKGDLQ SSLGAG        1196

SEQ ID NO: 258          moltype = DNA  length = 2379
FEATURE                 Location/Qualifiers
source                  1..2379
                        mol_type = genomic DNA
                        organism = Mycobacterium tuberculosis
SEQUENCE: 258
catatgcatc accatcacca tcacatgccg gacaccatgg tgaccaccga tgtcatcaag    60
agcgcggtgc agttggcctg ccgcgcaccg tcgctccaca acagccagcc ctggcgctgg   120
atagccgagg accacacggt tgcgctgttc ctcgacaagg atcgggtgct ttacgcgacc   180
gaccactccg gccgggaagc gctgctgggg tgcggcgccg tactcgacca ctttcgggtg   240
gcgatggcgg ccgcgggtac caccgccaat gtggaacggt ttcccaaccc caacgatcct   300
ttgcatctgg cgtcaattga cttcagcccg gccgatttcg tcaccgaggg ccaccgtcta   360
agggcggatg cgatcctact gcgccgtacc gaccggctgc ctttcgccga gccgccggat   420
tgggacttgg tggagtcgca gttgcgcacg accgtcaccg ccgacacggt gcgcatcgac   480
gtcatcgccg acgatatgcg tcccgaactg gcggcggcgt ccaaactcac cgaatcgctg   540
cggctctacg attcgtcgta tcatgccgaa ctcttttgct ggacaggggc ttttgagact   600
tctgagggca taccgcacag ttcattggta tcggcggccg aaagtgaccg ggtcaccttc   660
ggacgcgact tccggtcgt cgccaacacc gataggcgcc cggagtttgg ccacgaccgc    720
tctaaggtcc tggtgctctc cacctacgac aacgaacgcg ccagcctact cgctgcggc    780
gagatgcttt ccgccgtatt gcttgacgcc accatggctg ggcttgccac cgtcacgctg   840
acccacatca ccgaactgca cgccagccga gacctggtcg cagcgctgat tgggcagccc   900
gcaactccgc aagccttggt tcgcgtcggt ctggccccgg agatggaaga gccgccaccg   960
gcaacgcctc ggcgaccaat cgatgaagtg tttcacgttc gggctaagga tcaccggggt  1020
ggttctggcg gtagcggatt catgggcgat ctggtgggac ccggcgtgcc cggaatacgcg 1080
gcagccaatc ccactgggcc ggcctcggtg cagggaatgt cgcaggaccc ggtcgcggtg  1140
gcggcctcga acaatccgga gttgacaacg ctgacggctg cactgtcggg ccagctcaat  1200
ccgcaagtaa acctggtgga caccctcaac agcggtcagt acacggtgtt cgcaccgacc  1260
aacgcggcat ttagcaagct gccgcgcatcc acgatcgacg agctcaagac caattcgtca  1320
ctgctgacca gcatcctgac ctaccacgta gtgccggacc aaaaccagcc ggccaacgtc  1380
gtcggcaccc gtcagaccct ccagggcgcc agcgtgacgg tgaccggtca gggtaacagc  1440
ctcaaggtcg gtaacgccga cgtcgtctgt ggtggggtgt ctaccgccaa cgcgacggtg  1500
tacatgattg acagcgtgtc aatgcctccg gcgggcggaa gcggcggttc tgaattcatg  1560
ctccccgaga caaatcagga tgaggtccag cccaacgcac ccgttgccct ggtgacggtg  1620
gaaatccgtc acccgacaac ggattcgctc accgaatcag cgaaccggga gctcaaacac  1680
ctgcttatca atgatctacc gatcgaacgc caggcgcagg acgtcagctg ggggatgacg  1740
gcgcccggtc gagcccccac cccggtcgcg gatcgtttcg ttcgttatgt caatcgcgat  1800
aacaccgccg ccgcttcact gaagaaccag gcgatagtcg tggagaccac cgcctaccgc  1860
agctttgagg cctttaccga cgttgtgatg cgggtcgtgg atgctcgcgc gcaggtctcg  1920
tcaatcgttg ggttggagcg tatcggtctt cgctttgttc tggagatccg cgtccccgcg  1980
ggtgtcgacg gccggatcac gtggagcaac tggatcgacg agcagctgct cgggccgcag  2040
cgtttcactc ccggcggcct ggtcctgacc gagtggcagg gtgccgcagt ctaccgtgga  2100
ctacaaccag gcaaatcgct catcgtgcgc tacggcccgg gtatgggcca agcgcttgat  2160
cccaattacc atctgcgccg aataacaccc gccaaaccg gaccattctt cctgctggac   2220
atcgatagct tttggactcc cagtggcggc tccattcccg agtacaacag ggacgcctta  2280
gtgtcgacat tccaggacct gtacggtccg gcccaggtcg tgtttcagga gatgatcacc  2340
agtcgcctga aagatgagct gcttcgccag taaaagctt                         2379

SEQ ID NO: 259          moltype = DNA  length = 50
FEATURE                 Location/Qualifiers
misc_feature            1..50
                        note = Primer
source                  1..50
                        mol_type = other DNA
                        organism = synthetic construct
SEQUENCE: 259
gatacacata tgcaccatca ccatcaccac atgccggaca ccatggtgac                50

SEQ ID NO: 260          moltype = DNA  length = 48
FEATURE                 Location/Qualifiers
misc_feature            1..48
                        note = Primer
source                  1..48
                        mol_type = other DNA
                        organism = synthetic construct
SEQUENCE: 260
catggatccg ctaccgccag aaccaccccg gtgatcctta gcccgaac                  48

SEQ ID NO: 261          moltype = DNA  length = 45
FEATURE                 Location/Qualifiers
misc_feature            1..45
                        note = Primer
source                  1..45
                        mol_type = other DNA
                        organism = synthetic construct
SEQUENCE: 261
ggtggttctg gcggtagcgg attcatgggc gatctggtga gcccg                     45
```

```
SEQ ID NO: 262           moltype = DNA  length = 47
FEATURE                  Location/Qualifiers
misc_feature             1..47
                         note = Primer
source                   1..47
                         mol_type = other DNA
                         organism = synthetic construct
SEQUENCE: 262
catgaattca gaaccgccgc ttccgcccgc cggaggcatt agcacgc              47

SEQ ID NO: 263           moltype = DNA  length = 45
FEATURE                  Location/Qualifiers
misc_feature             1..45
                         note = Primer
source                   1..45
                         mol_type = other DNA
                         organism = synthetic construct
SEQUENCE: 263
ggcggaagcg gcggttctga attcatgctc cccgagacaa atcag                45

SEQ ID NO: 264           moltype = DNA  length = 35
FEATURE                  Location/Qualifiers
misc_feature             1..35
                         note = Primer
source                   1..35
                         mol_type = other DNA
                         organism = synthetic construct
SEQUENCE: 264
tagaattcaa gcttttactg gcgaagcagc tcatc                           35

SEQ ID NO: 265           moltype = AA  length = 790
FEATURE                  Location/Qualifiers
source                   1..790
                         mol_type = protein
                         organism = Mycobacterium tuberculosis
SEQUENCE: 265
HMHHHHHHMP DTMVTTDVIK SAVQLACRAP SLHNSQPWRW IAEDHTVALF LDKDRVLYAT   60
DHSGREALLG CGAVLDHFRV AMAAAGTTAN VERFPNPNDP LHLASIDFSP ADFVTEGHRL  120
RADAILLRRT DRLPFAEPPD WDLVESQLRT TVTADTVRID VIADDMRPEL AAASKLTESL  180
RLYDSSYHAE LFWWTGAFET SEGIPHSSLV SAAESDRVTF GRDFPVVANT DRRPEFGHDR  240
SKVLVLSTYD NERASLLRCG EMLSAVLLDA TMAGLATCTL THITELHASR DLVAALIGQP  300
ATPQALVRVG LAPEMEEPPP ATPRRPIDEV FHVRAKDHRG GSGGSGFMGD LVGPGCAEYA  360
AANPTGPASV QGMSQDPVAV AASNNPELTT LTAALSGQLN PQVNLVDTLN SGQYTVFAPT  420
NAAFSKLPAS TIDELKTNSS LLTSILTYHV VAGQTSPANV VGTRQTLQGA SVTVTGQGNS  480
LKVGNADVVC GGVSTANATV YMIDSVLMPP AGGSGGSEFM LPETNQDEVQ PNAPVALVTV  540
EIRHPTTDSL TESANRELKH LLINDLPIER QAQDVSWGMT APGGAPTVA DRFVRYVNRD  600
NTTAASLKNQ AIVVETTAYR SFEAFTDVVM RVVDARAQVS SIVGLERIGL RFVLEIRVPA  660
GVDGRITWSN WIDEQLLGPQ RFTPGGLVLT EWQGAAVYRE LQPGKSLIVR YGPGMGQALD  720
PNYHLRRITP AQTGPFFLLD IDSFWTPSGG SIPEYNRDAL VSTFQDLYGP AQVVFQEMIT  780
SRLKDELLRQ                                                        790

SEQ ID NO: 266           moltype = DNA  length = 2622
FEATURE                  Location/Qualifiers
source                   1..2622
                         mol_type = genomic DNA
                         organism = Mycobacterium tuberculosis
SEQUENCE: 266
atgggcagca gccatcatca tcatcatcac agcagcggcc tggtgccgcg cggcagccat   60
atgcataagg cgtcacaatc gatgatcacg cccaccaacg cagatcgcgg cgccggggtg  120
ctgggaaacg acagaaagcc ggatgagtcg tgcgcgcgtg cggcggccgc ggccgatccg  180
gggccaccga cccgaccagc gcacaatgcg gcgggagtca gcccggagat ggtgcaggtg  240
ccggcggagg cgcagcgcat cgtggtgctc tccggtgacc agctcgacgc gctgtgcgcg  300
ctgggcctgc aatcgcggat cgtcgccgcc gcgttgccga cagctcctc aagtcaacct  360
tcctatctgg gcacgaccgt gcatgatctg cccggtcgag tgactcgcag cgccccgac  420
ctgcgcgcca ttgcggcggc tcaccccgat ctgatcctgg gttcgcaggg tttgacgccg  480
cagttgtatc gcagctggc ggcgatcgcc ccgacggtgt ttaccgcggc accggggcgcg  540
gactgggaaa taaccctgcg tggtgtcggt gccgccacgg cccgtatcgc gcgcggtgac  600
gcgctgatca ccggggttcgc gaacacgcac acccaggtcg ggaccaagca tgacgcgaac  660
cacttccaag cgtcgatcgt gcactgacc gccaacacca tgcggtata cggcgccaac  720
aacttcccgg ccagcgtgct gagcgcggtc ggcgtcgacc gaccgccgtc tcaacggttc  780
accgacaagg cctacatcga gatcggcacc acggccgccg acctggcgaa atcaccggac  840
ttctcggcgg ccgacgccga tatcgtctac ctgtcgtgcg cgtcggaagc agccgcggaa  900
cgcgcggccg tcatcctgga tagcgaccca tggcgcaagc tgtccgccaa ccgtgacaac  960
cgggtcttcg tcgtcaacga caggtatgg cagacggtag agggtatggt cgctgccgcg 1020
ggcattgtcg atgatctgcg ctgggtcgac gcgccgatca acgagctcgg aggttctggt 1080
ggaagcgcat gcaaaacggt gacgttgacc gtcgacggaa ccgcgatgcg ggtgaccacg 1140
atgaaatcgc gggtgatcga catcgtcgaa gagaacgggt tctcagtcga cgaccgcgac 1200
gacctgtatc ccgcggccgg cgtgcaggtc catgacgccg acaccatcgt gctgcggcgt 1260
agccgtccgc tgcagatctc gctggatggt cacgacgcta gcaggtgtg gacgaccgcg 1320
```

```
tcgacggtgg acgaggcgct ggcccaactc gcgatgaccg acacggcgcc ggccgcggct   1380
tctcgcgcca gccgcgtccc gctgtccggg atggcgctac cggtcgtcag cgccaagacg   1440
gtgcagctca acgacggcgg gttggtgcgc acggtgcact tgccggcccc caatgtcgcg   1500
gggctgctga gtgcggccgg cgtgccgctg ttgcaaagcg accacgtggt gcccgccgcg   1560
acggccccga tcgtcgaagg catgcagatc caggtgaccg gcaatcggat caagaaggtc   1620
accgagcggc tgccgctgcc gccgaacgcg cgtcgtgtcg aggacccgga gatgaacatg   1680
agccgggagg tcgtcgaaga cccgggggtt ccggggaccc aggatgtgac gttcgcggta   1740
gctgaggtca acgcgtcgac gaccggccgt ttgcccgtcg ccaacgtcgt ggtgaccccg   1800
gcccacgaag ccgtggtgcg ggtgggcacc aagcccggta ccgaggtgcc cccggtgatc   1860
gacggaagca tctgggacgc gatcgccggc tgtgaggccg gtggcaactg ggcgatcaac   1920
accggcaacg ggtattacgg tggtgtgcag tttgaccagg gcacctggga ggccaacggc   1980
gggctgcggt atgcaccccg cgctgacctc gccaccgcg aagagcagat cgccgttgcc   2040
gaggtgaccc gactgcgtca aggttggggc gcctggccgg tatgtgctgc acgagcgggt   2100
gcgcgcgaat tcggtggaag cggaggttct atgacggcaa tctcgtgctc accgcgaccc   2160
aggtatgctt cccgaatgcc agttttgagc aagaccgtcg aggtcaccgc cgacgccgca   2220
tcgatcatgg ccatcgttgc cgatatcgag cgctacccag agtggaatga aggggtcaag   2280
ggcgcatggg tgctcgctcg ctacgatgac gggcgtccca gccaggtgcg gctcgacacc   2340
gctgttcaag gcatcgaggg cacctatatc cacgccgtgt actacccagg cgaaaaccag   2400
attcaaaccg tcatgcagca gggtgaactg tttgccaagc aggagcagct gttcagtgtg   2460
gtggcaaccg gcgccgcgag cttgctcacg gtggacatgg acgtccaggt caccatgccg   2520
gtgcccgagc cgatggtgaa gatgctgctc aacaacgtcc tggagcatct cgccgaaaat   2580
ctcaagcagc gcgccgagca gctggcggcc agctaaaagc tt                      2622

SEQ ID NO: 267          moltype = DNA   length = 52
FEATURE                 Location/Qualifiers
misc_feature            1..52
                        note = Primer
source                  1..52
                        mol_type = other DNA
                        organism = synthetic construct
SEQUENCE: 267
gatacacata tgcaccatca ccatcaccac atgggcagca gccatcatca tc          52

SEQ ID NO: 268          moltype = DNA   length = 32
FEATURE                 Location/Qualifiers
misc_feature            1..32
                        note = Primer
source                  1..32
                        mol_type = other DNA
                        organism = synthetic construct
SEQUENCE: 268
catatcgagc tcgttgatcg gcgcgtcgac cc                                32

SEQ ID NO: 269          moltype = DNA   length = 53
FEATURE                 Location/Qualifiers
misc_feature            1..53
                        note = Primer
source                  1..53
                        mol_type = other DNA
                        organism = synthetic construct
SEQUENCE: 269
atcaacgagc tcggaggttc tggtggaagc gcatgcaaaa cggtgacgtt gac         53

SEQ ID NO: 270          moltype = DNA   length = 33
FEATURE                 Location/Qualifiers
misc_feature            1..33
                        note = Primer
source                  1..33
                        mol_type = other DNA
                        organism = synthetic construct
SEQUENCE: 270
catatcgaat tcgcgcgcac ccgctcgtgc agc                               33

SEQ ID NO: 271          moltype = DNA   length = 52
FEATURE                 Location/Qualifiers
misc_feature            1..52
                        note = Primer
source                  1..52
                        mol_type = other DNA
                        organism = synthetic construct
SEQUENCE: 271
catgtcgaat tcggtggaag cggaggttct atgacggcaa tctcgtgctc ac          52

SEQ ID NO: 272          moltype = DNA   length = 33
FEATURE                 Location/Qualifiers
misc_feature            1..33
                        note = Primer
source                  1..33
                        mol_type = other DNA
```

-continued

```
                        organism = synthetic construct
SEQUENCE: 272
catatcaagc ttttagctgg ccgccagctg ctc                                 33

SEQ ID NO: 273          moltype = AA   length = 871
FEATURE                 Location/Qualifiers
source                  1..871
                        mol_type = protein
                        organism = Mycobacterium tuberculosis
SEQUENCE: 273
MGSSHHHHHH SSGLVPRGSH MHKASQSMIT PTTQIAGAGV LGNDRKPDES CARAAAAADP    60
GPPTRPAHNA AGVSPEMVQV PAEAQRIVVL SGDQLDALCA LGLQSRIVAA ALPNSSSSQP   120
SYLGTTVHDL PGVGTRSAPD LRAIAAAHPD LILGSQGLTP QLYPQLAAIA PTVFTAAPGA   180
DWENNLRGVG AATARIAAVD ALITGFAEHA TQVGTKHDAT HFQASIVQLT ANTMRVYGAN   240
NFPASVLSAV GVDRPPSQRF TDKAYIEIGT TAADLAKSPD FSAADADIVY LSCASEAAAE   300
RAAVILDSDP WRKLSANRDN RVFVVNDQVW QTGEGMVAAR GIVDDLRWVD APINELGGSG   360
GSACKTVTLT VDGTAMRVTT MKSRVIDIVE ENGFSVDDRD DLYPAAGVQV HDADTIVLRR   420
SRPLQISLDG HDAKQVWTTA STVDEALAQL AMTDTAPAAA SRASRVPLSG MALPVVSAKT   480
VQLNDGGLVR TVHLPAPNVA GLLSAAGVPL LQSDHVVPAA TAPIVEGMQI QVTRNRIKKV   540
TERLPLPPNA RRVEDPEMNM SREVVEDPGV PGTQDVTFAV AEVNGVETGR LPVANVVVTP   600
AHEAVVRVGT KPGTEVPPVI DGSIWDAIAG CEAGGNWAIN TGNGYYGGVQ FDQGTWEANG   660
GLRYAPRADL ATREEQIAVA EVTRLRQGWG AWPVCAARAG AREFGGSGGS MTAISCSPRP   720
RYASRMPVLS KTVEVTADAA SIMAIVADIE RYPEWNEGVK GAWVLARYDD GRPSQVRLDT   780
AVQGIEGTYI HAVYYPGENQ IQTVMQQGEL FAKQEQLFSV VATGAASLLT VDMDVQVTMP   840
VPEPMVKMLL NNVLEHLAEN LKQRAEQLAA S                                  871

SEQ ID NO: 274          moltype = DNA   length = 3171
FEATURE                 Location/Qualifiers
source                  1..3171
                        mol_type = genomic DNA
                        organism = Mycobacterium tuberculosis
SEQUENCE: 274
catatgcacc atcaccatca ccacatggaa aaaatgtcac atgatccgat cgctgccgac    60
attggcacgc aagtgagcga caacgctctg cacggcgtga cggccggctc gacggcgctg   120
acgtcggtca ccgggctggt tcccgcgggg gccgatgagg tctccgccca agcgcgcacg   180
gcgttcacat cggagggcat ccaattgctg gcttccaatg catcggccca agaccagctc   240
caccgtgcgg gcgaagcggt ccaggacgtc gcccgcacct attcgcaaat cgacgacggc   300
gccgccggcg tcttcgccga agagctcgga ggttccggtg aagcatgctg gtggcacgca   360
atgccaccgg agctaaatac cgcacgcgct atggccggtc cggtccggc tccaatgctt   420
gcggcagccg cggatggca gacgctttcg gcggctctgg acgctcaggc cgtcgagttg   480
accgcgcgcc tgaactctct gggagaagcc tggactggag gtggcagcga caaggcgctt   540
gcggctgcaa cgccgatggt ggtctggcta caaaccgcgt caacacaggc caagacccgt   600
gcgatgcagg cgacggcgca agcccgggca tacacccagg ccatggccac agcgccgtcg   660
ctgccggaga tcgccgccaa ccacatcacc caggccgtcc ttacggccac caacttcttc   720
ggtatcaaca cgatcccgat cgccgttgcc gagatggatt atttcatccg tatgtggaac   780
caggcagccc tggcaatgga ggtctaccag gccgagaccc ggttaacac gcttttcgag   840
aagctcgacg cgatggcgtc gatccttgat ccccggccga gccagacgac gacgaacccg   900
atcttcggaa tgccctcccc tggcagctca acaccggttg gccagttgcc gccggcggct   960
acccagaccc tcgccaacct gggtgagatg agcggcccga tgcagcagct gacccagccg  1020
ctgcagcagg tgacgtcgtt gttcagccag gtgggcggca ccggcggcgg caacccagcc  1080
gacgaggaag ccgcgcagat gggcctgctg ggcaccagtc cgctgtcgaa ccatccgctg  1140
gctggtggat caggccccag cgcgggcgcg ggcctgctgc gcgcggagtc gctacctggc  1200
gcaggtgggt cgttgacccg cacgccgctg atgtctcagc tgatcgaaaa gccggttgcc  1260
ccctcggtga tgcggcggc tgctgccgga tcgtcggcga cgggtggcgc cgctccggta  1320
ggtcggggag cgatgggcca gggtcgcaa tccggcggct ccaccaggcc gggtctggtc  1380
gcgccggcac cgctcgcgca ggagcgtgaa gaagacgacg aggacgctg ggacgaagag  1440
gacgactggg aattcggtgg cagtggagga tctatgacag agcagcagtg gaatttcgcg  1500
ggtatcgagg ccgcggcaag cgcaatccag ggaaatgtca cgtccattca ttccctcctt  1560
gacgagggga agcagtccct gaccaagctc gcagcggcct ggggcggtag cggttcggag  1620
gcgtaccagg gtgtccagca aaaatgggac gccacgcgcta ccagctgaa caacgcgctg  1680
cagaacctgg cgcggacgat cagcgaagcc ggtcaggcaa tggcttcgac gaaggcaac  1740
gtcactggga tgttcgcagc tagcggaggt tccggtggaa gcatgacgca gtcgcagacc  1800
gtgacggtgg atcagcaaga gattttgaac agggccaacg aggtggaggc cccgatggcg  1860
gacccaccga ctgatgtccc catcacaccg tgcgaactca tgcggccgct aaaacgccgcc  1920
caacagctgg tattgtccgc cgacaacatg cgggaatacc tggcggccgg tgccaaaagag  1980
cggcagcgtc tggcgacctc gctgcgcaac gcggccaagg cgtatggcga ggttgatgag  2040
gaggctgcga ccgcgctgga caacgacggc gaaggaactg tgcaggcaga atcggccggg  2100
gccgtcggag gggacagttc ggccgaacta accgatacgc cgagggtggc cacggccggt  2160
gaacccaact tcatggatct caaagaagcg gcaaggagc tcgaaacgg cgaccaaggc  2220
gcatcgctcg cgcactttgc ggatgggtgg aacactttca acctgacgct gcaaggcgca  2280
gtcaagcggt tccgggggtt tgacaactgg gaaggcgatg cggctaccgc ttgcgaggct  2340
tcgctcgatc aacaacggca atggatactc cacatggcca aattgagcgc tgcgatggcc  2400
aagcaggctc aatatgtcgc gcagctgcac gtgtgggcta ggcgggaaca tccgacttat  2460
gaagacatag tcggacctcga acggctttac cggaaaaacc cttccgcccg cgaccaaatt  2520
ctccgggtgt acgcgggagta tcagcagagg tcggagaagg tgctgaccga atacaacaac  2580
aaggcagccc tggaaccggt aaacccgccg aagcctcccc cgccatcaa gatcgacccg  2640
cccccgcctc cgcaagagca gggattgatc cctggcttcc tgatgccgcc gtctgacggc  2700
tccggtgtga ctcccggtac cgggatgcca ccgcaccga tggttccgcc taccggatcg  2760
ccgggtggtg gcctcccggc tgacacgcg gcacagctga cgtcggctgg gcggaagcc  2820
```

```
gcagcgctgt cgggygacgt ggcggtcaaa gcggcatcgc tcggtggygg tggaggcggc   2880
ggggtgccgt cggcgccgtt gggatccgcg atcgggggcg ccgaatcggt gcggccgct   2940
ggcgctggtg acattgccgg cttaggccag ggaagggccg gcggcggcgc cgcgctgggc   3000
ggcggtggca tggaatgcc gatgggtgcc gcgcatcagg acaaggggg cgccaagtcc   3060
aagggttctc agcaggaaga cgaggcgctc tacaccgagg atcgggcatg gaccgaggcc   3120
gtcattggta accgtcggcg ccaggacagt aaggagtcga agtgaaagct t             3171
```

```
SEQ ID NO: 275          moltype = DNA  length = 52
FEATURE                 Location/Qualifiers
misc_feature            1..52
                        note = Primer
source                  1..52
                        mol_type = other DNA
                        organism = synthetic construct
SEQUENCE: 275
gatacacata tgcaccatca ccatcaccac atggaaaaaa tgtcacatga tc             52

SEQ ID NO: 276          moltype = DNA  length = 34
FEATURE                 Location/Qualifiers
misc_feature            1..34
                        note = Primer
source                  1..34
                        mol_type = other DNA
                        organism = synthetic construct
SEQUENCE: 276
gatacatgag ctcttcggcg aagacgccgg cggc                                 34

SEQ ID NO: 277          moltype = DNA  length = 50
FEATURE                 Location/Qualifiers
misc_feature            1..50
                        note = Primer
source                  1..50
                        mol_type = other DNA
                        organism = synthetic construct
SEQUENCE: 277
gatacagagc tcggaggttc cggtggaagc atgctgtggc acgcaatgcc                50

SEQ ID NO: 278          moltype = DNA  length = 34
FEATURE                 Location/Qualifiers
misc_feature            1..34
                        note = Primer
source                  1..34
                        mol_type = other DNA
                        organism = synthetic construct
SEQUENCE: 278
gatacagaat tcccagtcgt cctcttcgtc ccag                                 34

SEQ ID NO: 279          moltype = DNA  length = 49
FEATURE                 Location/Qualifiers
misc_feature            1..49
                        note = Primer
source                  1..49
                        mol_type = other DNA
                        organism = synthetic construct
SEQUENCE: 279
gacagaattc ggtggcagtg gaggatctat gacagagcag cagtggaat                 49

SEQ ID NO: 280          moltype = DNA  length = 35
FEATURE                 Location/Qualifiers
misc_feature            1..35
                        note = Primer
source                  1..35
                        mol_type = other DNA
                        organism = synthetic construct
SEQUENCE: 280
catatcagct agctgcgaac atcccagtga cgttg                                35

SEQ ID NO: 281          moltype = DNA  length = 52
FEATURE                 Location/Qualifiers
misc_feature            1..52
                        note = Primer
source                  1..52
                        mol_type = other DNA
                        organism = synthetic construct
SEQUENCE: 281
catatcagct agcggaggtt ccggtggaag catgacgcag tcgcagaccg tg             52

SEQ ID NO: 282          moltype = DNA  length = 34
FEATURE                 Location/Qualifiers
```

```
misc_feature         1..34
                     note = Primer
source               1..34
                     mol_type = other DNA
                     organism = synthetic construct
SEQUENCE: 282
catatcaaag ctttcacttc gactccttac tgtc                                  34

SEQ ID NO: 283       moltype = AA   length = 1054
FEATURE              Location/Qualifiers
source               1..1054
                     mol_type = protein
                     organism = Mycobacterium tuberculosis
SEQUENCE: 283
HMHHHHHHME KMSHDPIAAD IGTQVSDNAL HGVTAGSTAL TSVTGLVPAG ADEVSAQAAT      60
AFTSEGIQLL ASNASAQDQL HRAGEAVQDV ARTYSQIDDG AAGVFAEELG GSGGSMLWHA     120
MPPELNTARL MAGAGPAPML AAAAGWQTLS AALDAQAVEL TARLNSLGEA WTGGGSDKAL     180
AAATPMVVWL QTASTQAKTR AMQATAQAAA YTQAMATTPS LPEIAANHIT QAVLTATNFF     240
GINTIPIALT EMDYFIRMWN QAALAMEVYQ AETAVNTLFE KLEPMASILD PGASQSTTNP     300
IFGMPSPGSS TPVGQLPPAA TQTLGQLGEM SGPMQQLTQP LQQVTSLFSQ VGGTGGGNPA     360
DEEAAQMGLL GTSPLSNHPL AGGSGPSAGA GLLRAESLPG AGGSLTRTPL MSQLIEKPVA     420
PSVMPAAAAG SSATGGAAPV GAGAMGQGAQ SGGSTRPGLV APAPLAQERE EDDEDDWDEE     480
DDWEFGGSGG SMTEQQWNFA GIEAAASAIQ GNVTSIHSLL DEGKQSLTKL AAAWGGSGSE     540
AYQGVQQKWD ATATELNNAL QNLARTISEA GQAMASTEGN VTGMFAASGG SGGSMTQSQT     600
VTVDQQEILN RANEVEAPMA DPPTDVPITP CELTAAKNAA QQLVLSADNM REYLAAGAKE     660
RQRLATSLRN AAKAYGEVDE EAATALDNDG EGTVQAESAG AVGGDSSAEL TDTPRVATAG     720
EPNFMDLKEA ARKLETGDQG ASLAHFADGW NTFNLTLQGD VKRFRGFDNW EGDAATACEA     780
SLDQQRQWIL HMAKLSAAMA KQAQYVAQLH VWARREHPTY EDIVGLERLY AENPSARDQI     840
LPVYAEYQQR SEKVLTEYNN KAALEPVNPP KPPPAIKIDP PPPPQEQGLI PGFLMPPSDG     900
SGVTPGTGMP AAPMVPPTGS PGGGLPADTA AQLTSAGREA AALSGDVAVK AASLGGGGGG     960
GVPSAPLGSA IGGAESVRPA GAGDIAGLGQ GRAGGGAALG GGGMGMPMGA AHQGQGGAKS    1020
KGSQQEDEAL YTEDRAWTEA VIGNRRRQDS KESK                                1054

SEQ ID NO: 284       moltype = DNA  length = 2613
FEATURE              Location/Qualifiers
source               1..2613
                     mol_type = genomic DNA
                     organism = Mycobacterium tuberculosis
SEQUENCE: 284
catatggagc tggtccgggt gaccgaggcc ggagccatgg ccgcgggccg ctgggtaggc      60
cgcggcgaca aggagggcgg cgacggcgcg gcggtcgacg cgatgcgcga actggtcaac     120
tcggtttcca tgcgcggggt ggtggtcatc ggcgaaggcc aaaaggacca cgcaccaatg     180
ctctacaacg gcgaagaagt gggcaacggc gacggaccgg aatgcgactt tgccgtcgac     240
cccattgacg gcaccacgct gatgagcaag gcatgacca acgccatctc ggtgctggcc     300
gtagccgatc gcggcaccat gttcgacccg tcggcggtgt tctacatgaa caaaatcgcc     360
gtcggccccg atgccgcaca cgtgctggat atcaccgcgc cgatctcgga aaacatccga     420
gcggtcgcca aggtcaagga cctgtcggtg cgagacatga cggtgtgcat cctgacagg      480
ccgcggcacg cgcaactcat ccacgacgtc cgcgccaccg gggcccggat ccggctgatc     540
accgatggcg acgtcgccgg cgcgatctcg gcgtgccgac cgcactccgg caccgacctg     600
ctagctggga tcgcggcac cccggaggga atcatcgccg ccgcggcgat ccgctgcatg     660
ggcggggcga tccaggcgca gctcgccccg cgcgacgacg cggaacgccg caaggcccta     720
gaagccggtt acgacctgaa ccaggtcttg accaccgaag atctggtgtc cggggaaaac     780
gtcttcttct gcgccactgg ggtcaccgac ggcgacctgc tcaagggagt gcgttactac     840
cccggcggct gcaccaccca ttcgatcgtg atgcgctcga gtccggcac cgtccggatg     900
atcgaggcct accaccggct ttcaaagctc aacgaatact ccgcgatcga cttcaccggc     960
gacagcagcg ccgtgtaccc attgcccgga ggttctggtg aagcgaatt cgtgcgatac    1020
agtgactcat accacacaac gggccggtgg cagccacgag cgtcgacaga agggtttccc    1080
atgggcgtca gcatcgaggt caacggacta acgaagtcct tcgggtcctc gaggatctgg    1140
gaagatgtca cgctaacgat cccccgccgg gaggtcagcg tgctgctggg cccatcgggt    1200
accggcaaat cggtgtttct gaaatctctg atcggcctcc tgccgccgga gcgcggccng    1260
atcatcatcg acggcaccga catcatcgaa tgctcggcca aggagcttta cgagatccgc    1320
acattgttcg gcgtgctgtt tcaggacggt gccctgttcg ggtcgatgaa cctctacgac    1380
aacaccgcgt tccccctgcg tgagcacacc aagaaaaagg aaagcgagat ccgtgacatc    1440
gtcatggaga agctggccct agtcggcctg ggtgggaacg agaagaagtt ccccggccag    1500
atctccggcg gatgcgtaa gcgtgccggc ctagcgcgtg ccctggtcct tgacccgcag    1560
atcattctct gcgacgagcc cgactcgggt ctggaccgg ttcgtaccgc ctacctgagc    1620
cagctgatca tggacatcaa cgcccagatc gacgccacca tcctgatcgt gacgcacaac    1680
atcaacatcg cccgcaccgt gccggacaac atgggcatgt tgttccgcaa gcatttggtg    1740
atgttcggc gcggggaggt gctactcacc agcgacgac cggtggtgcg gcagttcctc    1800
aacggccggc gcatcggccc gatcggcatg tccgaggaga aggacgaggc caccatggcc    1860
gaagagcagg ccctgctcga tgccggccac cacgcgggcg tgtcgaggga aatcgagggc    1920
gtgccgccgc agatcagcgc gacaccgggc atgccggagc gcaaagcggt cgcccggcgt    1980
caggctcggt tcgcgagat gttgcacacg ctgcccaaaa aggcccaggc ggcgatcctc    2040
gacgatctcg agggcacgca caagtacgcg gtgcacgaaa tctgctccgg tggaagcggc    2100
ggttctgagc tcgtgctgg tgacaccacc atcaccatcg tcggaaatct gaccgctgac    2160
cccgagctgc ggttcacccc gtccggtgcg gccgtggcga atttcaccgt ggcgtcaacg    2220
cccccggatct atgaccgtca gaccggcgaa tggaaagacg cgaagcgct gttcctccgg    2280
tgcaatatct ggcgggaggc ggccgagaac gtgcccgaga gctcacccg gggggcacga    2340
gtcatcgtta gcggcggct taagcagcgg tcgtttgaaa cccgtgaggg cgagaagcgc    2400
```

```
accgtcatcg aggtcgaggt cgatgagatt gggccttcgc ttcggtacgc caccgccaag    2460
gtcaacaagg ccagccgcag cggcgggttt ggcagcggat cccgtccggc gccggcgcag    2520
accagcagcg cctcgggaga tgacccgtgg ggcagcgcac cggcgtcggg ttcgttcggc    2580
ggcggcgatg acgaaccgcc attctgaaag ctt                                 2613

SEQ ID NO: 285          moltype = DNA   length = 32
FEATURE                 Location/Qualifiers
misc_feature            1..32
                        note = Primer
source                  1..32
                        mol_type = other DNA
                        organism = synthetic construct
SEQUENCE: 285
taggatccca tatggagctg gtccgggtga cc                                    32

SEQ ID NO: 286          moltype = DNA   length = 47
FEATURE                 Location/Qualifiers
misc_feature            1..47
                        note = Primer
source                  1..47
                        mol_type = other DNA
                        organism = synthetic construct
SEQUENCE: 286
cacgaattcg cttccaccag aacctccggg caatgggtac acggcgc                    47

SEQ ID NO: 287          moltype = DNA   length = 45
FEATURE                 Location/Qualifiers
misc_feature            1..45
                        note = Primer
source                  1..45
                        mol_type = other DNA
                        organism = synthetic construct
SEQUENCE: 287
ggaggttctg gtggaagcga attcgtgcga tacagtgact catac                      45

SEQ ID NO: 288          moltype = DNA   length = 50
FEATURE                 Location/Qualifiers
misc_feature            1..50
                        note = Primer
source                  1..50
                        mol_type = other DNA
                        organism = synthetic construct
SEQUENCE: 288
gccacgagct cagaaccgcc gcttccaccc tggccgattt cgtgcaccgc                 50

SEQ ID NO: 289          moltype = DNA   length = 50
FEATURE                 Location/Qualifiers
misc_feature            1..50
                        note = Primer
source                  1..50
                        mol_type = other DNA
                        organism = synthetic construct
SEQUENCE: 289
gccagggtgg aagcggcggt tctgagctcg tggctggtga caccaccatc                 50

SEQ ID NO: 290          moltype = DNA   length = 36
FEATURE                 Location/Qualifiers
misc_feature            1..36
                        note = Primer
source                  1..36
                        mol_type = other DNA
                        organism = synthetic construct
SEQUENCE: 290
caattaaagc tttcagaatg gcggttcgtc atcgcc                                36

SEQ ID NO: 291          moltype = AA    length = 887
FEATURE                 Location/Qualifiers
source                  1..887
                        mol_type = protein
                        organism = Mycobacterium tuberculosis
SEQUENCE: 291
MGSSHHHHHH SSGLVPRGSH MELVRVTEAG AMAAGRWVGR GDKEGGDGAA VDAMRELVNS      60
VSMRGVVVIG EGEKDHAPML YNGEEVGNGD GPECDFAVDP IDGTTLMSKG MTNAISVLAV     120
ADRGTMFDPS AVFYMNKIAV GPDAAHVLDI TAPISENIRA VAKVKDLSVR DMTVCILDRP     180
RHAQLIHDVR ATGARIRLIT DGDVAGAISA CRPHSGTDLL AGIGGTPEGI IAAAAIRCMG     240
GAIQAQLAPR DDAERRKALE AGYDLNQVLT TEDLVSGENV FFCATGVTDG DLLKGVRYYP     300
GGCTTHSIVM RSKSGTVRMI EAYHRLSKLN EYSAIDFTGD SSAVYPLPGG SGGSEFVRYS     360
DSYHTTGRWQ PRASTEGFPM GVSIEVNGLT KSFGSSRIWE DVTLTIPAGE VSVLLGPSGT     420
GKSVFLKSLI GLLRPERGSI IIDGTDIIEC SAKELYEIRT LFGVLFQDGA LFGSMNLYDN     480
```

```
TAFPLREHTK KKESEIRDIV MEKLALVGLG GDEKKFPGEI SGGMRKRAGL ARALVLDPQI      540
ILCDEPDSGL DPVRTAYLSQ LIMDINAQID ATILIVTHNI NIARTVPDNM GMLFRKHLVM      600
FGPREVLLTS DEPVVRQFLN GRRIGPIGMS EEKDEATMAE EQALLDAGHH AGGVEEIEGV      660
PPQISATPGM PERKAVARRQ ARVREMLHTL PKKAQAAILD DLEGTHKYAV HEIGQGGSGG      720
SELVAGDTTI TIVGNLTADP ELRFTPSGAA VANFTVASTP RIYDRQTGEW KDGEALFLRC      780
NIWREAAENV AESLTRGARV IVSGRLKQRS FETREGEKRT VIEVEVDEIG PSLRYATAKV      840
NKASRSGGFG SGSRPAPAQT SSASGDDPWG SAPASGSFGG GDDEPPF                    887

SEQ ID NO: 292              moltype = AA   length = 95
FEATURE                     Location/Qualifiers
source                      1..95
                            mol_type = protein
                            organism = Mycobacterium tuberculosis
SEQUENCE: 292
MTEQQWNFAG IEAAASAIQG NVTSIHSLLD EGKQSLTKLA AAWGGSGSEA YQGVQQKWDA       60
TATELNNALQ NLARTISEAG QAMASTEGNV TGMFA                                  95

SEQ ID NO: 293              moltype = DNA  length = 318
FEATURE                     Location/Qualifiers
source                      1..318
                            mol_type = genomic DNA
                            organism = Mycobacterium tuberculosis
SEQUENCE: 293
catatgcatc accatcacca tcacatgaca gagcagcagt ggaatttcgc gggtatcgag        60
gccgcgcaa gcgcaatcca gggaaatgtc acgtccattc attccctcct tgacgagggg       120
aagcagtccc tgaccaagct cgcagcggcc tggggcggta gcggttcaga ggcgtaccag      180
ggtgtccagc aaaaatggga cgccacggct accgagctga acaacgcgct gcagaacctg      240
gcgcggacga tcagcgaagc cggtcaggca atggcttcga ccgaaggcaa cgtcactggg      300
atgttcgcat aggaattc                                                    318

SEQ ID NO: 294              moltype = AA   length = 102
FEATURE                     Location/Qualifiers
source                      1..102
                            mol_type = protein
                            organism = Mycobacterium tuberculosis
SEQUENCE: 294
MHHHHHHMTE QQWNFAGIEA AASAIQGNVT SIHSLLDEGK QSLTKLAAAW GGSGSEAYQG       60
VQQKWDATAT ELNNALQNLA RTISEAGQAM ASTEGNVTGM FA                         102

SEQ ID NO: 295              moltype = DNA  length = 33
FEATURE                     Location/Qualifiers
misc_feature                1..33
                            note = Primer
source                      1..33
                            mol_type = other DNA
                            organism = synthetic construct
SEQUENCE: 295
caattacata tgagagtttt gttgctggga ccg                                    33

SEQ ID NO: 296              moltype = DNA  length = 35
FEATURE                     Location/Qualifiers
misc_feature                1..35
                            note = Primer
source                      1..35
                            mol_type = other DNA
                            organism = synthetic construct
SEQUENCE: 296
caattaaagc ttctactttc cagagcccgc aacgc                                  35

SEQ ID NO: 297              moltype = DNA  length = 32
FEATURE                     Location/Qualifiers
misc_feature                1..32
                            note = Primer
source                      1..32
                            mol_type = other DNA
                            organism = synthetic construct
SEQUENCE: 297
caattacata tgaccggccc caccaccgcg cc                                     32

SEQ ID NO: 298              moltype = DNA  length = 36
FEATURE                     Location/Qualifiers
misc_feature                1..36
                            note = Primer
source                      1..36
                            mol_type = other DNA
                            organism = synthetic construct
SEQUENCE: 298
caattaaagc tttcaggtgt ctttgggtgt tccgag                                 36
```

```
SEQ ID NO: 299          moltype = DNA   length = 33
FEATURE                 Location/Qualifiers
misc_feature            1..33
                        note = Primer
source                  1..33
                        mol_type = other DNA
                        organism = synthetic construct
SEQUENCE: 299
caattacata tgagagtttt gttgctggga ccg                                  33

SEQ ID NO: 300          moltype = DNA   length = 35
FEATURE                 Location/Qualifiers
misc_feature            1..35
                        note = Primer
source                  1..35
                        mol_type = other DNA
                        organism = synthetic construct
SEQUENCE: 300
caattaaagc ttctactttc cagagcccgc aacgc                                35

SEQ ID NO: 301          moltype = DNA   length = 54
FEATURE                 Location/Qualifiers
misc_feature            1..54
                        note = Primer
source                  1..54
                        mol_type = other DNA
                        organism = synthetic construct
SEQUENCE: 301
caattacata tgcatcacca tcaccatcac gtggtggacc gcgatcccaa tacc           54

SEQ ID NO: 302          moltype = DNA   length = 33
FEATURE                 Location/Qualifiers
misc_feature            1..33
                        note = Primer
source                  1..33
                        mol_type = other DNA
                        organism = synthetic construct
SEQUENCE: 302
caattagaat tctcagcgat tcctgatctt gtg                                  33

SEQ ID NO: 303          moltype = DNA   length = 33
FEATURE                 Location/Qualifiers
misc_feature            1..33
                        note = Primer
source                  1..33
                        mol_type = other DNA
                        organism = synthetic construct
SEQUENCE: 303
ctggatccca tatggccttc ccggaatatt cgc                                  33

SEQ ID NO: 304          moltype = DNA   length = 33
FEATURE                 Location/Qualifiers
misc_feature            1..33
                        note = Primer
source                  1..33
                        mol_type = other DNA
                        organism = synthetic construct
SEQUENCE: 304
ctagctgaat tctcatccga cgtgtttccg ccg                                  33

SEQ ID NO: 305          moltype = DNA   length = 33
FEATURE                 Location/Qualifiers
misc_feature            1..33
                        note = Primer
source                  1..33
                        mol_type = other DNA
                        organism = synthetic construct
SEQUENCE: 305
caattacata tggcgcccaa gacctactgc gag                                  33

SEQ ID NO: 306          moltype = DNA   length = 36
FEATURE                 Location/Qualifiers
misc_feature            1..36
                        note = Primer
source                  1..36
                        mol_type = other DNA
                        organism = synthetic construct
SEQUENCE: 306
caattaaagc ttctaggcca gcatcgagtc gatcgc                               36
```

```
SEQ ID NO: 307          moltype = DNA   length = 51
FEATURE                 Location/Qualifiers
misc_feature            1..51
                        note = Primer
source                  1..51
                        mol_type = other DNA
                        organism = synthetic construct
SEQUENCE: 307
caattacata tgcatcacca tcaccatcac atgcaattcg acgtgaccat c          51

SEQ ID NO: 308          moltype = DNA   length = 36
FEATURE                 Location/Qualifiers
misc_feature            1..36
                        note = Primer
source                  1..36
                        mol_type = other DNA
                        organism = synthetic construct
SEQUENCE: 308
caattagaat tctcagtgtg taccggcctt gaagcg                           36

SEQ ID NO: 309          moltype = DNA   length = 51
FEATURE                 Location/Qualifiers
misc_feature            1..51
                        note = Primer
source                  1..51
                        mol_type = other DNA
                        organism = synthetic construct
SEQUENCE: 309
caattacata tgcatcacca tcaccatcac acttccggcg atatgtcgag c          51

SEQ ID NO: 310          moltype = DNA   length = 33
FEATURE                 Location/Qualifiers
misc_feature            1..33
                        note = Primer
source                  1..33
                        mol_type = other DNA
                        organism = synthetic construct
SEQUENCE: 310
caattagaat tctcagcgcg gaatacttgc ctg                              33

SEQ ID NO: 311          moltype = DNA   length = 33
FEATURE                 Location/Qualifiers
misc_feature            1..33
                        note = Primer
source                  1..33
                        mol_type = other DNA
                        organism = synthetic construct
SEQUENCE: 311
gtgctagcca tggaaaaaa atgtcacatg atc                               33

SEQ ID NO: 312          moltype = DNA   length = 35
FEATURE                 Location/Qualifiers
misc_feature            1..35
                        note = Primer
source                  1..35
                        mol_type = other DNA
                        organism = synthetic construct
SEQUENCE: 312
ctggatccaa gcttctattc ggcgaagacg ccggc                            35

SEQ ID NO: 313          moltype = DNA   length = 33
FEATURE                 Location/Qualifiers
misc_feature            1..33
                        note = Primer
source                  1..33
                        mol_type = other DNA
                        organism = synthetic construct
SEQUENCE: 313
gtgctagcca tgctgtgg cacgcaatgc cac                                33

SEQ ID NO: 314          moltype = DNA   length = 35
FEATURE                 Location/Qualifiers
misc_feature            1..35
                        note = Primer
source                  1..35
                        mol_type = other DNA
                        organism = synthetic construct
SEQUENCE: 314
```

-continued

```
ctggatccaa gctttcacca gtcgtcctct tcgtc                              35

SEQ ID NO: 315          moltype = DNA  length = 51
FEATURE                 Location/Qualifiers
misc_feature            1..51
                        note = Primer
source                  1..51
                        mol_type = other DNA
                        organism = synthetic construct
SEQUENCE: 315
caattacata tgcatcacca tcaccatcac gtgaagcgag cgctcatcac c            51

SEQ ID NO: 316          moltype = DNA  length = 35
FEATURE                 Location/Qualifiers
misc_feature            1..35
                        note = Primer
source                  1..35
                        mol_type = other DNA
                        organism = synthetic construct
SEQUENCE: 316
caattagaat tctcatgtcc ggccggcgat catcg                              35

SEQ ID NO: 317          moltype = DNA  length = 50
FEATURE                 Location/Qualifiers
misc_feature            1..50
                        note = Primer
source                  1..50
                        mol_type = other DNA
                        organism = synthetic construct
SEQUENCE: 317
ccattacata tgcatcacca tcaccatcac atgacagagc agcagtggaa              50

SEQ ID NO: 318          moltype = DNA  length = 33
FEATURE                 Location/Qualifiers
misc_feature            1..33
                        note = Primer
source                  1..33
                        mol_type = other DNA
                        organism = synthetic construct
SEQUENCE: 318
ccattagaat tcctatgcga acatcccagt gac                                33
```

IMMUNOGENIC COMPOSITIONS COMPRISING *MYCOBACTERIUM TUBERCULOSIS* POLYPEPTIDES AND FUSIONS THEREOF

CROSS-REFERENCE TO RELATED APPLICATION(S)

This non-provisional application is a division of U.S. patent application Ser. No. 17/367,812, filed on Jul. 6, 2021, which is a division of U.S. patent application Ser. No. 15/815,512, filed on Nov. 16, 2017, now issued as U.S. Pat. No. 11,091,521, which is a divisional of U.S. patent application Ser. No. 13/791,511, filed on Mar. 8, 2013, now issued as U.S. Pat. No. 9,822,152, which is a continuation of U.S. patent application Ser. No. 12/594,806, filed on Jan. 6, 2010, now issued as U.S. Pat. No. 8,486,414, which is a 371 national phase entry of international patent number PCT/US2008/059500, filed Apr. 4, 2008 which claims the benefit and priority of U.S. provisional application Ser. No. 60/910,169, filed on Apr. 4, 2007, all of which are hereby incorporated by reference herein in their entirety, including all references and appendices cited therein, for all purposes, as if fully set forth herein.

STATEMENT OF GOVERNMENT INTEREST

This invention was made in part with government support under Grant Nos. AI-025038 and AI-067251 awarded by the National Institutes of Health. The government has certain rights in this invention.

STATEMENT REGARDING SEQUENCE LISTING

The content of the Sequence Listing XML of the sequence listing named "5-US-4_SequenceListingXML.xml" which is 470,512 bytes in size was created on Jan. 5, 2024, and electronically submitted is incorporated herein by reference in its entirety.

BACKGROUND

Technical Field

The present invention relates generally to compositions comprising antigenic and/or immunogenic combinations of *Mycobacterium tuberculosis* antigens and their use in the diagnosis, treatment, and prevention of tuberculosis.

Description of the Related Art

Tuberculosis is a chronic infectious disease caused by infection with *Mycobacterium tuberculosis* and other *Mycobacterium* species. It is a major disease in developing countries, as well as an increasing problem in developed areas of the world, with several million new cases each year. Although infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are critical. Currently, vaccination with live bacteria is the most widely used method for inducing protective immunity. The most common *Mycobacterium* employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to mycobacterial antigens. Sensitivity and specificity have, however, been problematic, and individuals vaccinated with BCG cannot be distinguished from infected individuals.

Accordingly, there is a need for improved reagents and methods for diagnosing, preventing and treating tuberculosis. The present invention fulfills these needs and offers other related advantages.

BRIEF SUMMARY

The present invention relates generally to compositions comprising at least two heterologous antigens, fusion polypeptides comprising the antigens and polynucleotides encoding the antigens, where the antigens are from a *Mycobacterium* species, particularly *Mycobacterium tuberculosis*. The present invention also relates methods of using the polypeptides and polynucleotides of the invention in the diagnosis, treatment and prevention of *Mycobacterium* infection. The antigens of the invention, when employed in combination and/or as fusion polypeptides or polynucleotides as described herein, offer improved and unexpected levels of immunogenicity, resulting in decrease in lung bacterial burden, and thus are particularly useful in the context of vaccine development.

For example, in one aspect of the invention, there are provided compositions comprising an immunostimulant and a combination of two or more *Mycobacterium tuberculosis* antigens, or immunogenic fragments thereof, wherein the antigens are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292) and antigens having at least 80%, 90% or 95% identity to any of the foregoing sequences.

In certain embodiments, the combination of two or more antigens is selected from the group consisting of:
(a) a combination comprising Rv1813 (SEQ ID NO: 16); Rv3620 (SEQ ID NO: 51) and Rv2608 (SEQ ID NO: 26);
(b) a combination comprising Rv2608 (SEQ ID NO: 26) and Rv3619 (SEQ ID NO: 46); and
(c) a combination comprising Rv3478 (SEQ ID NO: 41) and Rv3619 (SEQ ID NO: 46).

In a particular embodiment, the composition of (a) above, comprising Rv2608 (SEQ ID NO: 26), Rv1813 (SEQ ID NO: 16) and Rv3620 (SEQ ID NO: 51), further comprises one or more antigens selected from the group consisting of: Rv1886 (SEQ ID NO: 145), Rv2389 (SEQ ID NO: 21), Rv3478 (SEQ ID NO: 41), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3619 (SEQ ID NO: 46) and Rv3020 (SEQ ID NO: 36).

In a more particular embodiment, the composition comprises Rv1813 (SEQ ID NO: 16); Rv3620 (SEQ ID NO: 51), Rv2608 (SEQ ID NO: 26) and Rv2389 (SEQ ID NO: 21).

In related particular embodiment, the composition comprises Rv2608 (SEQ ID NO: 26); Rv1813 (SEQ ID NO: 16), Rv3620 (SEQ ID NO: 51) and Rv3619 (SEQ ID NO: 46).

In certain other embodiments of the invention, the composition of (b) above, comprising Rv2608 (SEQ ID NO: 26) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv3478 (SEQ ID NO: 41), and Rv3020 (SEQ ID NO: 36).

In a particular embodiment, the composition comprises Rv2608 (SEQ ID NO: 26), Rv3619 (SEQ ID NO: 46), and Rv1886 (SEQ ID NO: 145).

In another particular embodiment, the composition further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51) and Rv3020 (SEQ ID NO: 36).

In a more particular embodiment, the composition comprises Rv2608 (SEQ ID NO: 26), Rv3619 (SEQ ID NO: 46), Rv1813 (SEQ ID NO: 16) and Rv3620 (SEQ ID NO: 51).

In certain other embodiments of the invention, the composition of (c) above, comprising Rv3478 (SEQ ID NO: 41) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv2608 (SEQ ID NO: 26), and Rv3020 (SEQ ID NO: 36).

In a particular embodiment, the composition comprises Rv3478 (SEQ ID NO: 41), Rv3619 (SEQ ID NO: 46) and Rv1886 (SEQ ID NO: 145).

In another embodiment, the combination further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187) and Rv3020 (SEQ ID NO: 36).

The combination of two or more antigens described herein can include a combination of two or more separate recombinant antigens, or antigenic/immunogenic fragments thereof. Alternatively, the two or more antigens, or antigenic/immunogenic fragments thereof, may be covalently linked in the form of a fusion polypeptide.

According to another aspect of the invention, there are provided isolated fusion polypeptides comprising a combination of two or more covalently linked *Mycobacterium tuberculosis* antigens, or immunogenic fragments thereof, wherein the antigens are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214), and Rv3875 (SEQ ID NO: 292) and antigens having at least 80%, 90% or 95% identity to any of the foregoing sequences.

In certain embodiments, the fusion polypeptide comprises a combination of covalently linked antigens selected from the group consisting of:
(a) a combination comprising Rv1813 (SEQ ID NO: 16); Rv3620 (SEQ ID NO: 51) and Rv2608 (SEQ ID NO: 26);
(b) a combination comprising Rv2608 (SEQ ID NO: 26) and Rv3619 (SEQ ID NO: 46); and
(c) a combination comprising Rv3478 (SEQ ID NO: 41) and Rv3619 (SEQ ID NO: 46).

In a particular embodiment, the fusion polypeptide of (a) above, comprising Rv2608 (SEQ ID NO: 26), Rv1813 (SEQ ID NO: 16) and Rv3620 (SEQ ID NO: 51), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO:154), Rv0733 (SEQ ID NO: 190), Rv0577 (SEQ ID NO: 184), Rv3044 (SEQ ID NO:

166), Rv1626 (SEQ ID NO: 187), Rv3619 (SEQ ID NO: 46), Rv3478 (SEQ ID NO: 41) and Rv3020 (SEQ ID NO: 36).

In a more particular embodiment, the fusion polypeptide comprises Rv1813 (SEQ ID NO: 16); Rv3620 (SEQ ID NO: 51); Rv2608 (SEQ ID NO: 26) and Rv2389 (SEQ ID NO: 21).

In a related particular embodiment, the fusion polypeptide comprises Rv1813 (SEQ ID NO: 16); Rv3620 (SEQ ID NO: 51); Rv2608 (SEQ ID NO: 26) and Rv3619 (SEQ ID NO: 46).

In certain other embodiments of the invention, the fusion polypeptide of (b) above, comprising Rv2608 (SEQ ID NO: 26) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv3478 (SEQ NO: 41), and Rv3020 (SEQ ID NO: 36).

In a particular embodiment, the fusion polypeptide comprises Rv2608 (SEQ ID NO: 26), Rv1813 (SEQ NO: 16), Rv3619 (SEQ NO: 46), and Rv1886 (SEQ NO: 145). In another particular embodiment, the fusion polypeptide further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ NO: 190), Rv0577 (SEQ ID NO: 184), Rv3044 (SEQ ID NO: 166), Rv1626 (SEQ NO: 187), Rv3620 (SEQ ID NO: 51) and Rv3020 (SEQ ID NO: 36).

In a more particular embodiment, the fusion polypeptide comprises Rv2608 (SEQ ID NO: 26), Rv3619 (SEQ ID NO: 46), Rv1813 (SEQ NO: 16) and Rv3620 (SEQ NO: 51).

In certain other embodiments of the invention, the fusion polypeptide of (c) above, comprising Rv3478 (SEQ NO: 41) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ NO: 163), Rv2220 (SEQ NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv2608 (SEQ ID NO: 26), and Rv3020 (SEQ ID NO: 36).

In a particular embodiment, the fusion polypeptide comprises Rv3478 (SEQ ID NO: 41), Rv3619 (SEQ ID NO: 46) and Rv1886 (SEQ ID NO: 145).

In another embodiment, the fusion polypeptide further comprises one or more antigens selected from the group consisting of: Rv2389 (SEQ ID NO: 21), Rv1813 (SEQ ID NO: 16), Rv2875 (SEQ ID NO: 163), Rv2220 (SEQ NO: 154), Rv0733 (SEQ NO: 190), Rv0577 (SEQ ID NO: 184), Rv3044 (SEQ NO: 166), Rv1626 (SEQ ID NO: 187) and Rv3020 (SEQ ID NO: 36).

In certain particular embodiments, fusion polypeptides are provided which comprise an amino acid sequence selected from the group consisting of: ID83 (SEQ NO: 91), ID94 (SEQ ID NO: 95), ID93 (SEQ ID NO: 226), ID91 (SEQ ID NO: 236), ID71 (SEQ ID NO: 245), ID114 (SEQ NO: 251), ID125 (SEQ ID NO: 257).

According to another aspect of the invention, there are provided isolated polynucleotides encoding any of the antigens and/or fusion polypeptides described herein.

It will be understood that, in many embodiments, the compositions, polypeptides and polynucleotides of the invention are preferably formulated in combination with one or more immunostimulants in order to improve the immune response elicited by the antigens described herein. Numerous immunostimulant and adjuvant systems are known and available in the art and can be used in the context of the present invention, illustrative examples of which include AS-2, ENHANZYN™, MPL™, 3D-MPL™, IFA, QS21, CWS, TDM, AGPs, CpG-containing oligonucleotides, Toll-like receptor agonists (e.g., TLR9 agonists, TLR7 agonists, TLR7/8 agonists, TLR5 agonists, TLR4 agonists, TLR2 agonists, TLR3 agonists, etc.), LeIF, saponins, saponin mimetics, and biological and synthetic lipid A, imiquimod, gardiquimod, resiquimod, polyI:C, flagellin, or a combination thereof.

The fusion polynucleotides, fusion polypeptides, or compositions of the invention have been found to be highly antigenic. Therefore, according to another aspect of the invention, there are provided vaccines and related methods for stimulating a protective immune response in a subject by administering an effective amount of a composition as described herein. Isolated or purified polynucleotides may be used to produce recombinant fusion polypeptide antigens in vitro, which are then administered as a vaccine. Alternatively, the polynucleotides may be administered directly to a subject as a DNA-based vaccine to cause antigen expression in the subject, and the subsequent induction of an anti *Mycobacterium tuberculosis* immune response.

In addition, the compositions, fusion polypeptides and polynucleotides are useful as diagnostic tools in patients that may have been infected with *Mycobacterium*. For example, the compositions, fusion polypeptides, and polynucleotides of the invention may be used in in vitro and in vivo assays for detecting humoral antibodies or cell-mediated immunity against *Mycobacterium tuberculosis* for diagnosis of infection, monitoring of disease progression and/or test-of-cure evaluation. In one embodiment, there are provided diagnostic kits for detecting *Mycobacterium tuberculosis* infection in a biological sample, comprising (a) a polypeptide comprising at least an immunogenic portion of an antigen or fusion polypeptide described herein, (b) a detection reagent.

In another embodiment, methods are provided for detecting the presence of *Mycobacterium tuberculosis* infection in a biological sample, comprising (a) contacting a biological sample with a monoclonal antibody that binds to an antigen or fusion polypeptide described herein; and (b) detecting in the biological sample the presence of *Mycobacterium tuberculosis* proteins that bind to the monoclonal antibody.

In yet another embodiment, methods are provided for detecting *Mycobacterium tuberculosis* infection in a biological sample, comprising (a) contacting the biological sample with an antigen combination or fusion polypeptide as described herein and (b) detecting in the biological sample the presence of antibodies and/or T-cells that bind thereto.

In a particular embodiment, methods are provided for detecting *Mycobacterium tuberculosis* infection in a biological sample, comprising (a) contacting the biological sample with a combination of two or more antigens selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions thereof; and (b) detecting in the biological sample the presence of antibodies and/or T-cells that bind thereto.

In a particular embodiment, a method for detecting *Mycobacterium tuberculosis* infection in a biological sample comprises: contacting the biological sample with a fusion polypeptide selected from the group consisting of: DID85 (SEQ ID NO: 265); DID92 (SEQ ID NO: 273); DID108 (SEQ ID NO: 283) and DID93 (SEQ ID NO: 291); and detecting in the biological sample the presence of antibodies and/or T-cells that bind thereto.

In another particular embodiment, the invention provides diagnostic kits for detecting *Mycobacterium tuberculosis* infection in a biological sample, comprising: (a) a combination of two or more antigens selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO:208), Rv3873 (SEQ ID NO: 211), Rv1511 (SEQ ID NO: 214) and Rv3875 (SEQ ID NO: 292), or immunogenic portions thereof; and (b) a detection reagent.

In a particular embodiment, a kit of the present invention for detecting *Mycobacterium tuberculosis* infection in a biological sample comprises: a fusion polypeptide selected from the group consisting of: DID85 (SEQ ID NO: 265), DID92 (SEQ ID NO: 273), DID108 (SEQ ID NO: 283) and DID93 (SEQ ID NO: 291), and a detection reagent.

BRIEF DESCRIPTION OF THE SEVERAL VIEWS OF THE DRAWINGS

FIGS. 2A and 2B show the levels of TNF+ splenocytes upon in vitro antigen stimulation with different Mtb recombinant proteins. Splenocytes from mice infected with a low dose of virulent *M. tuberculosis* H37Rv were collected 4 wks (FIG. 2A) and 12 wks (FIG. 2B) post infection (p.i.) and tested for antigen specific TNF cytokine responses by ELISPOT. The splenocytes were incubated for 48 h in media, 10 μg/ml Mtb lysate, or 10 μg/ml of the Mtb recombinant proteins. The data shown is the mean±SD (n=2) in a representative experiment.

FIGS. 3A-3D shows protection against *M. tuberculosis* infection and antigen specific immune responses.

FIG. 3A shows Log 10 CFU in the lung of immunized mice after an aerosol challenge with *M. tuberculosis*. Lungs from mice (n=7) immunized with CpG, 3 various Mtb Rv antigens, or a combination thereof were collected 4 wks after an aerosol challenge with 50-100 Mtb bacilli. CFU were counted after 2 wks of in vitro growth on agar plate. The data shown is the mean±SEM of a representative experiment.

FIG. 3B shows serum IgG2c antibody endpoint titers. Sera from mice (n=3-6) immunized with CpG, 3 various Mtb Rv antigens, or a combination thereof were collected 1 week after the 3$^{rd}$ immunization and tested for antigen specific IgG2c antibodies by ELISA. The sera from CpG groups were tested against all Rv antigens, while the other sera were tested against the Rv antigen used for immunization. The data shown is the mean±SD of a representative experiment.

FIG. 3C shows IFN-y released by antigen stimulated splenocytes. Splenocytes from mice immunized with CpG, 3 various Mtb Rv antigens, or a combination thereof were collected 3 weeks after the 3$^{rd}$ immunization and tested for antigen specific IFN-y cytokine responses by ELISA. The splenocytes were incubated for 72 h in media, or 10 μg/ml of the Rv antigens used for the immunization. The data shown is the mean±SD (n=3) in a representative experiment.

FIG. 3D shows relative frequencies of TNF$^+$ splenocytes in response to antigen specific stimulation. Splenocytes from mice immunized with CpG, 3 various Mtb Rv antigens, or a combination thereof were collected 3 weeks after the 3$^{rd}$ immunization and tested for antigen specific TNF cytokine responses by ELISPOT. The splenocytes were incubated for 48 h in media, or 10 μg/ml of the Rv antigens used for the immunization. The data shown is the mean±SD (n=3) in a representative experiment

FIG. 4A shows antigen specific serum IgG1 and IgG2c antibody endpoint titers. Sera from mice (n=3-6) immunized with saline, ID83, or ID93 fusion protein in GLA-SE adjuvant formulations were collected 1 week after the 3$^{rd}$ immunization and tested for ID83 and ID93 specific IgG1 and IgG2c antibodies by ELISA. The data shown is the mean±SD in a representative experiment.

FIG. 4B shows levels of IFN-y released by antigen stimulated splenocytes. Splenocytes from mice immunized with ID83 or ID93 in GLA-SE adjuvant formulation were collected 3 weeks after the 3$^{rd}$ immunization and tested for antigen specific IFN-y cytokine responses by ELISA. The splenocytes were incubated for 72 h in media, 3 μg/ml ConA, or 10 μg/ml of ID83 or ID93 fusion proteins. The data shown is the mean±SD (n=3) in a representative experiment.

FIGS. 5A and 5B show the immunogenicity of ID83 with different adjuvant formulations in C578L/6 mice.

FIG. 5A shows antigen specific serum IgG1 and IgG2c antibody endpoint titers. Sera from mice (n=3-6) immunized with saline, or ID83 fusion protein with different adjuvant formulations were collected 1 week after the 3rd immunization and tested for ID83 specific IgG1 and IgG2c antibodies by ELISA. The data shown is the mean±SD in a representative experiment.

FIG. 5B shows levels of IFN-y released by antigen stimulated splenocytes. Splenocytes from mice immunized with saline or ID83 with different adjuvant formulation were collected 3 weeks after the 3rd immunization and tested for antigen specific IFN-y cytokine responses by ELISA. The splenocytes were incubated for 72 h in media, 3 µg/ml ConA, or 10 µg/ml of ID83 fusion proteins. The data shown is the mean±SD (n=3) in a representative experiment.

FIGS. 7A and 7B show Ad5-ID83-specific immune responses and protection against an *M. tuberculosis* challenge.

FIG. 7A shows relative frequencies of IFN-y+ splenocytes in response to antigen specific stimulation. Splenocytes from mice immunized with saline, or 5×10⁹ Ad5-ID83 viral particles were collected 3 weeks after the 3rd immunization and tested for antigen specific IFN-y cytokine responses by ELISPOT. The splenocytes were incubated for 48 h in media, or 10 µg/ml ID83 fusion protein. The data shown is the mean±SD (n=3) in a representative experiment.

FIG. 7B shows Log 10 CFU in the lung of immunized mice after an aerosol challenge with *M. tuberculosis*. Lungs from mice (n=7) immunized with saline, or 5×10⁹ Ad5-ID83 viral particles were collected 4 wks after an aerosol challenge with 50-100 Mtb bacilli. CFU were counted after 2 wks of in vitro growth on agar plate. The data shown is the mean±SEM of a representative experiment.

BRIEF DESCRIPTION OF SEQUENCE IDENTIFIERS

Figure 1:
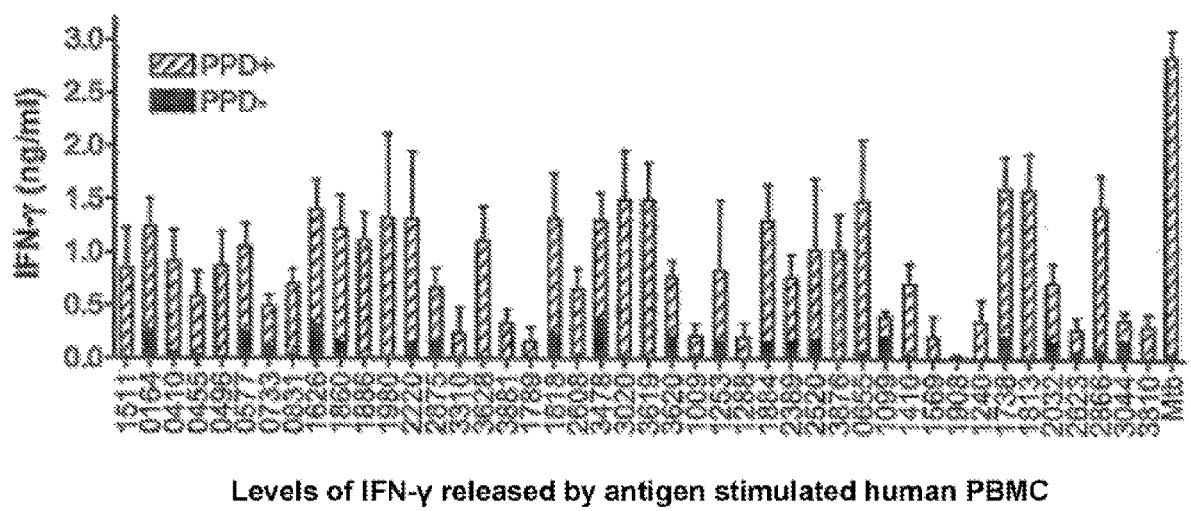
FIG. 1 shows the levels of IFN-y released by antigen stimulated human PBMC. PPD$^-$ and PPD$^+$ PBMC were incubated for 72 h in media, 10 μm/ml PHA, 10 μg/ml Mtb lysate, 50 μg/ml of the Mtb recombinant proteins. Mean (Mean$_{Ag}$–Mean$_{media}$)±SEM are shown for PPD$^+$ (n=18) and PPD$^-$ (n=7) PBMC.

SEQ ID NO: 1 represents the predicted amino acid sequence for Mtb Rv0164.

SEQ ID NO: 2 represents the sequence of a PCR amplified nucleic sequence encoding Mtb Rv0164.

SEQ ID NO: 3 represents the amino acid sequence of a recombinant Mtb Rv0164, including His tag.

SEQ ID NOs: 4 and 5 represent primers used to amplify Mtb Rv0164.

SEQ ID NO: 6 represents the predicted amino acid sequence for Mtb Rv0496.

SEQ ID NO: 7 represents the sequence of a PCR amplified nucleic sequence encoding Mtb Rv0496.

SEQ ID NO: 8 represents the amino acid sequence of a recombinant Mtb Rv0496, including His tag.

SEQ ID NOs: 9 and 10 represent primers used to amplify Mtb Rv0496.

SEQ ID NO: 11 represents the predicted amino acid sequence for Mtb Rv1738.

SEQ ID NO: 12 represents the sequence of a PCR amplified nucleic sequence encoding Mtb Rv1738.

SEQ ID NO: 13 represents the amino acid sequence of a recombinant Mtb Rv1738, including His tag.

SEQ ID NOs: 14 and 15 represent primers used to amplify Mtb Rv1738.

SEQ ID NO: 16 represents the predicted amino acid sequence for Mtb Rv1813.

SEQ ID NO: 17 represents the sequence of a PCR amplified nucleic sequence encoding Mtb Rv1813.

SEQ ID NO: 18 represents the amino acid sequence of a recombinant Mtb Rv1813, including His tag.

SEQ ID NOs: 19 and 20 represent primers used to amplify Mtb Rv1813.

SEQ ID NO: 21 represents the predicted amino acid sequence for Mtb Rv2389.

SEQ ID NO: 22 represents the sequence of a PCR amplified nucleic sequence encoding Mtb Rv2389.

SEQ ID NO: 23 represents the amino acid sequence of a recombinant Mtb Rv2389, including His tag.

SEQ ID NOs: 24 and 25 represent primers used to amplify MtbRv2389.

SEQ ID NO: 26 represents the predicted amino acid sequence for Mtb Rv2608.

SEQ ID NO: 27 represents the sequence of a PCR amplified nucleic sequence encoding Mtb Rv2608.

SEQ ID NO: 28 represents the amino acid sequence of a recombinant Mtb Rv2608, including His tag.

SEQ ID NOs: 29 and 30 represent primers used to amplify Mtb Rv2608.

SEQ ID NO: 31 represents the predicted amino acid sequence for Mtb Rv2866.

SEQ ID NO: 32 and 33 represent primers used to amplify Mtb Rv2866.

SEQ ID NO: 34 represents the sequence of a PCR amplified nucleic sequence encoding Mtb Rv2866.

SEQ ID NO: 35 represents the amino acid sequence of a recombinant Mtb Rv2866, including His tag.

SEQ ID NO: 36 represents the predicted amino acid sequence for Mtb Rv3020.

SEQ ID NO: 37 represents the sequence of a PCR amplified nucleic sequence encoding Mtb Rv3020.

SEQ ID NO: 38 represents the amino acid sequence of a recombinant Mtb Rv3020, including His tag.

SEQ ID NOs: 39 and 40 represent primers used to amplify Mtb Rv3020.

SEQ ID NO: 41 represents the predicted amino acid sequence for Mtb Rv3478.

SEQ ID NO: 42 represents the sequence of a PCR amplified nucleic sequence encoding Mtb Rv3478.

SEQ ID NO: 43 represents the amino acid sequence of a recombinant Mtb Rv3478, including His tag.

SEQ ID NOs: 44 and 45 represent primers used to amplify Mtb Rv3478.

SEQ ID NO: 46 represents the predicted amino acid sequence for Mtb Rv3619.

SEQ ID NO: 47 represents the sequence of a PCR amplified nucleic sequence encoding Mtb Rv3619.

SEQ ID NO: 48 represents the amino acid sequence of a recombinant Mtb Rv3619, including His tag.

SEQ ID NOs: 49 and 50 represent primers used to amplify MtbRv3619. Mtb Rv3620.

SEQ ID NO: 51 represents the predicted amino acid sequence for

SEQ ID NO: 52 represents the sequence of a PCR amplified nucleic sequence encoding Mtb Rv3620.

SEQ ID NO: 53 represents the amino acid sequence of a recombinant Mtb Rv3620, including His tag.

SEQ ID NOs: 54 and 55 represent primers used to amplify Mtb Rv3620.

SEQ ID NO: 56 represents the predicted amino acid sequence for Mtb Rv3810.

SEQ ID NO: 57 represents the sequence of a PCR amplified nucleic sequence encoding Mtb Rv3810.

SEQ ID NO: 58 represents the amino acid sequence of a recombinant Mtb Rv3810, including His tag.

SEQ ID NOs: 59 and 60 represent primers used to amplify Mtb Rv3810.

SEQ ID NO: 61 represents the predicted amino acid sequence for Mtb Rv3876.

SEQ ID NO: 62 represents the sequence of a PCR amplified nucleic sequence encoding Mtb Rv3876.

SEQ ID NO: 63 represents the amino acid sequence of a recombinant Mtb Rv3876, including His tag.

SEQ ID NOs: 64 and 65 represent primers used to amplify Mtb Rv3876.

SEQ ID NO: 66 represents a polynucleotide sequence encoding the fusion polypeptide Mtb36f.1.

SEQ ID NO: 67 represents the amino acid sequence of the recombinant Mtb fusion polypeptide Mtb36f 1, including His tag.

SEQ ID NOs: 68-71 represent primers used in the amplification and cloning of Mtb36f.1.

SEQ ID NO: 72 represents a polynucleotide sequence encoding the fusion polypeptide ID58.

SEQ ID NOs: 73-78 represent primers used in the amplification and cloning of ID58.

SEQ ID NO: 79 represents the amino acid sequence of the recombinant Mtb fusion polypeptide ID58, including His tag.

SEQ ID NO: 80 represents a polynucleotide sequence encoding the fusion polypeptide ID69.

SEQ ID NOs: 81-82 represent primers used in the amplification and cloning of ID69.

SEQ ID NO: 83 represents the amino acid sequence of the recombinant Mtb fusion polypeptide ID69, including His tag.

SEQ ID NO: 84 represents a polynucleotide sequence encoding the fusion polypeptide ID83.

SEQ ID NOs: 85-90 represent primers used in the amplification and cloning of ID83.

SEQ ID NO: 91 represents the amino acid sequence of the recombinant Mtb fusion polypeptide ID83, including His tag.

SEQ ID NO: 92 represents a polynucleotide sequence encoding the fusion polypeptide ID94.

SEQ ID NOs: 93-94 represent primers used in the amplification and cloning of ID94.

SEQ ID NO: 95 represents the amino acid sequence of the recombinant Mtb fusion polypeptide ID94, including His tag.

SEQ ID NO: 96 represents a polynucleotide sequence encoding the fusion polypeptide ID95.

SEQ ID NO: 97 represents the amino acid sequence of the recombinant Mtb fusion polypeptide ID95, including His tag.

SEQ ID NO: 98 represents a polynucleotide sequence encoding the fusion polypeptide ID120.

SEQ ID NO: 99 represents the amino acid sequence of the recombinant Mtb fusion polypeptide ID120, including His tag.

SEQ ID NO: 100 represents the predicted amino acid sequence for Rv0054.

SEQ ID NO: 101 represents the sequence of a PCR amplified nucleic sequence encoding Rv0054.

SEQ ID NO: 102 represents the amino acid sequence of a recombinant Rv0054, including His tag.

SEQ ID NO: 103 represents the predicted amino acid sequence for Rv0164.

SEQ ID NO: 104 represents the sequence of a PCR amplified nucleic sequence encoding Rv0164.

SEQ ID NO: 105 represents the amino acid sequence of a recombinant Rv0164, including His tag.

SEQ ID NO: 106 represents the predicted amino acid sequence for Rv0410.

SEQ ID NO: 107 represents the sequence of a PCR amplified nucleic sequence encoding Rv0410.

SEQ ID NO: 108 represents the amino acid sequence of a recombinant Rv0410, including His tag.

SEQ ID NO: 109 represents the predicted amino acid sequence for Rv0496.

SEQ ID NO: 110 represents the sequence of a PCR amplified nucleic sequence encoding Rv0496.

SEQ ID NO: 111 represents the amino acid sequence of a recombinant Rv0496, including His tag.

SEQ ID NO: 112 represents the predicted amino acid sequence for Rv0655.

SEQ ID NO: 113 represents the sequence of a PCR amplified nucleic sequence encoding Rv0655.

SEQ ID NO: 114 represents the amino acid sequence of a recombinant Rv0655, including His tag.

SEQ ID NO: 115 represents the predicted amino acid sequence for Rv0831.

SEQ ID NO: 116 represents the sequence of a PCR amplified nucleic sequence encoding Rv0831.

SEQ ID NO: 117 represents the amino acid sequence of a recombinant Rv0831, including His tag.

SEQ ID NO: 118 represents the predicted amino acid sequence for Rv1009.

SEQ ID NO: 119 represents the sequence of a PCR amplified nucleic sequence encoding Rv1009.

SEQ ID NO: 120 represents the amino acid sequence of a recombinant Rv1009, including His tag.

SEQ ID NO: 121 represents the predicted amino acid sequence for Rv1099.

SEQ ID NO: 122 represents the sequence of a PCR amplified nucleic sequence encoding Rv1099.

SEQ ID NO: 123 represents the amino acid sequence of a recombinant Rv1099, including His tag.

SEQ ID NO: 124 represents the predicted amino acid sequence for Rv1240.

SEQ ID NO: 125 represents the sequence of a PCR amplified nucleic sequence encoding Rv1240.

SEQ ID NO: 126 represents the amino acid sequence of a recombinant Rv1240, including His tag.

SEQ ID NO: 127 represents the predicted amino acid sequence for Rv1288.

SEQ ID NO: 128 represents the sequence of a PCR amplified nucleic sequence encoding Rv1288.

SEQ ID NO: 129 represents the amino acid sequence of a recombinant Rv1288, including His tag.

SEQ ID NO: 130 represents the predicted amino acid sequence for Rv1410.

SEQ ID NO: 131 represents the sequence of a PCR amplified nucleic sequence encoding Rv1410.

SEQ ID NO: 132 represents the amino acid sequence of a recombinant Rv1410, including His tag.

SEQ ID NO: 133 represents the predicted amino acid sequence for Rv1569.

SEQ ID NO: 134 represents the sequence of a PCR amplified nucleic sequence encoding Rv1569.

SEQ ID NO: 135 represents the amino acid sequence of a recombinant Rv1569, including His tag.

SEQ ID NO: 136 represents the predicted amino acid sequence for Rv1789.

SEQ ID NO: 137 represents the sequence of a PCR amplified nucleic sequence encoding Rv1789.

SEQ ID NO: 138 represents the amino acid sequence of a recombinant Rv1789, including His tag.

SEQ ID NO: 139 represents the predicted amino acid sequence for Rv1818.

SEQ ID NO: 140 represents the sequence of a PCR amplified nucleic sequence encoding Rv1818.

SEQ ID NO: 141 represents the amino acid sequence of a recombinant Rv1818, including His tag.

SEQ ID NO: 142 represents the predicted amino acid sequence for Rv1860.

SEQ ID NO: 143 represents the sequence of a PCR amplified nucleic sequence encoding Rv1860.

SEQ ID NO: 144 represents the amino acid sequence of a recombinant Rv1860, including His tag.

SEQ ID NO: 145 represents the predicted amino acid sequence for Rv1886.

SEQ ID NO: 146 represents the sequence of a PCR amplified nucleic sequence encoding Rv1886.

SEQ ID NO: 147 represents the amino acid sequence of a recombinant Rv1886, including His tag.

SEQ ID NO: 148 represents the predicted amino acid sequence for Rv1908.

SEQ ID NO: 149 represents the sequence of a PCR amplified nucleic sequence encoding Rv1908.

SEQ ID NO: 150 represents the amino acid sequence of a recombinant Rv1908, including His tag.

SEQ ID NO: 151 represents the predicted amino acid sequence for Rv2032.

SEQ ID NO: 152 represents the sequence of a PCR amplified nucleic sequence encoding Rv2032.

SEQ ID NO: 153 represents the amino acid sequence of recombinant Rv2032, including His tag.

SEQ ID NO: 154 represents the predicted amino acid sequence for Rv2220.

SEQ ID NO: 155 represents the sequence of a PCR amplified nucleic sequence encoding Rv2220.

SEQ ID NO: 156 represents the amino acid sequence of a recombinant Rv2220, including His tag.

SEQ ID NO: 157 represents the predicted amino acid sequence for Rv2608.

SEQ ID NO: 158 represents the sequence of a PCR amplified nucleic sequence encoding Rv2608.

SEQ ID NO: 159 represents the amino acid sequence of a recombinant Rv2608, including His tag.

SEQ ID NO: 160 represents the predicted amino acid sequence for Rv2623.

SEQ ID NO: 161 represents the sequence of a PCR amplified nucleic sequence encoding Rv2623.

SEQ ID NO: 162 represents the amino acid sequence of a recombinant Rv2623, including His tag.

SEQ ID NO: 163 represents the predicted amino acid sequence for Rv2875.

SEQ ID NO: 164 represents the sequence of a PCR amplified nucleic sequence encoding Rv2875.

SEQ ID NO: 165 represents the amino acid sequence of a recombinant Rv2875, including His tag.

SEQ ID NO: 166 represents the predicted amino acid sequence for Rv3044.

SEQ ID NO: 167 represents the sequence of a PCR amplified nucleic sequence encoding Rv3044.

SEQ ID NO: 168 represents the amino acid sequence of a recombinant Rv3004, including His tag.

SEQ ID NO: 169 represents the predicted amino acid sequence for Rv3310.

SEQ ID NO: 170 represents the sequence of a PCR amplified nucleic sequence encoding Rv3310.

SEQ ID NO: 171 represents the amino acid sequence of a recombinant Rv3310, including His tag.

SEQ ID NO: 172 represents the predicted amino acid sequence for Rv3619.

SEQ ID NO: 173 represents the sequence of a PCR amplified nucleic sequence encoding Rv3619.

SEQ ID NO: 174 represents the amino acid sequence of a recombinant Rv3619, including His tag.

SEQ ID NO: 175 represents the predicted amino acid sequence for Rv3810.

SEQ ID NO: 176 represents the sequence of a PCR amplified nucleic sequence encoding Rv3810.

SEQ ID NO: 177 represents the amino acid sequence of a recombinant Rv3810, including His tag.

SEQ ID NO: 178 represents the predicted amino acid sequence for Rv3881.

SEQ ID NO: 179 represents the sequence of a PCR amplified nucleic sequence encoding Rv3881.

SEQ ID NO: 180 represents the amino acid sequence of a recombinant Rv3881, including His tag.

SEQ ID NO: 181 represents the predicted amino acid sequence for Rv0455.

SEQ ID NO: 182 represents the sequence of a PCR amplified nucleic sequence encoding Rv0455.

SEQ ID NO: 183 represents the amino acid sequence of a recombinant Rv0455, including His tag.

SEQ ID NO: 184 represents the predicted amino acid sequence for Rv0577.

SEQ ID NO: 185 represents the sequence of a PCR amplified nucleic sequence encoding Rv0577.

SEQ ID NO: 186 represents the amino acid sequence of a recombinant Rv0577, including His tag.

SEQ ID NO: 187 represents the predicted amino acid sequence for Rv1626.

SEQ ID NO: 188 represents the sequence of a PCR amplified nucleic sequence encoding Rv1626.

SEQ ID NO: 189 represents the amino acid sequence of a recombinant Rv1626, including His tag.

SEQ ID NO: 190 represents the predicted amino acid sequence for Rv0733.

SEQ ID NO: 191 represents the sequence of a PCR amplified nucleic sequence encoding Rv0733.

SEQ ID NO: 192 represents the amino acid sequence of a recombinant Rv0733, including His tag.

SEQ ID NO: 193 represents the predicted amino acid sequence for Rv2520.

SEQ ID NO: 194 represents the sequence of a PCR amplified nucleic sequence encoding Rv2520.

SEQ ID NO: 195 represents the amino acid sequence of a recombinant Rv2520, including His tag.

SEQ ID NO: 196 represents the predicted amino acid sequence for Rv1253.

SEQ ID NO: 197 represents the sequence of a PCR amplified nucleic sequence encoding Rv1253.

SEQ ID NO: 198 represents the amino acid sequence of a recombinant Rv1253, including His tag.

SEQ ID NO: 199 represents the predicted amino acid sequence for Rv1980.

SEQ ID NO: 200 represents the sequence of a PCR amplified nucleic sequence encoding Rv1980.

SEQ ID NO: 201 represents the amino acid sequence of a recombinant Rv1980, including His tag.

SEQ ID NO: 202 represents the predicted amino acid sequence for Rv3628.

SEQ ID NO: 203 represents the sequence of a PCR amplified nucleic sequence encoding Rv3628.

SEQ ID NO: 204 represents the amino acid sequence of a recombinant Rv3628, including His tag.

SEQ ID NO: 205 represents the predicted amino acid sequence for Rv1884.

SEQ ID NO: 206 represents the sequence of a PCR amplified nucleic sequence encoding Rv1884.

SEQ ID NO: 207 represents the amino acid sequence of a recombinant Rv1884, including His tag.

SEQ ID NO: 208 represents the predicted amino acid sequence for Rv3872.

SEQ ID NO: 209 represents the sequence of a PCR amplified nucleic sequence encoding Rv3872.

SEQ ID NO: 210 represents the amino acid sequence of a recombinant Rv3872, including His tag.

SEQ ID NO: 211 represents the predicted amino acid sequence for Rv3873.

SEQ ID NO: 212 represents the sequence of a PCR amplified nucleic sequence encoding Rv3873.

SEQ ID NO: 213 represents the amino acid sequence of a 10 recombinant Rv3873, including His tag.

SEQ ID NO: 214 represents the predicted amino acid sequence for Rv1511.

SEQ ID NO: 215 represents the sequence of a PCR amplified nucleic sequence encoding Rv1511.

SEQ ID NO: 216 represents the amino acid sequence of a recombinant Rv1511, including His tag.

SEQ ID NO: 217 represents a polynucleotide sequence encoding the fusion polypeptide ID93.

SEQ ID NOs: 218-225 represent primers used in the amplification and cloning of ID93.

SEQ ID NO: 226 represents the amino acid sequence of the recombinant Mtb fusion polypeptide ID93, including His tag.

SEQ ID NO: 227 represents a polynucleotide sequence encoding the fusion polypeptide ID91.

SEQ ID NOs: 228-235 represent primers used in the amplification and cloning of ID91.

SEQ ID NO: 236 represents the amino acid sequence of the recombinant Mtb fusion polypeptide ID91, including His tag.

SEQ ID NO: 237 represents a polynucleotide sequence encoding the fusion polypeptide ID71.

SEQ ID NOs: 238-244 represent primers used in the amplification and cloning of ID71.

SEQ ID NO: 245 represents the amino acid sequence of the recombinant Mtb fusion polypeptide ID71, including His tag.

SEQ ID NO: 246 represents a polynucleotide sequence encoding the fusion polypeptide ID114.

SEQ ID NOs: 247-250 represent primers used in the amplification and cloning of ID114.

SEQ ID NO: 251 represents the amino acid sequence of the recombinant Mtb fusion polypeptide ID114, including His tag.

SEQ ID NO: 252 represents a polynucleotide sequence encoding the fusion polypeptide ID125.

SEQ ID NOs: 253-256 represent primers used in the amplification and cloning of ID125.

SEQ ID NO: 257 represents the amino acid sequence of the recombinant Mtb fusion polypeptide ID125, including His tag.

SEQ ID NO: 258 represents a polynucleotide sequence encoding the fusion polypeptide DID85.

SEQ ID NOs: 259-264 represent primers used in the amplification and cloning of DID85.

SEQ ID NO: 265 represents the amino acid sequence of the recombinant Mtb fusion polypeptide DID85, including His tag.

SEQ ID NO: 266 represents a polynucleotide sequence encoding the fusion polypeptide DID92.

SEQ ID NOs: 267-272 represent primers used in the amplification and cloning of DID92.

SEQ ID NO: 273 represents the amino acid sequence of the recombinant Mtb fusion polypeptide DID92, including His tag.

SEQ ID NO: 274 represents a polynucleotide sequence encoding the fusion polypeptide DID108.

SEQ ID NOs: 275-282 represent primers used in the amplification and cloning of DID108.

SEQ ID NO: 283 represents the amino acid sequence of the recombinant Mtb fusion polypeptide DID108, including His tag.

SEQ ID NO: 284 represents a polynucleotide sequence encoding the fusion polypeptide DID93.

SEQ ID NOs: 285-290 represent primers used in the amplification and cloning of DID93.

SEQ ID NO: 291 represents the amino acid sequence of the recombinant Mtb fusion polypeptide DID93, including His tag.

SEQ ID NO: 292 represents the predicted amino acid sequence for Rv3875.

SEQ ID NO: 293 represents the sequence of a PCR amplified nucleic sequence encoding Rv3875.

SEQ ID NO: 294 represents the amino acid sequence of a recombinant Rv3875, including His tag.

SEQ ID NOs: 295-296 represent primers used in the amplification and cloning of Rv0577.

SEQ ID NOs: 297-298 represent primers used in the amplification and cloning of Rv1626.

SEQ ID NOs: 299-300 represent primers used in the amplification and cloning of Ry0733.

SEQ ID NOs: 301-302 represent primers used in the amplification and cloning of Rv2520.

SEQ ID NOs: 303-304 represent primers used in the amplification and cloning of Rv1253.

SEQ ID NOs: 305-306 represent primers used in the amplification and cloning of Rv1980.

SEQ ID NOs: 307-308 represent primers used in the amplification and cloning of Rv3628.

SEQ ID NOs: 309-310 represent primers used in the amplification and cloning of Rv1844.

SEQ ID NOs: 311-312 represent primers used in the amplification and cloning of Ry3872.

SEQ ID NOs: 313-314 represent primers used in the amplification and cloning of Ry3873.

SEQ ID NOs: 315-316 represent primers used in the amplification and cloning of Ry1511.

SEQ ID NOs: 317-318 represent primers used in the amplification and cloning of Rv3875.

DETAILED DESCRIPTION

The present invention relates to highly antigenic/immunogenic compositions comprising *Mycobacterium* antigens. The compositions of the present invention generally comprise at least two heterologous polypeptides of a *Mycobacterium* species of the tuberculosis complex. A *Mycobacterium* species of the tuberculosis complex includes those species traditionally considered as causing the disease tuberculosis, as well as *Mycobacterium* environmental and opportunistic species that cause tuberculosis and lung disease in immune compromised patients, such as patients with AIDS, e.g., *Mycobacterium tuberculosis* (Mtb), *Mycobacterium bovis*, or *Mycobacterium africanum*, BCG, *Mycobacterium avium, Mycobacterium intracel/ulare, Mycobacterium celatum, Mycobacterium genavense, Mycobacterium haemophilum, Mycobacterium kansasii, Mycobacterium simiae, Mycobacterium vaccae, Mycobacterium fortuitum*, and *Mycobacterium scrofulaceum* (see, e.g., Harrison's Principles of Internal Medicine, volume 1, pp. 1004-1014 and 1019-1020. In a preferred embodiment, the *Mycobacterium* species to be prevented, treated or diagnosed according to the invention is *Mycobacterium tuberculosis* (Mtb). The sequences of antigens from *Mycobacterium* species are readily available. For example, *Mycobacterium tuberculosis* sequences can be found in Cole et al., *Nature* 393:537 (1998) and can be found at websites such as those maintained by the Wellcome Trust Sanger Institute and Institut Pasteur.

A. *Mycobacterium* Antigens and Fusions Thereof

The present invention, in one aspect, provides isolated *Mycobacterium* polypeptides, as described herein, including fusion polypeptides, and compositions containing same. Generally, a polypeptide of the invention will be an isolated polypeptide and may be a fragment (e.g., an antigenic/immunogenic portion) from an amino acid sequence disclosed herein, or may comprise an entire amino acid sequence disclosed herein. Polypeptides of the invention, antigenic/immunogenic fragments thereof, and other variants may be prepared using conventional recombinant and/or synthetic techniques.

In certain preferred embodiments, the polypeptides of the invention are antigenic/immunogenic, i.e., they react detectably within an immunoassay (such as an ELISA or T cell stimulation assay) with antisera and/or T cells from an infected subject. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T cell surface antigen receptors that recognize the polypeptide. Immunogenic portions may generally be identified using well known techniques, such as those summarized in Paul, *Fundamental Immunology,* 3rd ed., 243-247 (Raven Press, 1993) and references cited therein. Such techniques include screening polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein, and using well-known techniques.

In a particular embodiment, an antigenic/immunogenic portion of a polypeptide of the present invention is a portion that reacts with antisera and/or T cells at a level that is not substantially less than the reactivity of the full-length polypeptide (e.g., in an ELISA and/or T cell reactivity assay). Preferably, the level of immunogenic activity of the antigenic/immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

A polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous polynucleotide sequences contained in the polynucleotide sequences disclosed herein, or immunogenic fragments or variants thereof, or to one or more polynucleotide sequences which hybridize to one or more of these sequences under conditions of moderate to high stringency.

The present invention also provides polypeptide fragments, including antigenic/immunogenic fragments, comprising at least about 5, 10, 15, 20, 25, 50, or 100 contiguous amino acids, or more, including all intermediate lengths, of a polypeptide composition set forth herein, or those encoded by a polynucleotide sequence set forth herein.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., about 1-30 amino acids) has been removed from the N- and/or C-terminal of a mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutemic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUG | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | COG | CGU |
| Serine | Ser | S | AGC | AGU | UCA | UCC | UCG | UCU |
| Threonine | Thr | T | ACA | ACC | ACC | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, CA; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, CA; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain preferred embodiments of the invention, there are provided *Mycobacterium tuberculosis* fusion polypeptides, and polynucleotides encoding fusion polypeptides. Fusion polypeptide and fusion proteins refer to a polypeptide having at least two heterologous *Mycobacterium* sp. polypeptides, such as *Mycobacterium tuberculosis* polypeptides, covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein. *Mycobacterium tuberculosis* antigens are described in Cole et al., *Nature* 393:537 (1998), which discloses the entire *Mycobacterium tuberculosis* genome. Antigens from other *Mycobacterium* species that correspond to *Mycobacterium tuberculosis* antigens can be identified, e.g., using sequence comparison algorithms, as described herein, or other methods known to those of skill in the art, e.g., hybridization assays and antibody binding assays.

The fusion polypeptides of the invention generally comprise at least two antigenic polypeptides as described herein, and may further comprise other unrelated sequences, such as a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques. Preferably, a fusion protein is expressed as a recombinant protein. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Within preferred embodiments, an immunological fusion partner for use in a fusion polypeptide of the invention is derived from protein D, a surface protein of the gram-negative bacterium *Haemophilus* influenza B (WO 91/18926). Preferably, a protein D derivative comprises approximately the first third of the protein (e.g., the first N-terminal 100 110 amino acids), and a protein D derivative may be lipidated. Within certain preferred embodiments, the first 109 residues of a lipoprotein D fusion partner is included on the N-terminus to provide the polypeptide with additional exogenous T cell epitopes and to increase the expression level in *E. coli* (thus functioning as an expression enhancer). The lipid tail ensures optimal presentation of the antigen to antigen presenting cells. Other fusion partners include the non-structural protein from *influenzae* virus, NS1 (hemaglutinin). Typically, the N-terminal 81 amino acids are used, although different fragments that include T-helper epitopes may be used.

In another embodiment, an immunological fusion partner comprises an amino acid sequence derived from the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

B. Polynucleotide Compositions

The present invention also provides isolated polynucleotides, particularly those encoding the fusion polypeptides of the invention, as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein. The term "variants" also encompasses homologous genes of xenogenic origin.

In additional embodiments, the present invention provides isolated polynucleotides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200 500; 500 1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*Mycobacterium* polynucleotides and fusions thereof may be prepared, manipulated and/or expressed using any of a variety of well established techniques known and available in the art.

For example, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or immunogenicity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of □-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

C. Pharmaceutical and Vaccine Compositions

In another aspect, the present invention concerns formulations of one or more of the polynucleotide, polypeptide or other compositions disclosed herein in pharmaceutically-acceptable or physiologically-acceptable solutions for administration to a cell or an animal, either alone, or in combination with one or more other modalities of therapy. Such pharmaceutical compositions are particularly preferred for use as vaccines when formulated with a suitable immunostimulant/adjuvant system. The compositions are also suitable for use in a diagnostic context.

It will also be understood that, if desired, the compositions of the invention may be administered in combination with other agents as well, such as, e.g., other proteins or polypeptides or various pharmaceutically-active agents. There is virtually no limit to other components that may also be included, provided that the additional agents do not cause a significant adverse effect upon the objectives according to the invention.

In certain preferred embodiments the compositions of the invention are used as vaccines and are formulated in combination with one or more immunostimulants. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), Bortadella pertussis or *Mycobacterium* species or *Mycobacterium* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

In certain preferred embodiments, the adjuvant used in the present invention is a glucopyranosyl lipid A (GLA) adjuvant, as described in pending U.S. patent application Ser. No. 11/862,122, the disclosure of which is incorporated herein by reference in its entirety. For example, certain GLA compounds of interest are represented by the following formula:

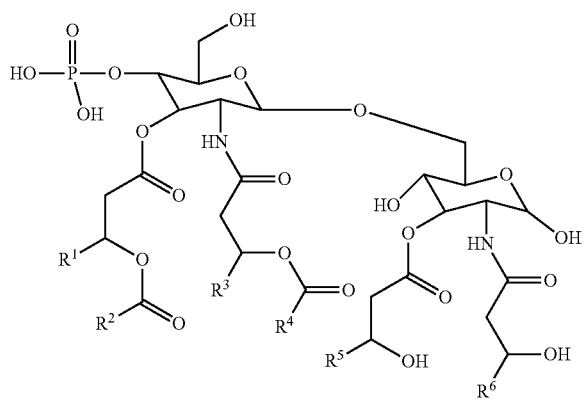

where: $R^1$, $R^3$, $R^5$ and $R^6$ are $C_{11}$-$C_{20}$ alkyl; and $R^2$ and $R^4$ are $C_{12}$-$C_{20}$ alkyl. In a more particular embodiment, $R^1$, $R^2$, $R^3$, $R^4$, $R^5$ and $R^6$ are $C_{14}$.

Other illustrative adjuvants useful in the context of the invention include Toll-like receptor agonists, such as TLR7 agonists, TLR7/8 agonists, and the like. Still other illustrative adjuvants include imiquimod (IMQ), gardiquimod (GDQ), resiquimod (RSQ), and related compounds.

Certain preferred vaccines employ adjuvant systems designed to induce an immune response predominantly of the Th1 type. High levels of Th1-type cytokines (e.g., IFN-γ, TNF, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman & Coffman, *Ann. Rev. Immunol.* 7:145-173 (1989).

Certain adjuvants for use in eliciting a predominantly Th1-type response include, for example, a combination of monophosphoryl lipid A, preferably 3-de-O-acylated monophosphoryl lipid A (3D-MPL™), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other illustrative formulations include more than one saponin in the adjuvant combinations of the present invention, for example combinations of at least two of the following group comprising QS21, QS7, Quil A, escin, or digitonin.

In a particular embodiment, the adjuvant system includes the combination of a monophosphoryl lipid A and a saponin derivative, such as the combination of QS21 and 3D-MPL™ adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL™ adjuvant and tocopherol in an oil-in-water emulsion is described in WO 95/17210.

Another enhanced adjuvant system involves the combination of a CpG-containing oligonucleotide and a saponin derivative as disclosed in WO 00/09159.

Other illustrative adjuvants include Montanide ISA 720 (Seppic, France), SAF (Novartis, Calif., United States), ISCOMS (CSL), MF-59 (Chiron), the SBAS series of adjuvants (e.g., SBAS-2, AS2', AS2," SBAS-4, or SBAS6, available from GlaxoSmithKline, Rixensart, Belgium), Detox, RC-529 (GlaxoSmithKline, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Compositions of the invention may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intradermal, subcutaneous, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641, 515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington: The Science and Practice of Pharmacy,* 20th Edition. Baltimore, MD: Lippincott Williams & Wilkins, 2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

D. Diagnostic Methods and Kits

As noted above, the compositions, fusion polypeptides and polynucleotides are also useful as diagnostic reagents for detecting and/or monitoring *Mycobacterium tuberculosis* infection in a patient. For example, the compositions, fusion polypeptides, and polynucleotides of the invention may be used in in vitro and in vivo assays for detecting humoral antibodies or cell-mediated immunity against *Mycobacte-*

*rium tuberculosis* for diagnosis of infection, monitoring of disease progression or test-of-cure evaluation.

Therefore, in certain embodiments, the invention provides improved diagnostic antigens for differentially diagnosing *Mycobacterium tuberculosis* infection based on serological examination, wherein the *Mycobacterium* antigens used in the diagnosis are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions or variants thereof, in any combination thereof mixed as separate antigens, or in fusion gene constructs. As demonstrated herein, combinations of the disclosed diagnostic antigens offer improved sensitivity in serological diagnostic testing.

The diagnostic methods and kits preferably employ a combination of two or more antigens as described herein. In certain embodiments, it will be preferred to use a multiple antigens as described herein, e.g., three or more, four or more, five or more, six or more, etc., in a diagnostic method of the invention. The antigens may be used in essentially any assay format desired, e.g., as individual antigens assayed separately, as multiple antigens assays simultaneously, as antigens immobilized on a solid support such as an array, or the like.

In a particular embodiment, the diagnostic antigens used in the methods herein are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions or variants thereof, in any combination thereof mixed as separate antigens, or in fusion gene constructs.

In one embodiment, there are provided diagnostic kits for detecting *Mycobacterium tuberculosis* infection in a biological sample, comprising (a) a polypeptide comprising at least an immunogenic portion of an antigen or fusion polypeptide described herein, and (b) a detection reagent.

In another embodiment, there are provided diagnostic kits for detecting *Mycobacterium tuberculosis* infection in a biological sample, comprising (a) an antibody or antigen binding fragment thereof that is specific for a polypeptide comprising at least an immunogenic portion of an antigen or fusion polypeptide described herein, and (b) a detection reagent.

In another embodiment, methods are provided for detecting the presence of *Mycobacterium tuberculosis* infection in a biological sample, comprising (a) contacting a biological sample with a monoclonal antibody that binds to an antigen or fusion polypeptide described herein; and (b) detecting in the biological sample the presence of *Mycobacterium tuberculosis* proteins that bind to the monoclonal antibody.

In yet another embodiment, methods are provided for detecting *Mycobacterium tuberculosis* infection in a biological sample, comprising (a) contacting the biological sample with an antigen combination or fusion polypeptide as described herein and (b) detecting in the biological sample the presence of antibodies and/or T-cells that bind thereto.

There are a variety of assay formats known to those of ordinary skill in the art for using purified antigen or fusion polypeptide to detect antibodies in a sample. See, e.g., Harlow and Lane, *Antibodies: A Laboratory Manual*, Cold Spring Harbor Laboratory, 1988. In one embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using any of a variety of techniques known and available in the art. The term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time.

In certain embodiments, the diagnostic assay employed is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin or Tween 20™ (Sigma Chemical Co., St. Louis, MO). The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody to *Mycobacterium tuberculosis* within an infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. The detection reagent generally contains a binding agent (such as, for example, Protein A, Protein G, immunoglobulin, lectin or free antigen) conjugated to a reporter group. Illustrative reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art.

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *Mycobacterium tuberculosis* antibodies in a sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the mean is considered positive for *Mycobacterium tuberculosis* antibodies and *Mycobacterium tuberculosis* infection. In another embodiment, the cut-off value is determined using a Receiver Operator Curve, according to the method of Sackett et al., *Clinical Epidemiology: A Basic Science for Clinical Medicine*, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for *Mycobacterium tuberculosis* infection.

In another embodiment, a diagnostic assay may be performed in a flow-through or strip test format, wherein the antigen or fusion polypeptide is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of *Mycobacterium tuberculosis* antibodies in the sample. Such tests can typically be performed with a very small amount (e.g., one drop) of patient serum or blood.

In yet another embodiment, methods are provided for detecting *Mycobacterium tuberculosis* in a biological sample using antibodies (which may be polyclonal or monoclonal) and/or T-cells specific for one or more antigens, fusion polypeptides and/or immunogenic portions of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

EXAMPLES

Example 1

Cloning and Expression of Recombinant Rv0164

Using H37Rv genomic DNA as template, Rv0164 was PCR amplified using the primers set forth in SEQ ID NOs: 4 and 5, below:

```
Primer 5'-Rv0164-5his-NdeI:
                                   (SEQ ID NO: 4)
TAGGATCCCATATGACGGCAATCTCGTGCTCAC Primer 3'-Rv0164-3HindIII:
                                   (SEQ ID NO: 5)
TAGAATTCAAGCTTTTAGCTGGCCGCCAGCTGCTC
```

The following amplification conditions were used: 94° C. 0.5 min., 55° C. 0.5 min., 68° C. 1 min for 30 cycles to give the product set forth in SEQ ID NO: 2. The PCR product was digested with NdeI/HindIII and cloned into pET 28a. Plasmid containing the Rv0164 gene was transformed into expression host and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000× g and stored at −20° C. After lysis of a 1 L induction by sonication and clarification of the supernatant, the Rv0164 protein remained in the insoluble fraction. This fraction was then washed 2× in 1% CHAPS detergent, 20 mM Tris HCl pH 8.0, and then solublized in 8M Urea. Purification was achieved using 2 rounds of Ni-NTA affinity chromatography (Qiagen) under denaturing conditions with and the Rv0164 protein was eluted using 300 mM Imidazole. After SDS-PAGE analysis, fractions containing the purified protein were dialyzed against 10 mM Tris pH 8.0. Protein concentration was determined by Bradford Assay and residual endotoxin levels were determined by the Llimulus Amoebcyte Assay. The amino acid sequence of the recombinant protein is set forth in SEQ ID NO: 3.

Example 2

Cloning and Expression of Recombinant Rv0496

Using H37Rv genomic DNA as template, Rv0496 was PCR amplified using the following primers:

```
5'-Rv0496-5his-NdeI
                                   (SEQ ID NO: 9)
TAGGATCCCATATGGTCGATGCCCACCGCGGC 3'-Rv0496-3HindIII
                                   (SEQ ID NO: 10)
TAGAATTCAAGCTTTCATGGTTTGCTGCCTCTCGA
```

Amplification was performed under the following conditions: 94° C. 0.5 min., 55° C. 0.5 min., 68° C. 2 min for 30 cycles, to give the product set forth in SEQ ID NO: 7. The PCR product was digested with NdeI/HindIII and cloned into pET28a. Rv0496 was transformed into expression hosts and Rosetta2 plysS. After lysis of a 1 L induction, it went into the inclusion body. Ni-NTA was performed twice under denaturing conditions, then dialyzed against 10 mM Tris pH 10. The amino acid sequence of the recombinant protein is set forth in SEQ ID NO: 8.

Example 3

Cloning and Expression of Recombinant Rv1738

Using H37Rv genomic DNA as template, Rv1738 was PCR amplified using the following primers:

```
5'-Rv1738-5his-NdeI
                                   (SEQ ID NO: 14)
CAATTACATATGCATCACCATCACCATCACATGTGCGGCGAC

CAGTCGGAT

3'-Rv1738-3EcoRI
                                   (SEQ ID NO: 15)
CAATTAGAATTCTCAATACAACAATCGCGCCGG
```

Amplification was performed using the following conditions: 95° C. 1 min., 58° C. 1 min., 72° C. 1 min for 35 cycles, to give the product set forth as SEQ ID NO: 12. The PCR product was digested with NdeI/EcoRI and cloned into pET 17b. Rv1738 was transformed into expression hosts BL-21plysE and plysS. After lysis of a 1 L induction, protein remained in the soluble supernatant. Ni-NTA was performed under denaturing conditions, then dialyzed against 10 mM Tris pH 8.0. The amino acid sequence of the recombinant protein is set forth in SEQ ID NO: 13.

Example 4

Cloning and Expression of Recombinant Rv1813

Using H37Rv genomic DNA as template, Rv1813 was PCR amplified using the following primers:

```
5'-Rv1813-5his33-NdeI-
                                   (SEQ ID NO: 19)
CAATTACATATGCATCACCATCACCATCACCATCTCGCCAAC GGtTTCGATG 3'-Rv1813-3EcoRI-
                                   (SEQ ID NO: 20)
CAATTAGAATTCTTAGTTGCACGCCCAGTTGAC
```

The amplification was performed using the following conditions 95° C. 1 min., 58° C. 1 min., 72° C. 1 min for 35 cycles, to give the product set forth in SEQ ID NO: 17. The PCR product was digested with NdeI/EcoRI and cloned into pET 17b. Rv1813 was transformed into expression hosts BL-21plysE and Rosetta plysS. After lysis of a 1 L induction, protein went into the inclusion body. Ni-NTA was performed under denaturing conditions, then dialyzed against 10 mM Tris pH 8.0. The amino acid sequence of the recombinant protein is set forth in SEQ ID NO: 18.

Example 5

Cloning and Expression of Recombinant Rv2389 (RPF-D)

Using H37Rv genomic DNA as template, Rv2389 was PCR amplified using the following primers:

```
5'-Rv2389-5his50-NdeI-
                                      (SEQ ID NO: 24)
CAATTACATATGCATCACCATCACCATCACGACGACATCGATT

GGGACGCC

3'-Rv2389-3EcoRI-
                                      (SEQ ID NO: 25)
CAATTAGAATTCTCAATCGTCCCTGCTCCCCGA
```

Amplification was performed under the following conditions: 95° C. 1 min., 58° C. 1 min., 72° C. 1 min for 35 cycles, to give the product set forth in SEQ ID NO: 22. The PCR product was digested with NdeI/EcoRI and cloned into pET 17b (pET construct begins at aa49). Rv2389 was transformed into expression hosts BL-21plysE and Rosetta plysS. After lysis of a 1 L induction, protein remained in the soluble fraction. Ni-NTA was performed under denaturing conditions, then dialyzed against 10 mM Tris pH 8.0. The amino acid sequence of the recombinant protein is set forth in SEQ ID NO: 23.

Example 6

Cloning and Expression of Recombinant Rv2608

Using H37Rv genomic DNA as template, Rv2608 was PCR amplified using the following primers:

```
5'-Rv2608-5-NdeI-
                                      (SEQ ID NO: 29)
TAGGATCCCATATGAATTTCGCCGTTTTGCCG

3'-Rv2608-3-HindIII-
                                      (SEQ ID NO: 30)
TAGAATTCAAGCTTTTAGAAAAGTCGGGGTAGCGCC
```

Amplification was performed using the following conditions 94° C. 0.5 min., 55° C. 0.5 min., 68° C. 2 min for 30 cycles, to give the product set forth in SEQ ID NO: 27. The gel purified PCR product was digested with NdeI/HindIII and cloned into the expression vector pET28a (Clonetech) (pET construct begins at amino acid 1). Rv2608 was transformed into expression hosts and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000× g and stored at −20° C. After lysis of a 1 L induction by sonication and clarification of the supernatant, the Rv2608 protein remained in the insoluble fraction. This fraction was then washed 2× in 1% CHAPS detergent, 10 mM Tris HCl pH 8.0, and then solublized in 8M Urea. Purification was performed using Ni-NTA affinity chromatography (Qiagen) 2× under denaturing conditions with and the Rv2608 protein was eluted using 300 mM Imidazole. After SDS-PAGE analysis, fractions containing the purified protein were dialyzed against 10 mM Tris pH 8.0. Protein concentration was determined by BCA assay and residual endotoxin levels were determined by the Llimulus Amoebcyte Assay. The amino acid sequence of the recombinant protein is set forth in SEQ ID NO: 28.

Example 7

Cloning and Expression of Recombinant Rv2866

Rv2866 was amplified from genomic template by PCR, using the following primers:

```
5'-Rv2866-5NdeI-
                                      (SEQ ID NO: 32)
CAATTACATATGCCTTCCACCGTGCCCTTCACC

3'-Rv2866-3HindIII-
                                      (SEQ ID NO: 33)
CAATTAAAGCTTCTATCGGCGGTAGATGTCCGCGCG.
```

The following amplification conditions were used: 94° C. for 0.5 min., 66° C. for 0.50 min., 68° C. for 1.50 min., 35 cycles), to give the product set forth in SEQ ID NO: 34. Product was digested with NdeI/HindIII and cloned into pET28.a vector. Rv2866 was expressed by host strain BL-21 plysS. The pellet and supernatant were bound with Ni resin under denaturing conditions. Dialysis was performed in 20 mM Tris pH 6. The amino acid sequence of the recombinant protein is set forth in SEQ ID NO: 35.

Example 8

Cloning and Expression of Recombinant Rv3020

Using H37 genomic DNA as template, Rv3020 was PCR amplified using the following primers:

```
5'-Rv3020-5his-NdeI-
                                      (SEQ ID NO: 39)
TAGGATCCCATATGAGTTTGTTGGATGCCCATAT 3'-Rv3020-3HindIII-
                                      (SEQ ID NO: 40)
TAGAATTCAAGCTTTTAAAACCCGGTGTAGCTGGAC
```

The following amplification conditions were employed: 94° C. 0.5 min., 55° C. 0.5 min., 68° C. 1 min. for 30 cycles, yielding the product set forth in SEQ ID NO: 37. The PCR product was digested with NdeI/HindIII and cloned into pET 28a. Plasmid containing the Rv3020 gene was transformed into expression host and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000× g and stored at −20° C. After lysis of a 1 L induction by sonication and clarification of the supernatant, the Rv3020 protein remained in the insoluble fraction. This fraction was then washed 2× in 1% CHAPS detergent, 20 mM Tris HCl pH 8.0, and then solublized in 8M Urea. Purification was performed using Ni-NTA affinity chromatography (Qiagen) under denaturing conditions with and the Rv3020 protein was eluted using 250 mM Imidazole. After SDS-PAGE analysis, fractions containing the purified protein were dialyzed against 10 mM Tris pH 8.0. Protein concentration was determined by Bradford Assay and residual endotoxin levels were determined by the Llimulus Amoebcyte Assay. The amino acid sequence of the recombinant protein is set forth in SEQ ID NO: 38.

Example 9

Cloning and Expression of Recombinant Rv3478

Using H37Rv genomic DNA as template, Rv3478 was amplified using the following primers:

```
5'-Rv3478-5his-NdeI-
                                    (SEQ ID NO: 44)
TAGGATCCCATATGGTGGATTTCGGGGCGTTAC 3'-Rv3478-3HindIII-
                                    (SEQ ID NO: 45)
TAGAATTCAAGCTTCTATCCGGCGGCCGGTGTGCG
```

Rv3478 was amplified using polymerase chain reaction (PCR) with the following conditions 94° C. 0.5 min., 55° C. 0.5 min., 68° C. 2 min. for 30 cycles. The gel purified PCR product (SEQ ID NO: 42) was digested with NdeI/HindIII and cloned into the expression vector pET28a (Clonetech). Rv3478 was transformed into expression hosts and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000×g and stored at −20° C. After lysis of a 1 L induction by sonication and clarification of the supernatant, the Rv3478 protein remained in the insoluble fraction. This fraction was then washed 2× in 1% CHAPS detergent, 10 mM Tris HCl pH 8.0, and then solublized in 8M Urea. Purification was done using Ni-NTA affinity chromatography (Qiagen) 2× under denaturing conditions with and the Rv3478 protein was eluted using 300 mM Imidazole. After SDS-PAGE analysis, fractions containing the purified protein were dialyzed against 10 mM Tris pH 8.0. Protein concentration was determined by BCA assay and residual endotoxin levels were determined by the Llimulus Amoebcyte Assay. The amino acid sequence of the recombinant protein is set forth in SEQ ID NO: 43.

Example 10

Cloning and Expression of Recombinant Rv3619

Using H37Rv genomic DNA as template, Rv3619 was amplified using the following primers.

```
5'-Rv3619-5his-NdeI-
                                    (SEQ ID NO: 49)
TAGGATCCCATATGACCAT

CAACTATCAATTCG

3'-Rv3619-3HindIII-
                                    (SEQ ID NO: 50)
TAGAATTCAAGCTTTTAGG

CCCAGCTGGAGCCGAC
```

Rv3619 was amplified using polymerase chain reaction (PCR) with the following conditions 94° C. 0.5 min., 55° C. 0.5 min., 68° C. 1 min. for 30 cycles. The gel purified PCR product (SEQ ID NO: 47) was digested with NdeI/HindIII and cloned into the expression vector pET28a (Clonetech). Rv3619 was transformed into expression hosts and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000× g and stored at −20° C. After lysis of a 1 L induction by sonication and clarification of the supernatant, the Rv3619 protein remained in the insoluble fraction. This fraction was then washed 2× in 1% CHAPS detergent, 10 mM Tris HCl pH 8.0, and then solublized in 8M Urea. Purification was performed using Ni-NTA affinity chromatography (Qiagen) under denaturing conditions with and the Rv3619 protein was eluted using 300 mM Imidazole. After SDS-PAGE analysis, fractions containing the purified protein were dialyzed against 10 mM Tris pH 8.0. Protein concentration was determined by Bradford Assay and residual endotoxin levels were determined by the Llimulus Amoebcyte Assay. The amino acid sequence of the recombinant protein is set forth in SEQ ID NO: 48.

Example 11

Cloning and Expression of Recombinant Rv3620

Using H37Rv genomic DNA as template, Rv3620 was PCR amplified using the following primers:

```
5'-Rv3620-5his-NdeI-
                                    (SEQ ID NO: 54)
TAGGATCCCATATGACCT

CGCGTTTTATGACG

3'-Rv3620-3HindIII-
                                    (SEQ ID NO: 55)
TAGAATTCAAGCTTTCAGC

TGCTGAGGATCTGCTG
```

Rv3620 was PCR amplified with conditions 94° C. 0.5 min., 55° C. 0.5 min., 68° C. 1 min. for 30 cycles. The PCR product (SEQ ID NO: 52) was digested with NdeI/HindIII and cloned into pET28a. Rv3620 was transformed into expression host Rosetta2 plysS. After lysis of a 1 L induction, protein went into the inclusion body. Ni-NTA was performed under denaturing conditions, then purified antigen dialyzed against 20 mM Tris pH 8.0, 50 mM NaCl. The amino acid sequence of the recombinant protein is set forth in SEQ ID NO: 53.

Example 12

Cloning and Expression of Recombinant Rv3810

Using H37Rv genomic DNA as template, Rv3810 was PCR amplified using the following primers:

```
5'-Rv3810-5his23-NdeI-
                                    (SEQ ID NO: 59)
CAATTACATATGCATCACCATCA

CCATCACAGTCCTTGTGCATATT

TTCTTGTC

3'-Rv3810-3XhoI-
                                    (SEQ ID NO: 60)
CAATTACTCGAGTT

AGGCGACCGGCACGGTGATTGG
```

Rv3810 was PCR amplified with conditions 95° C. 1 min., 58° C. 1 min., 72° C. 1.5 min. for 35 cycles. The PCR product (SEQ ID NO: 57) was digested with NdeI/XhoI and cloned into pET 17b (pET construct begins at amino acid 23). Rv3810 was transformed into expression hosts BL-21plysE and Rosetta plysS. After lysis of a 1 L induction, protein went into the inclusion body. Ni-NTA was performed under denaturing conditions, then dialyzed against 10 mM Tris pH 8.0. The amino acid sequence of the recombinant protein is set forth in SEQ ID NO: 58.

Example 13

Cloning and Expression of Recombinant Rv3876

Rv3876 was PCR amplified from genomic DNA using the following amplification primers:

```
Rv3876F-Nde-5':
                                      (SEQ ID NO: 64)
GATCCCATGGGCATATGGCGGCCGACTACGAC

Rv3876R-EcorRI-3':
                                      (SEQ ID NO: 65)
GTCAGAATTCTCAACGACGTCCAGCCCT
```

Amplification was performed using the following conditions: 94° C. 30 sec., 55° C. 30 sec., 72° C. 2 min. for 30 cycles. The PCR product was ligated into the shuttle vector pGemT. Positive clones were identified on LB agar-x-gal plates by blue/white selection. The Rv3876 gene product was digested with NdeI/EcoRI and cloned into pET 28a. Rv3876c was transformed into expression host BL-21 (DE3) plysS. After lysis of a 1 L induction, protein remained in the insoluble fraction. Ni-NTA was performed under denaturing conditions, then dialyzed against 20 mM Tris pH 8.0. The amino acid sequence of the recombinant protein is set forth in SEQ ID NO: 63.

Example 14

Cloning and Expression of Recombinant Fusion Protein MTB36F.1

The following primers were used in the construction of fusion construct Mtb36f.1:

```
5'-Rv2389-5NdeI50-
                                      (SEQ ID NO: 68)
CAATTACATATGGACGAC

ATCGATTGGGACGCC

3'-Rv2389-3SacIgo-
                                      (SEQ ID NO: 69)
CAATTAGAGCTCATCGTCC

CTGCTCCCCGAACA

5'-Rv3810-5SacI23-
                                      (SEQ ID NO: 70)
CAATTAGAGCTCAGTCCT

TGTG]CATATTTTCTTG

3'-Rv3810-3HindIII-KpnI-
                                      (SEQ ID NO. 71)
CAATTAAAGCTTTTAGGTACCGG

CGACCGGCACGGTGATTGG
```

Using previously cloned plasmid DNA of Rv2389 and Rv3810, the Mtb36f.1 components were PCR amplified using the following conditions: 94° C. 30 sec., 58° C. 30 sec., 68° C. 1 min. for 35 cycles. The 5' Rv2389 PCR product as digested with NdeI/SacI and cloned into pET 28a. The 3' Rv3810 PCR product was digested with SacI/HindIII and cloned into the Rv2389 containing pET 28a construct. Mtb36f.1 (SEQ ID NO: 66) was transformed into expression host BL-21(DE3)plysS. After lysis of a 1 L induction, protein remained in the soluble fraction. Ni-NTA was performed under native conditions, then dialyzed against 20 mM Tris pH 8.0. The amino acid sequence of the recombinant fusion protein is set forth in SEQ ID NO: 67.

Example 15

Cloning and Expression of Recombinant Fusion Protein ID58

The following primers were used in for cloning the fusion construct ID58, which comprises fusion partners derived from Mtb Rv1813, Rv3620 and Rv0496

```
5': Rv1813mat-5NdeI-KpnI
                                      (SEQ ID NO: 73)
CAATTACATATGGGTACCCATCT

CGCCAACGGTTCGATG

3': Rv1813mat-3SacIgo
                                      (SEQ ID NO: 74)
CAATTAGAGCTCGTTGCACGCC

CAGTTGACGAT

5': Rv3620-5SacI
                                      (SEQ ID NO: 75)
CAATTAGAGCTCATGACCTCGC

GTTTTATGACG

3': Rv3620-3SalIgo
                                      (SEQ ID NO: 76)
CAATTAGTCGACGCTGCTGAGGA

TCTGCTGGGA

5': Rv0496-5SalI
                                      (SEQ ID NO: 77)
CAATTAGTCGACATGGTCGATGC

CCACCGCGGC

3': Rv0496-3ScaI-HindIII
                                      (SEQ ID NO: 78)
CAATTAAAGCTTTTAAGTACTTG

GTTTGCTGCCTCTCGATCG
```

Rv1813 and Rv3620 were PCR amplified from genomic template DNA (94° C. for 0.5 min., 58° C. for 0.5 min., 58° C. for 1:5 min.; 35 cycles). Rv1813 was digested with NdeI/SacI then cloned into pET28.a vector. Rv3620 was digested with SacI/SalI then ligated into the Rv1813pET construct. Rv0496 was amplified from plasmid template by PCR (94° C. for 0:30; 60° C. for 0:30; 68° C. for 1:30; 35 cycles). Product was digested with SalI/HindIII and cloned into pET28.a-Rv1813-3620 vector. ID58-pET28.a had some point mutations so site directed mutagenesis was used to insert the correct nucleic acids. The ID58 fusion construct has a polynucleotide sequence set forth in SEQ ID NO: 72, encoding the fusion protein set forth in SEQ ID NO: 79. ID58 was expressed in host BL-21plysS 2XYT growth media, 37° C.). Induction was with 1 mM IPTG at OD 0.471 and cells were harvested at OD 1.36. Cell pellet was suspended in lysis buffer (20 mM Tris pH8, 100 mM NaCl, 2 mM PMSF) and froze. ID58 forms an inclusion body and was processed the same as ID83. Fractions from the flow through bind were dialyzed in 20 mM Tris pH 8.5.

Example 16

Cloning and Expression of Recombinant Fusion Protein ID69

The following primers were used in for cloning the fusion construct ID69, which comprises fusion partners derived from Rv2389, Rv1813, Rv3620 and Rv0496:

```
5': Rv2389mat-5NdeI
                                   (SEQ ID NO: 81)
CAATTACATATGGACGACATCGATTGGGACGC 3': Rv2389mat-3KpnI-HindIII
                                   (SEQ ID NO: 82)
CAATTAAAGCTTTTAAGTACTTGGTTTGCTGC

CTCTCGATCG
```

Rv2389 was PCR amplified from genomic template (94° C. for 0.5 min., 58° C. for 0.5 min., 68° C. for 1.5 min.; 35 cycles), digested with NdeI/HindIII, and ligated into pET28.a. ID58-pET28.a vector was digested with KpnI/HindIII to drop out the insert. ID58 was ligated into Rv2389-pET28.a vector (also digested with KpnI/HindIII). The fusion construct has a polynucleotide sequence set forth in SEQ ID NO: 80, encoding the fusion protein set forth in SEQ ID NO: 83. ID69 was expressed in host BL-21plysS (1 L, 2XYT growth media, 37° C.). Cell pellet was suspended in lysis buffer (20 mM Tris pH8, 100 mM NaCl, 2 mM PMSF) and froze. ID69 forms an inclusion body and was purified the same as ID83.

Example 17

Cloning and Expression of Recombinant Fusion Protein ID83

The following primers were used in for cloning the fusion construct ID83, which comprises fusion partners from Rv1813, Rv3620 and Rv2608:

```
5': Rv1813mat-5NdeI-KpnI
                                   (SEQ ID NO: 85)
CAATTACATATGGGTACCCATCTCGCCAACGGT TCGATG
3': Rv1813mat-3SacIgo
                                   (SEQ ID NO: 86)
CAATTAGAGCTCGTTGCACGCCCAGTTGACGAT 5': Rv3620-5SacI
                                   (SEQ ID NO: 87)
CAATTAGAGCTCATGACCTCGCGTTTTATGACG 3': Rv3620-3SalIgo
                                   (SEQ ID NO: 88)
CAATTAGTCGACGCTGCTGAGGATCTGCTGGGA 5': Rv2608-5SaII
                                   (SEQ ID NO: 89)
CAATTAGTCGACATGAATTTCGCCGTTTTGCCG 3': Rv2608-3ScaI-HindIII
                                   (SEQ ID NO: 90)
CAATTAAAGCTTTTAAGTACTGAAAAGTCGGGG

TAGCGCCGG
```

Rv1813 and Rv3620 were PCR amplified from genomic template DNA (94° C. for 0.5 min.; 58° C. for 0.5 min., 58° C. for 1.5 min.; 35 cycles). Rv1813 was digested with NdeI/SacI then cloned into pET28.a vector. Rv3620 was digested with SacI/SalI then ligated into the Rv1813pET construct. Rv2608 was amplified from plasmid template by PCR (94° C. for 0.5 min., 58° C. for 0.5 min., 68° C. for 1.5 min.; 35 cycles). Product was digested with SalI/HindIII and cloned into pET28.a-Rv1813-3620 vector. The fusion construct has a polynucleotide sequence set forth in SEQ ID NO: 84, encoding the fusion protein set forth in SEQ ID NO: 91.

ID83 was expressed in host BL-21plysS (2 L, 2XYT growth media, 37° C.). Induced with 1 mM IPTG at OD 0.77 and harvested at OD 1.93. Cell pellet was suspended in lysis buffer (20 mM Tris pH8, 100 mM NaCl, 2 mM PMSF) and froze. The cell pellet was then thawed, lysed by sonication, and spun at 7,000 rcf for 20 minutes. ID83 is an inclusion body protein. The pellet was washed 2× with 1% Chaps. The pellet was solubilized in 60 mL in binding buffer (8M urea, 20 mM Tris pH 8, 100 mM NaCl) and bound to 16 mL Ni-NTA resin at RT for 1 hour. The resin was washed (50 mL 0.5% DOC for 20 minutes; 80 mL 60% IPA for 30 minutes, 50 mL 0.5% DOC rinse) and then eluted with binding buffer with 300 mM imidazol. The supernatant from the first bind was bound to an additional 8 mL resin and processed as indicated above. The aforementioned purifications removed breakdown products. Another Ni-NTA bind was performed overnight at 4° C. in 160 mL (binding buffer with 50 mM NaCl) with 32 mL resin. The resin was washed and eluted as indicated above. The fractions from this bind were dialyzed in 20 mM Tris pH8.

Example 18

Cloning and Expression of Recombinant Fusion Protein ID94

The following primers were used in for cloning the fusion construct ID94, which comprises fusion partners derived from Rv2389, Rv1813, Rv3620 and Rv2608:

```
5': Rv2389mat-5NdeI
                                   (SEQ ID NO: 93)
CAATTACATATGGACGACATCGATTGGGACGCC 3': Rv2389mat-3KpnI-HindIII
                                   (SEQ ID NO: 94)
CAATTAAAGCTTTTAAGTACTTGGTTTGCTGCCT

CTCGATCG
```

Rv2389 was PCR amplified from genomic template (94° C. for 0.5 min., 58° C. for 0.5 min., 68° C. for 1.5 min., 35 cycles), digested with NdeI/HindIII, and ligated into pET28.a. ID83-pET28.a vector was digested with KpnI/HindIII to drop out the insert. ID83 was ligated into Rv2389-pET28.a vector (also digested with KpnI/HindIII). The fusion construct has a polynucleotide sequence set forth in SEQ ID NO: 92, encoding the fusion protein set forth in SEQ ID NO: 95. ID94 was expressed in host BL-21plysS (1 L, 2XYT growth media, 37° C.). Expression was induced with 1 mM IPTG at OD 0.50 and harvested at OD 1.41. Cell pellet was suspended in lysis buffer (20 mM Tris pH8, 100 mM NaCl, 2 mM PMSF) and froze. ID94 forms an inclusion body and was processed the same as ID83. ID94 did not bind well overnight so the volume was doubled with 8M urea and BME was added to 10 mM. The less concentrated solutions were bound the Ni-NTA resin at RT for 2 hours then overnight at 4° C. The resin was washed and eluted as previously indicated. The fractions from this purification were dialyzed in 20 mM Tris pH8.

Example 19

Cloning and Expression of Recombinant Fusion Protein ID95

ID95 is a fusion construct comprising fusion partners derived from Rv2389, Rv3810, Rv1813, Rv3620 and Rv0496. ID58-pET28.a vector was digested with KpnI/HindIII to drop out the insert. The ID58 insert was ligated into previously made 36f.1-pET28.a vector (also digested with KpnI/HindIII). The fusion construct has a polynucleotide sequence set forth in SEQ ID NO: 96, encoding the fusion protein set forth in SEQ ID NO: 97. ID95 was expressed in host BL-21plysS (1 L, 2XYT growth media, 37° C.). Cell pellet was suspended in lysis buffer (20 mM Tris pH8, 100 mM NaCl, 2 mM PMSF) and froze. ID95 forms an inclusion body and was purified the same as ID83.

Example 20

Cloning and Expression of Recombinant Fusion Protein ID120

ID120 is a fusion construct comprising fusion partners derived from Rv2389, Rv3810, Rv1813, Rv3620 and Rv2608. ID83-pET28.a vector was digested with KpnI/HindIII to drop out the insert. The ID83 insert was ligated into previously made 36f.1-pET28.a vector (also digested with KpnI/HindIII). The fusion construct has a polynucleotide sequence set forth in SEQ ID NO: 98, encoding the fusion protein set forth in SEQ ID NO: 99. ID120 was expressed in host BL-21plysS (1 L, 2XYT growth media, 37° C.). Expression was induced with 1 mM IPTG at OD 0.50 and cells were harvested at OD 1.41. Cell pellet was suspended in lysis buffer (20 mM Tris pH8, 100 mM NaCl, 2 mM PMSF) and froze. ID120 forms an inclusion body and was processed the same as ID83. ID120 did not bind well overnight so the volume was doubled with 8M urea and BME was added to 10 mM. The less concentrated solutions were bound to Ni-NTA resin at RT for 2 hours then overnight at 4° C. The resin was washed and eluted as previously indicated. The fractions from this purification were dialyzed in 20 mM Tris pH8.

Example 21

Recognition of Mtb Antigens by PPD+ Human PBMC and Splenocytes from Mtb Infected Mice This example demonstrates that Mtb antigen of the invention induce memory recall responses in human PBMC from PPD+ healthy donors, and splenocytes isolated from mice infected with *Mycobacterium tuberculosis.*

Material & Methods:

Human PBMC In Vitro Stimulation and Cytokine ELISA

PBMC were obtained through apheresis or purified from heparinized blood from 7 PPD−, and 15 PPD+ healthy donors. PBMC were plated in triplicate 96-well tissue culture plates at 2-2.5×10$^5$ cells/well and cultured with medium, PHA (10 µg/ml), *Mycobacterium tuberculosis* (Mtb) lysate (10 µg/ml), or each recombinant protein (50 µg/ml) for 72 h. Supernatants were harvested and analyzed for IFN-γ by a double-sandwich ELISA using specific mAb (eBioscience), and following the manufacturer's protocol.

Mouse Cytokine ELISPOT

Spleen from *Mycobacterium tuberculosis*-infected mice were harvested at different times post-infection, and single splenocyte suspensions were obtained by conventional procedures. An ELISPOT assay was used to determine the relative number of IFN-γ or TNF-expressing splenocytes. MultiScreen 96-well filtration plates (Millipore, Bedford, MA) were coated with 10 µg/ml rat anti-mouse IFN-γ, or TNF, capture Ab (eBioscience) and incubated overnight at 4° C. Plates were washed with PBS, blocked with RPMI 1640 and 10% FBS for at least 1 h at room temperature, and washed again. Spleen cells were plated, in duplicate, at 2×10$^5$ cells/well, and stimulated with the specific rAg at a 10 µg/ml for 48 h at 37° C. The plates were subsequently washed with PBS and 0.1% Tween and incubated overnight at 4° C. with a biotin-conjugated, rat anti-mouse IFN-γ, or TNF, secondary Ab (eBioscience) at 5 µg/ml in PBS, 0.5% BSA, and 0.1% Tween. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted.

Results:

Recognition of Mtb Recombinant Proteins by Human PPD+ PBMC

PBMC from PPD+ and PPD− donors were cultured for 72 h with Mtb Rv0164, Rv0455, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, and Rv1511 recombinant proteins. A description of the production of these recombinant antigens is described elsewhere herein. The concentration of IFN-γ was further analyzed in the cell culture supernatants.

All the recombinant proteins tested, except Rv1908, were presented to and activated T cells from PPD+ donors to produce IFN-γ (FIG. 1). Only background levels of IFN-γ were detected in response to these antigens using PBMC from PPD− controls. 5- to 70-fold increases in IFN-γ concentration were measured in PBMC cultures from PPD+ donors compared to PPD-controls, indicating antigen specific recognition of these recombinant proteins from donors previously exposed to *Mycobacterium tuberculosis* or *Mycobacterium bovis* (vaccinated with BCG).

Recognition of Mtb Recombinant Proteins by Splenocytes from *M. tuberculosis*-Infected Mice Mice were infected by low dose aerosol exposure with *Mycobacterium tuberculosis* H37Rv strain, and spleens were harvested at different time post-infection. An ELISPOT assay was used to determine the relative number of TNF-expressing splenocytes in response to Mtb recombinant Rv0164, Rv0455, Rv0496, Rv2608, Rv3020, Rv3478, Rv3619, Rv3620, Rv1738, Rv1813, Rv3810, Rv2389, Rv2866, Rv0054, Rv0655, Rv0831, Rv1009, Rv1240, Rv1288, Rv1410, Rv1569, Rv1789, Rv1818, Rv1860, Rv1886, Rv1908, Rv2220, Rv2032, Rv2875, Rv3044, Rv3310, Rv3881, Rv0577, Rv1626, Rv0733, Rv1253, Rv1980, Rv3628, Rv1884, Rv3875, Rv1511 and ID83 proteins during a 48 h in vitro culture.

All the recombinant and fusion proteins tested induced an increase in the number of TNF+ splenocytes from *Mycobacterium tuberculosis*-infected mice 28 days (FIG. 2, upper panel), 60 days (data not shown), and 90 days post-infection (FIG. 2, lower panel).

Together these data indicate that *Mycobacterium tuberculosis* infection in mice induced immune responses to Mtb proteins, including to Rv0164, Rv0455, Rv0496, Rv2608, Rv3020, Rv3478, Rv3619, Rv3620, Rv1738, Rv1813, Rv3810, Rv2389, Rv2866, Rv0054, Rv0655, Rv0831, Rv1009, Rv1240, Rv1288, Rv1410, Rv1569, Rv1789, Rv1818, Rv1860, Rv1886, Rv1908, Rv2220, Rv2032, Rv2875, Rv3044, Rv3310, Rv3881, Rv0577, Rv1626, Rv0733, Rv1253, Rv1980, Rv3628, Rv1884, Rv1511 and ID83 proteins.

Thus, both humans naturally exposed to, and mice infected by an aerosol challenge with virulent, *Mycobacterium tuberculosis*-mounted immune responses to bacterial proteins, as evidenced by recall responses to Mtb lysate and PPD. In addition, increase in IFN-γ and TNF cytokine responses to Rv0164, Rv0455, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv1511 and ID83 protein upon in vitro stimulation indicates that these antigens (1) are recognized by previously exposed individuals (presence of memory T cells), (2) could be used as immuno-therapeutics or (3) could be used as diagnostics.

Example 22

Immune Responses to Mtb Antigens in C57BL/6 Mice and Protection Against Aerosol Challenge with Mtb This example demonstrates that immunization of mice with Mtb antigens of the invention is immunogenic and can provide protection against aerosol *Mycobacterium tuberculosis* challenge.

Material & Methods:
Recombinant Antigens and Adjuvant Formulations

Recombinant proteins were produced as described above. CpG 1826 was obtained from Coley Pharmaceuticals (Wellesley, MA).

Immunization

Female C57/BL6 mice were obtained from Charles River and age-matched (5-7 week) within each experiment. Mice were immunized three times (3 week apart) with 8 µg of recombinant Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), Rv1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv0831 (SEQ ID NO: 115), Rv1288 (SEQ ID NO: 127), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv0577 (SEQ ID NO: 184), Rv1626 (SEQ ID NO: 187), Rv0733 (SEQ ID NO: 190), Rv3628 (SEQ ID NO: 202), and Rv1884 (SEQ ID NO: 205) protein formulated with 25 µg of the adjuvant CpG. Mice in the saline, adjuvant only, and BCG control groups received three doses of PBS, three doses of adjuvant alone, or a single dose of 5×10⁴ BCG CFU respectively. Mice were injected with a total volume of 100 µl/mouse via the s.c. route.

Cytokine ELISA

Three weeks after the last boost, spleen from animals designated for immunogenicity studies were harvested, and splenocytes were obtained by conventional procedures. For cytokine analysis, splenocytes were plated in duplicate in 96-well tissue culture plates at $2.5 \times 10^5$ cells/well and cultured with medium, Con A 3 µg/ml, PPD 10 µg/ml, Mtb lysate 10 µg/ml, or each recombinant protein 10 µg/ml for 72 h. Supernatants were harvested and analyzed for IFN-γ by a double-sandwich ELISA using specific mAb (eBioscience), and following the manufacturer's protocol.

Cytokine ELISPOT

MultiScreen 96-well filtration plates (Millipore, Bedford, MA) were coated with 10 µg/ml rat anti-mouse IFN-γ or TNF capture Ab (eBioscience) and incubated overnight at 4° C. Plates were washed with PBS, blocked with RPMI 1640 and 10% FBS for at least 1 h at room temperature, and washed again. Splenocytes were plated in duplicate at $2 \times 10^5$ cells/well, and stimulated with medium, Con A 3 µg/ml, PPD 10 µg/ml, or each recombinant protein 10 µg/ml for 48 h at 37° C. The plates were subsequently washed with PBS and 0.1% Tween-20 and incubated for 2 h with a biotin-conjugated rat anti-mouse IFN-γ or TNF secondary Ab (eBioscience) at 5 µg/ml in PBS, 0.5% BSA, and 0.1% Tween-20. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted on a automated ELISPOT reader (C.T.L. Serie3A Analyzer, Cellular Technology Ltd, Cleveland, OH), and analyzed with Immunospot® (CTL Analyzer LLC).

IgG Isotype ELISA

Animals were bled 1 wk after the last immunization and serum IgG1 and IgG2c antibody titers were determined. Nunc-Immuno Polysorb plates were coated for 4 h at room temperature with 2 µg/ml of recombinant protein in 0.1 M bicarbonate buffer, blocked overnight at 4° C. with PBS Tween-20 0.05% BSA 1%, washed with PBS Tween-20 0.05%, incubated for 2 h at room temperature with sera at a 1:50 dilution and subsequent 5-fold serial dilutions, washed, and incubated for 1 h with anti-IgG1-HRP or anti-IgG2c-HRP 1:2000 in PBS Tween-20 0.05% BSA 0.1%. Plates were washed and developed using SureBlue TMB substrate (KPL Inc., Gaithersburg, MD). The enzymatic reaction was stopped with 1N $H_2SO_4$, and plates were read within 30 min at 450 nm with a reference filter set at 650 nm using a microplate ELISA reader (Molecular Devices, Sunnyvale, CA) and SoftMax Pro5. Endpoint titers were determined with GraphPad Prism 4 (GraphPad Software Inc., San Diego, CA) with a cutoff of 0.1.

Protection Experiment

Mice were immunized s.c., three times, 3 weeks apart, with 8 □g of each recombinant protein from a subset of Mtb antigens, and mixed with the adjuvant CpG. Positive control mice were immunized with BCG (5×10⁴ CFU) in the base of the tail (once), and negative control animals were injected with saline, or adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10 Reduction in CFU=Log 10 CFU for the vaccinated group−Log 10 CFU for the Saline treated group.

Results:

Immune Responses to Recombinant Mtb Antigens Adjuvanted with CpG.

C57BL/6 mice were immunized three times, three weeks apart, with recombinant Mtb Rv0164, Rv0455, Rv0496, Rv2608, Rv3020, Rv3478, Rv3619, Rv3620, Rv1738, Rv1813, Rv3810, Rv2389, Rv2866, Rv0831, Rv1818, Rv1886, Rv2032, Rv2623, Rv2875, Rv3044, Rv0577, Rv1626, Rv3628, and Rv1884 proteins formulated with 25 μg of the adjuvant CpG. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. IgG2c:IgG1 endpoint titer ratios were determined for each vaccine group (Table 1). Saline, CpG adjuvant alone, or BCG immunization did not induce an IgG1 or IgG2c antibody response specific to any or the Mtb recombinant proteins tested (data not shown). Immunization with each of the Mtb recombinant proteins with the adjuvant CpG induced antigen specific IgG1 and IgG2c.

TABLE 1

| Immune responses to Mtb antigens | | | | | | | |
|---|---|---|---|---|---|---|---|
| Antigen | IFN-γ[a] | TNF[a] | IrgG[b] | Antigen | IFN-γ | TNF | IgG |
| Rv0577 | 523(8) | 388(297) | 0.98 | Rv0496 | 68(52) | 24(5) | *1.21 |
| Rv1626 | 20(21) | 268(117) | *1.19 | Rv0831 | 24(12) | 24(8) | *1.19 |
| Rv2875 | 428(172) | 137(60) | *1.05 | Rv1886 | 590(106) | 102(37) | 1.00 |
| Rv2608 | 798(11) | 175(105) | 1.09 | Rv3020 | 48(27) | 20(16) | *1.18 |
| Rv3478 | 453(4) | 149(73) | 1.03 | Rv3619 | 604(184) | 1261(319) | *1.13 |
| Rv3044 | 331(161) | 57(1) | *1.05 | Rv1813 | 388(103) | 32(13) | *1.18 |
| Rv0164 | 163(87) | 94(58) | *1.17 | Rv2380 | 39(49) | 92(31) | 1.02 |
| Rv0455 | 24(12) | 44(24) | 1.06 | Rv2623 | 21(12) | 2(1) | *1.14 |
| Rv1738 | 24(16) | 32(16) | 1.23 | Rv2866 | 104(56) | 32(12) | *1.31 |
| Rv1818 | 155(72) | 10(2) | *0.90 | Rv3620 | 184(44) | 72(33) | *1.13 |
| Rv1684 | 1600(372) | ND[c] | 1.01 | Rv3628 | 16(8) | ND | 1.09 |
| Rv2032 | 28(16) | ND | *1.14 | Rv3810 | 44(56) | 7(10) | 1.08 |

[a]Spot-Forming-Unit per million cells (SD). Mice were immunized s.c. three times, three wks aport with Mtb antigens (RV#) + CpG. Cytokine responses to the antigens were determined by ELISPOT 3 wks after the last injection.

[b]IgG2c:IgG1 ratio,

*P < 0.05, Student's t Test,

[c]ND, not done.

Three weeks after the last immunization, splenocytes were prepared and assayed by ELISPOT to determine the relative number of IFN-γ or TNF-expressing splenocytes in response to medium alone, the mitogen ConA, PPD, Mtb lysate, and each of the recombinant Mtb proteins.

Injection with saline, or CpG adjuvant alone did not induce IFN-γ or TNF responses specific to any of the recombinant proteins (data not shown).

Immunization with each of the Mtb recombinant proteins with the adjuvant CpG induced antigen specific IFN-γ and/or TNF recall responses by activated splenocytes (Table 1). Lower levels of IFN-γ in response to Mtb lysate and PPD were also observed (data not shown), suggesting that these proteins are naturally found in mycobacterial lysates and partially purified derivatives.

Together, these results indicate that immunization with the different recombinant Mtb antigens in CpG induced a Th1-type memory response with predominant IgG2c, IFN-γ, and TNF.

Protection Afforded by the Different Mtb Recombinant Proteins, Adjuvanted with CpG, Against an Aerosol Challenge with Mtb H37Rv.

Number of viable bacilli, expressed as mean Log 10 CFU, in the lung and spleen of mice vaccinated with Mtb recombinant protein Rv0496, Rv2608, Rv3020, Rv3478, Rv3619, Rv3620, Rv1813, Rv1569, Rv1789, Rv1860, Rv1886, Rv2220, Rv2875, Rv3044, Rv0577, Rv1626, and Rv0733, adjuvanted with CpG, were determined 4 weeks post aerosol challenge with ~50 CFU of virulent *Mycobacterium tuberculosis* H37Rv. The mean Log 10 CFU in the lung of mice immunized with the different recombinant proteins was compared to the mean Log 10 CFU obtained in mice receiving placebo (saline) or BCG, the current and only vaccine against TB. The difference in mean Log 10 CFU in the saline group vs the vaccinated groups is expressed as Log 10 reduction in CFU.

Immunization of mice with three doses of Rv3478+CpG or Rv2608+CpG resulted in a decrease in viable Mtb bacilli, in lung (0.66, respectively 0.58) close to that afforded by BCG vaccination (0.78) (Table 2). Immunization with each of Rv0496, Rv3020, Rv3619, Rv3620, Rv1813, Rv1569, Rv1789, Rv1860, Rv1886, Rv2220, Rv2875, Rv3044, Rv0577, Rv1626, and Rv0733, adjuvanted with CpG, also afforded some protection against Mtb infection. CpG adjuvant alone did not reduce lung bacterial burden (−0.09).

TABLE 2

| Vaccine-induced protection against Mtb[a] CFU Reduction ($Log_{10}$)[b] | | | | | | | |
|---|---|---|---|---|---|---|---|
| Rv0496 | 0.11 | Rv0577 | 0.36 | Rv1886 | 0.20 | Rv3478 | 0.66 |
| Rv0733 | 0.23 | Rv1626 | 0.32 | Rv1569 | 0.12 | Rv3044 | 0.43 |
| Rv0831 | 0.13 | Rv2875 | 0.44 | Rv1789 | 0.15 | Rv2220 | 0.25 |
| Rv1411 | 0.11 | Rv2608 | 0.58 | Rv3020 | 0.17 | BCG | 0.78 |
| Rv1860 | 0.19 | Rv3619 | 0.24 | Rv1813 | 0.14 | CpG | −0.09 |

[a]Mice were immunized s.c. three times, three wks apart with 8 μg Mtb antigens (Rv#) + 25 μg CpG.

[b]Reduction of viable bacteria (CFU) in the lungs compared to saline immunized animals 4 wks after a low dose aerosol challenge with *M. tuberculosis* H37Rv or Erdman strains.

These results are surprising in that levels of protection against Mtb infection were achieved with 3 doses of a single recombinant protein adjuvanted with CpG.

Example 23

Immune Responses to a Mixture of Mtb Antigens in C57BL/6 Mice and Protection Against Aerosol Challenge with Mtb This example demonstrates that immunization of mice with a mixture of Mtb antigens of the invention is immunogenic and can provide protection against aerosol *Mycobacterium tuberculosis* challenge.

Material & Methods:

Recombinant Antigens and Adjuvant Formulations

Recombinant proteins were produced as described above. CpG 1826 was obtained from Coley Pharmaceuticals (Wellesley, MA).

Immunization

Female C57/BL6 mice were obtained from Charles River and age-matched (5-7 week) within each experiment. Mice were immunized three times (3 week apart) with 6 or 8 μg of recombinant Rv2608, Rv3620, and Rv1813 protein formulated with 25 μg of the adjuvant CpG. Mice in the adjuvant only, and BCG control groups received three doses of adjuvant alone, or a single dose of $5\times10^4$ BCG CFU respectively. Mice were injected with a total volume of 100 μl/mouse via the s.c. route.

Cytokine ELISA

Three weeks after the last boost, spleen from animals designated for immunogenicity studies were harvested, and splenocytes were obtained by conventional procedures. For cytokine analysis, splenocytes were plated in duplicate 96-well tissue culture plates at $2.5\times10^5$ cells/well and cultured with medium, Con A 3 μg/ml, PPD 10 μg/ml, Mtb lysate 10 μg/ml, or each recombinant protein 10 μg/ml for 72 h. Supernatants were harvested and analyzed for IFN-γ by a double-sandwich ELISA using specific mAb (eBioscience), and following the manufacturer's protocol.

Cytokine ELISPOT

MultiScreen 96-well filtration plates (Millipore, Bedford, MA) were coated with 10 μg/ml rat anti-mouse IFN-γ or TNF capture Ab (eBioscience) and incubated overnight at 4° C. Plates were washed with PBS, blocked with RPMI 1640 and 10% FBS for at least 1 h at room temperature, and washed again. Splenocytes were plated in duplicate at $2\times10^5$ cells/well, and stimulated with medium, Con A 3 μg/ml, PPD 10 μg/ml, or each recombinant protein 10 μg/ml for 48 h at 37° C. The plates were subsequently washed with PBS and 0.1% Tween-20 and incubated for 2 h with a biotin-conjugated rat anti-mouse IFN-γ or TNF secondary Ab (eBioscience) at 5 μg/ml in PBS, 0.5% BSA, and 0.1% Tween-20. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted on a automated ELISPOT reader (C.T.L. Serie3A Analyzer, Cellular Technology Ltd, Cleveland, OH), and analyzed with Immunospot® (CTL Analyzer LLC).

IgG Isotype ELISA

Animals were bled 1 wk after the last immunization and serum IgG1 and IgG2c antibody titers were determined. Nunc-Immuno Polysorb plates were coated for 4 h at room temperature with 2 μg/ml of recombinant protein in 0.1 M bicarbonate buffer, blocked overnight at 4° C. with PBS Tween-20 0.05% BSA 1%, washed with PBS Tween-20 0.05%, incubated for 2 h at room temperature with sera at a 1:50 dilution and subsequent 5-fold serial dilutions, washed, and incubated for 1 h with anti-IgG1-HRP or anti-IgG2c-HRP 1:2000 in PBS Tween-20 0.05% BSA 0.1%. Plates were washed and developed using SureBlue TMB substrate (KPL Inc., Gaithersburg, MD). The enzymatic reaction was stopped with 1N $H_2SO_4$, and plates were read within 30 min at 450 nm with a reference filter set at 650 nm using a microplate ELISA reader (Molecular Devices, Sunnyvale, CA) and SoftMax Pro5. Endpoint titers were determined with GraphPad Prism 4 (GraphPad Software Inc., San Diego, CA) with a cutoff of 0.1.

Protection Experiment

Mice were immunized s.c., three times, 3 weeks apart, with 6 or 8 μg of each recombinant protein from a subset of Mtb antigens, and mixed with the adjuvant CpG. Positive control mice were immunized with BCG ($5\times10^4$ CFU) in the base of the tail (once), and negative control animals were injected with adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% CO 2. Data are expressed as Log 10 of the mean number of bacteria recovered±SD, and Log 10 Reduction in CFU=Log 10 CFU for the vaccinated group−Log 10 CFU for the Saline treated group.

Results:

Immune Responses to a Mixture of Recombinant Mtb Antigens Adjuvanted with CpG.

C57BL/6 mice were immunized three times, three weeks apart, with each recombinant Mtb Rv2608, Rv3620, and Rv1813 proteins, separately (8 μg) or in a mixture (6 μg each), formulated with 25 μg of the adjuvant CpG. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. IgG2c endpoint titers were determined for each vaccine group. CpG adjuvant alone or BCG immunization did not induce an IgG1 or IgG2c antibody response specific to any or the Mtb recombinant proteins tested (FIG. 3B, and data not shown). Immunization with each of the Mtb recombinant proteins with the adjuvant CpG induced antigen specific IgG1 (data not shown) and IgG2c (FIG. 3B).

Three weeks after the last immunization, splenocytes were prepared and assayed by ELISA or ELISPOT to determine the relative level of IFN-y or number of TNF-expressing splenocytes in response to medium alone, the mitogen ConA, PPD, Mtb lysate, and each of the recombinant Mtb proteins.

Injection with CpG adjuvant alone did not induce IFN-γ or TNF responses specific to any of the recombinant proteins (FIG. 3C-D).

Immunization with each of the Mtb recombinant proteins with the adjuvant CpG induced antigen specific IFN-γ and TNF recall responses by activated splenocytes (FIG. 3C-D). Lower levels of cytokine responses were observed when the three antigens were used as a mixture.

Together, these results indicate that immunization with the different recombinant Mtb antigens, separately or as a mixture, in CpG induced a Th1-type memory response with predominant IgG2c, IFN-γ, and TNF.

Protection Afforded by a Mixture of Different Mtb Recombinant Proteins, Adjuvanted with CpG, Against an Aerosol Challenge with Mtb H37Rv.

Number of viable bacilli, expressed as mean Log 10 CFU, in the lung of mice vaccinated with Mtb recombinant protein Rv2608, Rv3620, and Rv1813, separately (8 μg) or in a mixture (6 μg each), adjuvanted with CpG, were determined 4 weeks post aerosol challenge with ~50 CFU of virulent *Mycobacterium tuberculosis* H37Rv. The mean Log 10 CFU in the lung of mice immunized with the different recombinant proteins was compared to the mean Log 10 CFU obtained in mice receiving adjuvant alone or BCG, the current and only vaccine against TB. The difference in mean Log 10 CFU in the adjuvant group vs the vaccinated groups is expressed as Log 10 reduction in CFU.

Immunization of mice with three doses of Rv2608+Rv3620+Rv1813+CpG resulted in a decrease in viable Mtb bacilli in lung (Log 10 reduction in CFU of 0.67) close to that afforded by BCG vaccination (0.71) (FIG. 3A). Immunization with Rv2608 or Rv1813, adjuvanted with CpG, also afforded some protection against Mtb infection (0.24 and 0.30 respectively). Immunization with Rv3620+CpG or CpG adjuvant alone did not reduce lung bacterial burden. The reduction in CFU achieved by injecting a mixture of three Mtb antigens was higher than adding up individual effects.

These results are surprising in that levels of protection against Mtb infection were increased with 3 doses of a mixture or three recombinant proteins adjuvanted with CpG, compared to 3 doses of individual proteins with CpG.

Example 24

Immune Responses to ID83 and ID93 Fusion Proteins in C57BL/6 Mice and Protection Against Aerosol Challenge with Mtb This example demonstrates that immunization of mice with fusion proteins of the invention is immunogenic and can provide protection against aerosol *Mycobacterium tuberculosis* challenge.

Material & Methods:

Fusion Proteins and Adjuvant Formulations

Fusion proteins were produced as described above. CpG 1826 was obtained from Coley Pharmaceuticals (Wellesley, MA). Glucopyranosyl lipid A (GLA) was obtained from Avanti (Alabaster, AL) and Gardiquimod (GDQ) was obtained from Invivogen (San Diego, CA). Oil-in-water sable emulsions (–SE) were prepared by standard techniques.

Immunization

Female C57/BL6 mice were obtained from Charles River and age-matched (5-7 week) within each experiment. Mice were immunized three times (3 week apart) with 8 μg of ID83 and ID93 fusion protein formulated with 20 μg of the adjuvant GLA-SE, or 8 μg ID83 fusion protein formulated with 20-25 μg of the adjuvant GLA-SE, GDQ-SE, CpG-SE, GLA/GDQ-SE, GLA/CpG-SE, CpG/GDQ-SE. Mice in the saline, adjuvant only, and BCG control groups received three doses of PBS, three doses of adjuvant alone, or a single dose of $5\times10^4$ BCG CFU respectively. Mice were injected with a total volume of 100 μl/mouse via the s.c. route.

Cytokine ELISA

Three weeks after the last boost, spleen from animals designated for immunogenicity studies were harvested, and splenocytes were obtained by conventional procedures. For cytokine analysis, splenocytes were plated in duplicate 96-well tissue culture plates at $2.5\times10^5$ cells/well and cultured with medium, Con A 3 μg/ml, PPD 10 μg/ml, Mtb lysate 10 μg/ml, or each fusion protein 10 μg/ml for 72 h. Supernatants were harvested and analyzed for IFN-γ by a double-sandwich ELISA using specific mAb (eBioscience), and following the manufacturer's protocol.

IgG Isotype ELISA

Animals were bled 1 wk after the last immunization and serum IgG1 and IgG2c antibody titers were determined. Nunc-Immuno Polysorb plates were coated for 4 h at room temperature with 2 μg/ml of recombinant protein in 0.1 M bicarbonate buffer, blocked overnight at 4° C. with PBS Tween-20 0.05% BSA 1%, washed with PBS Tween-20 0.05%, incubated for 2 h at room temperature with sera at a 1:50 dilution and subsequent 5-fold serial dilutions, washed, and incubated for 1 h with anti-IgG1-HRP or anti-IgG2c-HRP 1:2000 in PBS Tween-20 0.05% BSA 0.1%. Plates were washed and developed using SureBlue TMB substrate (KPL Inc., Gaithersburg, MD). The enzymatic reaction was stopped with 1N $H_2SO_4$, and plates were read within 30 min at 450 nm with a reference filter set at 650 nm using a microplate ELISA reader (Molecular Devices, Sunnyvale, CA) and SoftMax Pro5. Endpoint titers were determined with GraphPad Prism 4 (GraphPad Software Inc., San Diego, CA) with a cutoff of 0.1.

Protection Experiment

Mice were immunized s.c., three times, 3 weeks apart, with 8 μg of the fusion protein, formulated in the indicated adjuvant. Positive control mice were immunized with BCG ($5\times10^4$ CFU) in the base of the tail (once), and negative control animals were injected with saline, or adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10 Reduction in CFU=Log 10 CFU for the vaccinated group−Log 10 CFU for the Saline treated group.

Results:

Immune Responses to ID83 and ID93 Adjuvanted with GLA-SE

C57BL/6 mice were immunized three times, three weeks apart, with ID83 or ID93 fusion proteins formulated with 20 μg of the adjuvant GLA-SE. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. Endpoint titers were determined for each vaccine group. Saline did not induce an IgG1 or IgG2c antibody response specific to ID83 or ID93 fusion proteins (FIG. 4A) nor did GLA-SE adjuvant alone (data not shown). Immunization with ID83 or ID93 fusion protein with the adjuvant GLA-SE induced antigen specific IgG1 and IgG2c.

Three weeks after the last immunization, splenocytes were prepared and assayed by ELISA to determine the relative level of IFN-γ produced by splenocytes in response to medium alone, the mitogen ConA, and each of the fusion proteins.

Injection with saline or GLA-SE adjuvant alone did not induce IFN-γ responses specific to ID83 or ID93 fusion proteins (data not shown).

Figure 4A:
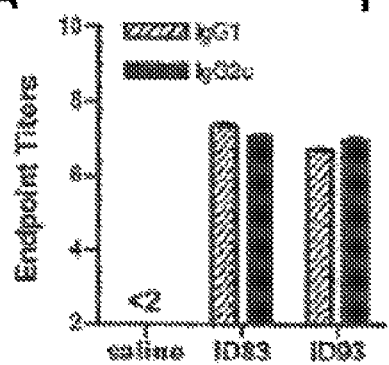
FIGS. 4A and 4B show the immunogenicity of ID83 and ID93 fusion proteins with GLA-SE in C57BL/6 mice.
Figure 4B:
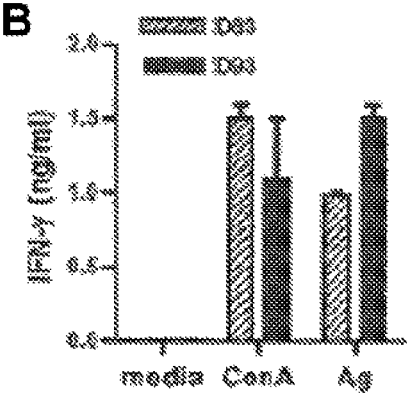
Figure 6:
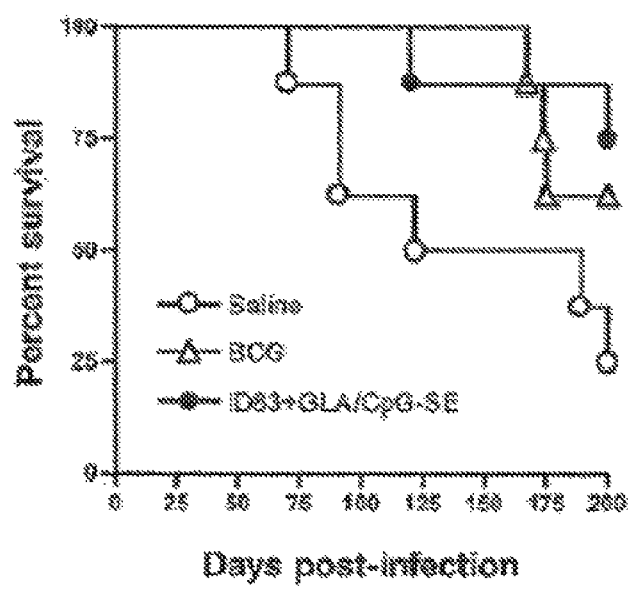
FIG. 6 shows the survival after infection with Mtb of guinea pigs immunized with ID83 fusion protein with GLA/CpG-SE. Guinea pigs were immunized with 1 dose of BCG, or 3 doses of ID83 with GLA/CpG-SE adjuvant and challenged with a low dose aerosol of *M. tuberculosis* H37Rv 4 wks after the last boost. Survival was monitored for 200 days until ¾ of the animal in the placebo group (saline) died.
Figure 8:
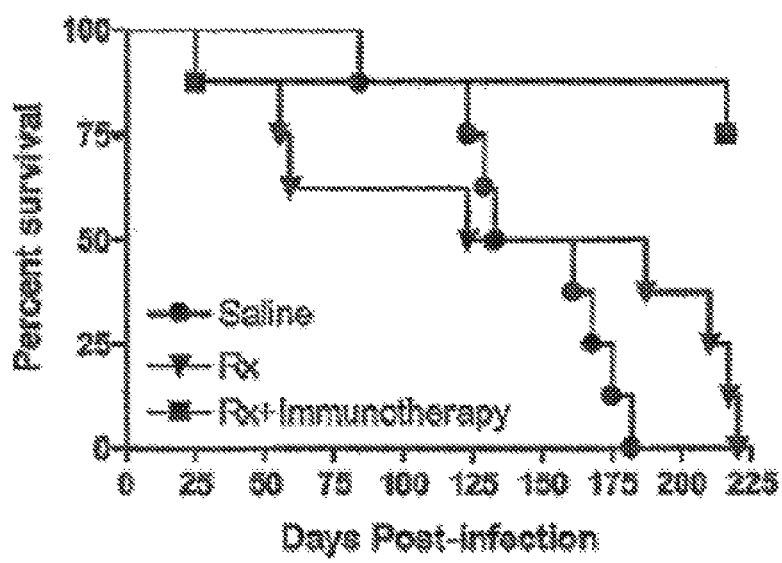
FIG. 8 shows the survival of *M. tuberculosis*-infected SWR mice (n=8) treated with a combination of antibiotics (Rx; rifampin+ioniazide for 60 days)+immunotherapy (three injections of a mixture containing Rv2608, Rv1813, and Rv3620 with GLA-SE), antibiotics alone (Rx; rifampin+ioniazide for 60 days) or left untreated (saline). The results demonstrate that the combination of drugs+immunotherapy extends the survival of mice infected with *M. tuberculosis*.
Figure 9:
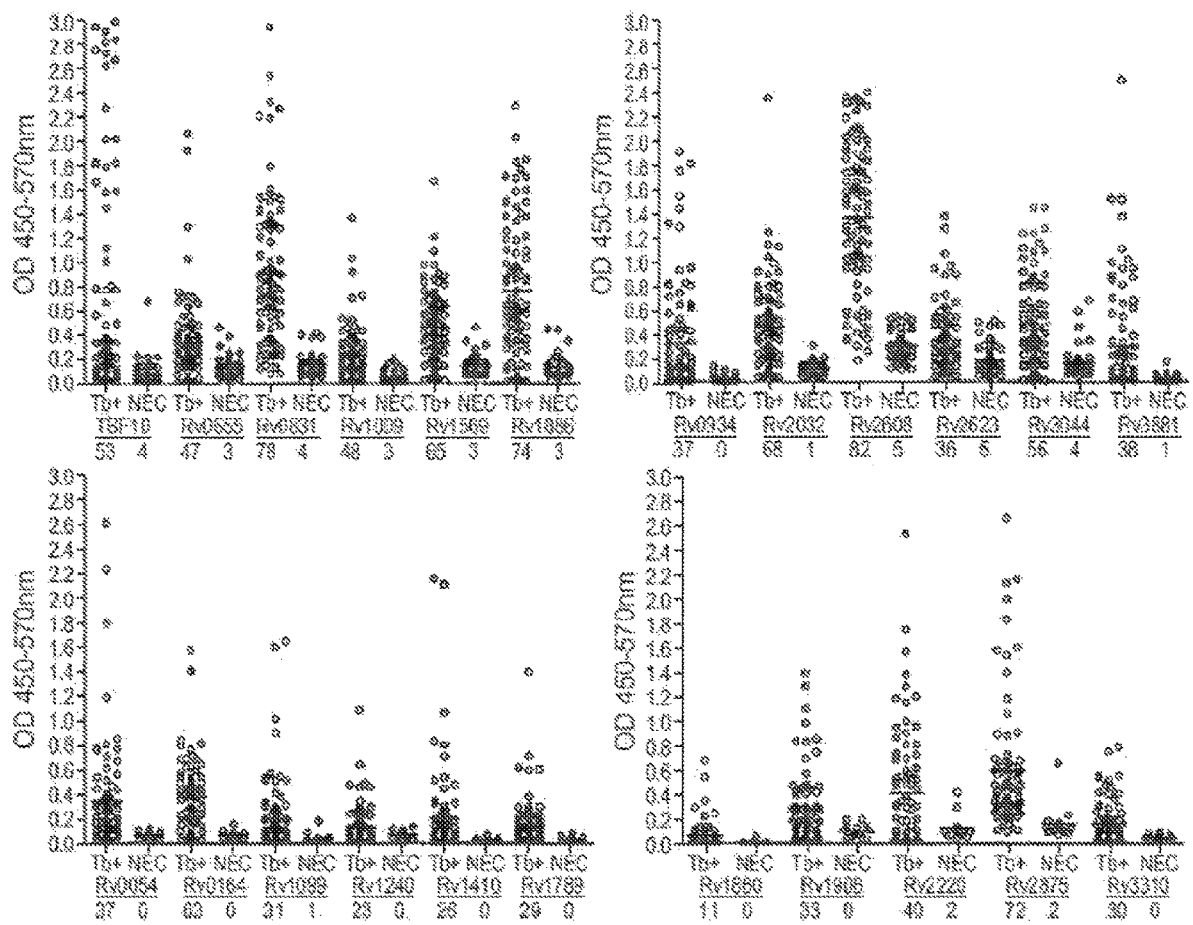
FIG. 9 shows the results of ELISA experiments in which a panel of sputum positive, Tb confirmed serum samples (n=80-92) and a panel of Tb negative, healthy control serum (n=40-46) were analyzed for reactivity with selected Tb antigens. The results demonstrate that 100% positive responses can be obtained by employing different antigen combinations.

Immunization with ID83 or ID93 fusion protein with the adjuvant GLA-SE induced antigen specific IFN-γ recall responses by activated splenocytes (FIG. 4B).

Together, these results indicate that immunization with the different fusion proteins in GLA-SE induced B and T cell immune responses.

The mean Log 10 CFU in the lung of mice immunized with the different fusion proteins was compared to the mean Log 10 CFU obtained in mice receiving placebo (saline) or BCG. The difference in mean Log 10 CFU in the saline group vs the vaccinated groups is expressed as Log 10 reduction in CFU.

Immunization of mice with three doses of ID83+GLA-SE or ID93+GLA-SE resulted in a decrease in viable Mtb bacilli in the lung of Mtb-infected mice of 0.34, respectively 0.48 Log 10 (Table 3). These results demonstrate that protection against Mtb infection was achieved with 3 doses of two different fusion proteins adjuvanted with GLA-SE.

TABLE 3

Number of viable bacilli in the lung of vaccinated mice.

| Groups | CFU[a] | SD | Diff[b] | Groups | CFU | SD | Diff. |
|---|---|---|---|---|---|---|---|
| Saline | 5.79 | 0.09 | N/A[c] | Saline | 5.94 | 0.15 | N/A |
| BCG | 5.06 | 0.18 | 0.73 | BCG | 5.07 | 0.20 | 0.57 |
| ID83 + GLA – SE | 5.45 | 0.23 | 0.34 | ID93 + GLA – SE | 5.46 | 0.21 | 0.48 |

[a]CFU = colony-forming-units. Values represent the number of viable bacilli in the lungs of infected mice and are expressed as $Log_{10}$.
[b]Difference = $Log_{10}$ CFU for the Saline group-$Log_{10}$ CFU for the vaccinated treated group.
[c]N/A = not applicable.

Immunogenicity of ID83 Formulated with Different Adjuvants

C57BL/6 mice were immunized three times, three weeks apart, with ID83 fusion protein formulated with 20-25 μg of the adjuvant GLA-SE, GDQ-SE, CpG-SE, GLA/GDQ-SE, GLA/CpG-SE, CpG/GDQ-SE. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. Endpoint titers were determined for each vaccine group. Saline did not induce an IgG1 or IgG2c antibody response specific to ID83 fusion proteins. Immunization with ID83 with the different adjuvants induced antigen specific IgG1 and IgG2c (FIG. 5A).

Three weeks after the last immunization, splenocytes were prepared and assayed by ELISA to determine the relative level of IFN-γ produced by splenocytes in response to medium alone, the mitogen ConA, and ID83 fusion protein.

Injection with saline did not induce IFN-γ responses specific to ID83 fusion protein. Immunization with ID83 fusion protein with the different adjuvants induced antigen specific IFN-γ recall responses by activated splenocytes (FIG. 5B).

Together, these results indicate that immunization with ID83 fusion protein in a variety of adjuvants induced B and T cell immune responses.

Protection Afforded by ID83 and ID93 Fusion Proteins, Formulated with the Adjuvant GLA-SE, Against an Aerosol Challenge with Mtb H37Rv.

Number of viable bacilli, expressed as mean Log 10 CFU, in the lung of mice vaccinated with ID83 or ID93 fusion proteins adjuvanted with GLA-SE, were determined 4 weeks post aerosol challenge with ~50 CFU of virulent *M. tuberculosis* H37RV.

Protection Afforded by ID83 Formulated with Different Adjuvants, in C57BL/6 Mice, Against an Aerosol Challenge with Mtb H37Rv.

Number of viable bacilli, expressed as mean Log 10 CFU, in the lung of mice vaccinated with ID83 fusion protein formulated with 20-25 μg of the adjuvant GLA-SE, CpG-SE, or GLA/CpG-SE were determined 4 weeks post aerosol challenge with ~50 CFU of virulent *M. tuberculosis* H37Rv.

The mean Log 10 CFU in the lung of mice immunized with ID83 in the different adjuvants was compared to the mean Log 10 CFU obtained in mice receiving placebo (saline) or BCG. The difference in mean Log 10 CFU in the saline group vs the vaccinated groups is expressed as Log 10 reduction in CFU.

Immunization of mice with three doses of ID83 with different adjuvants resulted in a decrease in viable Mtb bacilli in the lung of Mtb-infected mice (Table 4). These results are promising in that protection against Mtb infection was achieved with 3 doses of two different fusion proteins adjuvanted with GLA-SE.

TABLE 4

Number of viable bacilli in the lung of vaccinated mice.

| Groups | CFU[a] | SD[b] | CFU Reduction[c] | P value[d] |
|---|---|---|---|---|
| Saline | 6.28 | 0.22 | | |
| BCG | 5.01 | 0.15 | 1.27 | <0.01 |
| ID83 + GLA-SE | 5.75 | 0.22 | 0.53 | <0.01 |
| ID83 + CpG-SE | 5.79 | 0.12 | 0.49 | <0.01 |
| ID83 + GLA/CpG-SE | 5.62 | 0.22 | 0.66 | <0.01 |

[a]CFU = colony-forming-units. Values represents the number of viable bacilli in the lungs of infected mice and are expressed as $Log_{10}$.
[b]SD, standard deviation
[c]CFU Reduction = $Log_{10}$ CFU for the Saline group - $Log_{10}$ CFU for the vaccinated treated group.
[d]P value is calculated with one-way ANOVA followed by Dunnett's multiple comparison Test. P values <0.05 are considered statistically significant Together, these results indicate that vaccination with ID83 fusion protein adjuvanted with CpG-SE, GLA-SE, or CpG/

GLA-SE reduced the bacterial burden and partially protected mice from *M. tuberculosis* infection. ID83+CpG/GLA-SE was the most effective formulation in reducing the number of viable bacteria in the lungs of Mtb-infected mice.

Protection Afforded by ID83 Formulated with GLA/CpG-SE, in Guinea Pigs, Against an Aerosol Challenge with Mtb H37Rv.

Survival of guinea pigs vaccinated with ID83 fusion protein formulated with 20/25 μg of the adjuvant GLA/CpG-SE were followed for 200 days post aerosol challenge with ~50 CFU of virulent *M. tuberculosis* H37Rv.

The survival of guinea pigs immunized with ID83 in GLA/CpG-SE adjuvant was compared to the survival of guinea pigs receiving placebo (saline) or BCG.

Immunization of guinea pigs with three doses of ID83 with different adjuvants resulted in increased survival of Mtb-infected guinea pig (FIG. 6). At day 200 post-infection, 75% of the animals vaccinated with ID83+GLA/CpG-SE were still alive, compared with 25% of the guinea pigs in the placebo group. 62% of guinea pigs immunized with BCG were alive at day 200 post-infection with Mtb.

These results demonstrate that protection against Mtb infection was achieved with 3 doses of ID83 fusion protein formulated with GLA/CpG-SE. In addition, vaccination with ID83+GLA/CpG-SE protected Mtb-infected guinea pigs longer than BCG.

Together, these results indicate that vaccination with ID83 fusion protein adjuvanted with CpG-SE, GLA-SE, or CpG/GLA-SE reduced the bacterial burden in the lungs of Mtb-infected mice, and partially protected guinea pigs from *M. tuberculosis* infection. ID83+CpG/GLA-SE was the most effective formulation in reducing the number of viable bacteria in the lungs of Mtb-infected mice and prolonging the survival of Mtb-infected guinea pigs.

Vaccination of mice with three doses of ID83 or ID93 fusion protein, adjuvanted with GLA-SE, induced antibody and Th1 T cell memory responses along with reduction in viable bacilli counts in the lung of mice infected with *M. tuberculosis*. Furthermore, a combination of CpG and GLA-SE was observed to be most immunogenic and conferred increased protection to *M. tuberculosis* challenge.

Example 25

Immune Responses to AD5-ID83 in C57BL/6 Mice and Protection Against an Aerosol *M. Tuberculosis* Challenge This example demonstrates that immunization of mice with an adenovirus vector engineered to express ID83 fusion proteins of the invention is immunogenic in C57BL/6 mice.

Material & Methods:

Virus Construction and Purification

Ad5-ID83 was constructed using the AdEasy™ XL AdenoviralVector System (Stratagene #240010). Briefly, ID83 was amplified from plasmid DNA using PCR, digested with HinDIII and EcoRV, and ligated into pShuttle-CMV to make ID83-pShuttleCMV. ID83-pShuttleCMV was linearized by digesting with Pmel and electroporated (2.4 kV, 186Ω, 0.2 cm gap cuvette) into *Escherichia coli* BJ5183-AD-1 electro-competent cells (Stratagene #200157). Recombinant Ad5-ID83 plasmids were identified by digesting with PacI. PacI digested Ad5-ID83 plasmid (4 μg) was transfected into AD-239 cells in 60 mm plates using Polyfect reagent (Invitrogen #301107). After 4 days cells were harvested in 3 mL media and lysed by three cycles of freeze/thaw. Lysate supernatant was used to amplify virus for purification by CsCl gradient centrifugation.

Immunization

Female C57/BL6 mice were obtained from Charles River and age-matched (5-7 week) within each experiment. Mice were immunized two times (3 week apart) with $5\times10^8$ Ad5-ID83 viral particles. Mice in the saline, and BCG control groups received PBS or a single dose of $5\times10^4$ BCG CFU respectively. Mice were injected with a total volume of 100 μl/mouse via the i.m. route.

Cytokine ELISPOT

MultiScreen 96-well filtration plates (Millipore, Bedford, MA) were coated with 10 μg/ml rat anti-mouse IFN-γ or TNF capture Ab (eBioscience) and incubated overnight at 4° C. Plates were washed with PBS, blocked with RPMI 1640 and 10% FBS for at least 1 h at room temperature, and washed again. Splenocytes were plated in duplicate at $2\times10^5$ cells/well, and stimulated with medium, Con A 3 μg/ml, PPD 10 μg/ml, or each recombinant protein 10 μg/ml for 48 h at 37° C. The plates were subsequently washed with PBS and 0.1% Tween-20 and incubated for 2 h with a biotin-conjugated rat anti-mouse IFN-γ or TNF secondary Ab (eBioscience) at 5 μg/ml in PBS, 0.5% BSA, and 0.1% Tween-20. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted on a automated ELISPOT reader (C.T.L. Serie3A Analyzer, Cellular Technology Ltd, Cleveland, OH), and analyzed with Immunospot® (CTL Analyzer LLC).

Protection Experiment

Mice were immunized s.c., three times, 3 weeks apart, with 8 μg of the fusion protein, formulated in the indicated adjuvant. Positive control mice were immunized with BCG ($5\times10^4$ CFU) in the base of the tail (once), and negative control animals were injected with saline, or adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10 Reduction in CFU=Log 10 CFU for the vaccinated group−Log 10 CFU for the Saline treated group.

Results:

Immune Responses to Ad5-ID83

C57BL/6 mice were immunized two times, three weeks apart, with Ad5-ID83.

Three weeks after the last immunization, splenocytes were prepared and assayed by ELISPOT to determine the relative number of IFN-γ-expressing splenocytes in response to medium alone, the mitogen ConA, and each of the fusion proteins.

Immunization with Ad5-ID83 induced antigen specific IFN-γ recall responses by activated splenocytes (FIG. 7A). Injection with saline did not induce IFN-γ responses specific to ID83.

Protection Afforded by Ad5-ID83 Against an Aerosol Challenge with Mtb H37Rv.

Number of viable bacilli, expressed as mean Log 10 CFU, in the lung of mice vaccinated with 5×10$^8$ Ad5-ID83 viral particles, were determined 4 weeks post aerosol challenge with ~50 CFU of virulent *M. tuberculosis* H37RV.

The mean Log 10 CFU in the lung of mice immunized with Ad5-ID83 was compared to the mean Log 10 CFU obtained in mice receiving placebo (saline). The difference in mean Log 10 CFU in the saline group vs the vaccinated groups is expressed as Log 10 reduction in CFU.

Immunization of mice with two doses of Ad5-ID83 resulted in a decrease in viable Mtb bacilli in the lung of Mtb-infected mice of 0.27 (FIG. 7B). These results are promising in that protection against Mtb infection was achieved with only 2 doses of Ad5-ID83.

Together, these results indicate that immunization with Ad5-ID83 induced T cell immune responses and partially protected mice from an aerosol *M. tuberculosis* challenge.

Example 26

Immunotherapy with Mtb Rv1813, Rv2608, and Rv3620 Recombinant Proteins with the Adjuvant GLA-SE This example demonstrates that immunization of mice with a mixture of recombinant proteins of the invention along with standard antibiotic therapy can prolong the life of *M. tuberculosis*-infected mice.

Material & Methods:
Recombinant Proteins and Adjuvant Formulations

Recombinant proteins were produced as described above. Glucopyranosyl lipid A (GLA) was obtained from Avanti (Alabaster, AL). Stable oil-in-water emulsions (–SE) were prepared.

Aerosol Challenge with *M. tuberculosis*

Female SWR/J mice were obtained from Jackson Laboratories and age-matched (5-7 week) within each experiment. Mice were challenged by low dose aerosol exposure with *M. tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Survival of mice was monitored for 225 days post-infection Therapy Two weeks after an aerosol challenge with *M. tuberculosis*, standard antibiotic treatment was started. Mice were given 50 mg/l of rifampin and 85 mg/l isoniazide in their drinking water for 60 days. Some mice received additional immunotherapy and were immunized on day76, day97, and day118 post-infection with 6 μg of each Rv1813, Rv2608, and Rv3620 recombinant protein formulated with 20 μg of the adjuvant GLA-SE. Mice were injected with a total volume of 100 μl/mouse via the s.c. route. Mouse survival was monitored for 225 days.

Results:

Protection Afforded by a Combination of Antibiotics+ Rv1813, Rv2608, and Rv3620 with GLA-SE Immunotherapy, in *M. tuberculosis*-Infected Mice.

Survival of Mtb-infected mice treated with a standard regimen of rifampin+isoiazide antibiotics (Rx) or with a combination of Rx+immunization with Rv1813, Rv2608, and Rv3620 recombinant proteins formulated with 20 μg of the adjuvant GLA-SE (immunotherapy) was followed for 225 days post aerosol challenge with ~50 CFU of virulent *M. tuberculosis* H37Rv.

The survival of mice treated with Rx+immunotherapy was compared to the survival of mice receiving Rx alone or placebo (saline).

Treatment of mice with three doses of Rv1813, Rv2608, and Rv3620 recombinant proteins with GLA-SE, in addition to Rx, resulted in increased survival of Mtb-infected mice (FIG. 8). At day 225 post-infection, 75% of the animal vaccinated with Rv1813, Rv2608, and Rv3620 with GLA-SE were still alive, compared with 0% of the mice in the antibiotic (Rx) treatment alone group, and 0% in the placebo group.

These results demonstrate that protection against Mtb infection was achieved with antibiotics+3 doses of Rv1813, Rv2608, and Rv3620 with GLA-SE. In addition, treatment with antibiotics+Rv1813, Rv2608, and Rv3620 with GLA-SE protected Mtb-infected mice longer than antibiotics alone.

Together, these results indicate that immunotherapy with Rv1813, Rv2608, and Rv3620 with GLA-SE along with antibiotics induced immune responses that helped mice control an established *M. tuberculosis* infection.

Example 27

Serological Diagnosis of Tuberculosis

This example identifies *M. tuberculosis* antigens and antigen fusions having increased sensitivity and specificity for serological diagnosis of tuberculosis infection.

Polysorp 96 well plates (Nunc, Rochester, NY) were coated with 2 μg/ml recombinant antigen in bicarbonate buffer overnight at 4° C. and blocked for 2 hours at room temperature with PBST with 1% (w/v) BSA on a plate shaker. Serum were diluted appropriately to 1/200 in PBST with 0.1% BSA, added to each well and plates were incubated at room temperature for 2 hours with shaking. Plates were washed with PBST with 0.1% BSA and then HRP conjugated IgG immunoglobulin (Sigma, St. Louis, MO), diluted 1:10000 in PBST and 0.1% BSA, was added to each well and incubated at room temperature for 60 minutes with shaking. After washing, plates were developed with peroxidase color substrate (KPL, Baltimore MD) with reaction quenched by addition of 1N $H_2SO_4$ after 10 minutes. The corrected optical density of each well at 450-570 nm was read using a VERSAmax® microplate reader (Molecular Devices, Sunnyvale, CA).

The results of these experiments are summarized in FIG. 9. A panel of sputum positive, tuberculosis confirmed serum samples (TB, N=80-92) and a panel of tuberculosis negative, healthy control serum (NEC, N=40-46) were analyzed for reactivity with selected tuberculosis antigens. A previously characterized antigen, TBF10, was used as a positive control and found to give seropostive responses to 53 of the 92 tuberculosis positive serum samples. The reactivity of individual antigens are shown in FIGS. 9, with all the antigens listed displaying reactivity to 11-82 of the tuberculosis serum samples, with low or no reactivity to the healthy controls. The reactivity of a given antigen varied to the serum panel such that 100% positive responses could be obtained through selection of proper antigen combinations.

Example 28

Cloning and Expression of Recombinant Rv0577

Using H37Rv genomic DNA as template, Rv0577 was PCR amplified using the following primers:

```
5'-Rv0577-NdeI
                            (SEQ ID NO: 295)
CAATTACATATGAGAGTTTTGTTGCTGGGACCG

3'-Rv0577-HindIII-
                            (SEQ ID NO: 296)
CAATTAAAGCTTCTACTTTCCAGAGCCCGCAACGC
```

Amplification was performed under the following conditions: 94° C. 0.5 min., 55° C. 0.5 min., 68° C. 2 min for 30 cycles, to give the product set forth in SEQ ID NO:185. The PCR product was digested with NdeI/HindIII and cloned into pET28.a vector. Rv0733 was expressed by host strain BL-21plysS. The supernatant was bound with Ni resin under denaturing conditions. The Ni-NTA purification was followed by an anion exchange purification. Dialyzed in 20 mM Tris pH 8. The amino acid sequence of the recombinant protein is set forth in SEQ ID NO: 186.

Example 29

Cloning and Expression of Recombinant Rv1626

Using H37Rv genomic DNA as template, Rv1626 was PCR amplified using the following primers:

```
5'-Rv1626-NdeI
                            (SEQ ID NO: 297)
CAATTACATATGACCGGCCCCACCACCGCGCC

3'-Rv1628-HIndIII
                            (SEQ ID NO: 298)
CAATTAAAGCTTTCAGGTGTCTTTGGGTGTTCCGAG
```

Amplification was performed under the following conditions: 94° C. 0.5 min., 55° C. 0.5 min., 68° C. 2 min for 30 cycles, to give the product set forth in SEQ ID NO:188. The PCR product was digested with NdeI/HindIII and cloned into pET28.a vector._Rv1626 was expressed by host strain BL-21plysS. The supernatant was bound with Ni resin under denaturing conditions. The Ni-NTA purification was followed by an anion exchange purification. Dialyzed in 20 mM Tris pH 8. The amino acid sequence of the recombinant protein is set forth in SEQ ID NO: 189.

Example 30

Cloning and Expression of Recombinant Rv0733

Using H37Rv genomic DNA as template, Rv0733 was PCR amplified using the following primers:

```
5'-Rv0733-5NdeI
                            (SEQ ID NO: 299)
CAATTACATATGAGAGTTTTGTTGCTGGGACCG

3'-Rv0733-HindIII
                            (SEQ ID NO: 300)
CAATTAAAGCTTCTACTTTCCAGAGCCCGCAACGC
```

Amplification was performed under the following conditions: 94° C. 0.5 min., 55° C. 0.5 min., 68° C. 2 min for 30 cycles, to give the product set forth in SEQ ID NO: 191. The PCR product was digested with NdeI/HindIII and cloned into pET28.a vector. Rv0733 was expressed by host strain BL-21plysS. The supernatant was bound with Ni resin under denaturing conditions. The Ni-NTA purification was followed by an anion exchange purification. Dialyzed in 20 mM Tris pH 8. The amino acid sequence of the recombinant protein is set forth in SEQ ID NO: 192.

Example 31

Cloning and Expression of Recombinant Rv2520

Using H37Rv genomic DNA as template, Rv2520 was PCR amplified using the following primers:

```
5'-Rv2520-NdeI-6his
                            (SEQ ID NO: 301)
CAATTACATATGCATCACCATCACCATCACGTG

GTGGACCGCGATCCCAATACC

3'-Rv2520-EcoRI
                            (SEQ ID NO: 302)
CAATTAGAATTCTCAGCGATTCCTGATCTTGTG
```

Amplification was performed under the following conditions: 94° C. 0.5 min., 55° C. 0.5 min., 68° C. 2 min for 30 cycles, to give the product set forth in SEQ ID NO:194. The PCR product was digested with NdeI/EcoRI and cloned into a modified pET 28a missing the upstream 6 histidine and the 5'linker sequence. Rv2520 was transformed into expression hosts BL-21pLysS and Rosetta pLysS. Both expressed equally, but proceeded with the BL-21 pLysS cell strain. Following cell lysis, the supernatant fraction was bound with Ni-NTA resin under denaturing conditions. The Ni-NTA purification was followed by an anion exchange purification. Purified fractions were dialyzed into 20 mM Tris pH 8. The amino acid sequence of the recombinant protein is set forth in SEQ ID NO: 195.

Example 32

Cloning and Expression of Recombinant Rv1253

Using H37Rv genomic DNA as template, Rv1253 was PCR amplified using the following primers:

```
5'-Rv1253-NdeI
                            (SEQ ID NO: 303)
CTGGATCCCATATGGCCTTCCCGGAATATTCGC

3'-Rv1253-EcoRI
                            (SEQ ID NO: 304)
CTAGCTGAATTCTCATCCGACGTGTTTCCGCCG
```

Amplification was performed under the following conditions: 94° C. 0.5 min., 55° C. 0.5 min., 68° C. 2 min for 30 cycles, to give the product set forth in SEQ ID NO:197. The PCR product was digested with NdeI/EcoRII and cloned into the pET28.a vector. Rv1511 was transformed into expression host Rosetta plysS. After lysis of a 1 L induction, the recombinant protein was expressed in the inclusion body pellet. Ni-NTA affinity purification was done under denaturing conditions, then dialyzed against 20 mM Tris pH 8.0. The amino acid sequence of the recombinant protein is set forth in SEQ ID NO: 198.

Example 33

Cloning and Expression of Recombinant Rv1980

Using H37Rv genomic DNA as template, Rv1980 was PCR amplified using the following primers:

```
5'-Rv1980-NdeI-24
                                     (SEQ ID NO: 305)
CAATTACATATGGCGCCCAAGACCTACTGCGAG

3'-Rv1980-HindIII
                                     (SEQ ID NO: 306)
CAATTAAAGCTTCTAGGCCAGCATCGAGTCGATCGC
```

Amplification was performed under the following conditions: 94° C. 0.5 min., 55° C. 0.5 min., 68° C. 2 min for 30 cycles, to give the product set forth in SEQ ID NO: 200. The PCR product was digested with NdeI/HindIII and cloned into pET28.a vector. Rv1980 was transformed into expression host Rosetta plysS. After lysis of a 1 L induction, the recombinant protein was expressed in the inclusion body pellet. Ni-NTA affinity purification was done under denaturing conditions, then dialyzed against 20 mM Tris pH 8.0. The amino acid sequence of the recombinant protein is set forth in SEQ ID NO: 201.

Example 34

Cloning and Expression of Recombinant Rv3628

Using H37Rv genomic DNA as template, Rv3628 was PCR amplified using the following primers:

```
5'-Rv3628-Nde-6hisI
                                     (SEQ ID NO: 307)
CAATTACATATGCATCACCATCACCATCACATGCAATTCGACG

TGACCATC

3'-Rv3628-EcoRI
                                     (SEQ ID NO: 308)
CAATTAGAATTCTCAGTGTGTACCGGCCTTGAAGCG
```

Amplification was performed under the following conditions: 94° C. 0.5 min., 55° C. 0.5 min., 68° C. 2 min for 30 cycles, to give the product set forth in SEQ ID NO: 203. Using H37Rv genomic DNA as template, Rv3628 was PCR'd with conditions 95° C. 1 min., 58° C. 1 min., 72° C. 1.5 min for 35 cycles. The PCR product was digested with NdeI/EcoRI and cloned into pET 17b. Rv3628 was transformed into expression hosts BL-21plysE and Rosetta plysS. Both expressed equally, but proceeded with the plysE construct. After lysis of a 1 L induction, it went into the inclusion body. Ni-NTA was done under denaturing conditions, then dialyzed against 10 mM Tris pH 8.0. The amino acid sequence of the recombinant protein is set forth in SEQ ID NO: 204.

Example 35

Cloning and Expression of Recombinant Rv1844

Using H37Rv genomic DNA as template, Rv1844 was PCR amplified using the following primers:

```
5'-Rv1884-NdeI-6his30
                                     (SEQ ID NO: 309)
CAATTACATATGCATCACCATCACCATCACACTTCCGGCGAT

ATGTCGAGC
```

```
3'-Rv1884-EcoRI
                                     (SEQ ID NO: 310)
CAATTAGAATTCTCAGCGCGGAATACTTGCCTG
```

Amplification was performed under the following conditions: 94° C. 0.5 min., 55° C. 0.5 min., 68° C. 2 min for 30 cycles, to give the product set forth in SEQ ID NO: 206. The PCR product was digested with NdeI/EcoRI and cloned into pET 17b. Plasmid containing the Rv1884 gene was transformed into expression hosts BL-21plysE and plysS. Both expressed equally, but proceeded with the plysE. After lysis of a 1 L induction, it remained in the insoluble inclusion body fraction. Ni-NTA was done under denaturing conditions, then dialyzed against 10 mM Tris pH 8.0. The amino acid sequence of the recombinant protein is set forth in SEQ ID NO: 207.

Example 36

Cloning and Expression of Recombinant Rv3872

Using H37Rv genomic DNA as template, Rv3872 was PCR amplified using the following primers:

```
5'-Rv3872-NdeI
                                     (SEQ ID NO: 311)
GTGCTAGCCATATGGAAAAAATGTCACATGATC

3'-Rv3872-HindIII
                                     (SEQ ID NO: 312)
CTGGATCCAAGCTTCTATTCGGCGAAGACGCCGGC
```

Amplification was performed under the following conditions: 94° C. 0.5 min., 55° C. 0.5 min., 68° C. 2 min for 30 cycles, to give the product set forth in SEQ ID NO: 209. The PCR product was digested with NdeI/HindIII and cloned into pET28.a vector. Rv3872 was transformed into expression host Rosetta plysS. After lysis of a 1 L induction, the recombinant protein was expressed in the soluble supernatant fraction. Ni-NTA affinity purification was done 2× under native conditions, then dialyzed against 20 mM Tris pH 8.0. The amino acid sequence of the recombinant protein is set forth in SEQ ID NO: 210.

Example 37

Cloning and Expression of Recombinant Rv3873

Using H37Rv genomic DNA as template, Rv3873 was PCR amplified using the following primers:

```
5'-Rv3873-NdeI
                                     (SEQ ID NO: 313)
GTGCTAGCCATATGCTGTGGCACGCAATGCCAC

3'-3873-HindIII
                                     (SEQ ID NO: 314)
CTGGATCCAAGCTTTCACCAGTCGTCCTCTTCGTC
```

Amplification was performed under the following conditions: 94° C. 0.5 min., 55° C. 0.5 min., 68° C. 2 min for 30 cycles, to give the product set forth in SEQ ID NO: 212. The PCR product was digested with NdeI/HindII and cloned into pET28a vector. Plasmid containing the Rv3873 gene was transformed into expression host Rosetta plysS. After lysis of a 1 L induction, the recombinant protein was expressed in the soluble supernatant fraction. Ni-NTA affinity purification was done 2× under native conditions, then dialyzed against 20 mM Tris pH 8.0. The amino acid sequence of the recombinant protein is set forth in SEQ ID NO: 213.

Example 38

Cloning and Expression of Recombinant Rv1511

Using H37Rv genomic DNA as template, Rv1511 was PCR amplified using the following primers:

```
5'-Rv1511-NdeI
                                 (SEQ ID NO: 315)
CAATTACATATGCATCACCATCACCATCACGTGAAGCGAGCG

CTCATCACC

3'-Rv1511-EcoRI
                                 (SEQ ID NO: 316)
CAATTAGAATTCTCATGTCCGGCCGGCGATCATCG
```

Amplification was performed under the following conditions: 94° C. 0.5 min., 55° C. 0.5 min., 68° C. 2 min for 30 cycles, to give the product set forth in SEQ ID NO: 214. The PCR product was digested with NdeI/EcoRI and cloned into pET 28a, minus the 5' linker. Rv1511 was transformed into expression hosts BL-21plysS and Rosetta plysS. Both expressed equally, but proceeded with the BL-21 cells. After lysis of a 1 L induction, the recombinant protein was expressed in the inclusion body pellet. Ni-NTA affinity purification was done under denaturing conditions, then dialyzed against 10 mM Tris pH 9.5. The amino acid sequence of the recombinant protein is set forth in SEQ ID NO: 215.

Example 39

Cloning and Expression of Recombinant Fusion Protein ID93

The following primers were used in for cloning the fusion construct ID93, which comprises fusion partners derived from Rv3619, Rv1813, Rv3620 and Rv2608:

```
5': Rv1813mat-5NdeI-KpnI
                                 (SEQ ID NO: 218)
CAATTACATATGGGTACCCATCTCGCCAACGGTTCGATG 3': Rv1813mat-3SacIgo
                                 (SEQ ID NO: 219)
CAATTAGAGCTCGTTGCACGCCCAGTTGACGAT 5': Rv3620-5SacI
                                 (SEQ ID NO: 220)
CAATTAGAGCTCATGACCTCGCGTTTTATGACG 3': Rv3620-3SalIgo
                                 (SEQ ID NO: 221)
CAATTAGTCGACGCTGCTGAGGATCTGCTGGGA 5': Rv2608-5SalI
                                 (SEQ ID NO: 222)
CAATTAGTCGACATGAATTTCGCCGTTTTGCCG 3': Rv2608-3ScaI-HindIII
                                 (SEQ ID NO: 223)
CAATTAAAGCTTTTAAGTACTGAAAAGTCGGGGTAGCGCCGG 5': Rv3619-5NdeI
                                 (SEQ ID NO: 224)
CAATTACATATGACCATCAACTATCAATTC 3': Rv3619-3KpnI
                                 (SEQ ID NO: 225)
CAATTAGGTACCGGCCCAGCTGGAGCCGACGGC
```

Rv1813 and Rv3620 were PCR amplified from H37Rv genomic template DNA (94° C. for 0:30; 58° C. for 0:30; 58° C. for 1:30; 35 cycles). Rv1813 was digested with NdeI/SacI then cloned into pET28.a vector. Rv3620 was digested with SacI/SalI then ligated into the Rv1813pET construct. The fusion construct has a polynucleotide sequence set forth in SEQ ID NO: 217, encoding the fusion protein set forth in SEQ ID NO: 226. Rv2608 was amplified from plasmid template by PCR (94° C. for 0:30; 58° C. for 0:30; 68° C. for 1:30; 35 cycles). Product was digested with SalI/HindIII and cloned into pET28.a-Rv1813-3620 vector. Rv3619 was amplified same as above and digested with NdeI/KpnI then ligated into the ID83 vector. ID93 was expressed in host BL-21plysS (2 L, 2XYT growth media, 37° C.). Induced with 1 mM IPTG at OD 0.77 and harvested at OD 1.93. Cell pellet was suspended in lysis buffer (20 mM Tris pH8, 100 mM NaCl, 2 mM PMSF) and froze. The cell pellet was then thawed, lysed by sonication, and spun at 7,000 rcf for 20 minutes ID83 is an inclusion body protein. The pellet was washed 2× with 1% Chaps. The pellet was solubilized in 60 mL in binding buffer (8M urea, 20 mM Tris pH 8, 100 mM NaCl) and bound to 16 mL Ni-NTA resin at RT for 1 hour. The resin was washed (50 mL 0.5% DOC for 20 minutes; 80 mL 60% IPA for 30 minutes, 50 mL 0.5% DOC rinse) and then eluted with binding buffer with 300 mM imidazole. The supernatant from the first bind was bound to an additional 8 mL resin and processed as indicated above. The aforementioned purifications removed breakdown products. Another Ni-NTA bind was done overnight at 4° C. in 160 mL (binding buffer with 50 mM NaCl) with 32 mL resin. The resin was washed and eluted as indicated above. The fractions from this bind were dialyzed in 20 mM Tris pH8.

Example 40

Cloning and Expression of Recombinant Fusion Protein ID91

The following primers were used in for cloning the fusion construct ID91, which comprises fusion partners derived from Rv3619, Rv2389, Rv3478 and Rv1886:

```
5'-Rv3619-5NdeI
                                 (SEQ ID NO: 228)
CAATTACATATGACCATCAACTATCAATTC

3'-Rv3619-3KpnI
                                 (SEQ ID NO: 229)
CAATTAGGTACCGGCCCAGCTGGAGCCGACGG

5'-Rv2389-KpnI
                                 (SEQ ID NO: 230)
TGGGCCGGTACCGACGACATCGATTGGGACGCC

3'-Rv2389-BamHI
                                 (SEQ ID NO: 231)
AATCCACCACGGATCCATCGTCCCTGCTCCCCGAAC

5'-Rv3478-BamHI
                                 (SEQ ID NO: 232)
CAGGGACGATGGATCCGTGGTGGATTTCGGGGCGTTAC

3'-Rv3478-EcoRI
                                 (SEQ ID NO: 233)
CCGGGAGAAGAATTCTCCGGCGGCCGGTGTGCGGG

5'-Rv1886-EcoRI
                                 (SEQ ID NO: 234)
GCCGCCGGAGAATTCTTCTCCCGGCCGGGGTGCC
```

```
3'-Rv1886matR HindIII
                                        (SEQ ID NO: 235)
GATATCAAGCTTTCAGCCGGCGCCTAACGAAC
```

The fusion construct has a polynucleotide sequence set forth in SEQ ID NO: 227, encoding the fusion protein set forth in SEQ ID NO: 236.

Example 41

Cloning and Expression of Recombinant Fusion Protein ID71

The following primers were used in for cloning the fusion construct ID71, which comprises fusion partners derived from Rv3619, Rv2389, Rv3478 (N180) and Rv1886:

```
5'-Rv3619-5NdeI
                                        (SEQ ID NO: 238)
CAATTACATATGACCATCAACTATCAATTC

3'-Rv3619-3KpnI
                                        (SEQ ID NO: 239)
CAATTAGGTACCGGCCCAGCTGGAGCCGACGG

5'-Rv2389-KpnI
                                        (SEQ ID NO: 240)
TGGGCCGGTACCGACGACATCGATTGGGACGCC

3'-Rv2389-BamHI
                                        (SEQ ID NO: 241)
AATCCACCACGGATCCATCGTCCCTGCTCCCCGAAC

5'-Rv3478-N180-EcoRI
                                        (SEQ ID NO: 242)
CGGCCGGGAGAAGAATTCCCCGCCGGGGTTGGTGATCAG

5'-Rv1886-EcoRI
                                        (SEQ ID NO: 243)
GCCGCCGGAGAATTCTTCTCCCGGCCGGGGCTGCC

3'-Rv1886matR HindIII
                                        (SEQ ID NO: 244)
GATATCAAGCTTTCAGCCGGCGCCTAACGAAC
```

The fusion construct has a polynucleotide sequence set forth in SEQ ID NO: 237, encoding the fusion protein set forth in SEQ ID NO: 245.

Example 42

Cloning and Expression of Recombinant Fusion Protein ID114

The following primers were used in for cloning the fusion construct ID114, which comprises fusion partners derived from Rv1813, Rv3620, Rv2608 and Rv1886:

```
5': Rv2608-5SalI
                                        (SEQ ID NO: 247)
CAATTAGTCGACATGAATTTCGCCGTTTTGCCG

3': Rv2608-3ScaI-HindIII
                                        (SEQ ID NO: 248)
CAATTAAAGCTTTTAAGTACTGAAAAGTCGGGGTAGCGCCGG 5'-Rv1886-2608-ScaI
                                        (SEQ ID NO: 249)
CGGCGCTACCCCGACTTTTCAGTACTTTCTCCCGGCCGGGG
CTGCCG 3'-Rv1886matR HindIII
                                        (SEQ ID NO: 250)
GATATCAAGCTTTCAGCCGGCGCCTAACGAAC
```

Rv1813 and Rv3620 were PCR amplified from H37Rv genomic template DNA (94° C. for 0:30; 58° C. for 0:30; 58° C. for 1:30; 35 cycles). The fusion construct has a polynucleotide sequence set forth in SEQ ID NO: 246, encoding the fusion protein set forth in SEQ ID NO: 251.

Example 43

Cloning and Expression of Recombinant Fusion Protein ID125

The following primers were used in for cloning the fusion construct ID125, which comprises fusion partners derived from Rv3619, Rv1813, Rv3620, Rv2608 and Rv1886:

```
5': Rv2608-5SalI
                                        (SEQ ID NO: 253)
CAATTAGTCGACATGAATTTCGCCGTTTTGCCG

3': Rv2608-3ScaI-HindIII
                                        (SEQ ID NO: 254)
CAATTAAAGCTTTTAAGTACTGAAAAGTCGGGGTAGCGCCGG 5'-Rv1886-2608-ScaI
                                        (SEQ ID NO: 255)
CGGCGCTACCCCGACTTTTCAGTACTTTCTCCCGGCCGGGG
CTGCCG 3'-Rv1886matR HindIII
                                        (SEQ ID NO: 256)
GATATCAAGCTTTCAGCCGGCGCCTAACGAAC
```

The fusion construct has a polynucleotide sequence set forth in SEQ ID NO: 252, encoding the fusion protein set forth in SEQ ID NO: 257.

Example 44

Cloning and Expression of Recombinant Fusion Protein DID85

The following primers were used in for cloning the fusion construct DID85, which comprises fusion partners derived from Rv2032, Rv2875, and Rv0831:

```
5'-Rv2032-NdeI-6his
                                        (SEQ ID NO: 259)
GATACACATATGCACCATCACCATCACCACATGCCGGACACC
ATGGTGAC 3'-Rv2032-GGSGGS-BamHI
                                        (SEQ ID NO: 260)
CATGGATCCGCTACCGCCAGAACCACCCCGGTGATCCTTAG
CCCGAAC 5'-Rv2875-BamHI
                                        (SEQ ID NO: 261)
GGTGGTTCTGGCGGTAGCGGATTCATGGGCGATCTGGTGAG
CCCG 3'-Rv2875R-EcoRI
                                        (SEQ ID NO: 262)
CATGAATTCAGAACCGCCGCTTCCGCCCGCCGGAGGCATTA
GCACGC 5'-Rv0831F-EcoRI
                                        (SEQ ID NO: 263)
GGCGGAAGCGGCGGTTCTGAATTCATGCTCCCCGAGACAAA
TCAG
```

```
3'-Rv0831R-HindIII
                                      (SEQ ID NO: 264)
TAGAATTCAAGCTTTTACTGGCGAAGCAGCTCATC
```

The genes for Rv2032, Rv2875, and Rv0831 were PCR amplified from existing Plasmid DNA (94° C. for 0:30; 58° C. for 0:30; 58° C. for 1:30; 30 cycles) using the above primer sequences. The three amplified PCR products were used in a second round of PCR to amplify the full length fusion gene product using the 5'-Rv2032-NdeI-6his and 3'-Rv0831R-HindIII primers. The resulting PCR product was digested with NdeI/HindIII and cloned into pET29a vector. DID85 was expressed by host strain BL-21plysS. The fusion construct has a polynucleotide sequence set forth in SEQ ID NO: 258, encoding the fusion protein set forth in SEQ ID NO: 265. After lysis of a 1 L induction, it went into the inclusion body. Ni-NTA was done under denaturing conditions, followed by anion exchange chromatography. Purified fractions were dialyzed against 10 mM Tris pH 8.0.

Example 45

Cloning and Expression of Recombinant Fusion Protein DID92

The following primers were used in for cloning the fusion construct DID92, which comprises fusion partners derived from Rv3044, Rv1009, and Rv0614:

```
5'-Rv3044-NdeI-6his
                                      (SEQ ID NO: 267)
GATACACATATGCACCATCACCATCACCACATGGGCAGCAGC

CATCATCATC

3'-Rv3044-NcoI
                                      (SEQ ID NO: 268)
CATATCGAGCTCGTTGATCGGCGCGTCGACCC

5'-Rv1009-NcoI-GGSGGS linker
                                      (SEQ ID NO: 269)
ATCAACGAGCTCGGAGGTTCTGGTGGAAGCGCATGCAAAAC

GGTGACGTTGAC

3'-Rv1009-EcoRI
                                      (SEQ ID NO: 270)
CATATCGAATTCGCGCGCACCCGCTCGTGCAGC

5'-Rv0164-EcoRI-GGSGGS linker
                                      (SEQ ID NO. 271)
CATGTCGAATTCGGTGGAAGCGGAGGTTCTATGACGGCAAT

CTCGTGCTCAC

3'-Rv0164-HindIII
                                      (SEQ ID NO: 272)
CATATCAAGCTTTTAGCTGGCCGCCAGCTGCTC
```

The fusion construct has a polynucleotide sequence set forth in SEQ ID NO: 266, encoding the fusion protein set forth in SEQ ID NO: 273.

Example 46

Cloning and Expression of Recombinant Fusion Protein DID108

The following primers were used in for cloning the fusion construct DID108, which comprises fusion partners derived from Rv3872, Rv3873, Rv3875 and Rv3881:

```
5'-Rv3872-NdeI-6his
                                      (SEQ ID NO: 275)
GATACACATATGCACCATCACCATCACCACATGGAAAAAATG

TCACATGATC

3'-Rv3872-SacI
                                      (SEQ ID NO: 276)
GATACATGAGCTCTTCGGCGAAGACGCCGGCGGC

5'-Rv3873-SacI-GGSGGS linker
                                      (SEQ ID NO: 277)
GATACAGAGCTCGGAGGTTCCGGTGGAAGCATGCTGTGGCA

CGCAATGCC

3'-Rv3873-EcoRI
                                      (SEQ ID NO: 278)
GATACAGAATTCCCAGTCGTCCTCTTCGTCCCAG

5'-Rv3875-EcoRI-GGSGGS linker
                                      (SEQ ID NO: 279)
GACAGAATTCGGTGGCAGTGGAGGATCTATGACAGAGCAGC

AGTGGAAT

3'-Rv3875-NheI
                                      (SEQ ID NO: 280)
CATATCAGCTAGC TGCGAACATCCCAGTGACGTTG

5'-Rv3881-NheI-GGSGGS linker
                                      (SEQ ID NO: 281)
CATATCAGCTAGCGGAGGTTCCGGTGGAAGCATGACGCAGT

CGCAGACCGTG

3'-Rv3881-HindIII
                                      (SEQ ID NO: 282)
CATATCAAAGCTT TCACTTCGACTCCTTACTGTC
```

The fusion construct has a polynucleotide sequence set forth in SEQ ID NO: 274, encoding the fusion protein set forth in SEQ ID NO: 283.

Example 47

Cloning and Expression of Recombinant Fusion Protein DID93

The following primers were used in for cloning the fusion construct DID93, which comprises fusion partners derived from Rv1099, Rv0655, and Rv0054:

```
5'-Rv1099-NdeI
                                      (SEQ ID NO: 285)
TAGGATCCCATATGGAGCTGGTCCGGGTGACC

3'-Rv1099-EcoRI-GGSGGS linker
                                      (SEQ ID NO: 286)
CACGAATTCGCTTCCACCAGAACCTCCGGGCAATGGGTACA

CGGCGC

5'-Rv0655-EcoRI-GGSGGS Linker
                                      (SEQ ID NO: 287)
GGAGGTTCTGGTGGAAGCGAATTCGTGCGATACAGTGACTC

ATAC

3'-Rv0655-SacI
                                      (SEQ ID NO: 288)
GCCACGAGCTCAGAACCGCCGCTTCCACCCTGGCCGATTTC

GTGCACCGC
```

```
5'-Rv0054-SacI-GGSGGS linker
                                (SEQ ID NO: 289)
GCCAGGGTGGAAGCGGCGGTTCTGAGCTCGTGGCTGGTGA
CACCACCATC 3'Rv0054-HindIII
                                (SEQ ID NO: 290)
CAATTAAAGCTTTCAGAATGGCGGTTCGTCATCGCC
```

The fusion construct has a polynucleotide sequence set forth in SEQ ID NO:284, encoding the fusion protein set forth in SEQ ID NO: 291

Example 48

Cloning and Expression of Recombinant Fusion Protein Rv3875

Using H37Rv genomic DNA as template, Rv3875 was PCR amplified using the following primers:

```
5'-Rv3875-6His-NdeI
                                (SEQ ID NO: 317)
CCATTACATATGCATCACCATCACCATCACATGACAGAGCAG
CAGTGGAA

3'-Rv3875-EcoRI
                                (SEQ ID NO: 318)
CCATTAGAATTCCTATGCGAACATCCCAGTGAC
```

The amino acid sequence of the recombinant protein is set forth in SEQ ID NO: 294.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for stimulating an immune response comprising:

administering to a subject an effective amount of a composition comprising two or more *Mycobacterium tuberculosis* antigens, wherein the two or more antigens comprise the antigen Rv3478 comprising the amino acid sequence set forth in SEQ ID NO:41 and the antigen Rv3619 comprising the amino acid sequence set forth in SEQ ID NO:46, or an antigen comprising an amino acid sequence having at least 90% sequence identity to the amino acid sequence set forth in SEQ ID NO: 41 and an antigen comprising an amino acid sequence having at least 90% sequence identity to the amino acid sequence set forth in SEQ ID NO: 46; and wherein the two or more antigens are covalently linked in the form of a fusion polypeptide.

2. The method of claim 1, wherein the two or more antigens comprise an antigen comprising an amino acid sequence having at least 99% sequence identity to the amino acid sequence set forth in SEQ ID NO: 41 and an antigen comprising an amino acid sequence having at least 99% sequence identity to the amino acid sequence set forth in SEQ ID NO: 46.

3. The method of claim 1, wherein the two or more antigens are directly linked.

4. The method of claim 1, wherein the two or more antigens are linked via an amino acid linker.

5. The method of claim 1, wherein the composition further comprises an immunostimulant.

6. The method of claim 5, wherein the immunostimulant is selected from the group consisting of glucopyranosyl lipid adjuvant (GLA), adjuvant system-2 (AS-2), monophosphoryl lipid A, 3-de-O-acylated monophosphoryl lipid A, incomplete Freund's adjuvant (IFA), *Quillaja saponaria* 21 (QS21), cell wall skeleton (CWS), trehalose dicorynomycolate (TDM), aminoalkyl glucosaminide phosphates (AGPs), CpG-containing oligonucleotides, Toll-like receptor agonists, LeIF, saponins, saponin mimetics, biological and synthetic lipid A, imiquimod, gardiquimod, resiquimod, polyI:C, and flagellin, or a combination thereof.

7. The method of claim 6, wherein the immunostimulant is GLA.

8. The method of claim 1, wherein the two or more antigens further comprise the antigen Rv2389 comprising the amino acid sequence set forth in SEQ ID NO: 21 or an antigen comprising an amino acid sequence having at least 90% sequence identity to the amino acid sequence set forth in SEQ ID NO: 21.

9. The method of claim 8, wherein the two or more antigens further comprise an antigen comprising an amino acid sequence having at least 99% sequence identity to the amino acid sequence set forth in SEQ ID NO: 21.

10. The method of claim 1, wherein the two or more antigens further comprise the antigen Rv1886 comprising the amino acid sequence set forth in SEQ ID NO: 145 or an antigen comprising an amino acid sequence having at least 90% sequence identity to the amino acid sequence set forth in SEQ ID NO: 145.

11. The method of claim 10, wherein the two or more antigens further comprise an antigen comprising an amino acid sequence having at least 99% sequence identity to the amino acid sequence set forth in SEQ ID NO: 145.

12. The method of claim 1, wherein the two or more antigens further comprise the antigen Rv2389 comprising the amino acid sequence set forth in SEQ ID NO: 21 or an antigen comprising an amino acid sequence having at least 90% sequence identity to the amino acid sequence set forth in SEQ ID NO: 21 and the antigen Rv1886 comprising the amino acid sequence set forth in SEQ ID NO: 145 or an antigen comprising an amino acid sequence having at least 90% sequence identity to the amino acid sequence set forth in SEQ ID NO: 145.

13. The method of claim 12, wherein the two or more antigens further comprise an antigen comprising an amino acid sequence having at least 99% sequence identity to the amino acid sequence set forth in SEQ ID NO: 21 and an amino acid sequence having at least 99% sequence identity to the amino acid sequence set forth in SEQ ID NO: 145.

14. The method of claim 1, wherein the fusion polypeptide is ID91 comprising the amino acid sequence set forth in SEQ ID NO: 236 or an amino acid sequence having at least 90% sequence identity to the amino acid sequence set forth in SEQ ID NO: 236.

15. The method of claim 14, wherein the fusion polypeptide comprises an amino acid sequence having at least 99% sequence identity to the amino acid sequence set forth in SEQ ID NO: 236.

\* \* \* \* \*